(12) United States Patent
Gu et al.

(10) Patent No.: US 11,767,330 B2
(45) Date of Patent: Sep. 26, 2023

(54) CITRATE SALT, PHARMACEUTICAL COMPOSITIONS, AND METHODS OF MAKING AND USING THE SAME

(71) Applicant: Foghorn Therapeutics Inc., Cambridge, MA (US)

(72) Inventors: Chong-Hui Gu, Waban, MA (US); Joshua D. Waetzig, Waltham, MA (US)

(73) Assignee: FOGHORN THERAPEUTICS INC., Cambridge, MA (US)

( * ) Notice: Subject to any disclaimer, the term of this patent is extended or adjusted under 35 U.S.C. 154(b) by 0 days.

(21) Appl. No.: 17/858,875

(22) Filed: Jul. 6, 2022

(65) Prior Publication Data

US 2023/0064136 A1     Mar. 2, 2023

Related U.S. Application Data

(60) Provisional application No. 63/218,776, filed on Jul. 6, 2021.

(51) Int. Cl.
*C07D 519/00* (2006.01)
*C07D 201/00* (2006.01)
*A61K 31/4545* (2006.01)

(52) U.S. Cl.
CPC ........ *C07D 519/00* (2013.01); *C07B 2200/13* (2013.01)

(58) Field of Classification Search
CPC ............... C07D 519/00; C07D 201/00; C07B 2200/13; A61K 31/4545
See application file for complete search history.

(56) References Cited

U.S. PATENT DOCUMENTS

| | | | |
|---|---|---|---|
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,056,883 B2 | 6/2006 | Ito et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,205,103 B2 | 4/2007 | Emerson | |
| 7,232,566 B2 | 6/2007 | June et al. | |
| 9,271,978 B2 | 3/2016 | Liu et al. | |
| 9,353,051 B2 | 5/2016 | Byrd et al. | |
| 9,410,943 B2 | 8/2016 | Kadoch et al. | |
| 10,105,420 B2 | 10/2018 | Kadoch et al. | |
| 10,464,925 B2 | 11/2019 | Bradner et al. | |
| 10,646,575 B2 | 5/2020 | Phillips et al. | |
| 10,660,968 B2 | 5/2020 | Phillips et al. | |
| 10,725,057 B2 | 7/2020 | Tojo et al. | |
| 10,849,982 B2 | 12/2020 | Phillips et al. | |
| 10,905,768 B1 | 2/2021 | Phillips et al. | |
| 10,976,320 B2 | 4/2021 | Dykhuizen et al. | |
| 11,185,592 B2 | 11/2021 | Phillips et al. | |
| 11,414,416 B1 | 8/2022 | Ruppel et al. | |
| 2005/0079512 A1 | 4/2005 | Emerson et al. | |
| 2006/0121005 A1 | 6/2006 | Berenson et al. | |
| 2011/0053897 A1 | 3/2011 | Che et al. | |
| 2011/0061116 A1 | 3/2011 | Haidar et al. | |
| 2011/0201602 A1 | 8/2011 | Geuns-Meyer et al. | |
| 2016/0058872 A1 | 3/2016 | Crew et al. | |
| 2016/0200721 A1 | 7/2016 | Yukimasa et al. | |
| 2016/0347708 A1 | 12/2016 | Ebright et al. | |
| 2017/0014491 A1 | 1/2017 | Kadoch et al. | |
| 2017/0050968 A1 | 2/2017 | Bennett et al. | |
| 2017/0158709 A1 | 6/2017 | Boloor | |
| 2017/0190686 A1 | 7/2017 | Tojo et al. | |
| 2017/0340605 A1 | 11/2017 | Albrecht et al. | |
| 2018/0044335 A1 | 2/2018 | Martin et al. | |
| 2018/0085465 A1 | 3/2018 | Bradner et al. | |
| 2018/0187614 A1 | 7/2018 | Dudar | |
| 2018/0213422 A1 | 7/2018 | Kazmi et al. | |
| 2018/0215766 A1 | 8/2018 | Bair et al. | |
| 2018/0215866 A1 | 8/2018 | Zhao et al. | |
| 2018/0328913 A1 | 11/2018 | Kadoch et al. | |
| 2019/0076539 A1 | 3/2019 | Phillips et al. | |
| 2019/0219562 A1 | 7/2019 | Matyskiela et al. | |
| 2019/0247509 A1 | 8/2019 | Buckley et al. | |
| 2019/0322683 A1 | 10/2019 | Chan et al. | |
| 2020/0140456 A1 | 5/2020 | Phillips et al. | |

(Continued)

FOREIGN PATENT DOCUMENTS

| | | |
|---|---|---|
| CN | 107056772 A | 8/2017 |
| CN | 108690020 A | 10/2018 |

(Continued)

OTHER PUBLICATIONS

U.S. Appl. No. 17/425,013, Brucelle et al.
U.S. Appl. No. 17/425,153, Ruppel et al.
U.S. Appl. No. 17/696,656, Ruppel et al.
Baheti et al., "Excipients used in lyophilization of small molecules," J. Excipients and Food Chem. 1(1):41-54 (2010).
Brien et al., Targeted degradation of BRD9 reverses oncogenic gene expression in synovial sarcoma,eLIFE. 7:1-26 (2018).
Crawford et al., "Inhibition of bromodomain-containing protein 9 for the prevention of epigenetically-defined drug resistance," Bioorg Med Chem Lett. 27(15):3534-41(2017).
Hay et al., "Design and synthesis of potent and selective inhibitors of BRD7 and BRD9 bromodomains," Medchemcomm. 6:1381-86 (2015).

(Continued)

*Primary Examiner* — John M Mauro
(74) *Attorney, Agent, or Firm* — Clark & Elbing LLP

(57) ABSTRACT

The present disclosure features citrate salts and pharmaceutical compositions useful for the treatment of BAF complex-related disorders. Also disclosed are methods for preparing compounds.

12 Claims, 54 Drawing Sheets

(32 of 54 Drawing Sheet(s) Filed in Color)

(56) References Cited

U.S. PATENT DOCUMENTS

| | | |
|---|---|---|
| 2020/0206344 A1 | 7/2020 | Kadoch et al. |
| 2021/0009568 A1 | 1/2021 | Zhou et al. |
| 2021/0198256 A1 | 7/2021 | Nasveschuk et al. |
| 2021/0230190 A1 | 7/2021 | Ruppel et al. |
| 2022/0048906 A1 | 2/2022 | Ruppel et al. |
| 2022/0098190 A1 | 3/2022 | Ruppel et al. |
| 2022/0193205 A1 | 6/2022 | Zhou et al. |
| 2022/0289711 A1 | 9/2022 | Ruppel et al. |
| 2022/0315578 A1 | 10/2022 | Chen et al. |
| 2023/0077730 A1 | 3/2023 | Ruppel et al. |

FOREIGN PATENT DOCUMENTS

| | | | |
|---|---|---|---|
| WO | WO-2017/197051 A1 | 11/2017 | |
| WO | WO-2017/197056 A1 | 11/2017 | |
| WO | WO-2017/223452 A1 | 12/2017 | |
| WO | WO-2018/177297 A1 | 10/2018 | |
| WO | WO-2019/099868 A2 | 5/2019 | |
| WO | WO-2019/152437 A1 | 8/2019 | |
| WO | WO-2019/195201 A1 | 10/2019 | |
| WO | WO-2019/207538 A1 | 10/2019 | |
| WO | WO-2020/051235 A1 | 3/2020 | |
| WO | WO-2020/078933 A1 | 4/2020 | |
| WO | WO-2020/132561 A1 | 6/2020 | |
| WO | WO-2020/160192 A1 | 8/2020 | |
| WO | WO-2020/160193 A2 | 8/2020 | |
| WO | WO-2020/160198 A1 | 8/2020 | |
| WO | WO-2020/239103 A1 | 12/2020 | |
| WO | WO-2021/055295 A1 | 3/2021 | |
| WO | WO-2021/178920 A1 | 9/2021 | |

OTHER PUBLICATIONS

Hohmann et al., "Sensitivity and engineered resistance of myeloid leukemia cells to BRD9 inhibition," Nat Chem Biol. 12(9): 672-679 (2016) (12 pages).

International Search Report and Written Opinion for International Application No. PCT/US22/36252, dated Nov. 15, 2022 (15 pages).

Kadoch et al., "Mammalian SWI/SNF chromatin remodeling complexes and cancer: Mechanistic insights gained from human genomics," Sci Adv. 1(5):e1500447 (2015) (17 pages).

Kadoch et al., "Proteomic and bioinformatic analysis of mammalian SWI/SNF complexes identifies extensive roles in human malignancy," Nat Genet. 45(6):592-601 (2013) (11 pages).

Kadoch et al., "Reversible Disruption of mSWI/SNF (BAF) Complexes by the SS18-SSX Oncogenic Fusion in Synovial Sarcoma," Cell. 153(1):71-85 (2013).

Kotla et al., "Mechanism of action of lenalidomide in hematological malignancies," J Hematol Oncol. 2:36 (Aug. 12, 2009).

Martin et al., "Structure-Based Design of an in Vivo Active Selective BRD9 Inhibitor," J Med Chem. 59(10):4462-75 (2016).

McBride et al., "Disruption of mammalian SWI/SNF and polycomb complexes in human sarcomas: mechanisms and therapeutic opportunities," J Pathol. 244(5): 638-649 (2018).

Michel et al., "Abstract PR15: BRD9 defines a novel mammalian SWI/SNF (BAF) complex configuration which supports proliferation in AML," Clin Cancer Res. 23(24): (2017).

Pan et al., "A major chromatin regulator determines resistance of tumor cells to T cell-mediated killing," Science. 359(6377):770-75 (2018) (11 pages).

Picaud et al., "9H-purine scaffold reveals induced-fit pocket plasticity of the BRD9 bromodomain," J Med Chem. 58(6):2718-36(2015).

Remillard et al., "Degradation of the BAF Complex Factor BRD9 by Heterobifunctional Ligands," Angew Chem Int Ed Engl. 56(21):5738-43 (2017) (7 pages).

Teuscher et al., "A Versatile Method to Determine the Cellular Bioavailability of Small-Molecule Inhibitors," J Med Chem. 60(1): 157-169 (2017).

Theodoulou et al., "Discovery of I-BRD9, a Selective Cell Active Chemical Probe for Bromodomain Containing Protein 9 Inhibition," J Med Chem. 59(4):1425-39 (2015).

Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," Cancer Res. 75(18):3865-78 (2015).

Wang et al., "NMR Fragment Screening Hit Induces Plasticity of BRD7/9 Bromodomains," Chembiochem. 17(15):1456-63 (2016).

Zoppi et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," J Med Chem. 62(2):699-726 (2019).

Borold et al., "BRD9 is a druggable component of interferon-stimulated gene expression and antiviral activity," EMBO Rep. 22(10):e52823 (Aug. 16, 2021) (18 pages).

Hu et al., "Genomic characterization of genes encoding histone acetylation modulator proteins identifies therapeutic targets for cancer treatment," Nat Commun. 10(1):733 (2019) (17 pages).

Remillard et al., "Degradation of the BAF Complex Factor BRD9 by Heterobifunctional Ligands," available in PMC May 24, 2018, published in final edited form as: Angew Chem Int Ed Engl. 56(21):5738-5743 (2017) (14 pages).

Zhu et al., "Targeting BRD9 for Cancer Treatment: A New Strategy," Onco Targets Ther. 13:13191-13200 (Dec. 24, 2020).

U.S. Appl. No. 17/245,379, Sandoval et al.

Choi et al., "Correlation of computed tomography and positron emission tomography in patients with metastatic gastrointestinal stromal tumor treated at a single institution with imatinib mesylate: proposal of new computed tomography response criteria," J Clin Oncol. 25(13):1753-9 (May 1, 2007).

Extended European Search Report for European Patent Application No. 20749033.5, dated Sep. 29, 2022 (5 pages).

International Preliminary Report on Patentability for International Application No. PCT/US2020/015740, dated Jul. 27, 2021 (6 pages).

International Preliminary Report on Patentability for International Application No. PCT/US2020/044508, dated Feb. 10, 2022 (6 pages).

International Search Report and Written Opinion for International Application No. PCT/US20/44043, dated Nov. 9, 2020 (15 pages).

International Search Report and Written Opinion for International Application No. PCT/US20/44508, dated Jan. 12, 2021 (8 pages).

International Search Report and Written Opinion for International Application No. PCT/US20/15740, dated Jun. 26, 2020 (11 pages).

International Search Report and Written Opinion for International Application No. PCT/US21/15630, dated Apr. 8, 2021 (8 pages).

International Search Report and Written Opinion for International Application No. PCT/US22/38641, dated Nov. 17, 2022 (10 pages).

International Search Report and Written Opinion for International Application No. PCT/US22/38668 dated Jan. 20, 2023 (11 pages).

International Search Report and Written Opinion for PCT/US2022/028511, dated Aug. 1, 2022 (14 pages).

Muscal et al., "Plasma and cerebrospinal fluid pharmacokinetics of thalidomide and lenalidomide in nonhuman primates," Available in PMC Jun. 18, 2013. Published in final edited form as: Cancer Chemother Pharmacol. 69(4):943-7 (Apr. 2012) (10 pages).

PubChem CID 68310947, "7-Methyl-4-phenyl-2H-isoquinolin-1-one," created Nov. 30, 2012 (8 pages).

SYO1

HS-SY-II

ASKA

RD

HCT116

Calu6

CITRATE SALT, PHARMACEUTICAL COMPOSITIONS, AND METHODS OF MAKING AND USING THE SAME

BACKGROUND

Disorders can be affected by the BAF complex. BRD9 is a component of the BAF complex. The present invention relates to useful salts, compositions, and methods for the treatment of BAF complex-related disorders, such as cancer and infection.

SUMMARY

Bromodomain-containing protein 9 (BRD9) is a protein encoded by the BRD9 gene on chromosome 5. BRD9 is a component of the BAF (BRG1- or BRM-associated factors) complex, a SWI/SNF ATPase chromatin remodeling complex, and belongs to family IV of the bromodomain-containing proteins. BRD9 is present in several SWI/SNF ATPase chromatin remodeling complexes and is upregulated in multiple cancer cell lines. Accordingly, agents that reduce the levels and/or activity of BRD9 may provide new methods for the treatment of disease and disorders, such as cancer and infection. The inventors have found that depleting BRD9 in cells results in the depletion of the SS18-SSX fusion protein in those cells. The SS18-SSX fusion protein has been detected in more than 95% of synovial sarcoma tumors and is often the only cytogenetic abnormality in synovial sarcoma. Additionally, evidence suggests that the BAF complex is involved in cellular antiviral activities. Thus, agents that degrade BRD9 (e.g., compounds) are useful in the treatment of disorders (e.g., cancers or infections) related to BAF, BRD9, and/or SS18-SSX.

In one aspect, the invention provides a citrate salt of the compound of Formula I:

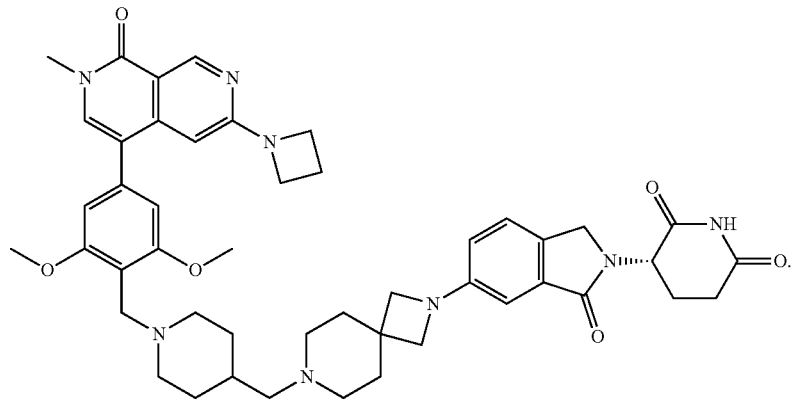

Formula I

In another aspect, the invention provides a citrate salt of the compound of Formula Ia:

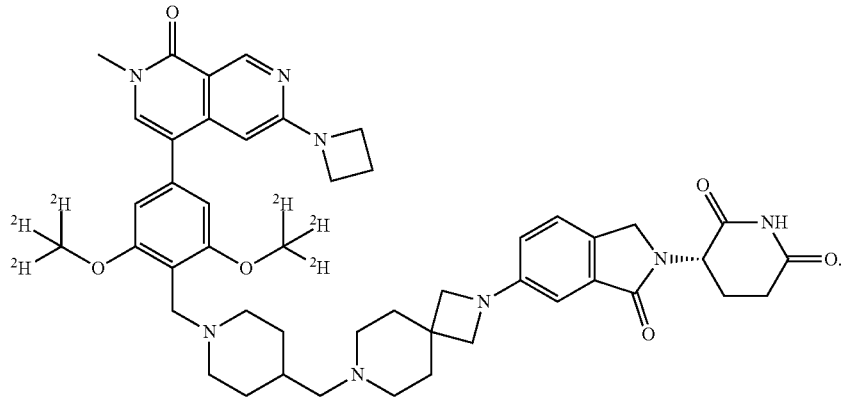

Formula Ia

In yet another aspect, the invention provides a pharmaceutical composition including the citrate salt described herein. In some embodiments, the pharmaceutical composition is liquid. In some embodiments, the pharmaceutical composition further includes a buffer (e.g., a citrate buffer).

In some embodiments, pH of the pharmaceutical composition is 3.5 to 5.5 (e.g., 3.5 to 5.0, 4.0 to 5.5, or 4.0 to 5.0).

In some embodiments, the pharmaceutical composition further includes a cyclodextrin-based solubilizer (e.g., sulfobutylether-β-cyclodextrin).

In some embodiments, the pharmaceutical composition further includes saline (e.g., isotonic saline).

In an aspect, the invention provides a crystalline form of the free-base solid form of the compound of Formula I:

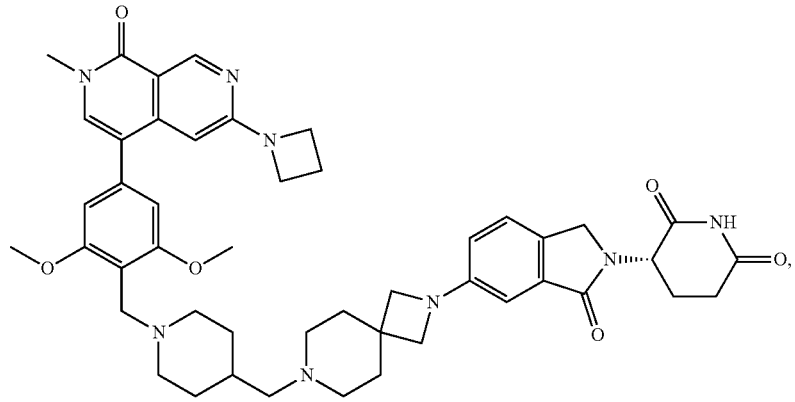

Formula I where the crystalline form is characterized by a powder x-ray diffraction pattern having peaks at 10.4±0.2 2θ and 26.9±0.2 2θ.

In some embodiments, the x-ray diffraction pattern further includes peaks at 17.7±0.2 2θ and at 17.9±0.2 2θ. In some embodiments, the x-ray diffraction pattern further includes a peak at 20.8±0.2 2θ. In some embodiments, the x-ray diffraction pattern further includes a peak at 13.8±0.2 2θ.

In another aspect, the invention provides a crystalline form of the free-base solid form of the compound of Formula I:

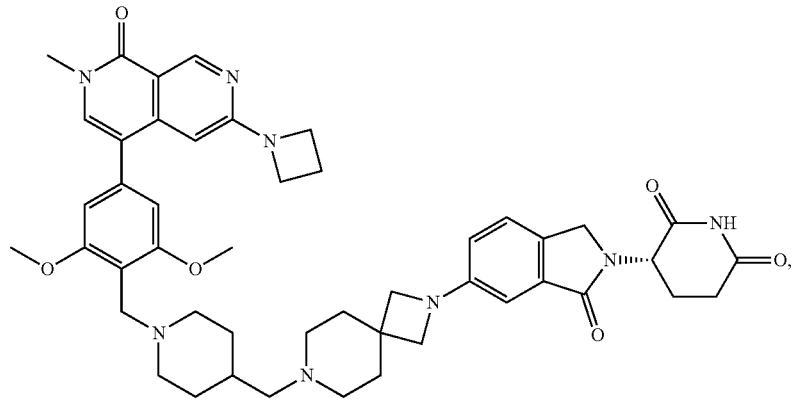

Formula I where the crystalline form is characterized by a powder x-ray diffraction pattern having peaks at 13.4±0.2 2θ and 17.4±0.2 2θ.

In some embodiments, the x-ray diffraction pattern further includes a peak at 26.3±0.2 2θ. In some embodiments, the x-ray diffraction pattern further includes a peak at 21.0±0.2 2θ. In some embodiments, the x-ray diffraction pattern further includes peaks at 13.6±0.2 2θ and 18.1±0.2 2θ.

In some embodiments, the crystalline form of any of the above aspects is in a pharmaceutical composition (e.g., a pharmaceutical composition described herein).

In a further aspect, the invention provides a pharmaceutical composition including the free-base solid form of the compound of Formula I:

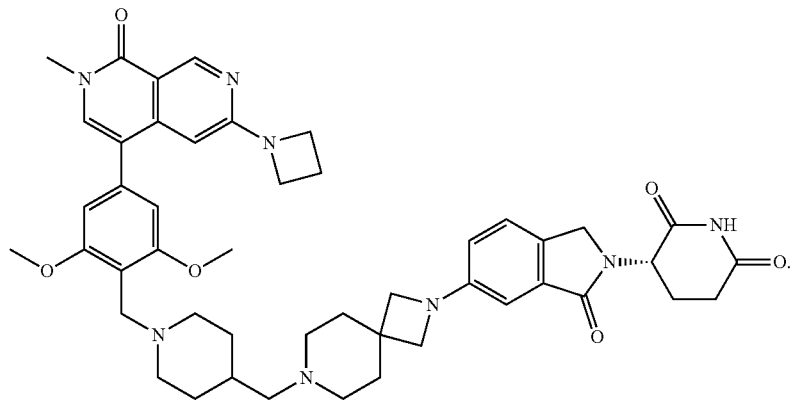

Formula I

In a yet further aspect, the pharmaceutical composition including the free-base solid form of the compound of Formula Ia:

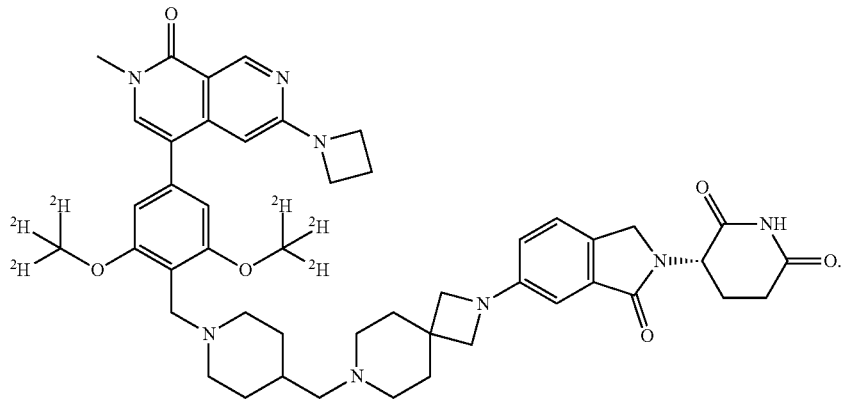

Formula Ia

In some embodiments, the free-base solid form is a lyophilizate.

In some embodiments, the pharmaceutical composition includes a buffer (e.g., a citrate buffer) in an amount sufficient produce a solution having pH of 3.5 to 5.5 upon dissolution in water at pH 7.

In still another aspect, the invention provides a pharmaceutical composition including an aqueous solvent and the compound of Formula I:

Formula I

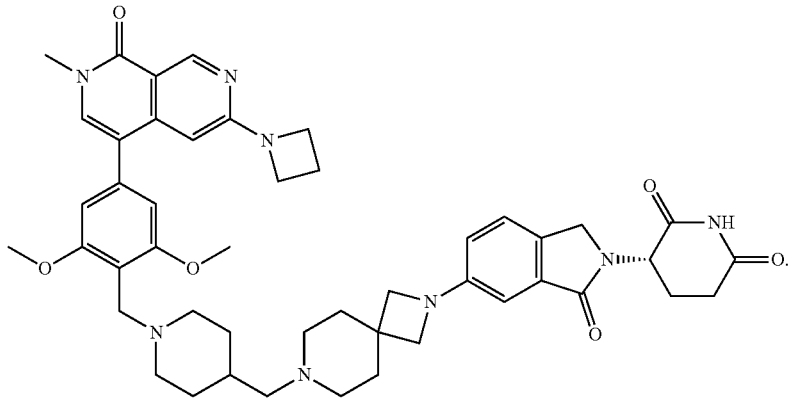

In a further aspect, the invention provides a pharmaceutical composition including an aqueous solvent and the compound of Formula Ia:

Formula Ia

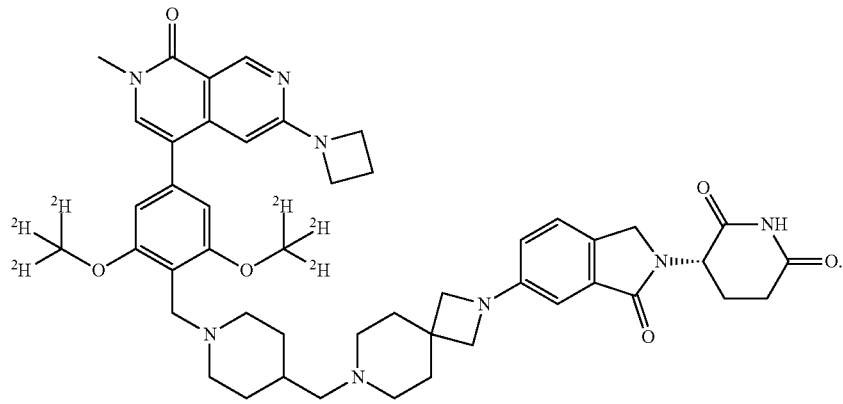

In some embodiments, pH of the pharmaceutical composition is 3.5 to 5.5 (e.g., 3.5 to 5.0, 4.0 to 5.5, or 4.0 to 5.0). In some embodiments, the pharmaceutical composition contains saline (e.g., isotonic saline). In some embodiments, the pharmaceutical composition further includes a cyclodextrin-based solubilizer (e.g., sulfobutylether-β-cyclodextrin).

In another aspect, the invention provides a method of administering to a subject the compound of Formula I:

Formula I

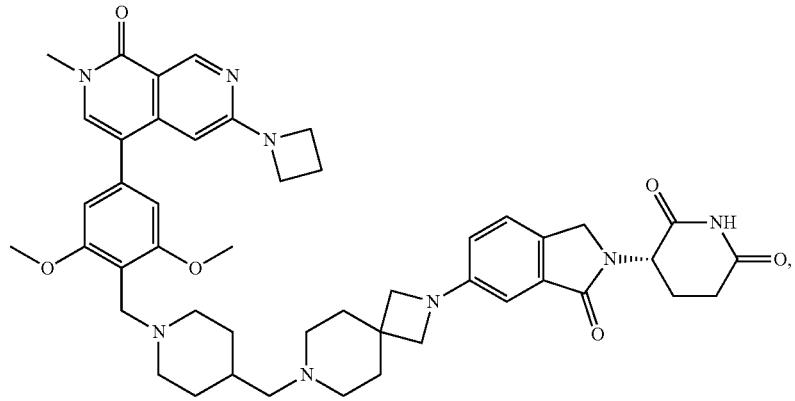

the method including combining the compound of Formula I in solid form with an aqueous solvent having pH of 3.5 to 5.5 to produce an aqueous solution, and administering the aqueous solution to the subject intravenously.

In yet another aspect, the invention provides a method of administering to a subject the compound of Formula Ia:

trointestinal stromal tumor, Kaposi sarcoma, liposarcoma, leiomyosarcoma, malignant mesenchymoma malignant peripheral nerve sheath tumors, myxofibrosarcoma, or low-grade rhabdomyosarcoma. In some embodiments, the sarcoma is synovial sarcoma. In some embodiments, the sarcoma is rhabdomyosarcoma. In some embodiments, the Formula Ia

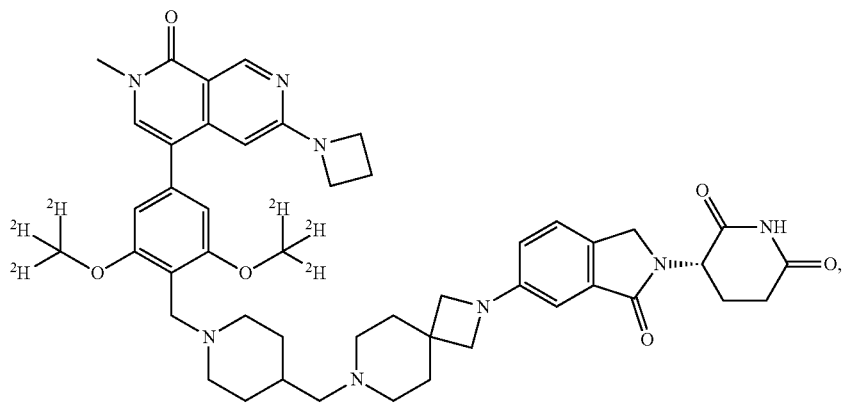

the method including combining the compound of Formula Ia in solid form with an aqueous solvent having pH of 3.5 to 5.5 to produce an aqueous solution, and administering the aqueous solution to the subject intravenously.

In still another aspect, the invention provides a method of treating a BAF complex-related disorder in a subject in need thereof, the method involving administering to the subject an effective amount of the citrate salt described herein, the crystalline form described herein, or the pharmaceutical composition described herein.

In a further aspect, the invention provides a method of treating an SS18-SSX fusion protein-related disorder in a subject in need thereof, the method involving administering to the subject an effective amount of the citrate salt described herein, the crystalline form described herein, or the pharmaceutical composition described herein.

In yet further aspect, the invention provides a method of treating a BRD9-related disorder in a subject in need thereof, the method involving administering to the subject an effective amount of the citrate salt described herein, the crystalline form described herein, or the pharmaceutical composition described herein.

In some embodiments, the disorder is cancer.

In still further aspect, the invention provides a method of treating cancer in a subject in need thereof, the method including administering to the subject an effective amount of the citrate salt described herein, the crystalline form described herein, or the pharmaceutical composition described herein.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma, non-small cell lung cancer, stomach cancer, or breast cancer. In some embodiments, the cancer is a sarcoma. In some embodiments, the sarcoma is a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gas-cancer is a prostate cancer. In some embodiments, the cancer is acute myeloid leukemia. In some embodiments, the cancer is a BRCA mutated cancer.

In some embodiments, the disorder is a viral infection.

In another aspect, the invention provides a method of treating a viral infection related to BAF47 in a subject in need thereof, the method including administering to the subject an effective amount of the citrate salt described herein, the crystalline form described herein, or the pharmaceutical composition described herein. In some embodiments, the viral infection is an infection with a virus of the Retroviridae family, Hepadnaviridae family, Flaviviridae family, Adenoviridae family, Herpesviridae family, Papillomaviridae family, Parvoviridae family, Polyomaviridae family, Paramyxoviridae family, or Togaviridae family. In some embodiments, the cell is a cancer cell.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In an aspect, the disclosure features a method of treating a BAF complex-related disorder in a subject in need thereof, the method involving administering to the subject an effective amount of any of the foregoing compounds, or pharmaceutically acceptable salts thereof, or a pharmaceutical composition thereof. In some embodiments, the BAF complex-related disorder is cancer. In some embodiments, the BAF complex-related disorder is infection.

In another aspect, the disclosure features a method of treating an SS18-SSX fusion protein-related disorder in a subject in need thereof, the method involving administering to the subject an effective amount of any of the foregoing compounds, or pharmaceutically acceptable salts thereof, or a pharmaceutical composition thereof. In some embodiments, the SS18-SSX fusion protein-related disorder is cancer. In some embodiments, the SS18-SSX fusion protein-related disorder is infection. In some embodiments of any of the foregoing methods, the SS18-SSX fusion protein is a SS18-SSX1 fusion protein, a SS18-SSX2 fusion protein, or a SS18-SSX4 fusion protein.

In yet another aspect, the disclosure features a method of treating a BRD9-related disorder in a subject in need thereof, the method involving administering to the subject an effective amount of any of the foregoing compounds, or pharmaceutically acceptable salts thereof, or a pharmaceutical composition thereof. In some embodiments, the BRD9-related disorder is cancer. In some embodiments, the BRD9-related disorder is infection.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histiocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In some embodiments, the infection is viral infection (e.g., an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)); Flaviviridae family (e.g. hepatitis C virus (HCV)); Adenoviridae family (e.g. Human Adenovirus); Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvirus K*, CMV, varicella-zoster virus); Papillomaviridae family (e.g. Human Papillomavirus (HPV, HPV E1)); Parvoviridae family (e.g. Parvovirus B19); Polyomaviridae family (e.g. JC virus and BK virus); Paramyxoviridae family (e.g. Measles virus); or Togaviridae family (e.g. Rubella virus)). In some embodiments, the disorder is Coffin Siris, Neurofibromatosis (e.g., NF-1, NF-2, or Schwannomatosis), or Multiple Meningioma. In an aspect, the disclosure features a method of treating a cancer in a subject in need thereof, the method including administering to the subject an effective amount of any of the foregoing compounds, or pharmaceutically acceptable salts thereof, or any of the foregoing pharmaceutical compositions.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histiocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In some embodiments of any of the foregoing methods, the cancer is a prostate cancer. In some embodiments of any of the foregoing methods, the cancer is a prostate cancer.

In some embodiments of any of the foregoing methods, the cancer is a BRCA mutated cancer.

In another aspect, the disclosure features a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)), Flaviviridae family (e.g. hepatitis C virus (HCV)), Adenoviridae family (e.g. Human Adenovirus), Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvirus K*, CMV, varicella-zoster virus), Papillomaviridae family (e.g. Human Papillomavirus (HPV, HPV E1)), Parvoviridae family (e.g. Parvovirus B19), Polyomaviridae family (e.g. JC virus and BK virus), Paramyxoviridae family (e.g. Measles virus), Togaviridae family (e.g. Rubella virus).

In another embodiment of any of the foregoing methods, the method further includes administering to the subject an additional anticancer therapy (e.g., chemotherapeutic or cytotoxic agent or radiotherapy).

In some embodiments, the additional anticancer therapy is a PARP inhibitor (e.g., niraparib, olaparib, rucaparib, talazoparib, veliparib, pamiparib, CK-102, or E7016). In particular embodiments, the additional anticancer therapy is: a chemotherapeutic or cytotoxic agent (e.g., doxorubicin or ifosfamide), a differentiation-inducing agent (e.g., retinoic acid, vitamin D, cytokines), a hormonal agent, an immunological agent, or an anti-angiogenic agent. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cisplatin). A list of additional compounds having anticancer activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

In particular embodiments, the compound of the invention and the additional anticancer therapy and any of the foregoing compounds or pharmaceutical compositions are administered within 28 days of each other (e.g., within 21, 14, 10, 7, 5, 4, 3, 2, or 1 days) or within 24 hours (e.g., 12, 6, 3, 2, or 1 hours, or concomitantly) each in an amount that together are effective to treat the subject.

In an aspect, the invention provides a method of preparing an enantioenriched compound of Formula I:

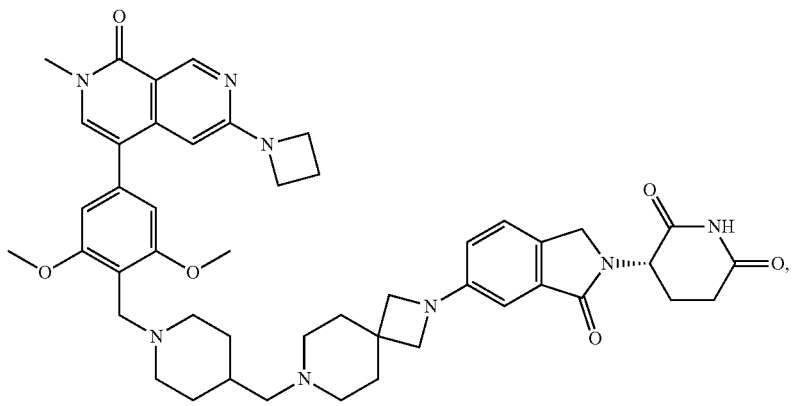

Formula I the method including reacting an enantioenriched compound of Formula Ib or a salt thereof and a compound of Formula Ic or a salt thereof under reductive amination reaction conditions, where the compound of Formula Ib is of the following structure:

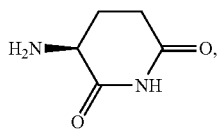

Formula Ib and the compound of formula of Formula Ic is of the following structure:

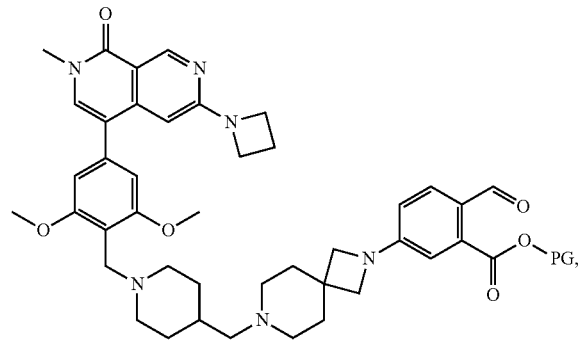

Formula Ic where PG is an O-protecting group.

In some embodiments, the reductive amination reaction conditions include the use of a borohydride agent as a reducing agent. In some embodiments, the borohydride agent is an NHC—$BH_3$ adduct, $NaBH_3CN$, or $NaBH(OAc)_3$. In some embodiments, the borohydride agent is the NHC—$BH_3$ adduct. In some embodiments, the borohydride agent is an adduct of N,N'-dimethylimidazolylidene and $BH_3$. In some embodiments, the reductive amination reaction conditions include the use of a Brønsted acid. In some embodiments, the Brønsted acid is acetic acid.

In some embodiments, the method includes the step of purifying the compound of Formula I.

In some embodiments, the step of purifying the compound of Formula I includes:

(i) an aqueous work-up to produce an aqueous layer and an organic layer, (ii) separating the organic layer away from the aqueous layer, (iii) concentrating the organic layer to produce a residue, (iv) forming a slurry of the residue with dichloromethane/acetonitrile to produce a liquid phase and a solid phase, (v) isolating the liquid phase, and (vi) concentrating the liquid phase to produce the compound of Formula I in purified form.

In some embodiments, the method includes the step of further purifying the compound of Formula I, the step of further purifying the compound of Formula I including:

dissolving the compound of Formula I from step (vi) in dichloromethane/acetonitrile to produce a solution, adding water to the solution to form a wet cake slurry, and separating the solid away from the wet cake slurry to produce a purified compound of Formula I, and optionally subjecting one or more times the purified compound of Formula I to the steps of dissolving, adding water, and separating the solid to increase the purity of the compound of Formula I.

In some embodiments, the purified compound of Formula I is subjected to the steps of dissolving, adding water, and separating the solid once.

The methods described herein for the preparation of an enantioenriched compound of Formula I may be adjusted to prepare an enantioenriched compound of Formula I':

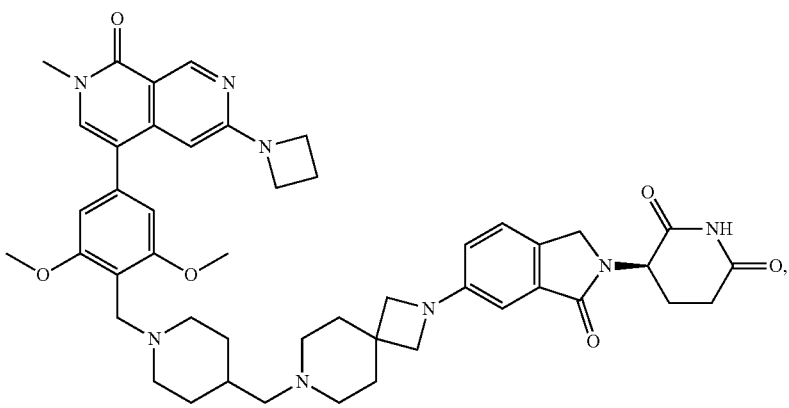

Formula I' the method including reacting an enantioenriched compound of Formula Ib' or a salt thereof and a compound of Formula Ic or a salt thereof under reductive amination reaction conditions, where the compound of Formula Ib' is of the following structure:

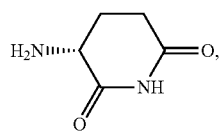

Formula Ib' and the compound of formula of Formula Ic is of the following structure:

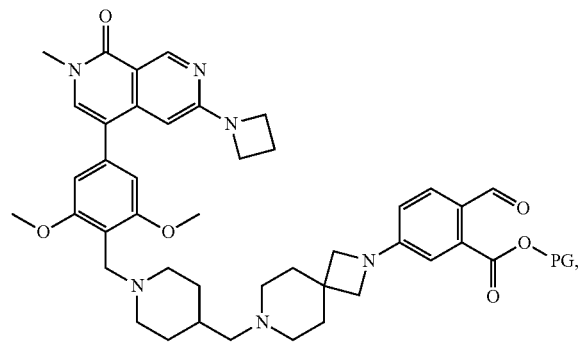

Formula Ic where PG is an O-protecting group.

In some embodiments, the reductive amination reaction conditions include the use of a borohydride agent as a reducing agent. In some embodiments, the borohydride agent is an NHC—BH$_3$ adduct, NaBH$_3$CN, or NaBH(OAc)$_3$. In some embodiments, the borohydride agent is the NHC—BH$_3$ adduct. In some embodiments, the borohydride agent is an adduct of N,N'-dimethylimidazolylidene and BH$_3$. In some embodiments, the reductive amination reaction conditions include the use of a Brønsted acid. In some embodiments, the Brønsted acid is acetic acid.

In some embodiments, the method includes the step of purifying the compound of Formula I'.

In some embodiments, the step of purifying the compound of Formula I' includes:
(i) an aqueous work-up to produce an aqueous layer and an organic layer,
(ii) separating the organic layer away from the aqueous layer,
(iii) concentrating the organic layer to produce a residue,
(iv) forming a slurry of the residue with dichloromethane/acetonitrile to produce a liquid phase and a solid phase,
(v) isolating the liquid phase, and
(vi) concentrating the liquid phase to produce the compound of Formula I' in purified form.

In some embodiments, the method includes the step of further purifying the compound of Formula I', the step of further purifying the compound of Formula I' including:
dissolving the compound of Formula I' from step (vi) in dichloromethane/acetonitrile to produce a solution,
adding water to the solution to form a wet cake slurry, and
separating the solid away from the wet cake slurry to produce a purified compound of Formula I', and optionally subjecting one or more times the purified compound of Formula I' to the steps of dissolving, adding water, and separating the solid to increase the purity of the compound of Formula I'.

In some embodiments, the purified compound of Formula I' is subjected to the steps of dissolving, adding water, and separating the solid once.

In an aspect, the invention provides a method of preparing an enantioenriched compound of Formula A:

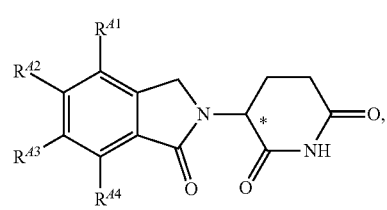

Formula A where
* designates an enantioenriched stereogenic center; and
each of $R^{A1}$, $R^{A2}$, $R^{A3}$, and $R^{A4}$ is, independently, H, A-L-, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{A1}$ and $R^{A2}$, $R^{A2}$ and $R^{A3}$, or $R^{A3}$ and $R^{A4}$, together with the carbon atoms to which each is attached, combine to form

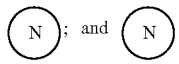

and is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with A-L-, where one of $R^{A1}$, $R^{A2}$, $R^{A3}$, and $R^{A4}$ is A-L-, or

is substituted with A-L-;
L is a linker; and
A is a BRD9 binding moiety;
the method including reacting an enantioenriched compound of Formula A1 or a salt thereof and a compound of Formula A2 or a salt thereof under reductive amination reaction conditions, where the compound of Formula A1 is of the following structure:

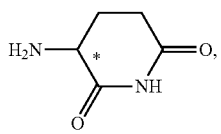

Formula A1 and the compound of formula of Formula A2 is of the following structure:

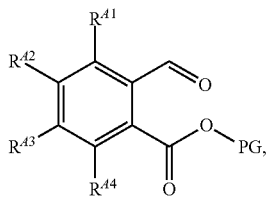

Formula A2 where PG is an O-protecting group.
In some embodiments, A-L- has the structure of Formula II:

$$A\text{-}(E^1)\text{-}(F^1)\text{—}(C^3)_m\text{-}(E^3)_n\text{—}(F^2)_{o1}\text{—}(F^3)_{o2}\text{-}(E^2)_p\text{-},\quad \text{Formula II}$$

where
each of m, n, o1, o2, and p is, independently, 0 or 1;
each of $E^1$ and $E^2$ is, independently, O, S, $NR^N$, optionally substituted $C_{1-10}$ alkylene, optionally substituted $C_{2-10}$ alkenylene, optionally substituted $C_{2-10}$ alkynylene, optionally substituted $C_2$-$C_{10}$ polyethylene glycol, or optionally substituted $C_{1-10}$ heteroalkylene;
$E^3$ is optionally substituted $C_1$-$C_6$ alkylene, optionally substituted $C_1$-$C_6$ heteroalkylene, O, S, or $NR^N$;
each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;
$C_3$ is carbonyl, thiocarbonyl, sulphonyl, or phosphoryl; and
each of $F^1$, $F^2$, and $F^3$ is, independently, optionally substituted $C_3$-$C_{10}$ carbocyclylene, optionally substituted $C_{2-10}$ heterocyclylene, optionally substituted $C_6$-$C_{10}$ arylene, or optionally substituted $C_2$-$C_9$ heteroarylene, In some embodiments, A-L- has the structure of Formula IIa:

$$A\text{-}(E^1)\text{-}(F^1)\text{—}(C^3)_m\text{-}(E^2)_p\text{-}.\quad \text{Formula IIa}$$

In some embodiments, A-L- has the structure of Formula IIb:

$$A\text{-}(E^1)\text{-}(F^1)\text{-}(E^2)_p\text{-}.\quad \text{Formula IIb}$$

In some embodiments, A-L- has the structure of Formula IIc:

$$A\text{-}(E^1)\text{-}(F^1)\text{-}.\quad \text{Formula IIIc}$$

In some embodiments, A-L- has the structure of Formula IId:

$$A\text{-}(E^1)\text{-}(F^1)\text{—}(C^3)_m\text{—}(F^2)_{o1}.\quad \text{Formula IId}$$

In some embodiments, A-L- has the structure of Formula IIe:

$$A\text{-}(E^1)\text{-}(F^1)\text{-}(E^3)_n\text{—}(F^2)_{o1}\text{-}(E^2)_p\text{-}.\quad \text{Formula IIe}$$

In some embodiments, A-L- has the structure of Formula IIf:

$$A\text{-}(E^1)\text{-}(F^1)\text{—}(C^3)_m\text{-}(E^3)_n\text{—}(F^2)_{o1}\text{-}(E^2)_p\text{-}.\quad \text{Formula IIf}$$

In some embodiments, A-L- has the structure of Formula Vg:

$$A\text{-}(E^1)\text{-}(F^1)\text{-}(E^3)_n\text{—}(F^2)_{o1},\quad \text{Formula IIg}$$

In some embodiments, each of $E^1$ and $E^2$ is, independently, $NR^N$, optionally substituted $C_{1-10}$ alkylene, optionally substituted $C_2$-$C_{10}$ polyethylene glycolene, or optionally substituted $C_{1-10}$ heteroalkylene.

In some embodiments, $E^3$ is optionally substituted $C_1$-$C_6$ alkylene, O, S, or $NR^N$. In some embodiments, $E^3$ is optionally substituted $C_1$-$C_6$ alkylene. In some embodiments, $E^3$ is optionally substituted $C_1$-$C_3$ alkylene. In some embodiments, $E^3$ is

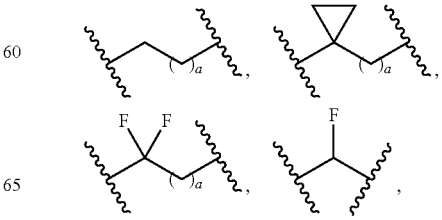

-continued
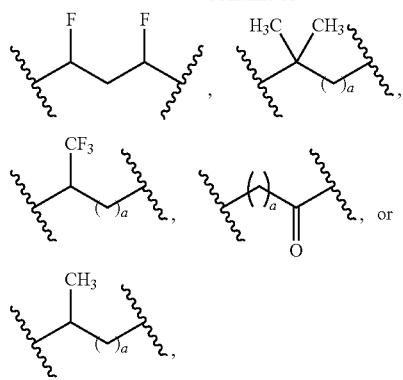
where a is 0, 1, 2, 3, 4, or 5.
In some embodiments, $E^3$ is
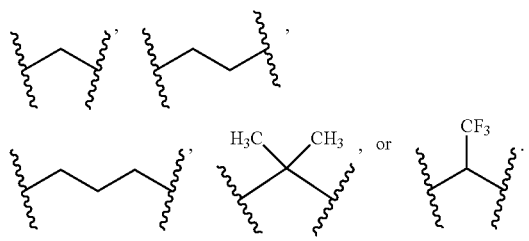
In some embodiments, $E^3$ is O. In some embodiments, each $R^N$ is, independently, H or optionally substituted $C_{1-4}$ alkyl. In some embodiments, each $R^N$ is, independently, H or methyl. In some embodiments, $E^1$ is
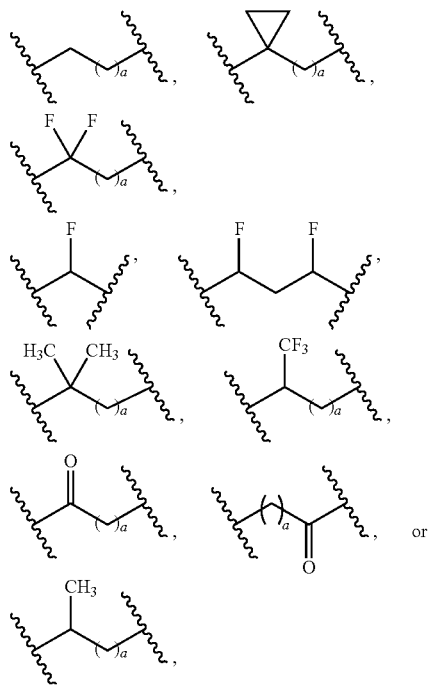
where a is 0, 1, 2, 3, 4, or 5.
In some embodiments, $E^1$ is
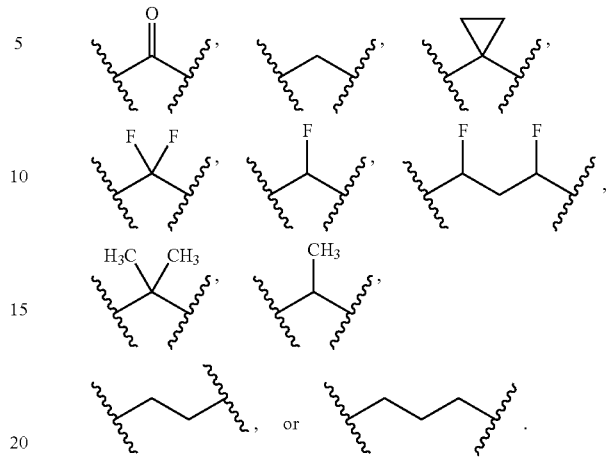
In some embodiments, $E^1$ is
In some embodiments, $E^1$ is
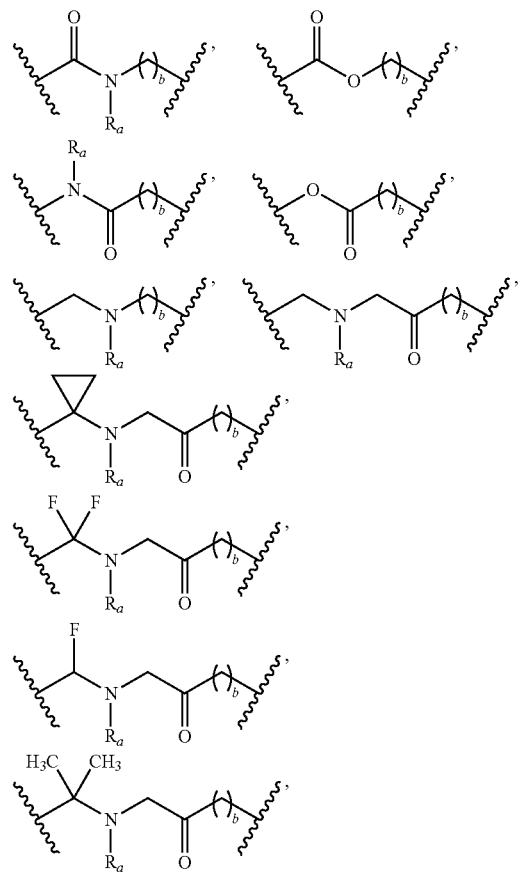

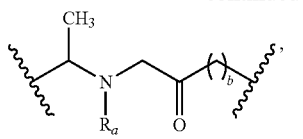

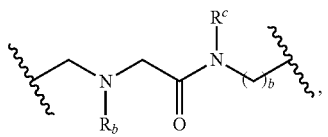

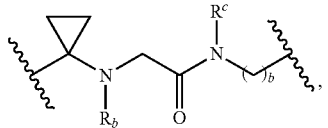

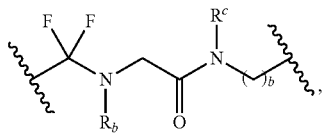

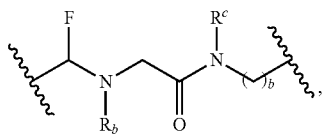

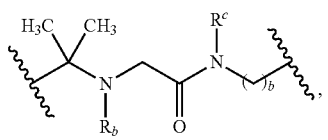

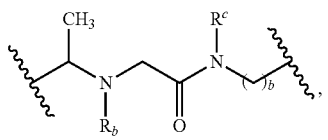

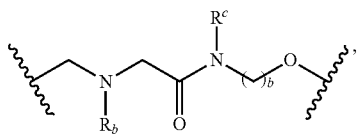

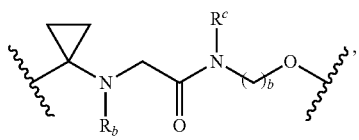

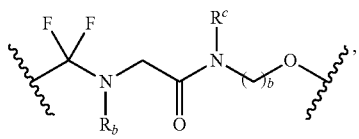

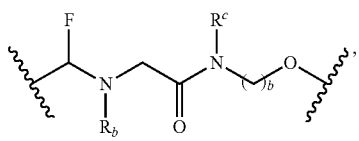

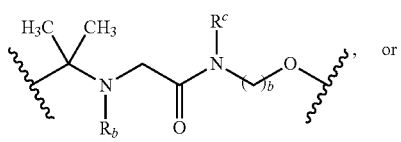

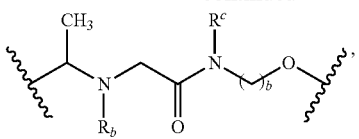

where b is 0, 1, 2, 3, 4, 5, or 6;

$R^a$ is H, optionally substituted $C_1$-$C_6$ alkyl, optionally substituted $C_1$-$C_6$ heteroalkyl, or optionally substituted $C_3$-$C_6$ carbocyclyl;

$R^b$ is H, optionally substituted $C_1$-$C_6$ alkyl, optionally substituted $C_1$-$C_6$ heteroalkyl, or optionally substituted $C_3$-$C_6$ carbocyclyl; and $R^c$ is H, optionally substituted $C_1$-$C_6$ alkyl, optionally substituted $C_1$-$C_6$ heteroalkyl, or optionally substituted $C_3$-$C_6$ carbocyclyl.

In some embodiments, $E^1$ is

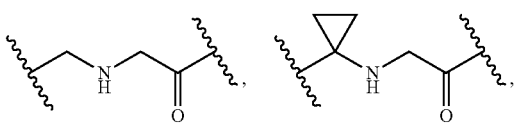

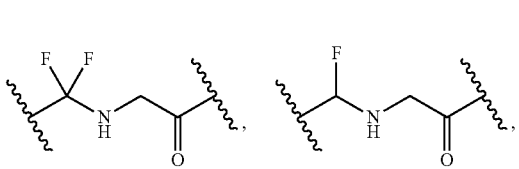

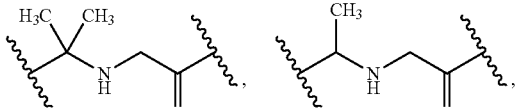

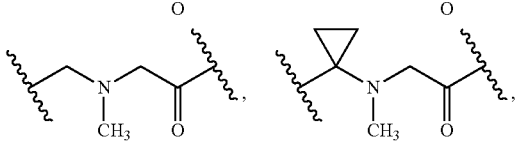

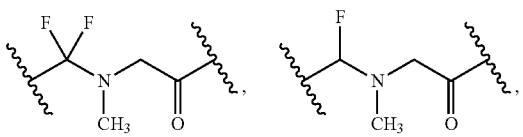

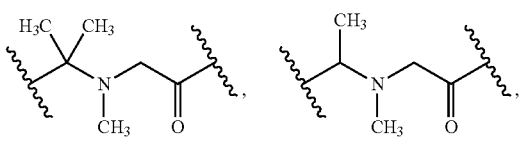

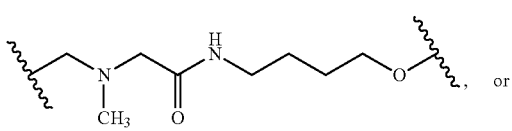

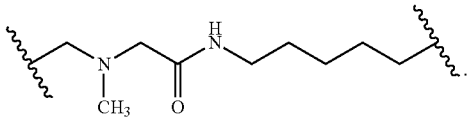

In some embodiments, $E^1$ is

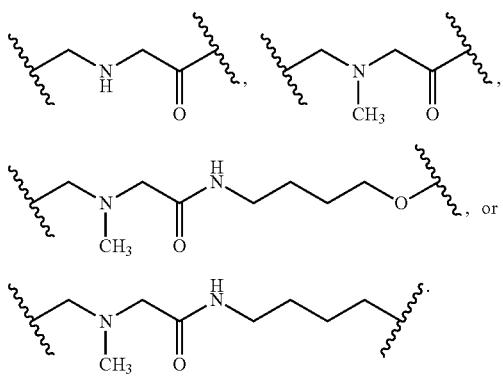

In some embodiments, $E^1$ is

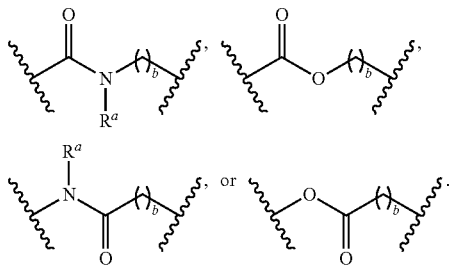

In some embodiments, $E^1$ is

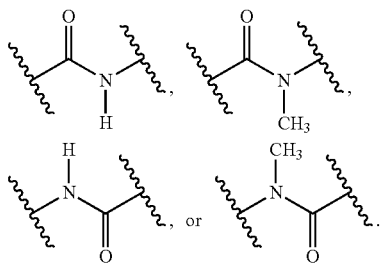

In some embodiments, $R^a$ is H or methyl. In some embodiments, $R^a$ is H. In some embodiments, $R^a$ is methyl.

In some embodiments, $E^2$ is O, $NR^w$,

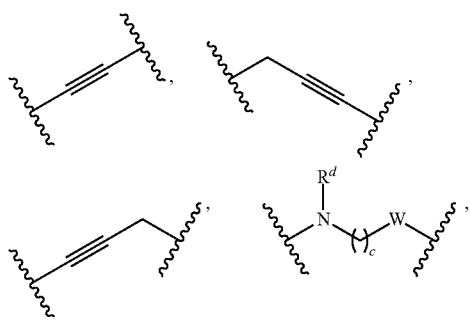

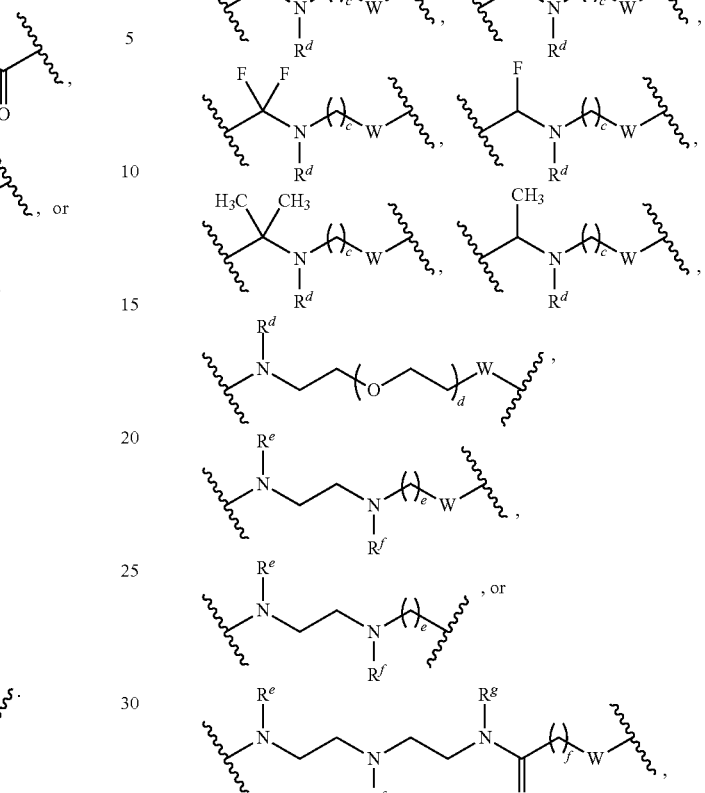

where
c is 0, 1, 2, 3, 4, 5, 6, 7, or 8;
d is 0, 1, 2, or 3;
e is 0, 1, 2, 3, 4, 5, or 6;
f is 0, 1, 2, 3, or 4;
$R^d$ is H, optionally substituted $C_1$-$C_6$ alkyl, optionally substituted $C_1$-$C_6$ heteroalkyl, or optionally substituted $C_3$-$C_6$ carbocyclyl;
$R^e$ is H, optionally substituted $C_1$-$C_6$ alkyl, optionally substituted $C_1$-$C_6$ heteroalkyl, or optionally substituted $C_3$-$C_6$ carbocyclyl;
$R^f$ is H, optionally substituted $C_1$-$C_6$ alkyl, optionally substituted $C_1$-$C_6$ heteroalkyl, or optionally substituted $C_3$-$C_6$ carbocyclyl;
$R^g$ is H, optionally substituted $C_1$-$C_6$ alkyl, optionally substituted $C_1$-$C_6$ heteroalkyl, or optionally substituted $C_3$-$C_6$ carbocyclyl; and
W is O or $NR^w$, where $R^w$ is H or optionally substituted $C_1$-$C_6$ alkyl.

In some embodiments, $E^2$ is O,

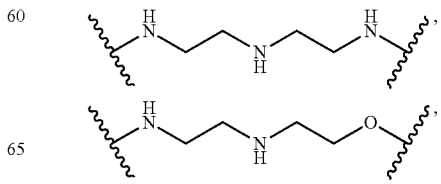

-continued

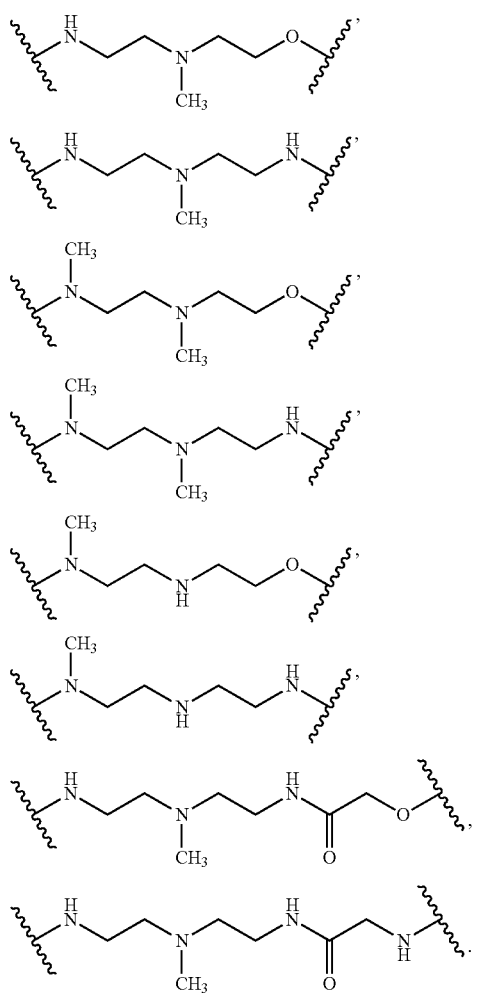

In some embodiments, each of $F^1$, $F^2$, or $F^3$ is, independently, optionally substituted $C_3$-$C_{10}$ carbocyclylene. In some embodiments, the $C_3$-$C_{10}$ carbocyclylene is monocyclic. In some embodiments, the $C_3$-$C_{10}$ carbocyclylene is polycyclic. In some embodiments, the $C_3$-$C_{10}$ carbocyclylene is fused. In some embodiments, the $C_3$-$C_{10}$ carbocyclylene is spirocyclic. In some embodiments, the $C_3$-$C_{10}$ carbocyclylene is bridged.

In some embodiments, the $C_3$-$C_{10}$ carbocyclylene is

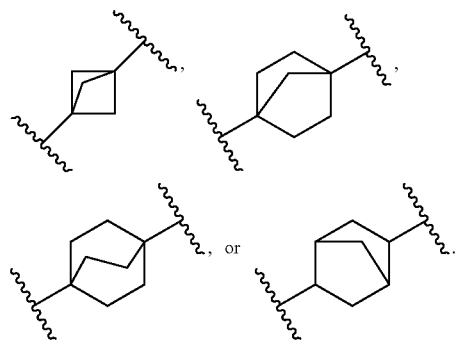

In some embodiments, the $C_3$-$C_{10}$ carbocyclylene is

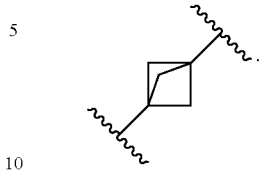

In some embodiments, each of $F^1$, $F^2$, or $F^3$ is, independently, optionally substituted $C_2$-$C_6$ heterocyclylene. In some embodiments, the $C_2$-$C_6$ heterocyclylene is monocyclic.

In some embodiments, the $C_2$-$C_6$ heterocyclylene is

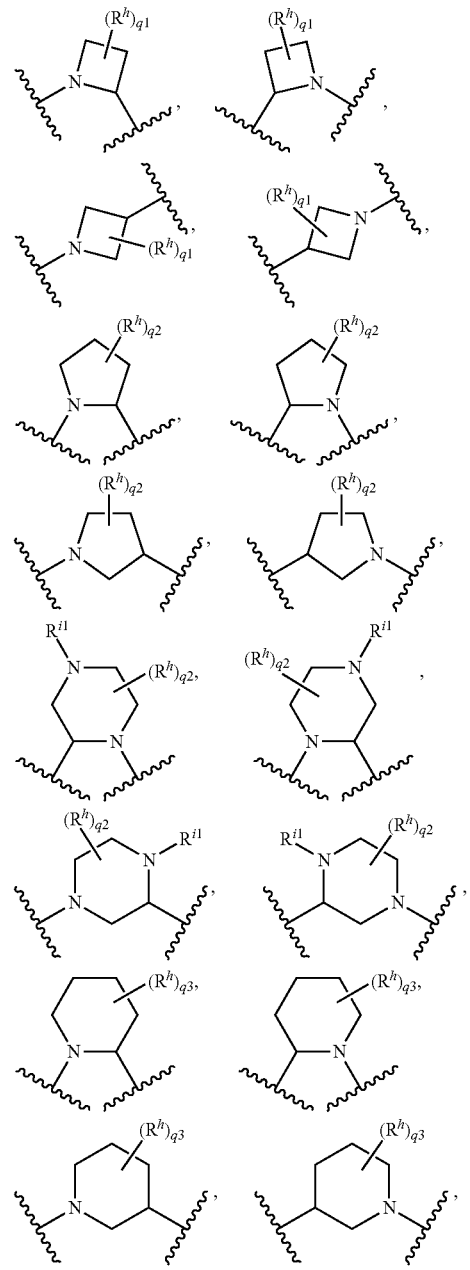

-continued

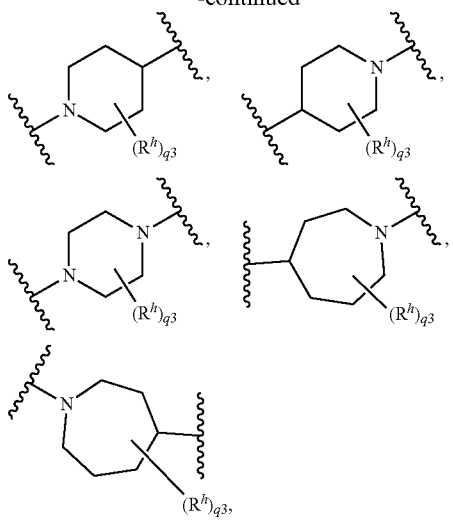

where
q1 is 0, 1, 2, 3, or 4;
q2 is 0, 1, 2, 3, 4, 5, or 6;
q3 is 0, 1, 2, 3, 4, 5, 6, 7, or 8;
each $R^h$ is, independently, $^2H$, halogen, optionally substituted $C_1$-$C_6$ alkyl, $OR^{i2}$, or $NR^{i3}R^{i4}$; or two $R^h$ groups, together with the carbon atom to which each is attached, combine to form optionally substituted $C_3$-$C_{10}$ carbocyclyl or optionally substituted $C_2$-$C_9$ heterocyclyl; or two $R^h$ groups, together with the carbon atoms to which each is attached, combine to form optionally substituted $C_3$-$C_{10}$ carbocyclyl or optionally substituted $C_2$-$C_9$ heterocyclyl;
$R^{i1}$ is H or optionally substituted $C_1$-$C_6$ alkyl;
$R^{i2}$ is H, optionally substituted $C_1$-$C_6$ alkyl, optionally substituted $C_1$-$C_6$ heteroalkyl, or optionally substituted $C_3$-$C_6$ carbocyclyl;
In some embodiments, the $C_2$-$C_9$ heterocyclylene is

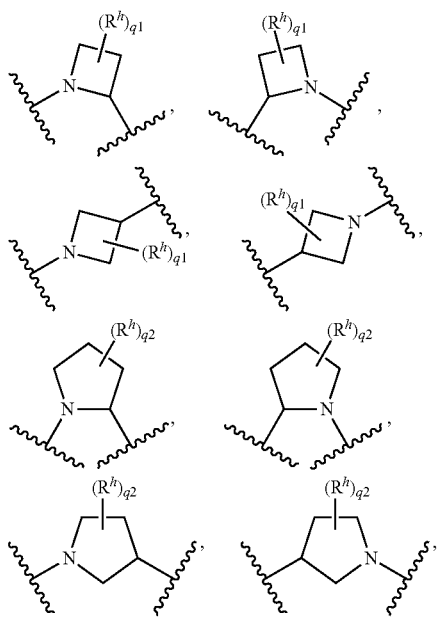

-continued

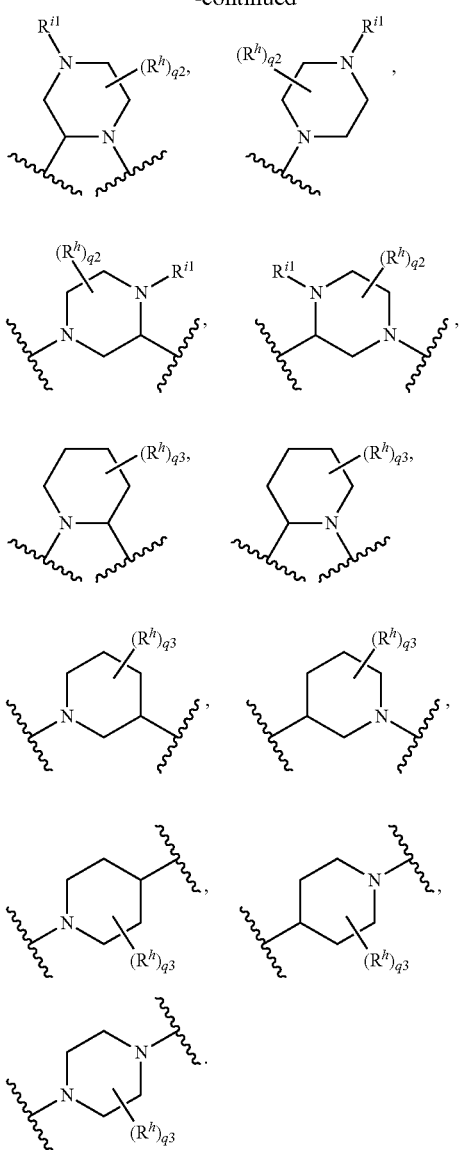

In some embodiments, each $R^h$ is, independently, $^2H$, halogen, cyano, optionally substituted $C_1$-$C_6$ alkyl, $OR^{i2}$, or $NR^{i3}R^{i4}$. In some embodiments, each $R^h$ is, independently, $^2H$, F, methyl,

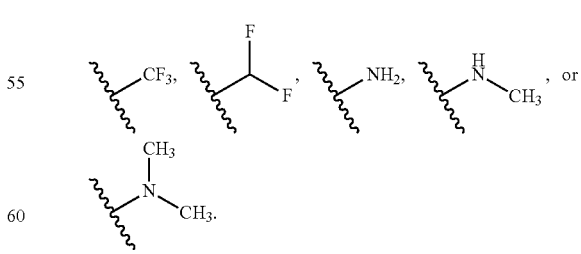

In some embodiments, each $R^h$ is, independently, F, methyl, or $NR^{i3}R^{i4}$. In some embodiments, q1 is 0, 1, or 2. In some embodiments, q2 is 0, 1, or 2. In some embodiments, q3 is 0, 1, or 2.

In some embodiments, the $C_2$-$C_9$ heterocyclylene is
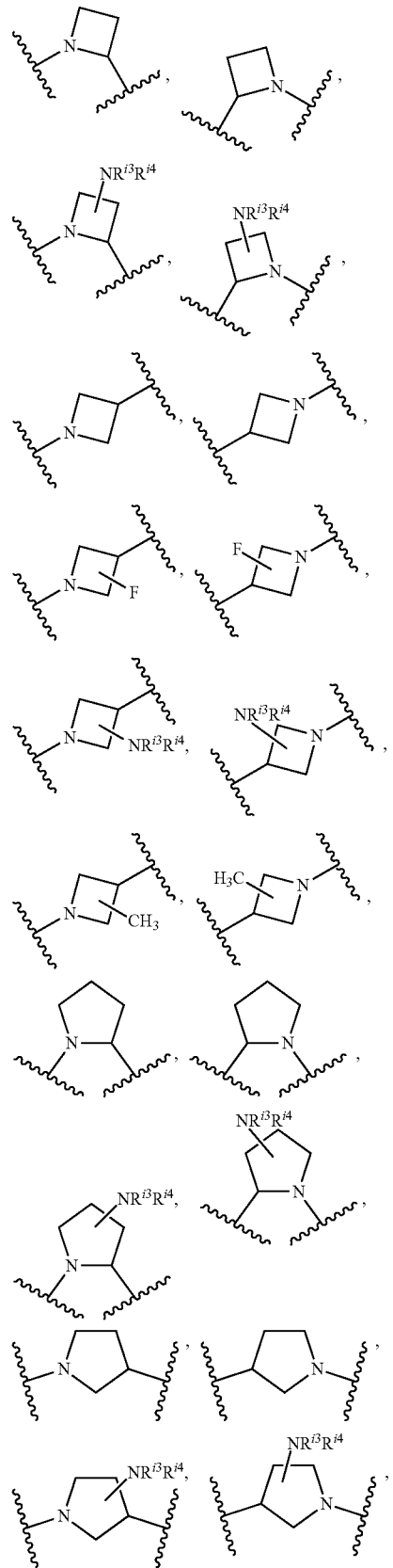
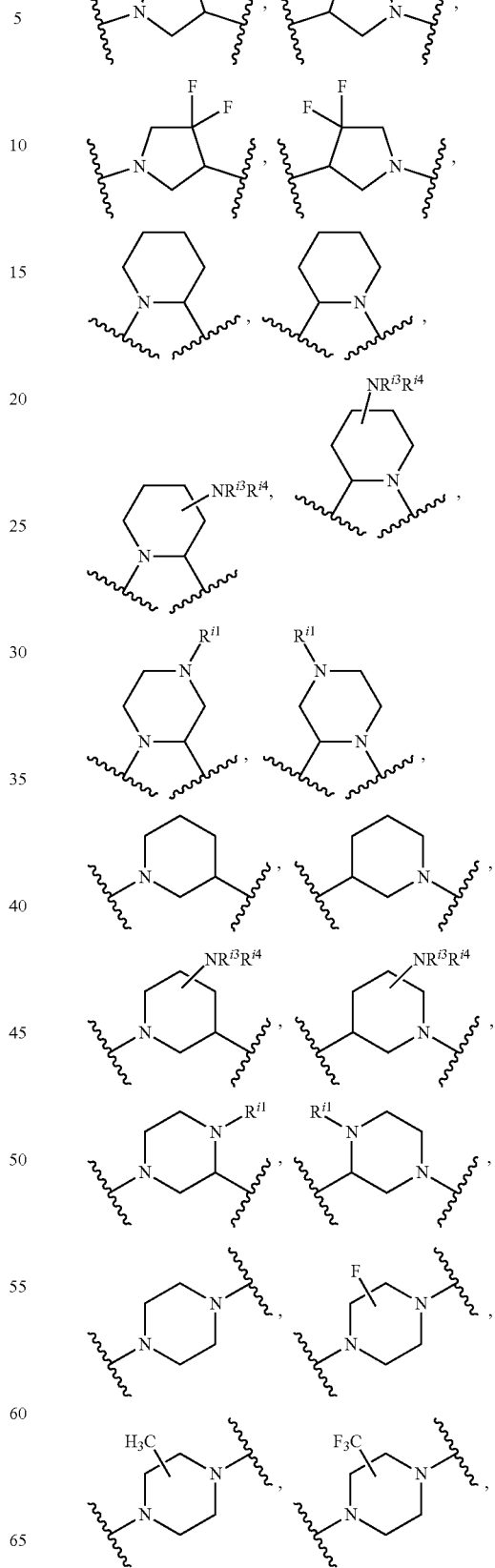
-continued

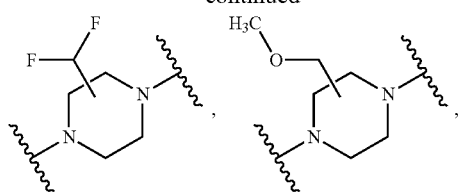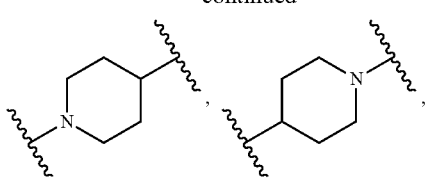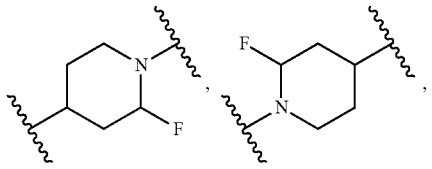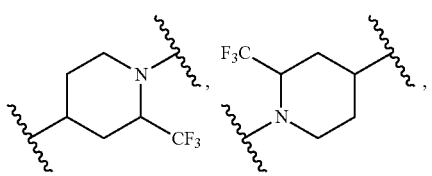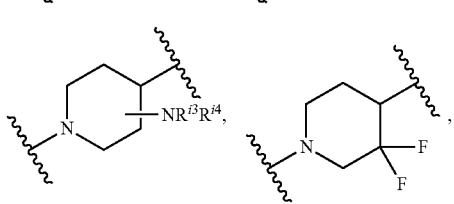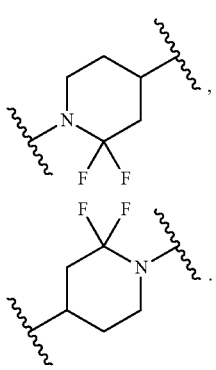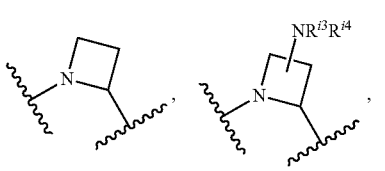
In some embodiments, the $C_2$-$C_9$ heterocyclylene is
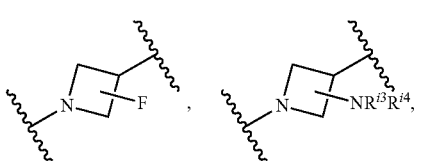

-continued
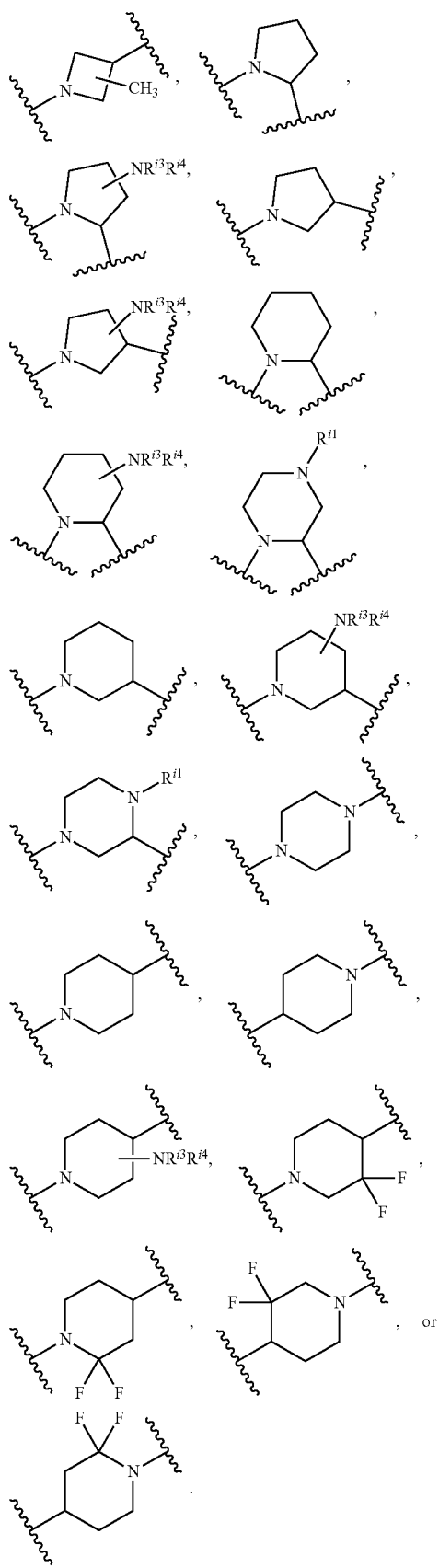
In some embodiments, the $C_2$-$C_9$ heterocyclylene is
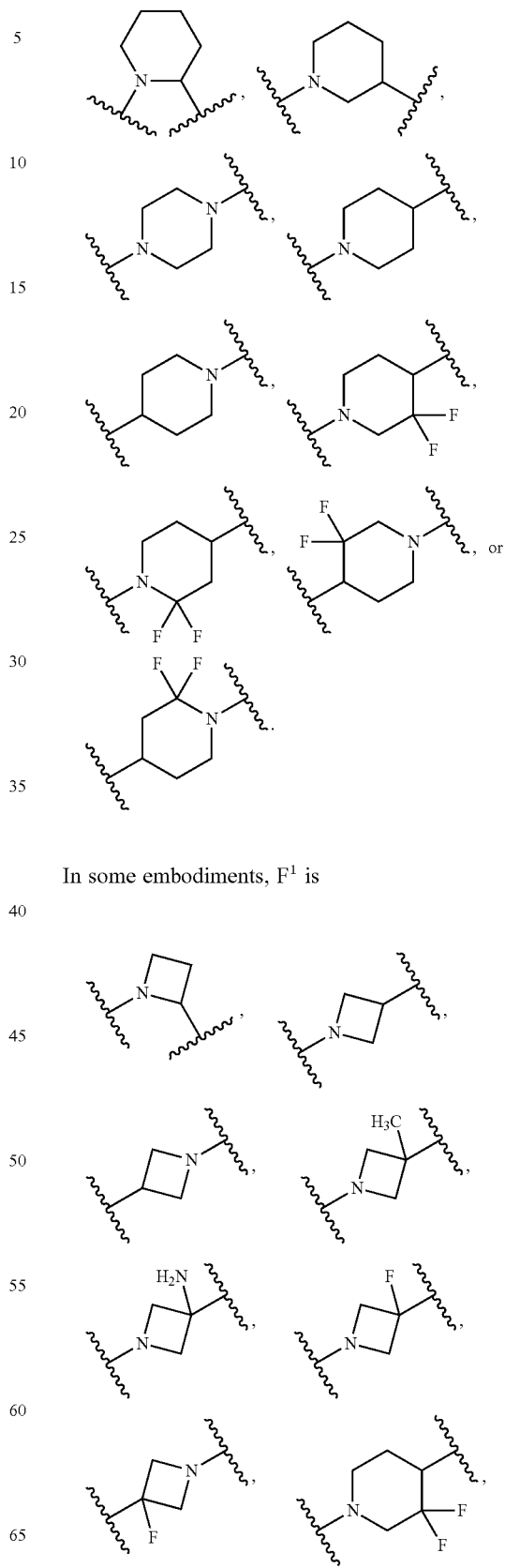
In some embodiments, $F^1$ is

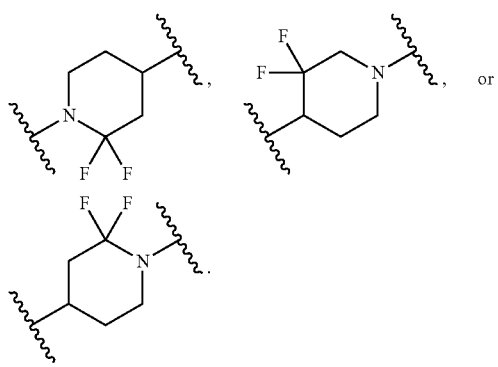

In some embodiments, $F^2$ is

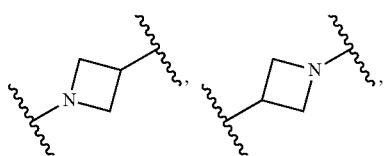

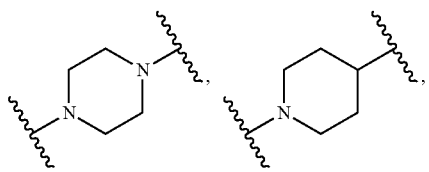

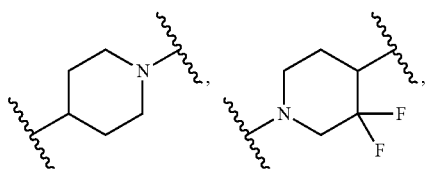

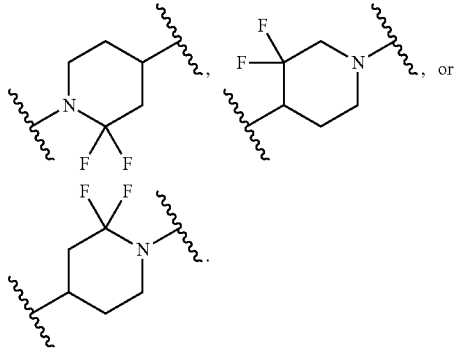

In some embodiments, $F^3$ is

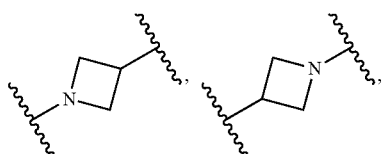

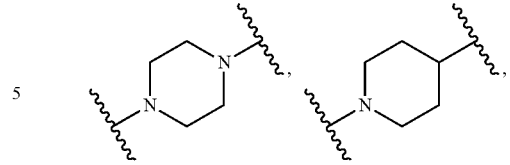

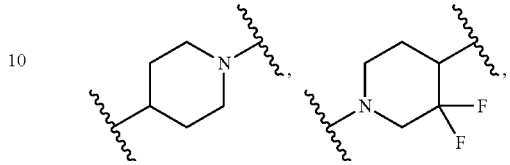

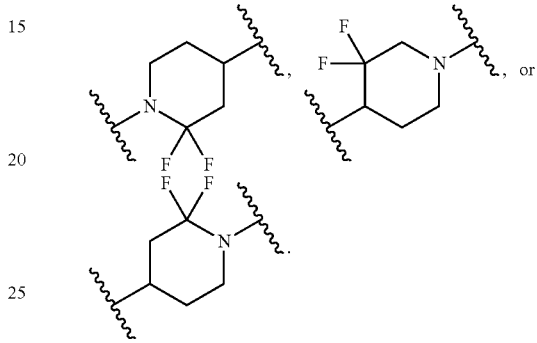

In some embodiments, the $C_2$-$C_6$ heterocyclylene is polycyclic. In some embodiments, the $C_2$-$C_6$ heterocyclylene is bicyclic. In some embodiments, the $C_2$-$C_6$ heterocyclylene is bridged.

In some embodiments, the $C_2$-$C_6$ heterocyclylene is

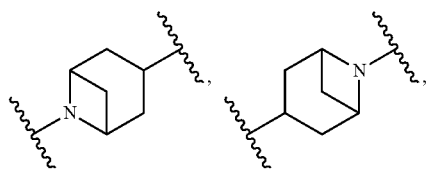

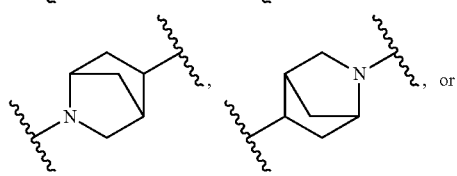

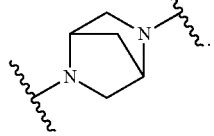

In some embodiments, the $C_2$-$C_6$ heterocyclylene is fused.

In some embodiments, the $C_2$-$C_9$ heterocyclylene is

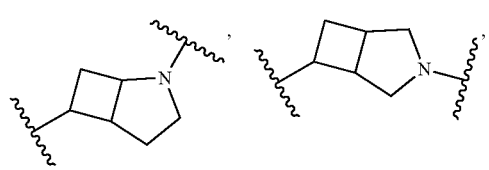

In some embodiments, $F^1$ is,

In some embodiments, $F^2$ is

-continued
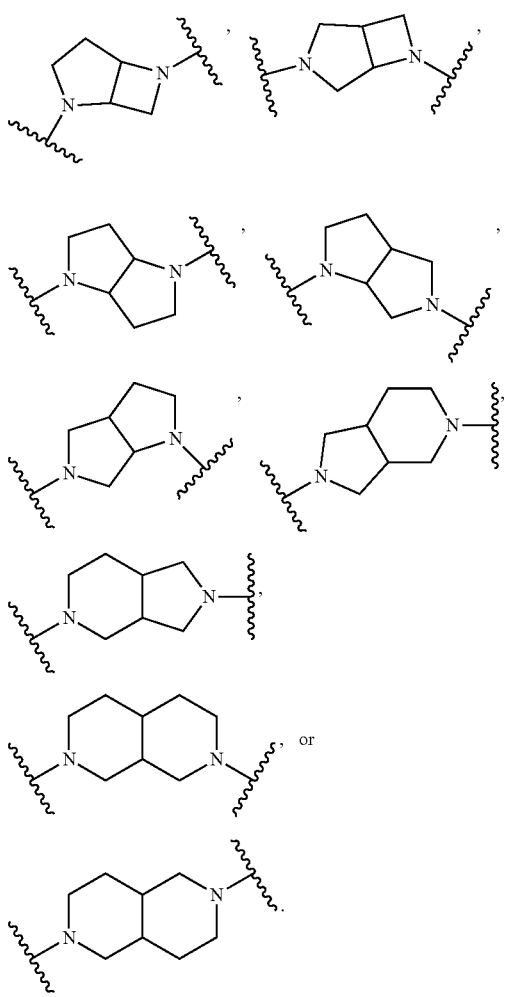
In some embodiments, the $C_2$-$C_6$ heterocyclylene is spirocyclic.
In some embodiments, the $C_2$-$C_6$ heterocyclylene is
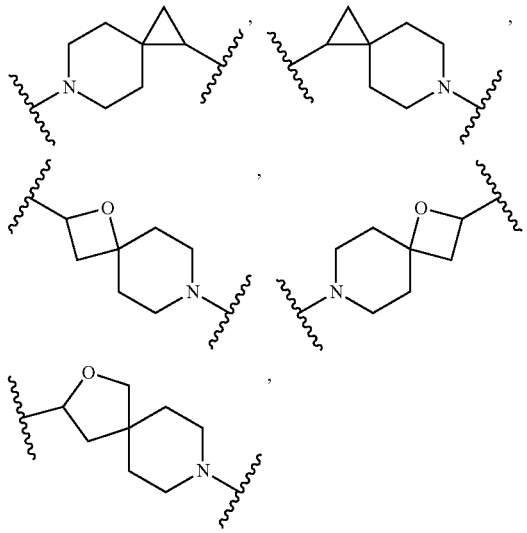
-continued
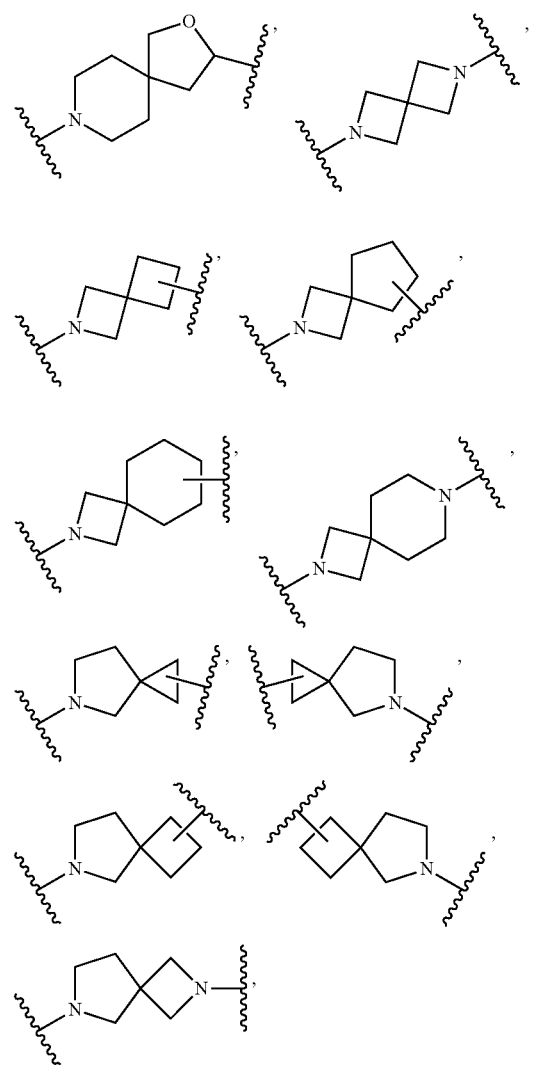
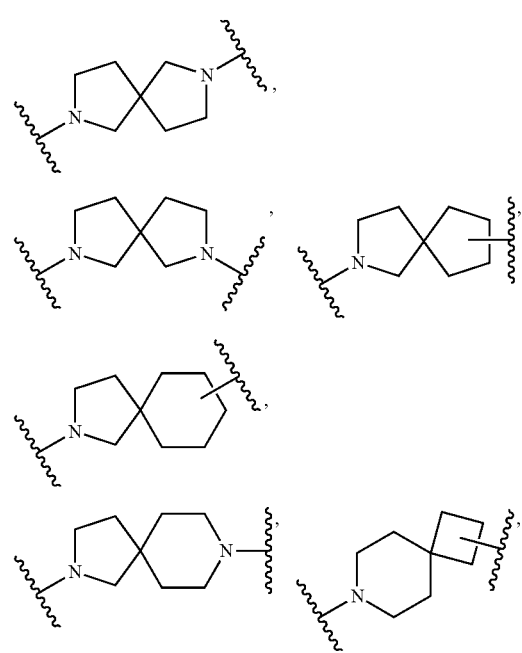

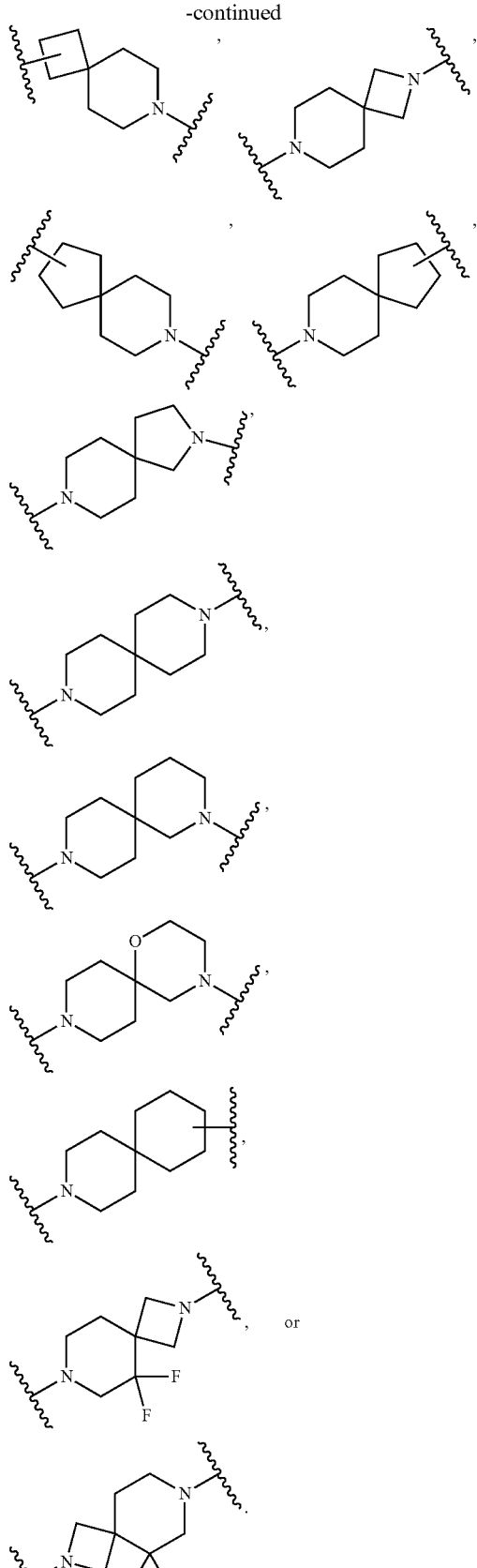
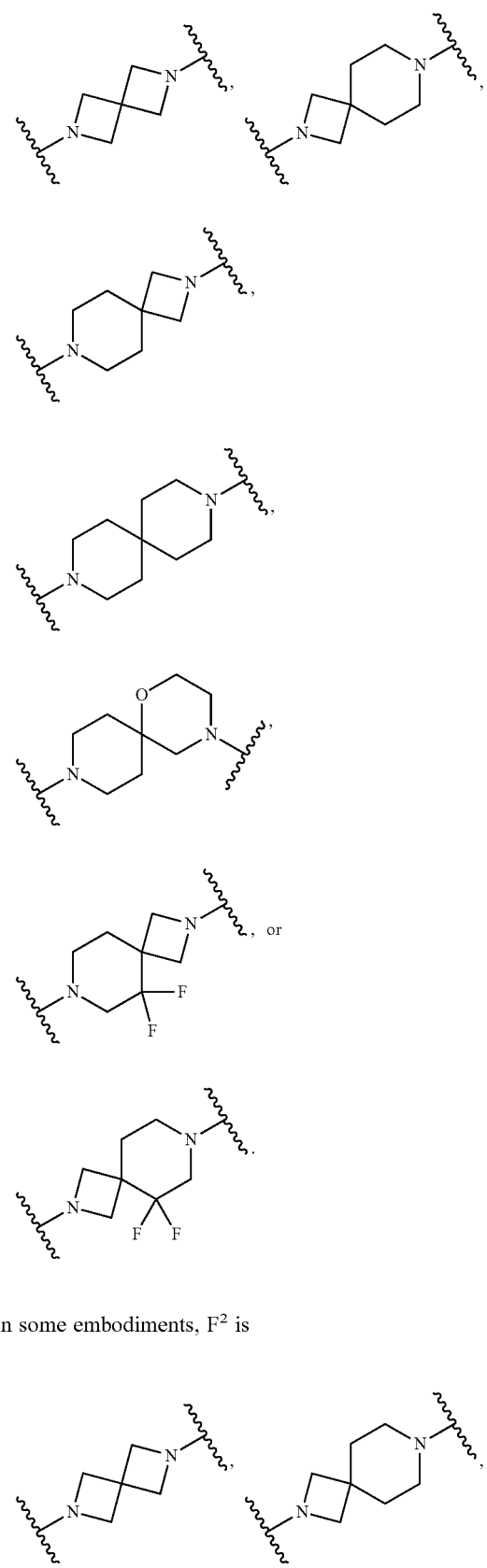
In some embodiments, $F^1$ is
In some embodiments, $F^2$ is -continued

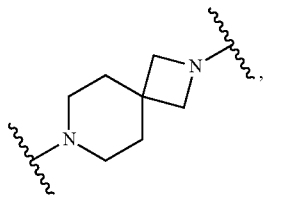

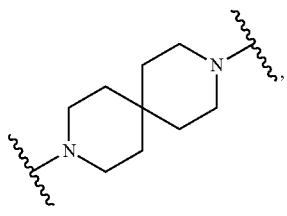

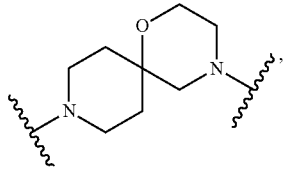

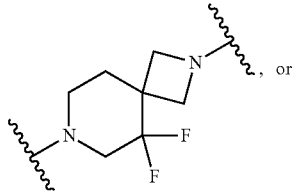, or

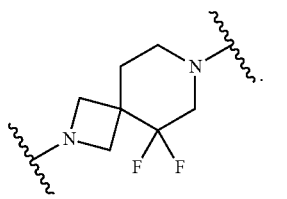.

In some embodiments, $F^3$ is

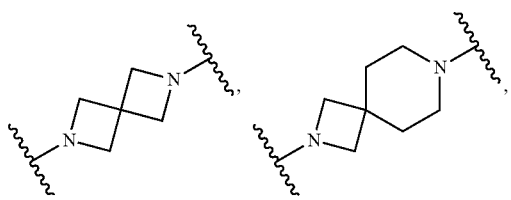

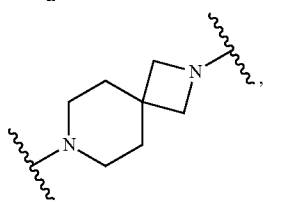,

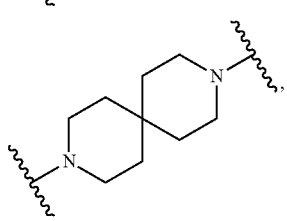,

-continued

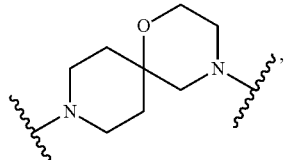,

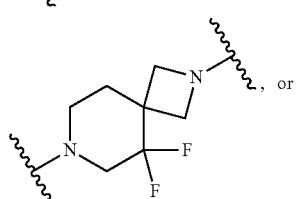, or

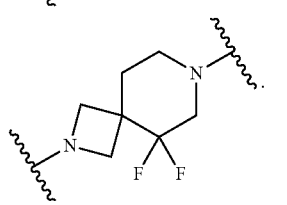.

In some embodiments, the $C_2$-$C_9$ heterocyclylene includes a quaternary amine.

In some embodiments, each of $F^1$, $F^2$, or $F^3$ is, independently, optionally substituted $C_6$-$C_{10}$ arylene.

In some embodiments, the $C_5$-$C_{10}$ arylene is

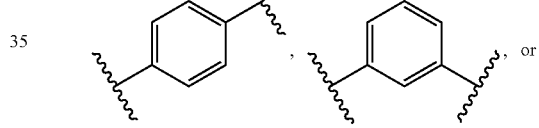, or

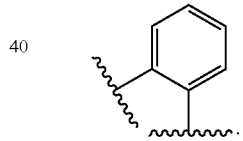.

In some embodiments, each of $F^1$, $F^2$, or $F^3$ is, independently, optionally substituted $C_2$-$C_9$ heteroarylene.

In some embodiments, the $C_2$-$C_9$ heteroarylene is

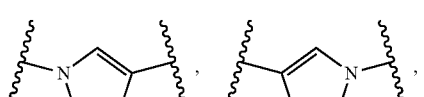

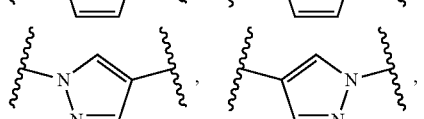

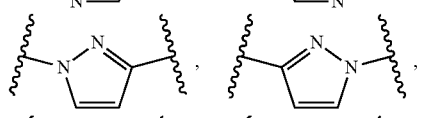

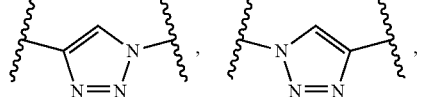

-continued

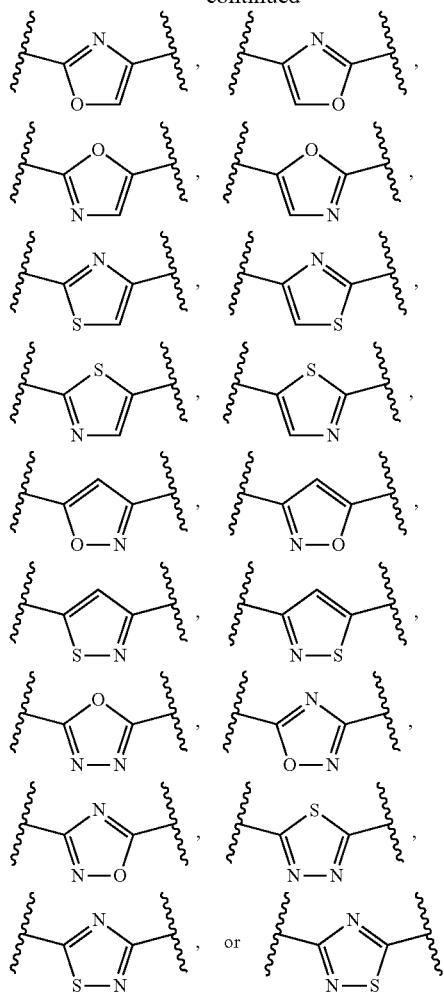

In some embodiments, $F^2$ is

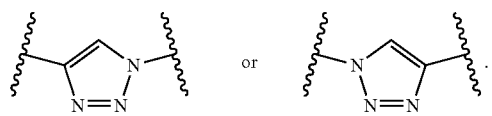 [SMILES: *c1cn(*)nn1 ; *c1cn(*)nn1]

In some embodiments, $F^2$ is

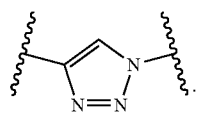

In some embodiments, $C^3$ is

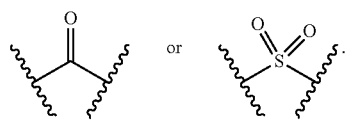

In some embodiments, $C^3$ is

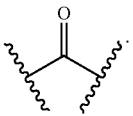

In some embodiments, m is 1. In some embodiments, m is 0. In some embodiments, p is 1. In some embodiments, p is 0. In some embodiments, o1 is 1. In some embodiments, o1 is 0. In some embodiments, o2 is 1. In some embodiments, o2 is 0. In some embodiments, n is 1. In some embodiments, n is 0.

In some embodiments, the linker has the structure of

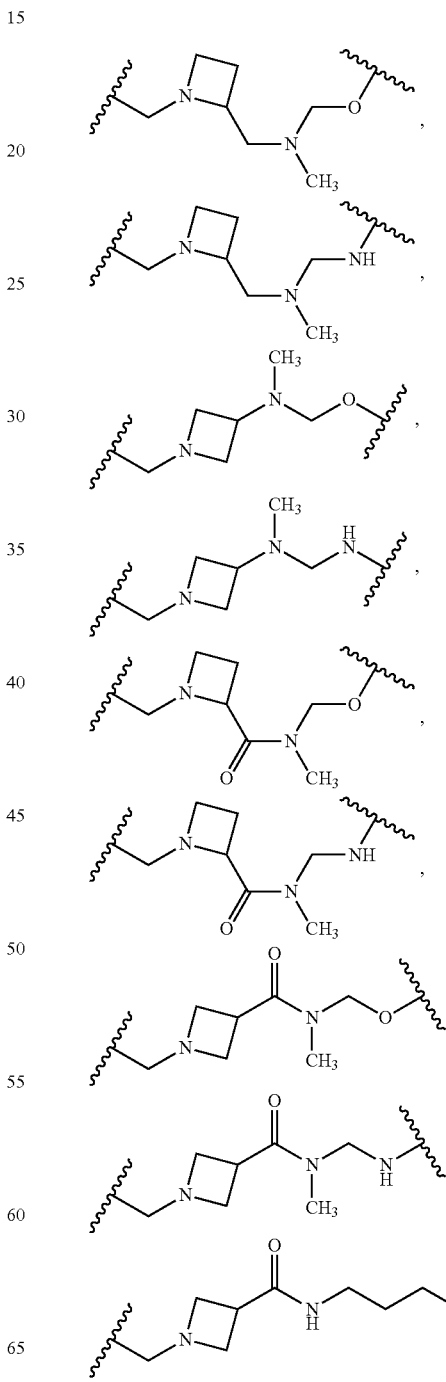

51
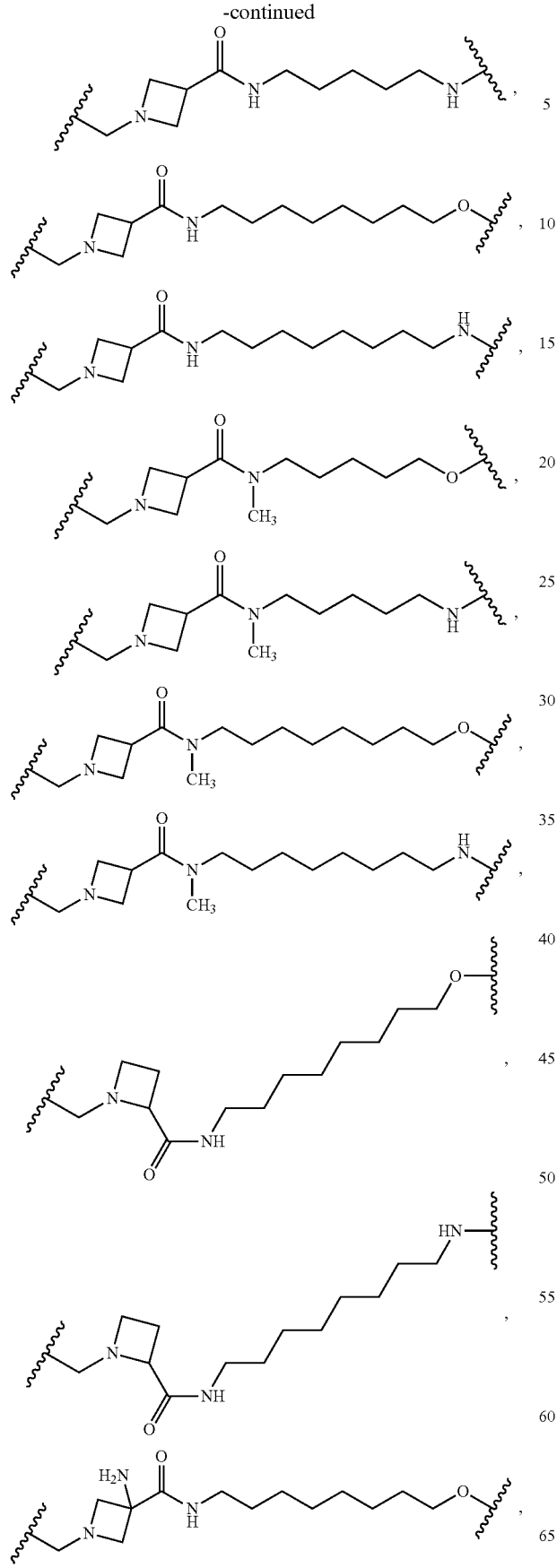
52
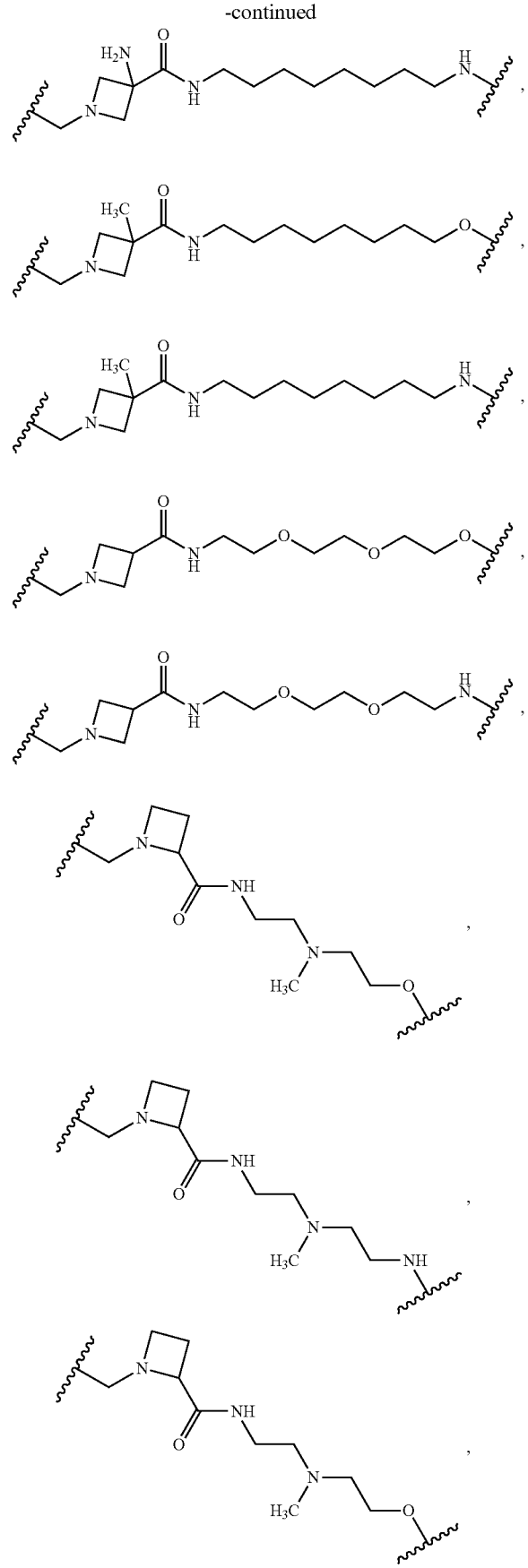

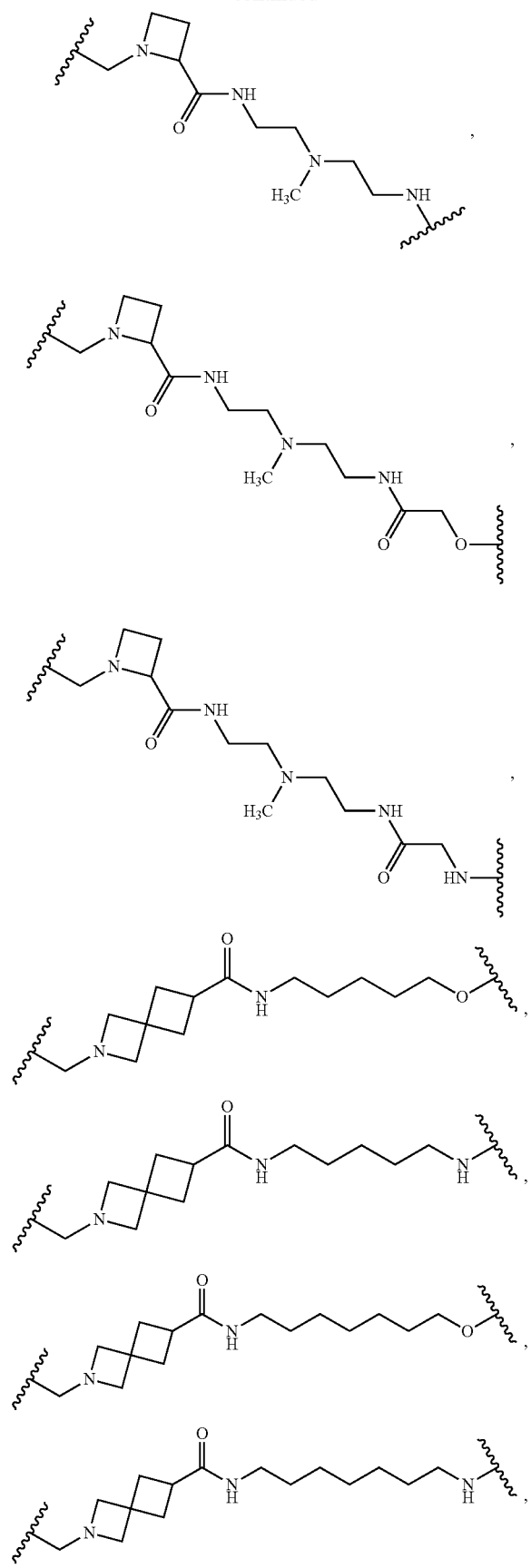
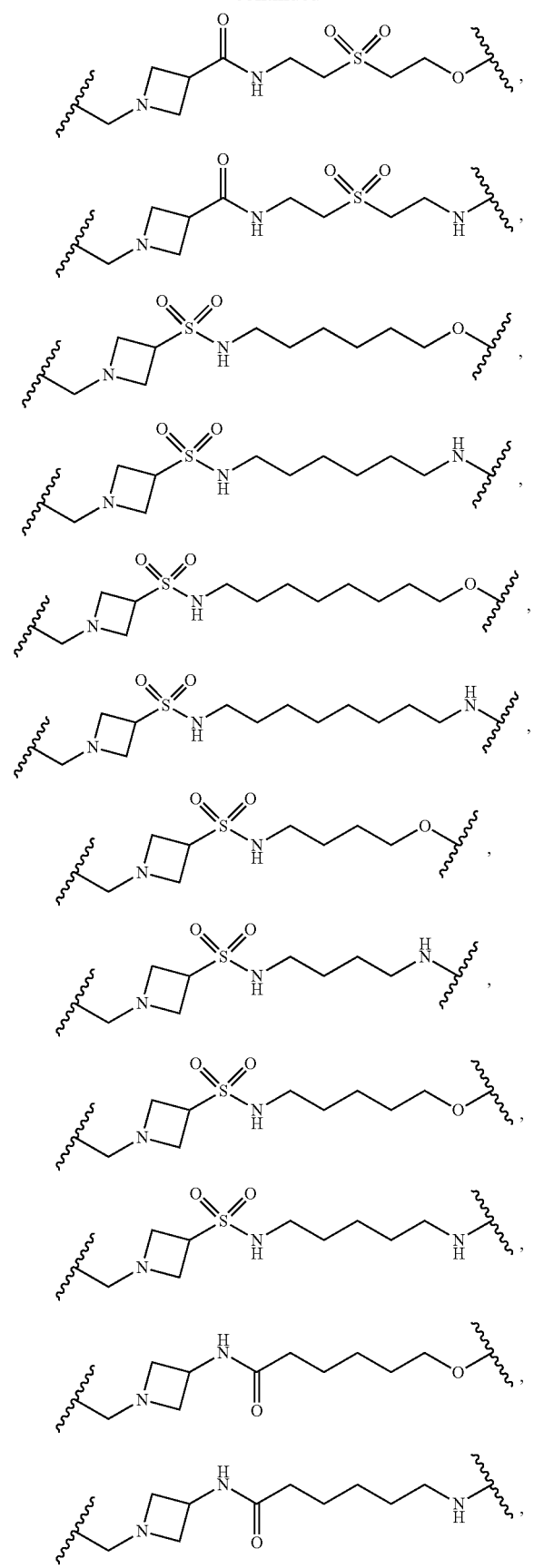

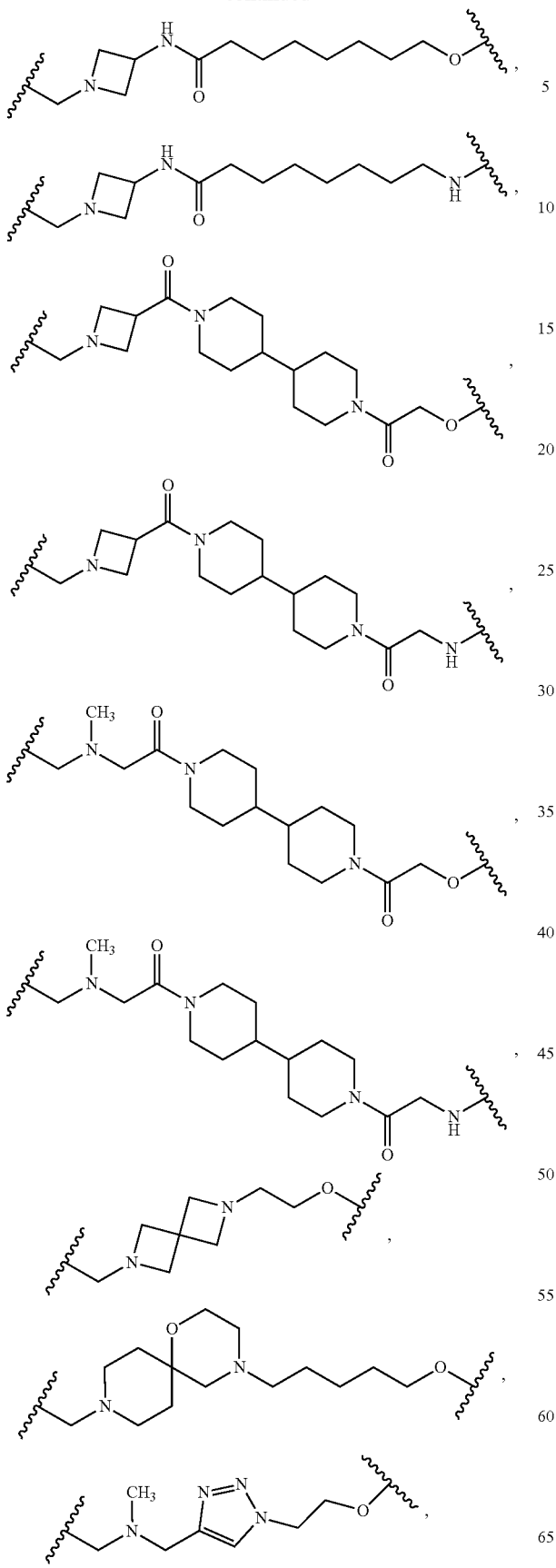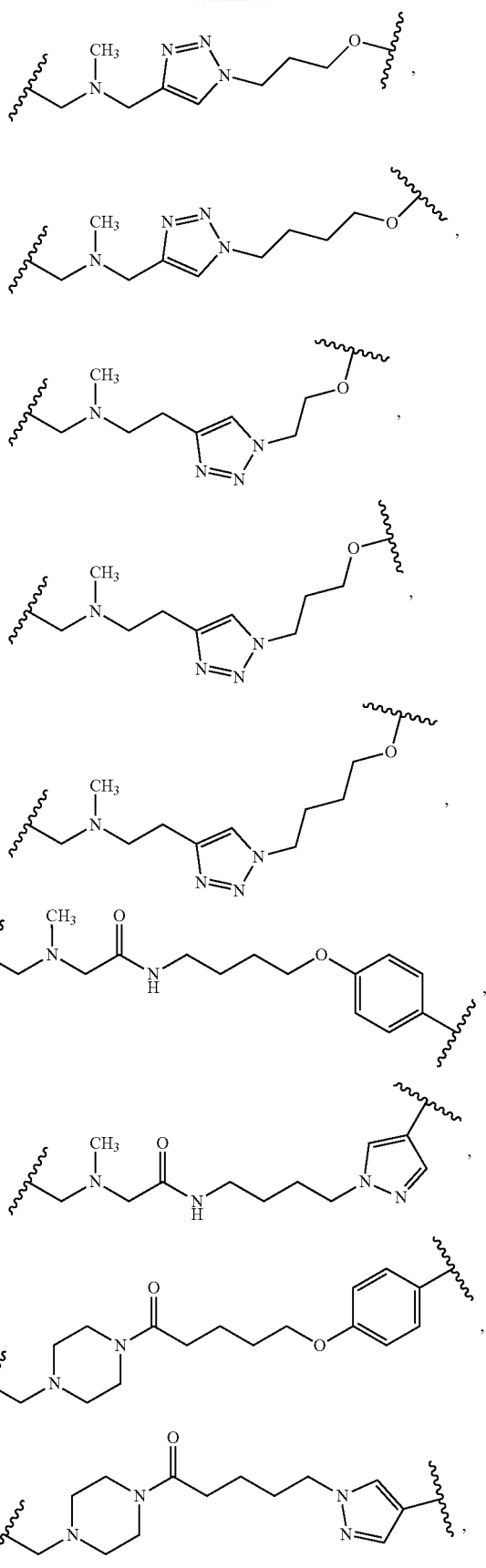

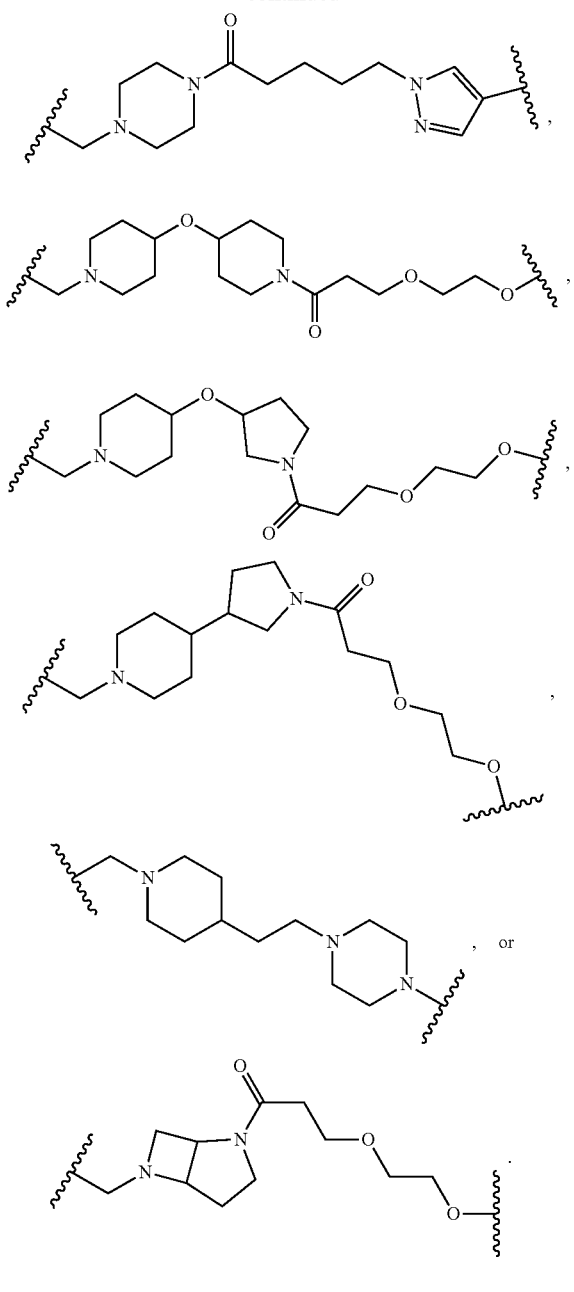
In some embodiments, the linker has the structure of
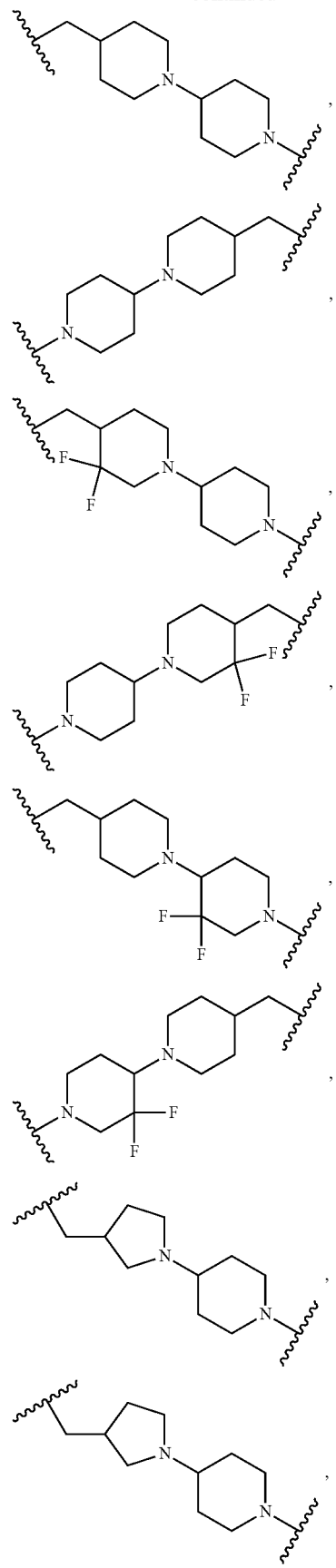

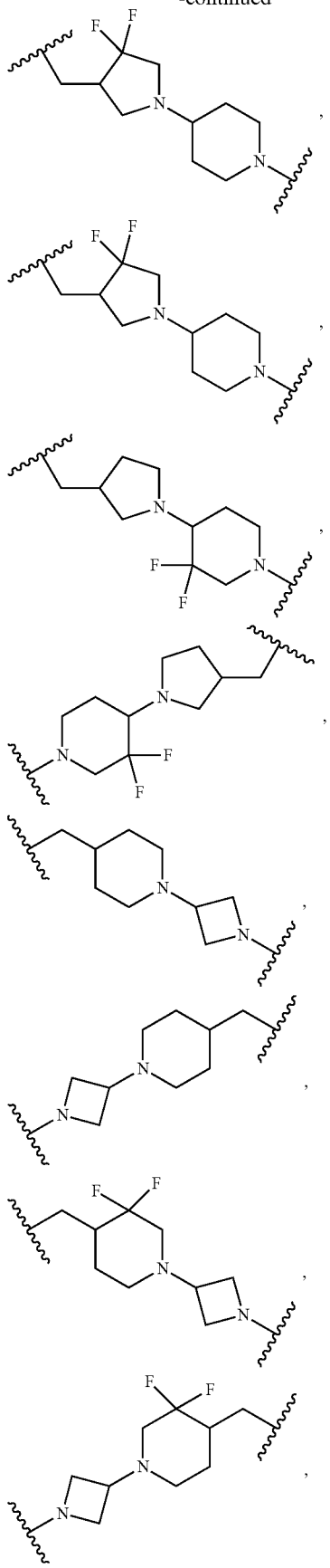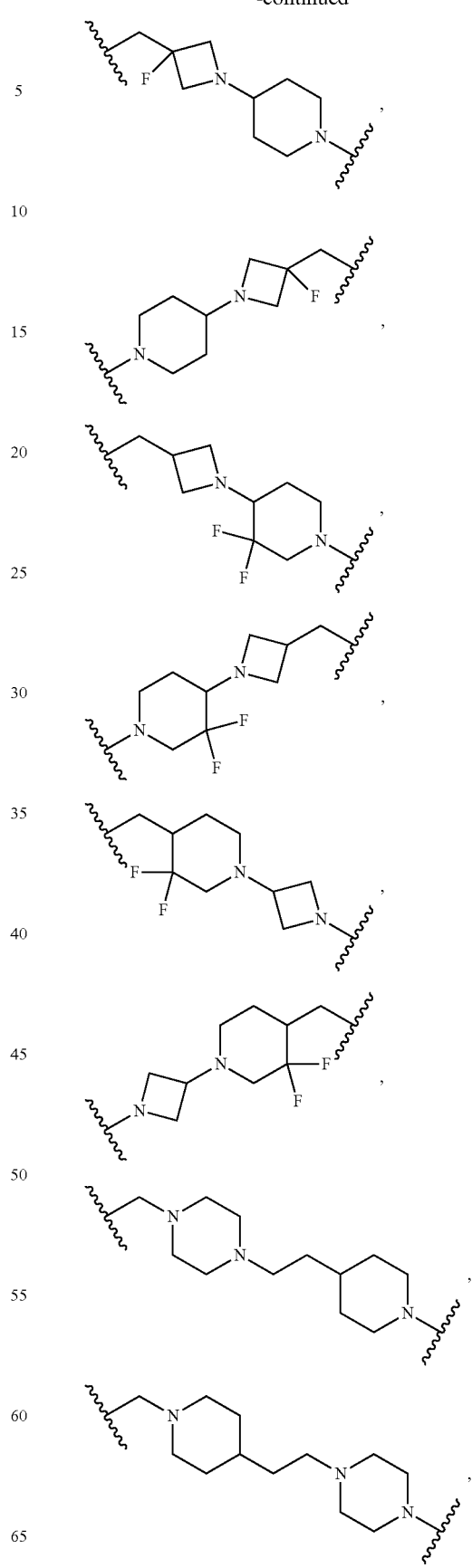

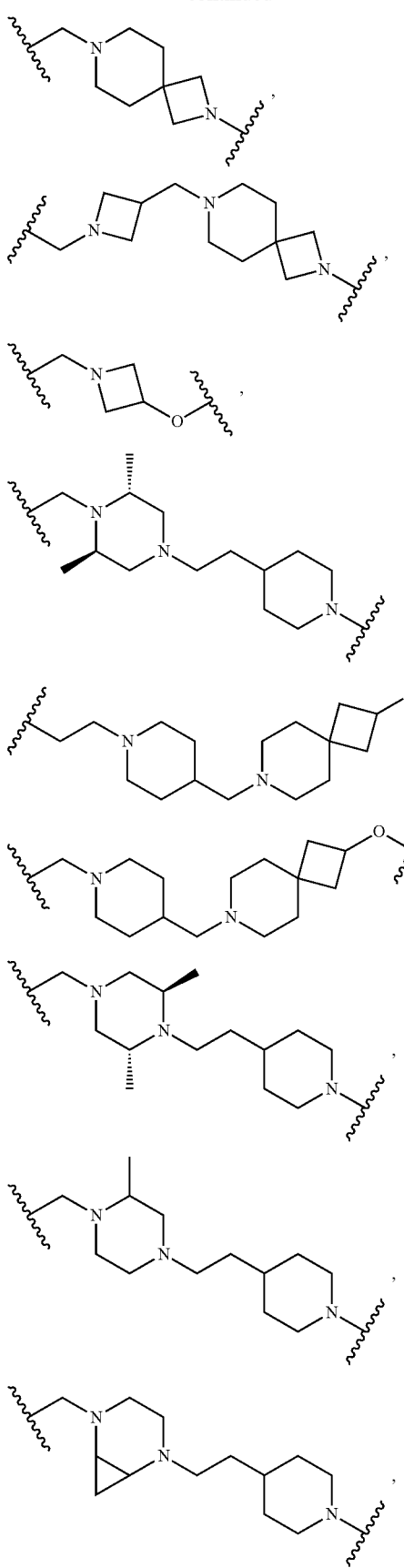
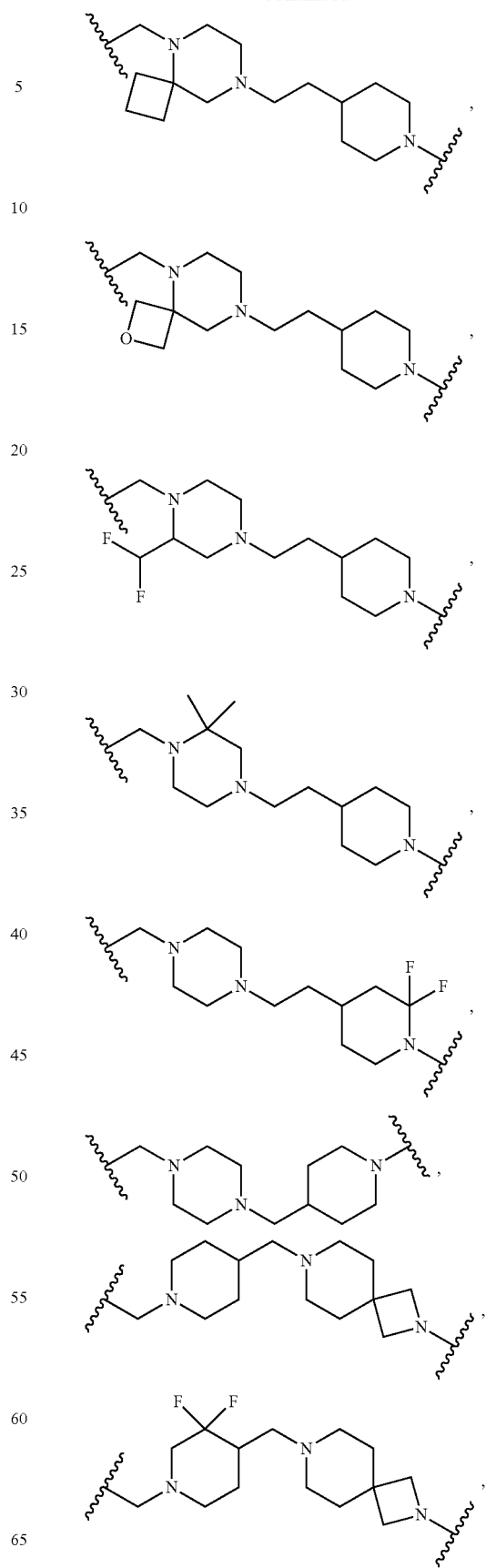

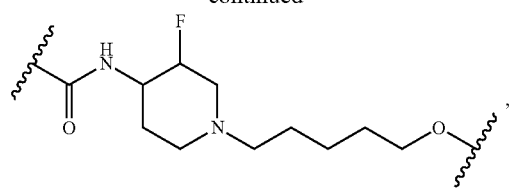,
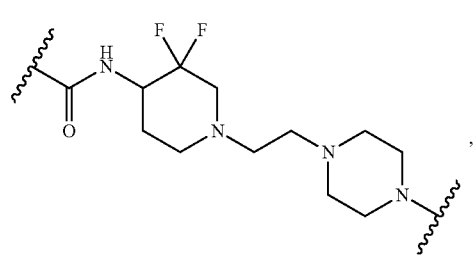,
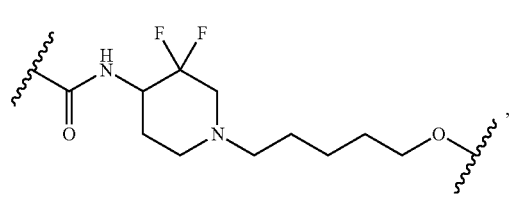,
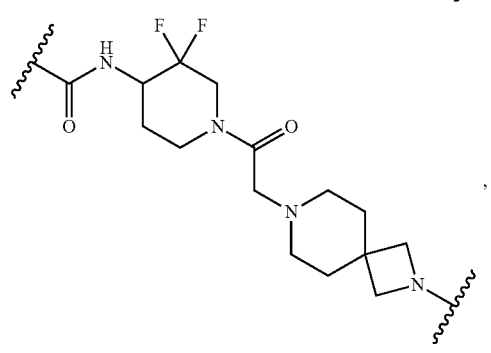,
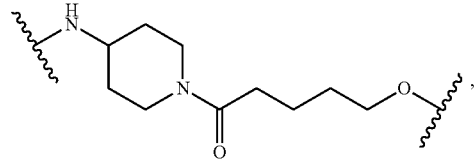,
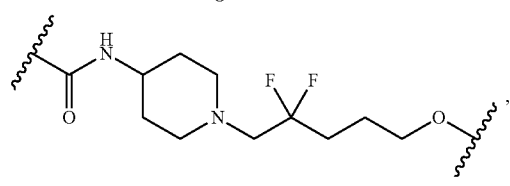,
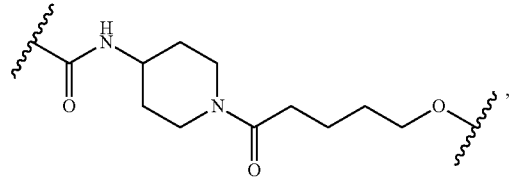,
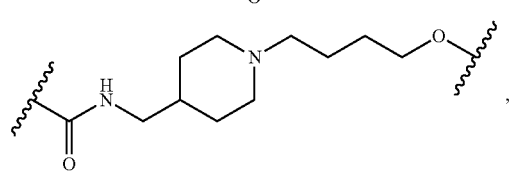,
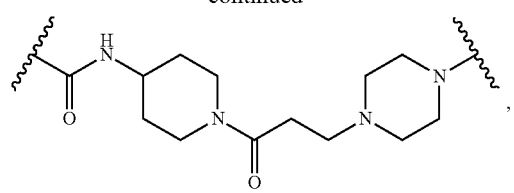,
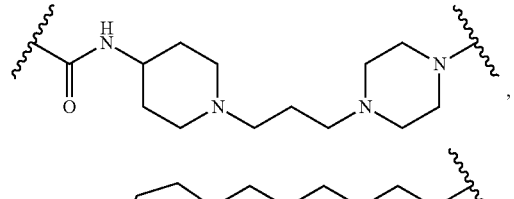,
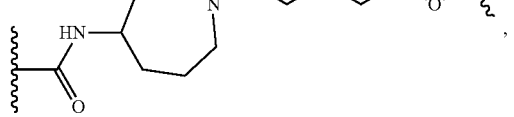,
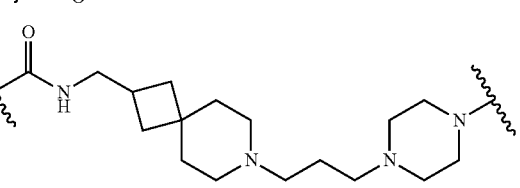,
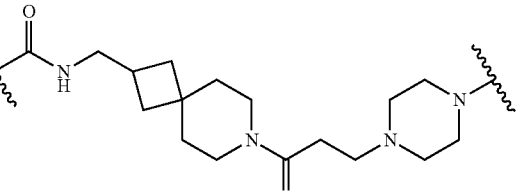,
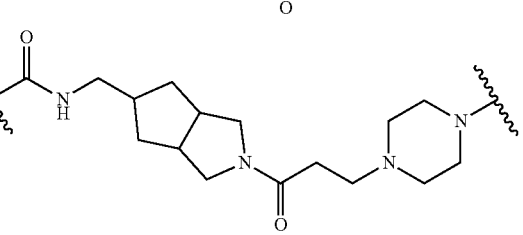,
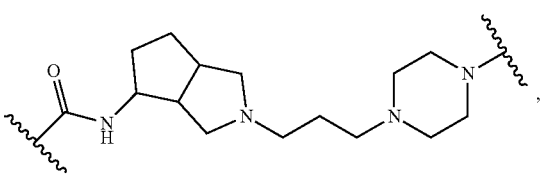,
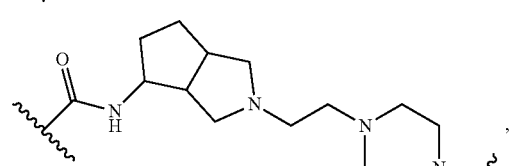,
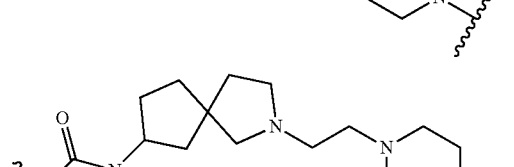, -continued

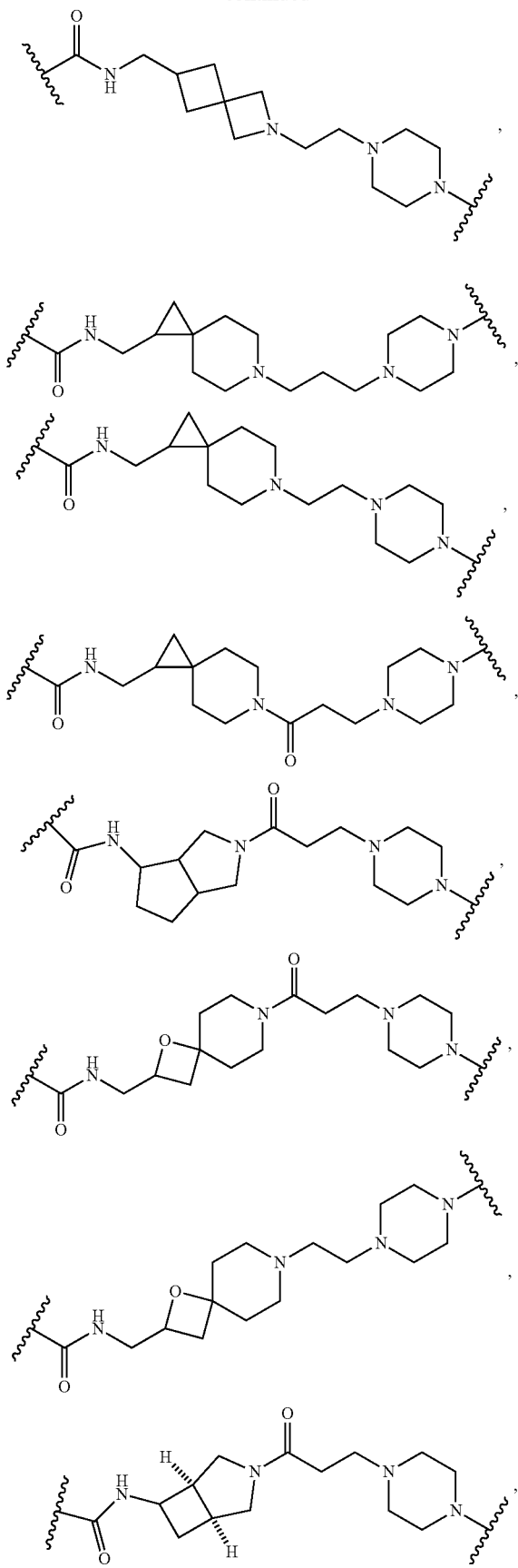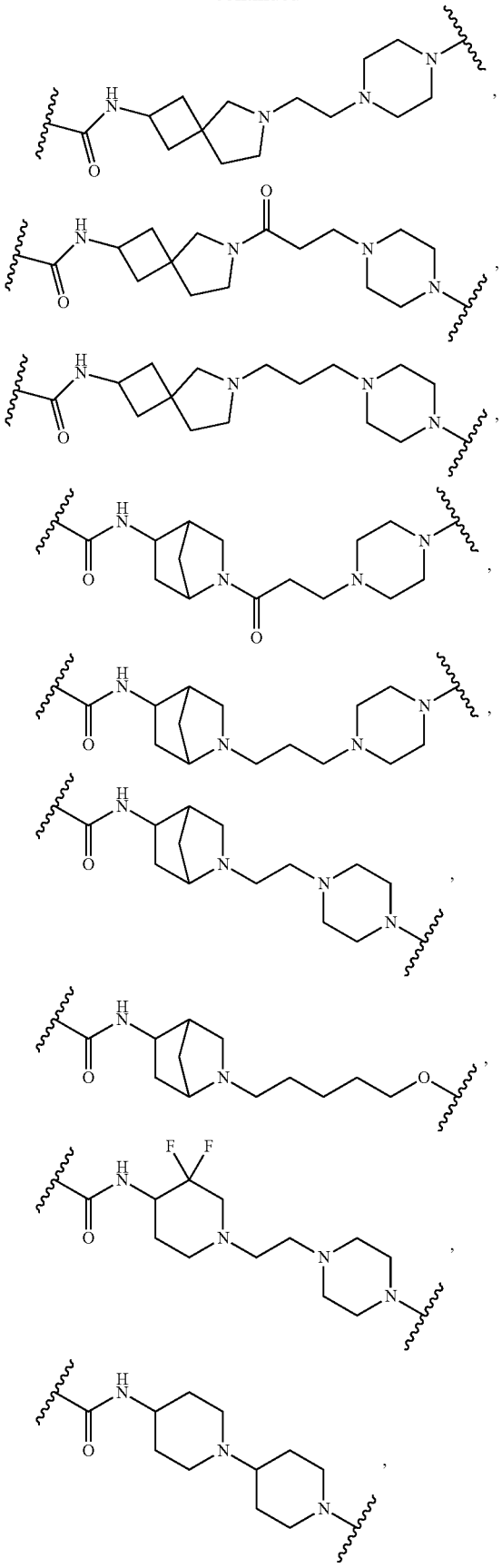

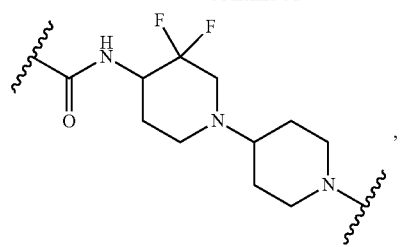,
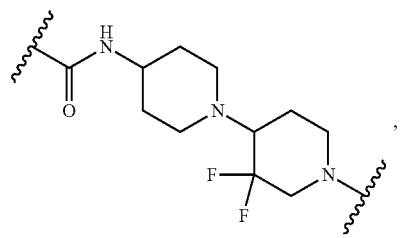,
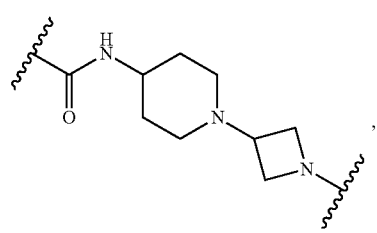,
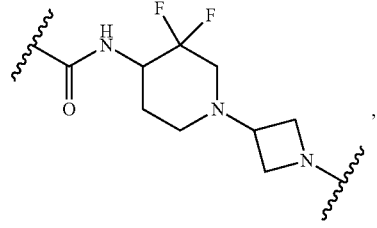,
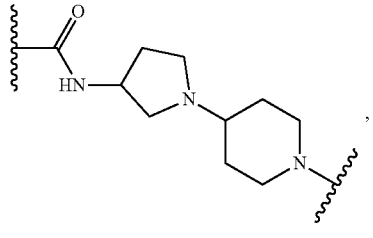,
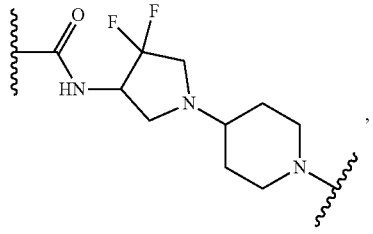,
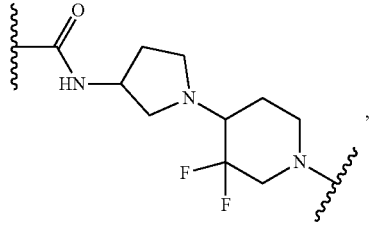,
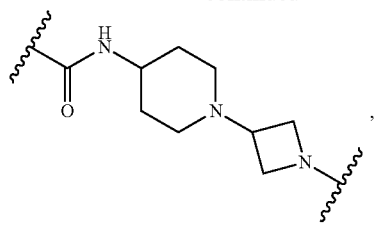,
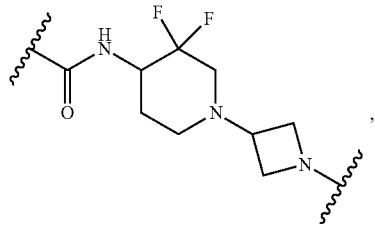,
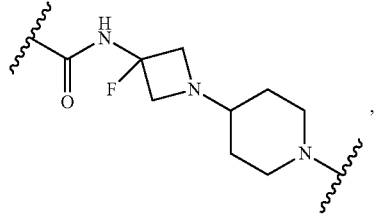,
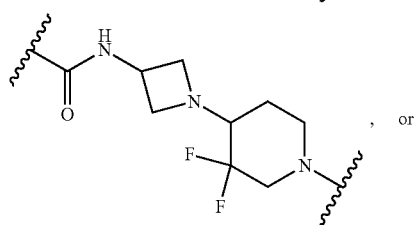, or
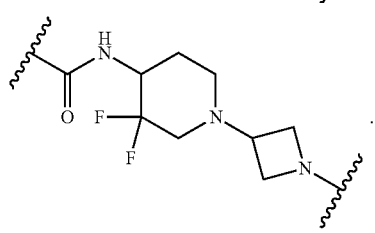.
In some embodiments, the linker has the structure of:
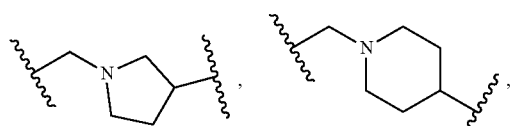
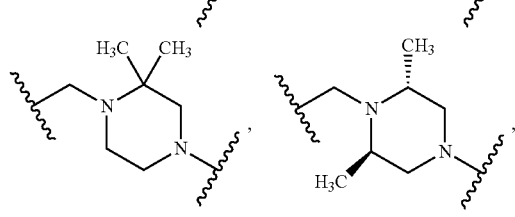

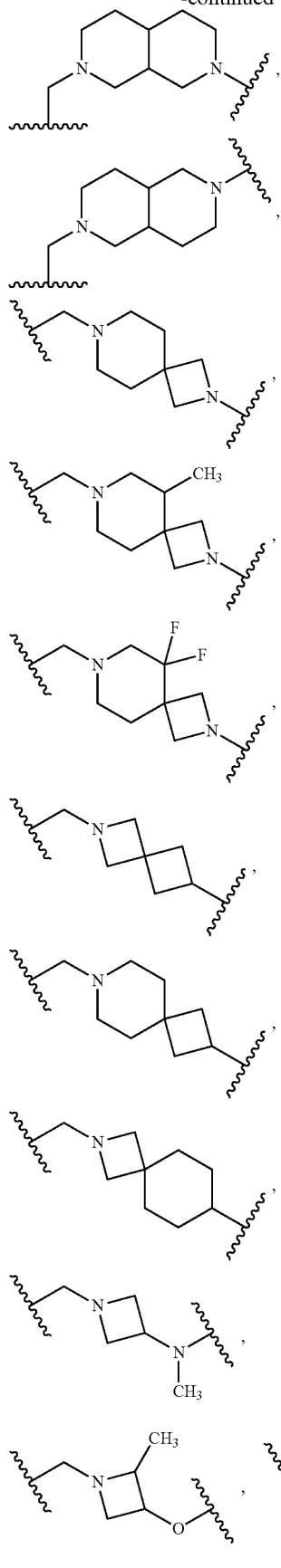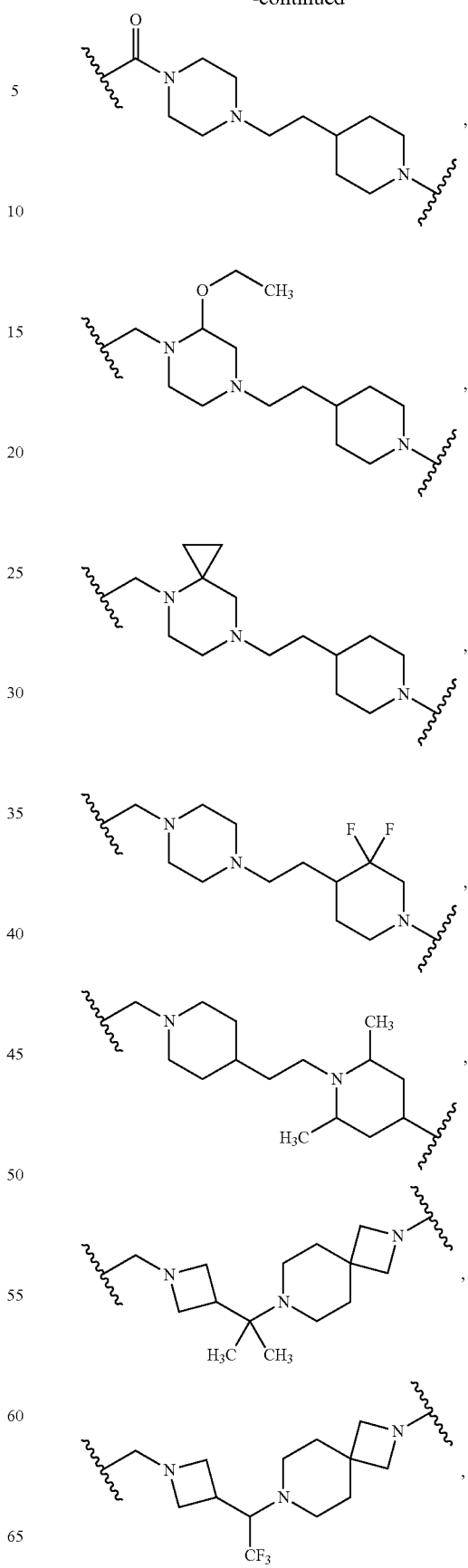

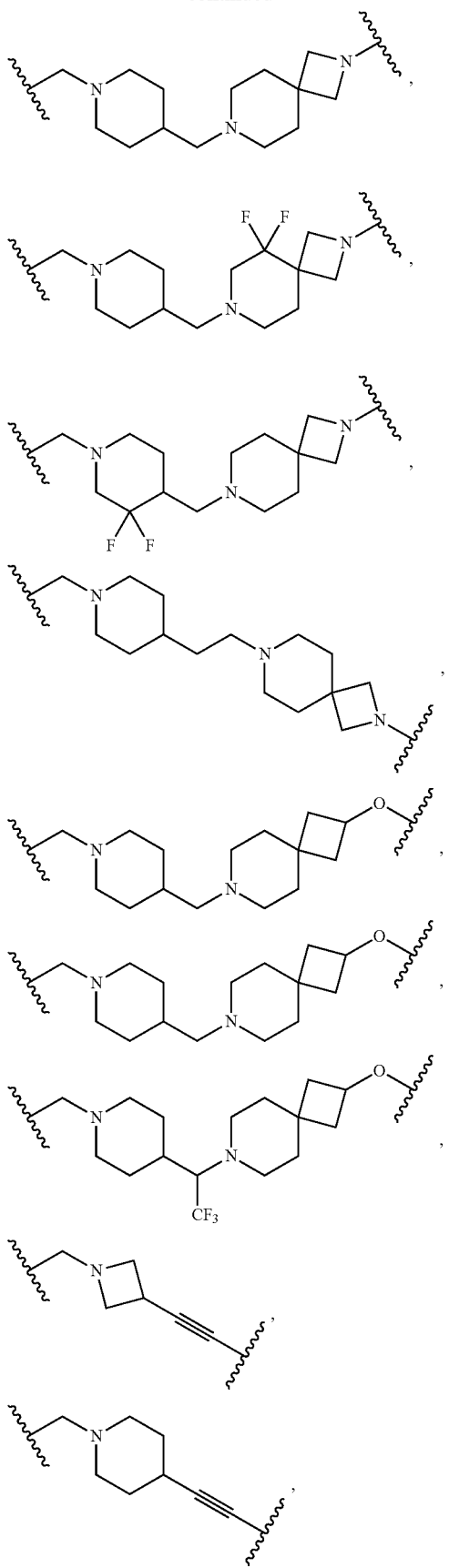

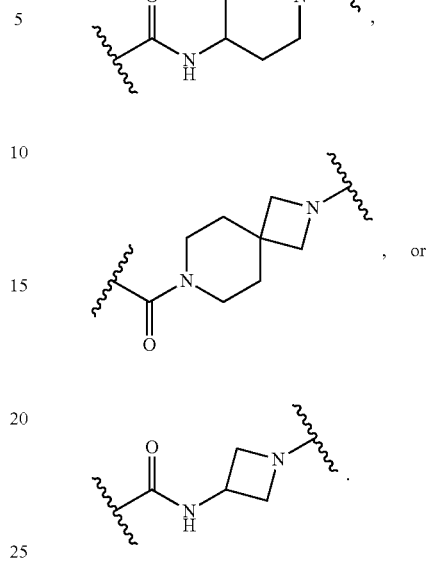

In some embodiments, the linker is optionally substituted $C_3$-$C_{10}$ carbocyclylene, optionally substituted $C_{2-10}$ heterocyclylene, optionally substituted $C_6$-$C_{10}$ arylene, or optionally substituted $C_2$-$C_9$ heteroarylene. In some embodiments, the linker is optionally substituted $C_{2-10}$ heterocyclylene.

In some embodiments, the linker has the structure of

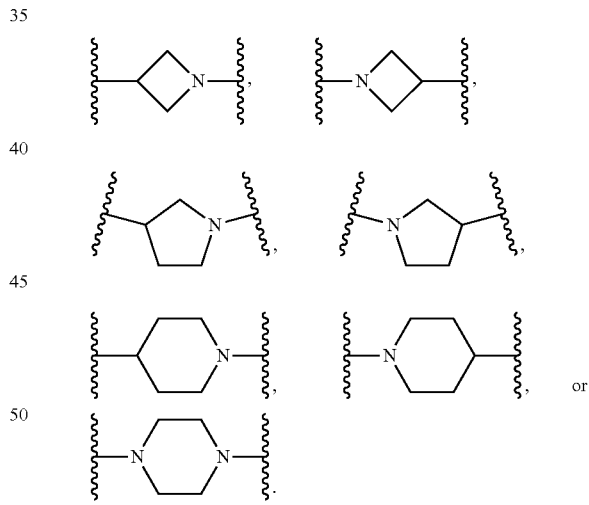

In some embodiments, the linker has the structure of

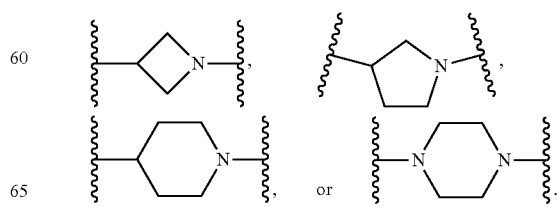

In some embodiments, the linker is absent.

In some embodiments, the BRD9 binding moiety ha the structure of Formula III:

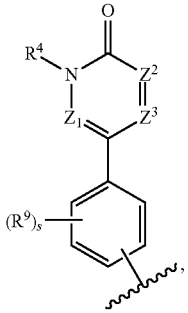

Formula III where $R^4$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl; $Z^1$ is N or $CR^5$;

$Z^2$ is N or $CR^{6a}$;

$Z^3$ is N or $CR^{6b}$;

$R^5$ is H, halogen, optionally substituted $C_1$-$C_6$ alkyl, optionally substituted $C_1$-$C_6$ heteroalkyl, optionally substituted $C_3$-$C_{10}$ carbocyclyl, or optionally substituted $C_6$-$C_{10}$ aryl;

$R^{6a}$ is H, halogen, cyano, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; $R^{6b}$ is H, halogen, cyano, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; or $R^{6a}$ and $R^{6b}$, together with the carbon atoms to which each is attached, combine to form optionally substituted $C_6$-$C_{10}$ aryl or optionally substituted $C_2$-$C_9$ heteroaryl;

s is 0, 1, 2, 3, or 4; and each $R^9$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, $Z^1$ is $CR^5$. In some embodiments, $Z^2$ is N. In some embodiments, $Z^2$ is $CR^{6a}$. In some embodiments, $Z^3$ is N. In some embodiments, $Z^3$ is $CR^{6b}$.

In some embodiments, $R^4$ is H, optionally substituted $C_1$-$C_6$ alkyl, optionally substituted $C_2$-$C_6$ alkenyl, or optionally substituted $C_3$-$C_{10}$ carbocyclyl. In some embodiments, $R^4$ is H, optionally substituted $C_1$-$C_6$ alkyl, optionally substituted $C_2$-$C_6$ alkenyl, or optionally substituted $C_3$-$C_{10}$ carbocyclyl. In some embodiments, $R^4$ is H. In some embodiments, $R^4$ is optionally substituted $C_1$-$C_6$ alkyl.

In some embodiments, $R^4$ is

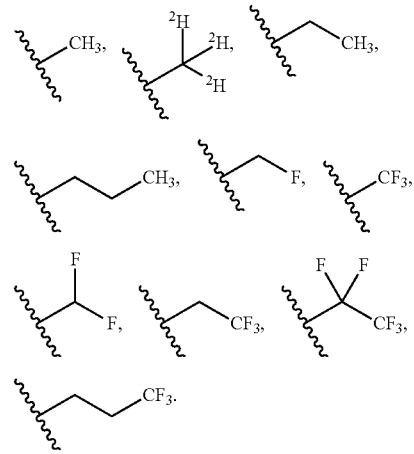

In some embodiments, $R^4$ is optionally substituted $C_2$-$C_6$ alkenyl. In some embodiments, $R^4$ is

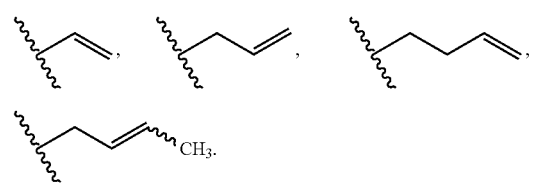

In some embodiments, $R^4$ is optionally substituted $C_3$-$C_{10}$ carbocyclyl. In some embodiments, $R^4$ is

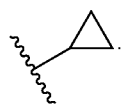 [SMILES: *C1CC1]

In some embodiments, $R^4$ is H,

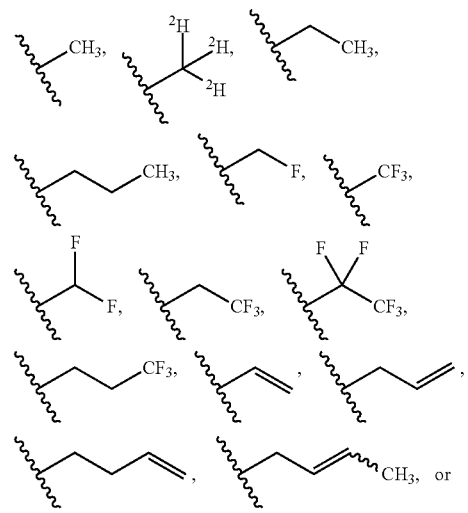

In some embodiments, $R^4$ is H or

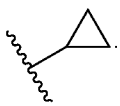

In some embodiments, $R^4$ is

In some embodiments, $R^4$ is H.

In some embodiments, $R^5$ is H, optionally substituted $C_1$-$C_6$ alkyl, or optionally substituted $C_6$-$C_{10}$ aryl. In some embodiments, $R^5$ is H, optionally substituted $C_1$-$C_6$ alkyl, or optionally substituted $C_3$-$C_{10}$ carbocyclyl.

In some embodiments, $R^5$ is H,

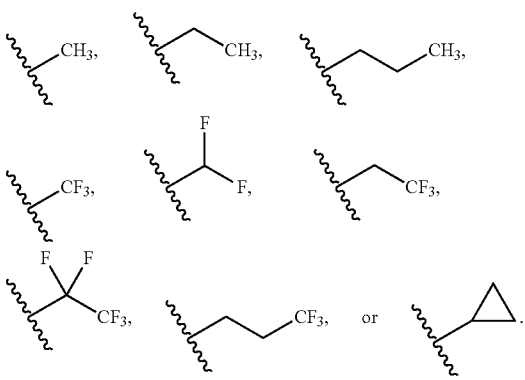

In some embodiments, $R^5$ is H or

In some embodiments, $R^5$ is

In some embodiments, $R^{6a}$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino. In some embodiments, $R^{6a}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{6a}$ is H, halogen, cyano, optionally substituted $C_1$-$C_6$ alkyl, or optionally substituted $C_1$-$C_6$ heteroalkyl. In some embodiments, $R^{6a}$ is H, halogen, cyano, or optionally substituted $C_1$-$C_6$ alkyl. In some embodiments, $R^{6a}$ is optionally substituted $C_1$-$C_6$ heteroalkyl.

In some embodiments, $R^{6a}$ is H, F, cyano,

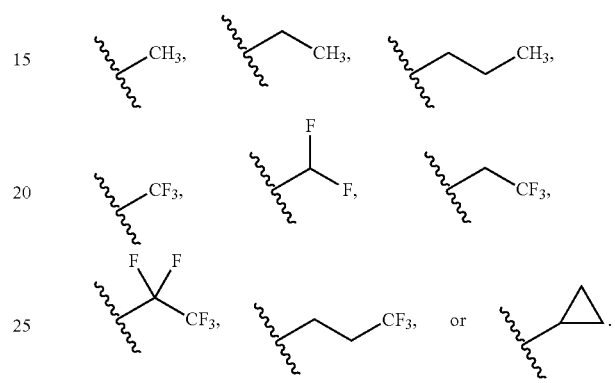

In some embodiments, $R^{6a}$ is H, F, cyano,

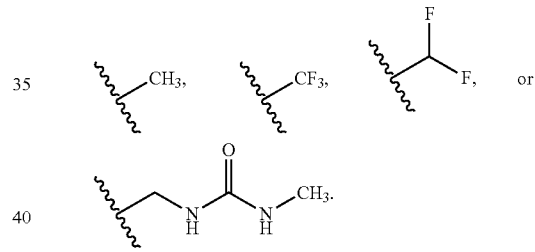

In some embodiments, $R^{6b}$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino. In some embodiments, $R^{6b}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{6a}$ is H, halogen, cyano, optionally substituted $C_1$-$C_6$ alkyl, or optionally substituted $C_1$-$C_6$ heteroalkyl. In some embodiments, $R^{6a}$ is H, halogen, cyano, or optionally substituted $C_1$-$C_6$ alkyl. In some embodiments, $R^{6a}$ is optionally substituted $C_1$-$C_6$ heteroalkyl.

In some embodiments, $R^{6b}$ is H, F, cyano,

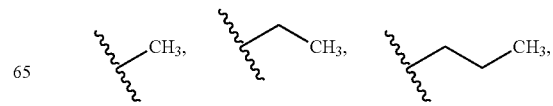

-continued

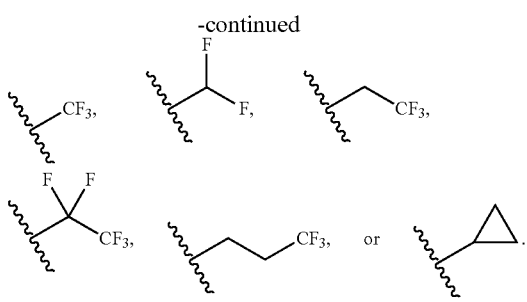

In some embodiments, $R^{6b}$ is H, F, cyano,

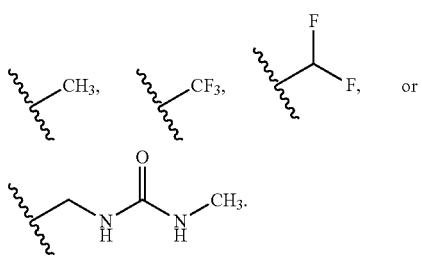

In some embodiments, s is 0, 1, or 2. In some embodiments, s is 2. In some embodiments, s is 1.

In some embodiments, each $R^9$ is, independently, halogen, optionally substituted $C_1$-$C_6$alkyl, or optionally substituted $C_1$-$C_6$ heteroalkyl. In some embodiments, each $R^9$ is, independently, optionally substituted $C_1$-$C_6$ alkyl or optionally substituted $C_1$-$C_6$ heteroalkyl. In some embodiments, each $R^9$ is, independently, halogen,

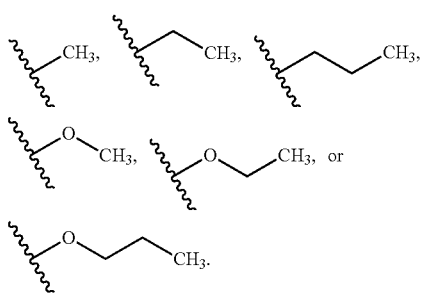

In some embodiments, the BRD binding moiety has the structure of Formula IIIa:

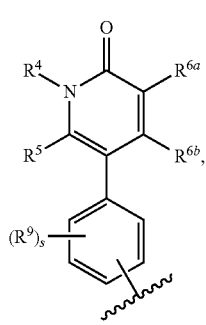

Formula IIIa or a pharmaceutically acceptable salt thereof.

In some embodiments, the BRD binding moiety has the structure of Formula IIIb:

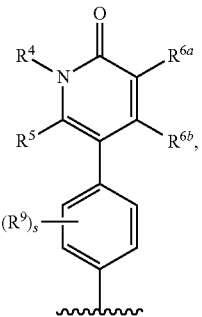

Formula IIIb or a pharmaceutically acceptable salt thereof.

In some embodiments, the BRD binding moiety has the structure of Formula IIIc:

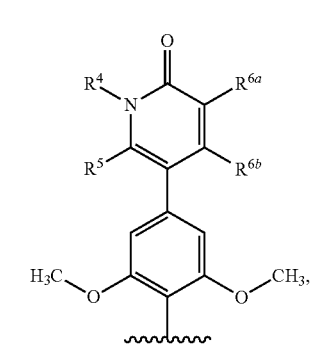

Formula IIIc or a pharmaceutically acceptable salt thereof.

In some embodiments, the BRD binding moiety has the structure of Formula IIId:

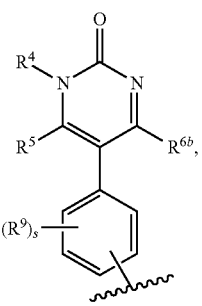

Formula IIId or a pharmaceutically acceptable salt thereof.

In some embodiments, the BRD binding moiety has the structure of Formula IIIe:

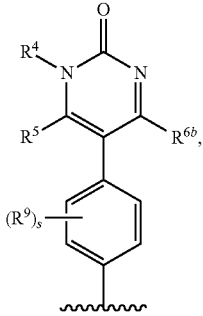

Formula IIIe or a pharmaceutically acceptable salt thereof.

In some embodiments, the BRD binding moiety has the structure of Formula IIIf:

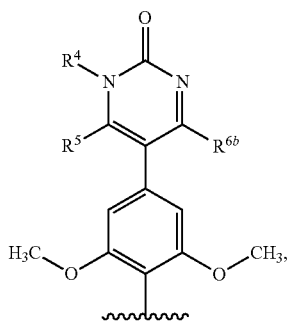

Formula IIIf or a pharmaceutically acceptable salt thereof.

In some embodiments, the BRD binding moiety has the structure of Formula IIIg:

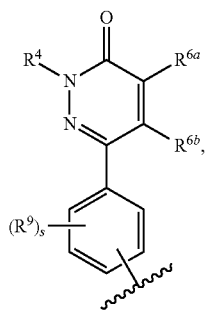

Formula IIIg or a pharmaceutically acceptable salt thereof.

In some embodiments, the BRD binding moiety has the structure of Formula IIIh:

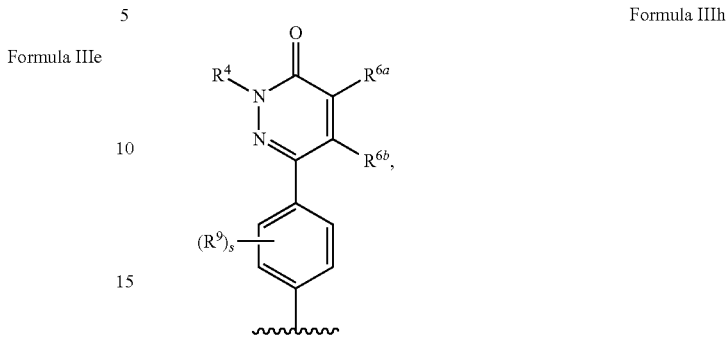

Formula IIIh or a pharmaceutically acceptable salt thereof.

In some embodiments, the BRD binding moiety has the structure of Formula IIIi:

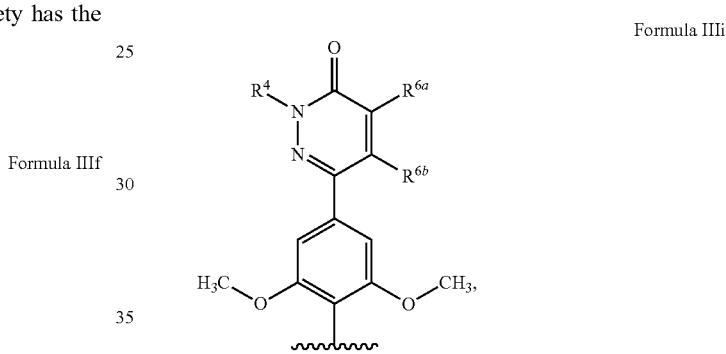

Formula IIIi or a pharmaceutically acceptable salt thereof.

In some embodiments, the BRD binding moiety has the structure of Formula IV:

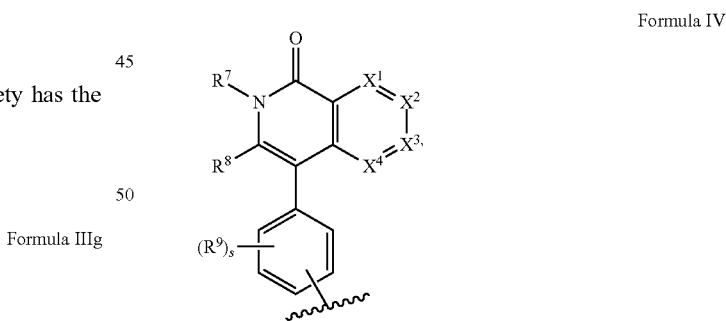

Formula IV where $R^7$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl;

$R^8$ is H, halogen, optionally substituted $C_1$-$C_6$ alkyl, optionally substituted $C_1$-$C_6$ heteroalkyl, optionally substituted $C_3$-$C_{10}$ carbocyclyl, or optionally substituted $C_6$-$C_{10}$ aryl;

s is 0, 1, 2, 3, or 4;

each $R^9$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

$X^1$ is N or $CR^{10a}$;

$X^2$ is N or $CR^{10b}$;

$X^3$ is N or $CR^{10c}$;

$X^4$ is N or $CR^{10d}$; and each of $R^{10a}$, $R^{10b}$, $R^{10c}$, and $R^{10d}$ is, independently, H, halogen, hydroxy, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, $X^1$ is $CR^{10a}$. In some embodiments, $X^2$ is N. In some embodiments, $X^2$ is $CR^{10b}$. In some embodiments, $X^3$ is N. In some embodiments, $X^3$ is $CR^{10c}$. In some embodiments, $X^4$ is $CR^{10d}$.

In some embodiments, $R^7$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl. In some embodiments, $R^7$ is H, optionally substituted $C_1$-$C_6$ alkyl, or optionally substituted $C_3$-$C_6$ carbocyclyl.

In some embodiments, $R^7$ is H,

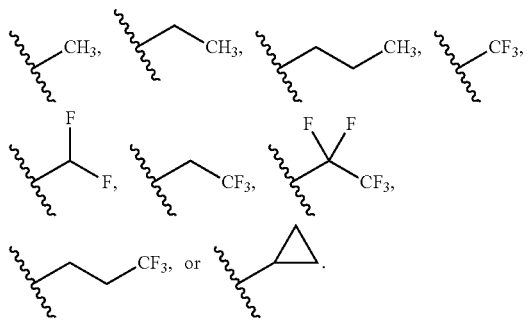

In some embodiments, $R^7$ is H or

In some embodiments, $R^7$ is

In some embodiments, $R^8$ is H, halogen, optionally substituted $C_1$-$C_6$ alkyl, or optionally substituted $C_6$-$C_{10}$ aryl. In some embodiments, $R^8$ is H, optionally substituted $C_1$-$C_6$ alkyl, or optionally substituted $C_1$-$C_6$ heteroalkyl.

In some embodiments, $R^8$ is H,

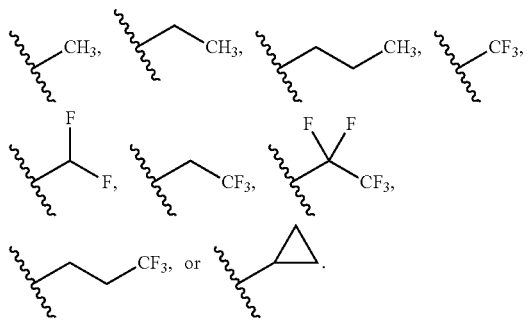

In some embodiments, $R^8$ is H or

In some embodiments, $R^8$ is

In some embodiments, s is 0, 1, or 2. In some embodiments, s is 2.

In some embodiments, each $R^9$ is, independently, halogen, optionally substituted $C_1$-$C_6$ alkyl, or optionally substituted $C_1$-$C_6$ heteroalkyl. In some embodiments, each $R^9$ is, independently, optionally substituted $C_1$-$C_6$ alkyl or optionally substituted $C_1$-$C_6$ heteroalkyl.

In some embodiments, each $R^9$ is, independently, halogen,

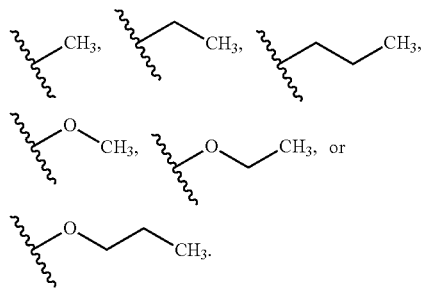

In some embodiments, each of $R^{10a}$, $R^{10b}$, $R^{10c}$, and $R^{10d}$ is, independently, optionally substituted $C_1$-$C_6$ alkyl, optionally substituted $C_1$-$C_6$ heteroalkyl, or optionally substituted amino.

In some embodiments, each of $R^{10a}$, $R^{10b}$, $R^{10c}$, and $R^{10d}$ is, independently, —NH$_2$,

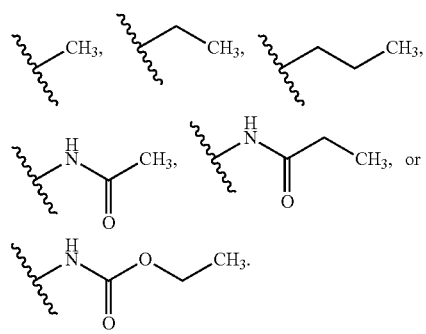

In some embodiments, $R^{10a}$ is H, F, cyano,

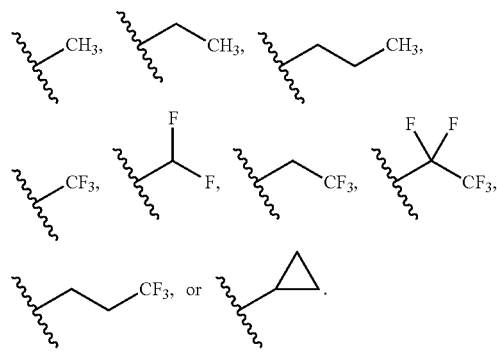

In some embodiments, $R^{10a}$ is H, F, cyano,

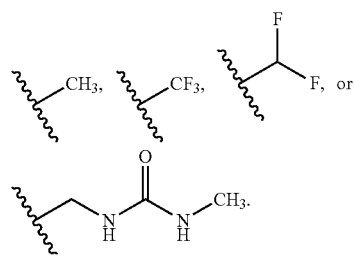

In some embodiments, $R^{10b}$ is H, F, cyano,

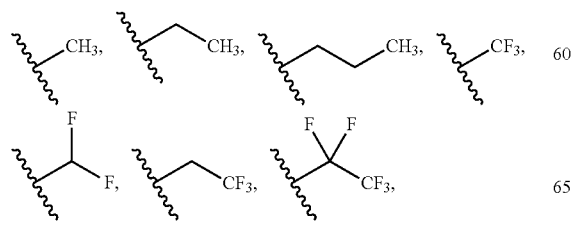

-continued

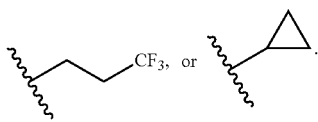

In some embodiments, $R^{10b}$ is H, F, cyano,

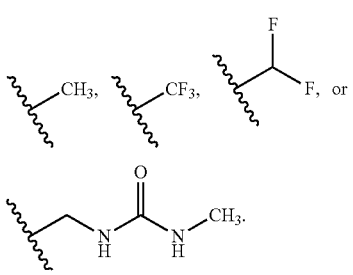

In some embodiments, $R^{10c}$ is H, F, cyano,

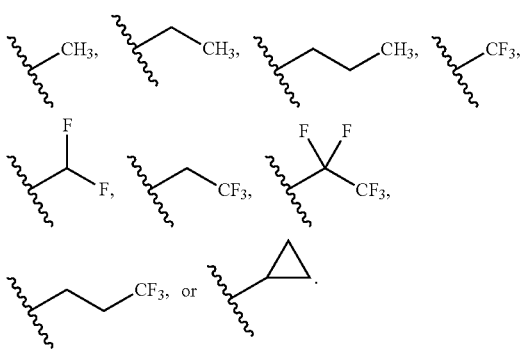

In some embodiments, $R^{10c}$ is H, F, cyano,

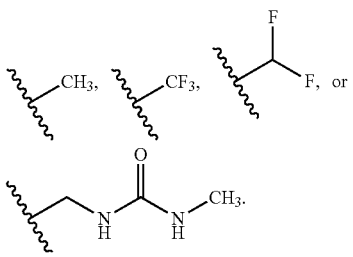

In some embodiments, $R^{10d}$ is H, F, cyano,

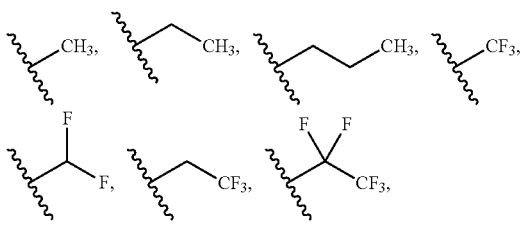

-continued

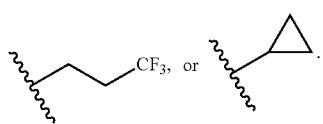

In some embodiments, $R^{10d}$ is H, F, cyano,

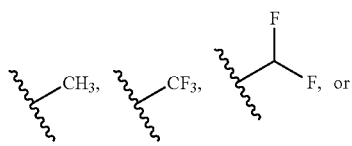

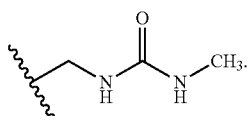

In some embodiments, the BRD binding moiety has the structure of Formula IVa:

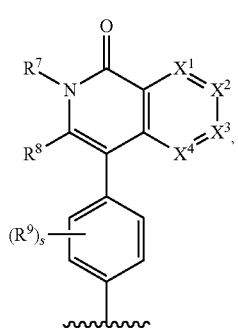
Formula IVa or a pharmaceutically acceptable salt thereof.

In some embodiments, the BRD binding moiety has the structure of Formula IVc:

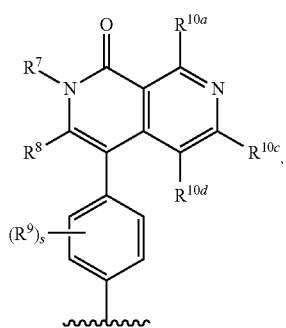
Formula IVc or a pharmaceutically acceptable salt thereof.

In some embodiments, the BRD binding moiety has the structure of Formula IVd:

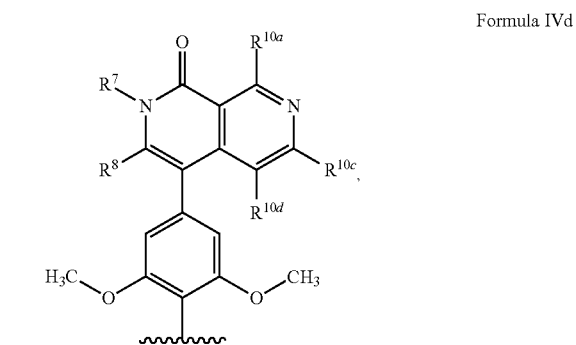
Formula IVd or a pharmaceutically acceptable salt thereof.

In some embodiments, the BRD binding moiety has the structure of Formula IVe:

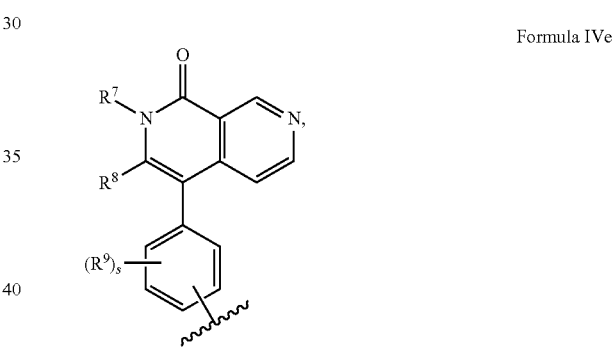
Formula IVe or a pharmaceutically acceptable salt thereof.

In some embodiments, the BRD binding moiety has the structure of Formula IVf:

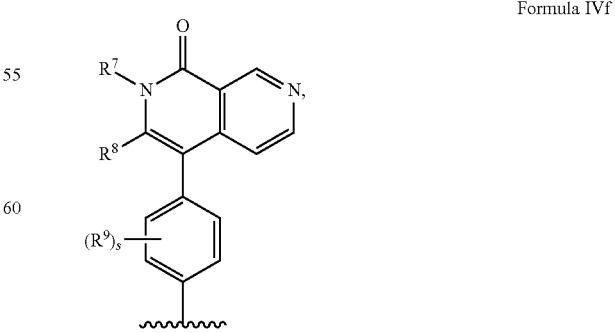
Formula IVf or a pharmaceutically acceptable salt thereof.

In some embodiments, the BRD binding moiety has the structure of Formula IVg:

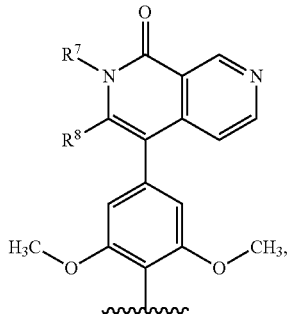

Formula IVg or a pharmaceutically acceptable salt thereof.

In some embodiments, the BRD binding moiety has the structure of Formula IVh:

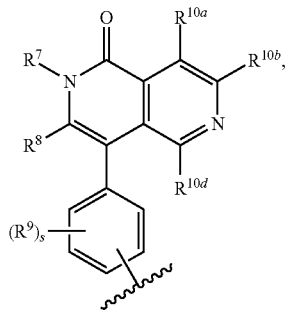

Formula IVh or a pharmaceutically acceptable salt thereof.

In some embodiments, the BRD binding moiety has the structure of Formula IVi:

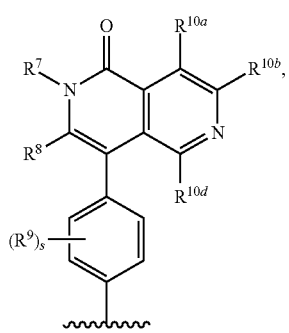

Formula IVi or a pharmaceutically acceptable salt thereof.

In some embodiments, the BRD binding moiety has the structure of Formula IVj:

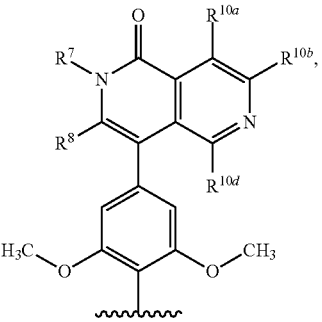

Formula IVj or a pharmaceutically acceptable salt thereof.

In some embodiments, the BRD binding moiety has the structure of Formula IVk:

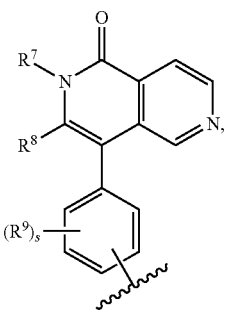

Formula IVk or a pharmaceutically acceptable salt thereof.

In some embodiments, the BRD binding moiety has the structure of Formula IVm:

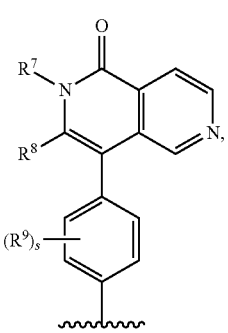

Formula IVm or a pharmaceutically acceptable salt thereof.

In some embodiments, the BRD binding moiety has the structure of Formula IVn:

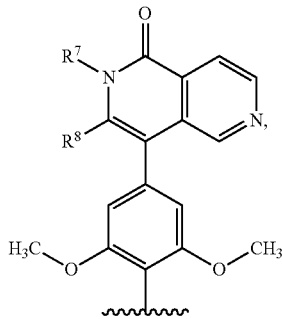

Formula IVn or a pharmaceutically acceptable salt thereof.

In some embodiments, the BRD9 binding moiety includes the structure of Formula V

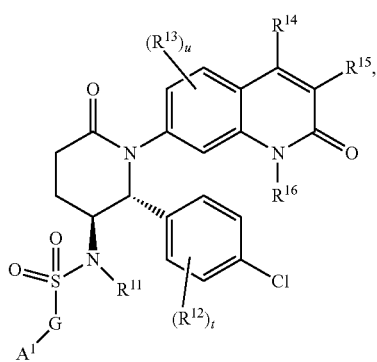

Formula V where
each $R^{11}$ and $R^{16}$ is, independently, H, optionally substituted $C_1$-$C_6$ alkyl, or optionally substituted $C_1$-$C_6$ heteroalkyl;
t is 0, 1, 2, 3, or 4;
each $R^{12}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
u is 0, 1, 2, 3, or 4;
each $R^{13}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
each $R^{14}$ and $R^{15}$ is, independently, selected form the group consisting of H, halogen, optionally substituted $C_1$-$C_6$ alkyl, or optionally substituted $C_6$-$C_{10}$ aryl;
$A^1$ is a bond between A and the linker; and
G is optionally substituted $C_1$-$C_6$ alkylene, optionally substituted $C_6$-$C_{10}$ arylene, or optionally substituted $C_3$-$C_6$ carbocyclylene;
or a pharmaceutically acceptable salt thereof.

In some embodiments, the BRD9 binding moiety includes the structure of Formula VI:

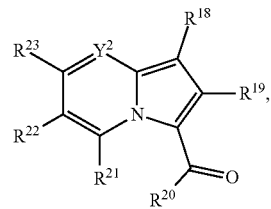

Formula VI where
$Y^2$ is $CR^{17}$ or N;
$R^{18}$ is a bond to the linker, optionally substituted $C_6$-$C_{10}$ aryl, or $C_2$-$C_9$ heteroaryl;
$R^{19}$ is H, halogen, optionally substituted $C_1$-$C_6$ alkyl, or optionally substituted $C_6$-$C_{10}$ aryl;
$R^{20}$ is H, optionally substituted $C_1$-$C_6$ alkyl, or optionally substituted $C_6$-$C_{10}$ aryl;
each $R^{17}$, $R^{21}$, and $R^{22}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
$R^{23}$ is H or —$NR^{24}R^{25}$; and
each of $R^{24}$ and $R^{25}$ is, independently, H, a bond to the linker, optionally substituted $C_1$-$C_6$ alkyl, or optionally substituted $C_1$-$C_6$ heteroalkyl, or $R^{24}$ and $R^{25}$ combine to form optionally substituted $C_2$-$C_9$ heterocyclyl,
where one of $R^{18}$, $R^{24}$, or $R^{25}$ is a bond to the linker,
or a pharmaceutically acceptable salt thereof.

In some embodiments, the BRD9 binding moiety includes the structure of Formula VII:

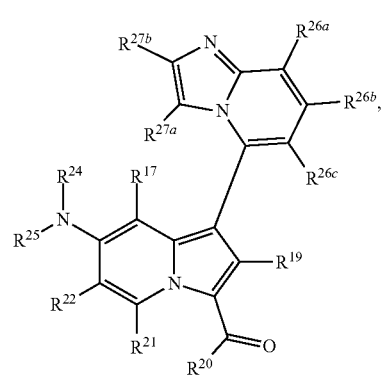

Formula VII where
each $R^{26a}$, $R^{26b}$, and $R^{26c}$ is, independently, H, a bond to the linker, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

each $R^{27a}$ and $R^{27b}$ is, independently, H, halogen, optionally substituted $C_1$-$C_6$ alkyl, or optionally substituted $C_6$-$C_{10}$ aryl;

$R^{19}$ is H, halogen, optionally substituted $C_1$-$C_6$ alkyl, or optionally substituted $C_6$-$C_{10}$ aryl;

$R^{20}$ is H, optionally substituted $C_1$-$C_6$ alkyl, or optionally substituted $C_6$-$C_{10}$ aryl;

each $R^{17}$, $R^{21}$, and $R^{22}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and each of $R^{24}$ and $R^{25}$ is, independently, H, a bond to the linker, optionally substituted $C_1$-$C_6$ alkyl, or optionally substituted $C_1$-$C_6$ heteroalkyl, or $R^{24}$ and $R^{25}$ combine to form optionally substituted $C_2$-$C_9$ heterocyclyl, where one of $R^{26a}$, $R^{26b}$, $R^{26c}$, $R^{24}$ or $R^{25}$ is a bond to the linker, or a pharmaceutically acceptable salt thereof.

In some embodiments, the BRD9 binding moiety includes the structure of Formula VIII:

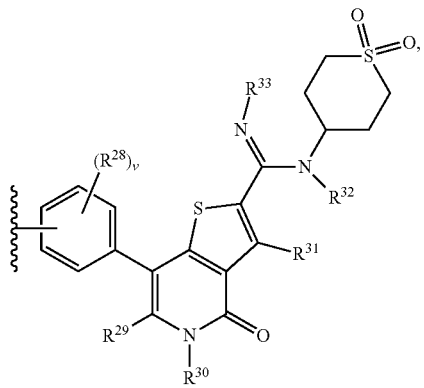

Formula VIII where v is 0, 1, 2, 3, or 4;

each $R^{28}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

$R^{29}$ is H, halogen, optionally substituted $C_1$-$C_6$ alkyl, or optionally substituted $C_6$-$C_{10}$ aryl;

$R^{31}$ is H, halogen, optionally substituted $C_1$-$C_6$ alkyl, or optionally substituted $C_6$-$C_{10}$ aryl; and each $R^{30}$, $R^{32}$, and $R^{33}$ is, independently, H, optionally substituted $C_1$-$C_6$ alkyl, or optionally substituted $C_1$-$C_6$ heteroalkyl, or a pharmaceutically acceptable salt thereof.

In some embodiments, the BRD9 binding moiety includes the structure of Formula IX:

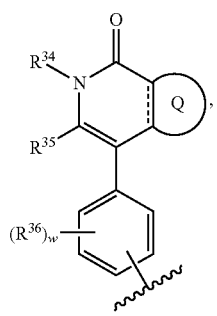

Formula IX where

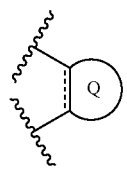

is

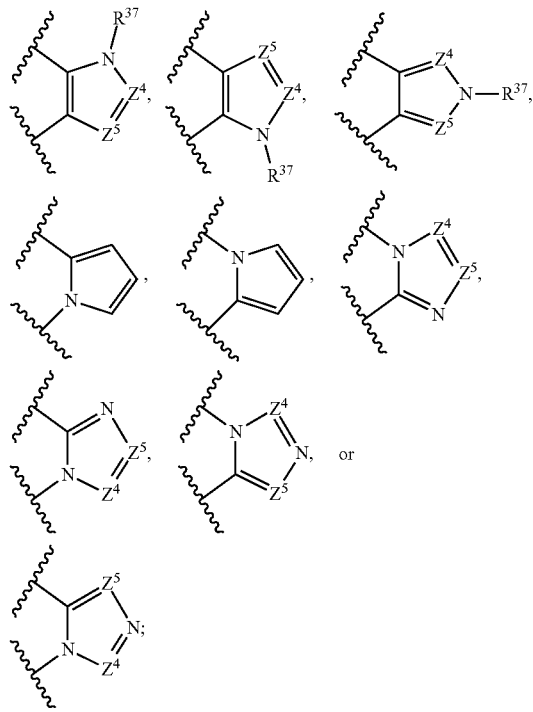

$Z^4$ is N or $CR^{38}$;

$Z^5$ is N or $CR^{39}$;

$R^{34}$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl;

$R^{35}$ is H, halogen, optionally substituted $C_1$-$C_6$ alkyl, optionally substituted $C_1$-$C_6$ heteroalkyl, optionally substituted $C_3$-$C_6$ carbocyclyl, or optionally substituted $C_6$-$C_{10}$ aryl;

$R^{37}$ is H, optionally substituted $C_1$-$C_6$ alkyl, or optionally substituted $C_1$-$C_6$ heteroalkyl;

$R^{38}$ is H, halogen, optionally substituted $C_1$-$C_6$ alkyl, or optionally substituted $C_6$-$C_{10}$ aryl;

$R^{39}$ is H, halogen, optionally substituted $C_1$-$C_6$ alkyl, or optionally substituted $C_6$-$C_{10}$ aryl;

w is 0, 1, 2, 3, or 4; and each $R^{36}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, $Z^4$ is N. In some embodiments, $Z^4$ is $R^{38}$.

In some embodiments, $Z^5$ is N. In some embodiments, $Z^5$ is $R^{39}$.

In some embodiments,

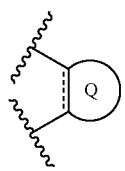

is

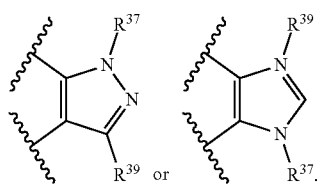

In some embodiments,

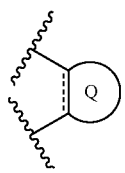

is

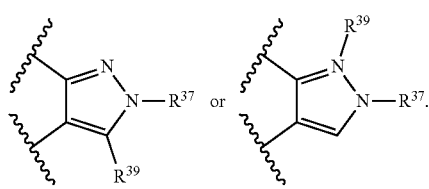

In some embodiments,

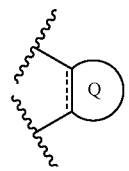

is

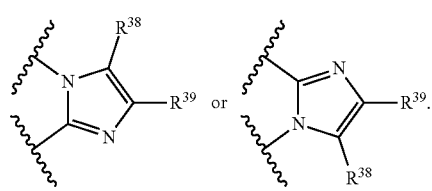

In some embodiments,

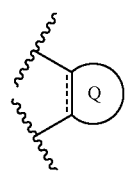

is

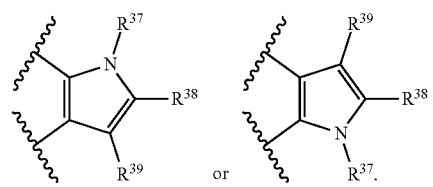

In some embodiments,

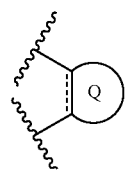

is

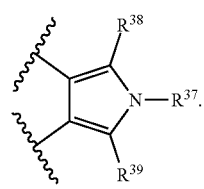

In some embodiments,

[structure with Q]

is

[imidazole structures with R38, R39] or [imidazole structure with R39, R38].

In some embodiments,

[structure with Q]

is

[pyrrole structure] or [pyrrole structure].

In some embodiments, $R^{37}$ is H or

[CH₃ structure].

In some embodiments, $R^{38}$ is H or

[CH₃ structure].

In some embodiments, $R^{39}$ is H or

[CH₃ structure].

In some embodiments, $R^{34}$ is H,

[CH₃], [CD₃ with ²H labels], [CH₃],

[ethyl CH₃], [CH₂F], [CF₃],

[CHF₂], [CH₂CF₃], [C(F)(F)CF₃ with CF₃],

[CH₂CH₂CF₃], [vinyl], [allyl],

[but-3-enyl], [propenyl CH₃], or

[cyclopropyl].

In some embodiments, $R^{35}$ is H,

[CH₃], [CH₂CH₃], [CH₂CH₂CH₃],

[CF₃], [CHF₂], [CH₂CF₃],

[C(F)(F)CF₃], [CH₂CH₂CF₃], or

[cyclopropyl].

In some embodiments, s is 0, 1, or 2.

In some embodiments, each $R^{36}$ is, independently, halogen,

[CH₃], [CH₂CH₃], [CH₂CH₂CH₃],

[OCH₃], [OCH₂CH₃], or

[OCH₂CH₂CH₃].

In some embodiments, the BRD binding moiety has the structure of Formula IXa:

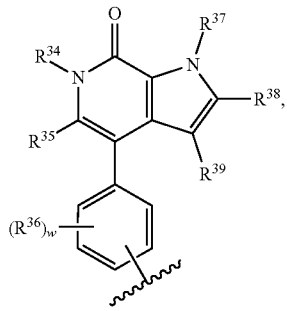

Formula IXa or a pharmaceutically acceptable salt thereof.

In some embodiments, the BRD binding moiety has the structure of Formula IXb:

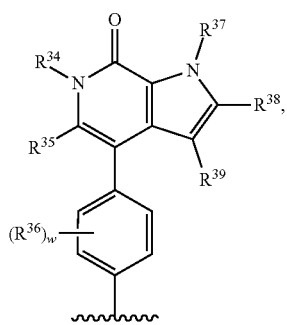

Formula IXb or a pharmaceutically acceptable salt thereof.

In some embodiments, the BRD binding moiety has the structure of Formula IXc:

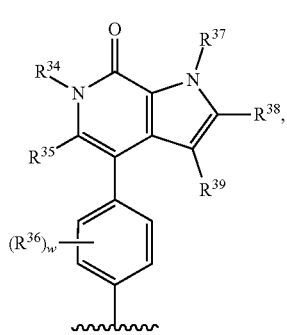

Formula IXc or a pharmaceutically acceptable salt thereof.

In some embodiments, the BRD binding moiety has the structure of Formula IXd:

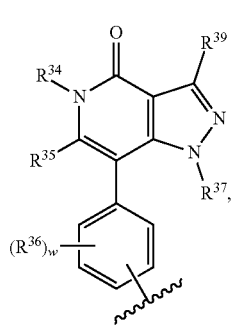

Formula IXd or a pharmaceutically acceptable salt thereof.

In some embodiments, the BRD binding moiety has the structure of Formula IXe:

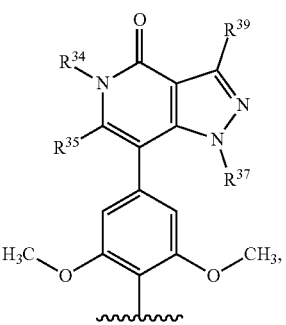

Formula IXe or a pharmaceutically acceptable salt thereof.

In some embodiments, the BRD binding moiety has the structure of Formula IXf:

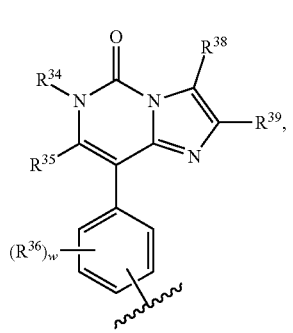

Formula IXf or a pharmaceutically acceptable salt thereof.

In some embodiments, the BRD binding moiety has the structure of Formula IXg:

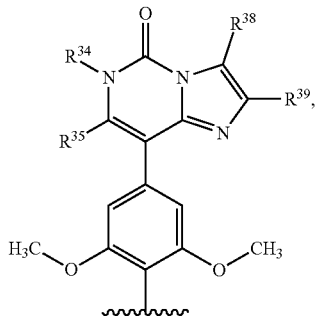

Formula IXg or a pharmaceutically acceptable salt thereof.

In some embodiments, the BRD binding moiety has the structure of Formula IXh:

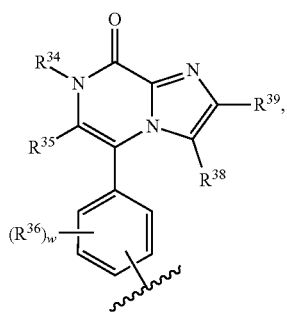

Formula IXh or a pharmaceutically acceptable salt thereof.

In some embodiments, the BRD binding moiety has the structure of Formula IXi:

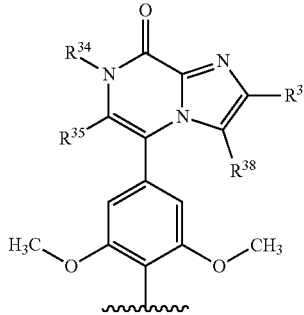

Formula IXi or a pharmaceutically acceptable salt thereof.

In some embodiments, the BRD9 binding moiety is:

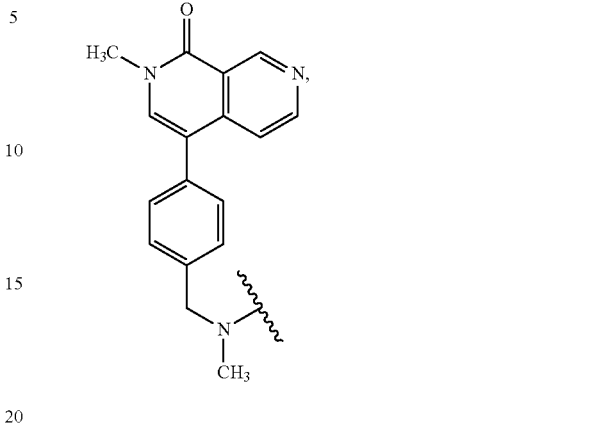

X2

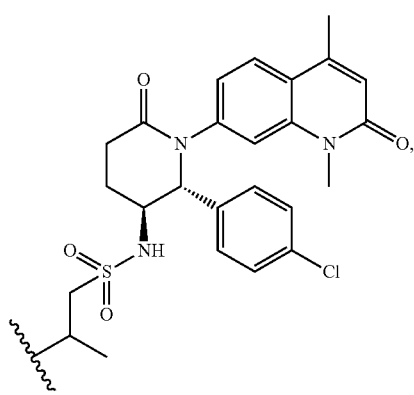

X3

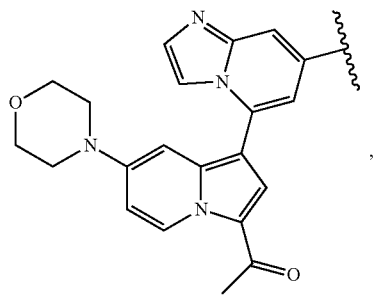

X4

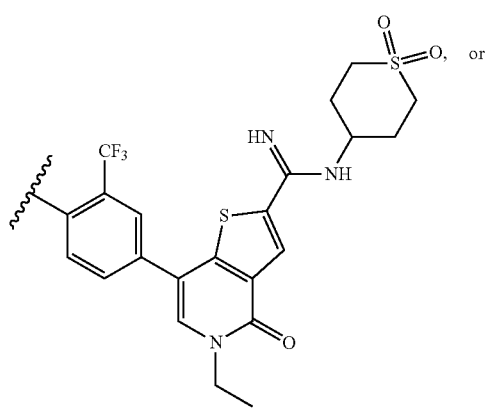

X5

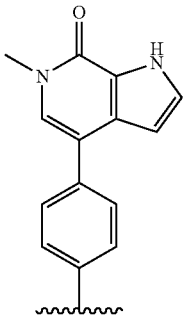

In some embodiments, the reductive amination reaction conditions include the use of a borohydride agent as a reducing agent.

In some embodiments, the borohydride agent is an NHC—$BH_3$ adduct, $NaBH_3CN$, or $NaBH(OAc)_3$. In some embodiments, the borohydride agent is the NHC—$BH_3$ adduct. In some embodiments, the borohydride agent is an adduct of N,N'-dimethylimidazolylidene and $BH_3$.

In some embodiments, the reductive amination reaction conditions include the use of a Brønsted acid. In some embodiments, the Brønsted acid is acetic acid.

In some embodiments, the method includes the step of purifying the compound of Formula A.

In some embodiments, the step of purifying the compound of Formula A includes:

(i) an aqueous work-up to produce an aqueous layer and an organic layer, (ii) separating the organic layer away from the aqueous layer, (iii) concentrating the organic layer to produce a residue, (iv) forming a slurry of the residue with dichloromethane/acetonitrile to produce a liquid phase and a solid phase, (v) isolating the liquid phase, and (vi) concentrating the liquid phase to produce the compound of Formula A in purified form.

In some embodiments, the method includes the step of further purifying the compound of Formula A, the step of further purifying the compound of Formula A including:

dissolving the compound of Formula A from step (vi) in dichloromethane/acetonitrile to produce a solution, adding water to the solution to form a wet cake slurry, and separating the solid away from the wet cake slurry to produce a purified compound of Formula A, and optionally subjecting one or more times the purified compound of Formula A to the steps of dissolving, adding water, and separating the solid to increase the purity of the compound of Formula A.

In some embodiments, the purified compound of Formula A is subjected to the steps of dissolving, adding water, and separating the solid once.

In some embodiments, PG is $C_{1-6}$ alkyl. In some embodiments, PG is methyl.

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The term "aliphatic," as used herein, refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$, or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic," as used herein, refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, and alkyl-O-haloalkyl.

The term "acyl," as used herein, represents a hydrogen or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms). An "alkylene" is a divalent alkyl group.

The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms). An "alkenylene" is a divalent alkenyl group.

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms). An "alkynylene" is a divalent alkynyl group.

The term "amino," as used herein, represents —N($R^{N1}$)$_2$, wherein each $R^{N1}$ is, independently, H, OH, NO$_2$, N($R^{N2}$)$_2$, SO$_2$O$R^{N2}$, SO$_2R^{N2}$, SO$R^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the compounds described herein can be an unsubstituted amino (i.e., —NH$_2$) or a substituted amino (i.e., —N($R^{N1}$)$_2$).

The term "aryl," as used herein, refers to an aromatic mono- or polycarbocyclic radical of, e.g., 6 to 12, carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —N$_3$ group.

The term "bridged cyclyl," as used herein, refers to a bridged polycyclic group of 5 to 20 atoms, containing from 1 to 3 bridges. Bridged cyclyl includes bridged carbocyclyl (e.g., norbornyl) and bridged heterocyclyl (e.g., 1,4-diazabicyclo[2.2.2]octane).

The term "cyano," as used herein, represents a —CN group.

The term "carbocyclyl," as used herein, refers to a non-aromatic $C_3$-$C_{12}$, monocyclic or polycyclic (e.g., bicyclic or tricyclic) structure in which the rings are formed by carbon atoms. Carbocyclyl structures include cycloalkyl groups (e.g., cyclohexyl) and unsaturated carbocyclyl radicals (e.g., cyclohexenyl). Polycyclic carbocyclyl includes spirocyclic carbocyclyl, bridged carbocyclyl, and fused carbocyclyl. A "carbocyclylene" is a divalent carbocyclyl group.

The term "cycloalkyl," as used herein, refers to a saturated, non-aromatic, monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The terms "halo" or "halogen," as used herein, mean a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers to alkyl-O— (e.g., methoxy and ethoxy), and an "alkylamino" which, as used herein, refers to —N(alkyl)$R^{Na}$, where $R^{Na}$ is H or alkyl (e.g., methylamino). A "heteroalkylene" is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers to alkenyl-O—. A "heteroalkenylene" is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers to alkynyl-O—. A "heteroalkynylene" is a divalent heteroalkynyl group.

The term "heteroaryl," as used herein, refers to an aromatic monocyclic or polycyclic structure of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl. A "heteroarylene" is a divalent heteroaryl group.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a monocyclic or polycyclic radical (e.g., bicyclic or tricyclic) having 3 to 12 atoms having at least one non-aromatic ring containing 1, 2, 3, or 4 ring atoms selected from N, O, or S, and no aromatic ring containing any N, O, or S atoms. Polycyclic heterocyclyl includes spirocyclic heterocyclyl, bridged heterocyclyl, and fused heterocyclyl. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl. A "heterocyclylene" is a divalent heterocyclyl group.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group. A carboxyl hydroxyl is a hydroxyl that is bonded to a carbonyl. An aliphatic hydroxyl is a hydroxyl that is bonded to an $sp^3$-hybridized carbon.

The term "imidazolium salt," as used herein, refers to a charge-balanced combination of an N,N'-disubstituted imidazole cation and a negatively charged counterion. Non-limiting examples of the negatively charged counterions include halides (e.g., chloride, bromide, or iodide) and tetrafluoroborate. Non-limiting examples of imidazolium salts include N,N'-dialkylimidazolium salts, e.g., N,N'-dimethylimidazolium salts (e.g., N,N'-dimethylimidazolium chloride, N,N'-dimethylimidazolium tetrafluoroborate, N,N'-dimethylimidazolium iodide), N,N'-methylethylimidazolium salts, and N,N'-methyl-t-butylimidazolium salts.

The term "imidazolinium salt," as used herein, refers to a charge-balanced combination of an N,N'-disubstituted 2-imidazoline cation and a negatively charged counterion. Non-limiting examples of the negatively charged counterions include halides (e.g., chloride, bromide, or iodide) and tetrafluoroborate. Non-limiting examples of imidazolium salts include N,N'-dialkylimidazolium salts, e.g., N,N'-dimethylimidazolium salts (e.g., N,N'-dimethylimidazolium chloride, N,N'-dimethylimidazolium tetrafluoroborate, N,N'-dimethylimidazolium iodide), N,N'-methylethylimidazolium salts, and N,N'-methyl-t-butylimidazolium salts.

The term "imine," as used herein, represents $=NR^N$ group, where $R^N$ is, e.g., H or alkyl.

The term "NHC—$BH_3$ adduct," as used herein, refers to an adduct of an imidazolylidene or imidazolinylidene and $BH_3$. Without wishing to be bound by theory, it is believed that an N-heterocyclic carbene (e.g., imidazolylidene or imidazolinylidene) is formed through deprotonation of the corresponding imidazolium or imidazolinium salt. This N-heterocyclic carbene is then believed to bind to $BH_3$. Non-limiting examples of NHC—$BH_3$ adducts include N,N'-dimethylimidazolylidene borane and N,N'-dimethylimidazolylidene borane. NHC—$BH_3$ adducts may be prepared in situ from the corresponding salt (e.g., imidazolium or imidazolinium salt) and borane or may be isolated.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "O-protecting group," as used herein, represents those groups intended to protect a hydroxyl (e.g., a carboxylic hydroxyl or an aliphatic hydroxyl) against undesirable reactions during synthetic procedures. Commonly used O-protecting groups are disclosed in Greene, "Protective Groups in Organic Synthesis," 3rd Edition (John Wiley & Sons, New York, 1999). Exemplary O-protecting groups include $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), ($C_{6-15}$)aryl($C_{1-6}$)alkyl, ($C_{4-19}$)heteroaryl($C_{1-6}$)alkyl, ($C_{1-6}$)heteroaryl($C_{1-6}$)alkyl, ($C_{1-6}$)alkoxy($C_{1-6}$)alkyl, ($C_{1-6}$)alkylthio($C_{1-6}$)alkyl, ($C_{6-10}$)aryl($C_{1-6}$)alkoxy($C_{1-6}$)alkyl, and silyl (e.g., tri($C_{1-6}$ alkyl)silyl, tri($C_{6-10}$ aryl or $C_{1-6}$ heteroaryl)silyl, di($C_{6-10}$ aryl or $C_{1-6}$ heteroaryl)($C_{1-6}$ alkyl)silyl, and ($C_{6-10}$ aryl or $C_{1-6}$ heteroaryl)di($C_{1-6}$ alkyl)silyl). Specific examples of alkylethers include methyl and t-butyl, and an example of an alkenyl ether is allyl. O-protecting groups can be used to protect a carboxyl group (e.g., with a $C_{1-12}$ alkyl (e.g., $C_{1-8}$, $C_{1-6}$, $C_{1-4}$, $C_{2-7}$, $C_{3-12}$, and $C_{3-6}$ alkyl), ($C_{6-15}$)aryl($C_{1-6}$)alkyl, ($C_{1-6}$)alkoxy($C_{1-6}$)alkyl, ($C_{1-6}$)alkylthio($C_{1-6}$)alkyl, or ($C_{6-10}$)aryl($C_{1-6}$)alkoxy($C_{1-6}$)alkyl). Examples of alkoxyalkyls and alkylthioalkyls that can be used as O-protecting groups include methoxymethyl, methylthiomethyl, (2-methoxyethoxy)methyl, and β-(trimethylsilyl)ethoxymethyl. Examples of arylalkyl groups that can be used as O-protecting groups include benzyl, p-methoxybenzyl (MPM), 3,4-dimethoxybenzyl, triphenylmethyl (trityl), o-nitrobenzyl, p-nitrobenzyl, p-halobenzyl, 2,6-dichlorobenzyl, p-cyanobenzyl, naphthylmethyl, and 2- and 4-picolyl ethers.

The term "nitro," as used herein, represents an —$NO_2$ group.

The term "oxo," as used herein, represents an =O group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, orthioalkoxy), heteroaryl, heterocyclyl, amino (e.g., $NH_2$ or mono- or dialkyl amino), azido, cyano, nitro, oxo, sulfonyl, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds described herein can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, where such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms.

Atropisomers are stereoisomers resulting from hindered rotation about single bonds where the steric strain barrier to rotation is high enough to allow for the isolation of the conformers. The compounds described herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O $^{32}$P, $^{33}$P, $^{35}$S, $^{18}$F, $^{36}$Cl, $^{123}$I and $^{125}$I. Isotopically-labeled compounds (e.g., those labeled with $^3$H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). In some embodiments, one or more hydrogen atoms are replaced by $^2$H or $^3$H, or one or more carbon atoms are replaced by $^{13}$C- or $^{14}$C-enriched carbon. Positron emitting isotopes such as $^{15}$O, $^{13}$N, $^{11}$C, and $^{18}$F are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "adult soft tissue sarcoma" refers to a sarcoma that develops in the soft tissues of the body, typically in adolescent and adult subjects (e.g., subjects who are at least 10 years old, 11 years old, 12 years old, 13 years old, 14 years old, 15 years old, 16 years old, 17 years old, 18 years old, or 19 years old). Non-limiting examples of adult soft tissue sarcoma include, but are not limited to, synovial sarcoma, fibrosarcoma, malignant fibrous histiocytoma, dermatofibrosarcoma, liposarcoma, leiomyosarcoma, hemangiosarcoma, Kaposi's sarcoma, lymphangiosarcoma, malignant peripheral nerve sheath tumor/neurofibrosarcoma, extraskeletal chondrosarcoma, extraskeletal osteosarcoma, extraskeletal myxoid chondrosarcoma, and extraskeletal mesenchymal.

As used herein, the term "BAF complex" refers to the BRG1- or HRBM-associated factors complex in a human cell.

As used herein, the term "BAF complex-related disorder" refers to a disorder that is caused or affected by the level and/or activity of a BAF complex.

As used herein, the terms "GBAF complex" and "GBAF" refer to a SWI/SNF ATPase chromatin remodeling complex in a human cell. GBAF complex subunits may include, but are not limited to, ACTB, ACTL6A, ACTL6B, BICRA, BICRAL, BRD9, SMARCA2, SMARCA4, SMARCC1, SMARCD1, SMARCD2, SMARCD3, and SS18. The term "cancer" refers to a condition caused by the proliferation of malignant neoplastic cells, such as tumors, neoplasms, carcinomas, sarcomas, leukemias, and lymphomas.

As used herein, the term "BRD9" refers to bromodomain-containing protein 9, a component of the BAF (BRG1- or BRM-associated factors) complex, a SWI/SNF ATPase chromatin remodeling complex, and belongs to family IV of the bromodomain-containing proteins. BRD9 is encoded by the BRD9 gene, the nucleic acid sequence of which is set forth in SEQ ID NO: 1. The term "BRD9" also refers to natural variants of the wild-type BRD9 protein, such as proteins having at least 85% sequence identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type BRD9, which is set forth in SEQ ID NO: 2.

As used herein, the term "BRD9-related disorder" refers to a disorder that is caused or affected by the level and/or activity of BRD9. The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

A "compound of the present invention" and similar terms as used herein, whether explicitly noted or not, refers to compounds useful for treating BAF-related disorders (e.g., cancer or infection) described herein, including, e.g., compound of Formula I or (Ia), as well as pharmaceutically acceptable salts (e.g., a citrate salt), solvates, hydrates, stereoisomers (including atropisomers), and tautomers thereof. Those skilled in the art will appreciate that certain compounds described herein can exist in one or more different isotopic (e.g., in which one or more atoms has been substituted with a different isotope of the atom, such as hydrogen substituted for deuterium) forms. Unless otherwise indicated or clear from context, a depicted structure can be understood to represent any such isotopic form, individually or in combination. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

As used herein, the term "degrader" refers to a small molecule compound including a degradation moiety, where the compound interacts with a protein (e.g., BRD9) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRD9. In one example, the moiety binds to a protease or a ubiquitin ligase that metabolizes the protein, e.g., BRD9.

By "determining the level of a protein" is meant the detection of a protein, or an mRNA encoding the protein, by methods known in the art either directly or indirectly.

"Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

As used herein, the terms "effective amount," "therapeutically effective amount," and "a "sufficient amount" of an agent that reduces the level and/or activity of BRD9 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating cancer, it is an amount of the agent that reduces the level and/or activity of BRD9 sufficient to achieve a treatment response as compared to the response obtained without administration of the agent that reduces the level and/or activity of BRD9. The amount of a given agent that reduces the level and/or activity of BRD9 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of BRD9 of the present disclosure is an amount which results in a beneficial or desired result in a subject as compared to a control. As defined herein, a therapeutically effective amount of an agent that reduces the level and/or activity of BRD9 of the present disclosure may be readily determined by one of ordinary skill by routine methods known in the art. Dosage regimen may be adjusted to provide the optimum therapeutic response.

As used herein, the term "inhibitor" refers to any agent which reduces the level and/or activity of a protein (e.g., BRD9). Non-limiting examples of inhibitors include small molecule inhibitors, degraders, antibodies, enzymes, or polynucleotides (e.g., siRNA).

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein or mRNA in a sample.

By "modulating the activity of a BAF complex," is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction $X/Y$)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid. The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

By "reducing the activity of BRD9," is meant decreasing the level of an activity related to an BRD9, or a related downstream effect. A non-limiting example of inhibition of an activity of BRD9 is decreasing the level of a BAF complex (e.g., GBAF) in a cell. The activity level of BRD9 may be measured using any method known in the art. In some embodiments, an agent which reduces the activity of BRD9 is a small molecule BRD9 inhibitor. In some embodiments, an agent which reduces the activity of BRD9 is a small molecule BRD9 degrader.

By "reducing the level of BRD9," is meant decreasing the level of BRD9 in a cell or subject. The level of BRD9 may be measured using any method known in the art.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the term "SS18-SSX fusion protein-related disorder" refers to a disorder that is caused or affected by the level and/or activity of SS18-SSX fusion protein.

As used herein, the terms "treat," "treated," or "treating" mean both therapeutic treatment and prophylactic or preventative measures where the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material. The details of one or more embodiments of the invention are set forth in the description below. Other features, objects, and advantages of the invention will be apparent from the description and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 32A and 32B are 100× magnification, and FIG. 32C is 400× magnification.

DETAILED DESCRIPTION

Figure 1:
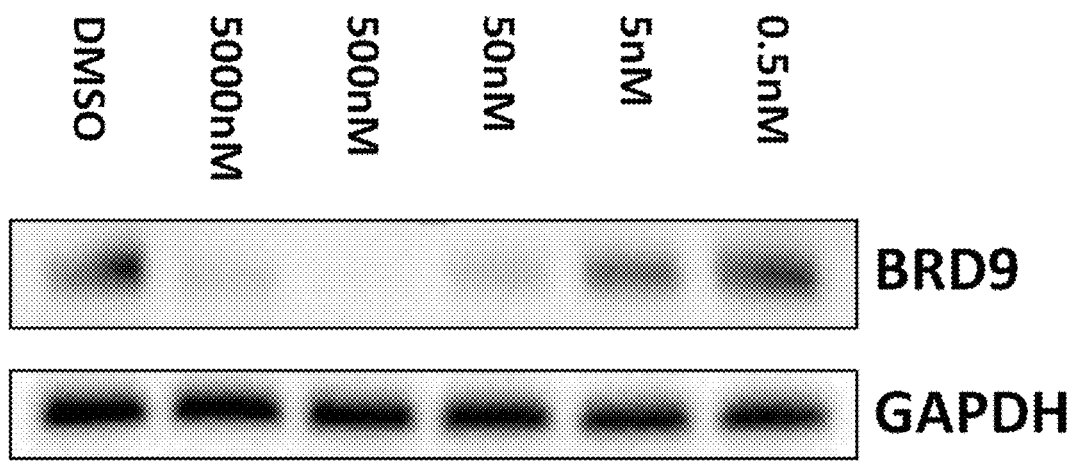
FIG. 1 is an image illustrating dose dependent depletion of BRD9 levels in a synovial sarcoma cell line (SYO1) in the presence of a BRD9 degrader.

The present disclosure features compositions and methods useful for the treatment of BAF-related disorders (e.g., cancer and infection) as well for the preparation of compounds. The disclosure further features compositions and methods useful for inhibition of the level and/or activity of BRD9, e.g., for the treatment of disorders such as cancer (e.g., sarcoma) and infection (e.g., viral infection), e.g., in a subject in need thereof.

The invention provides a citrate salt of the compound of Formula I:

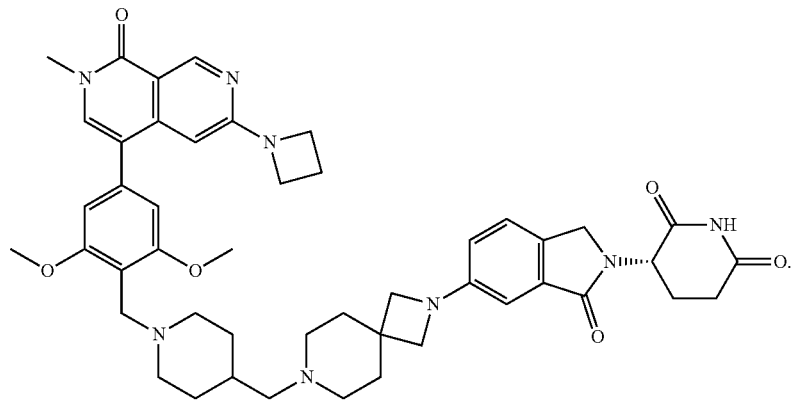

Formula I

The invention also provides a citrate salt of the compound of Formula Ia:

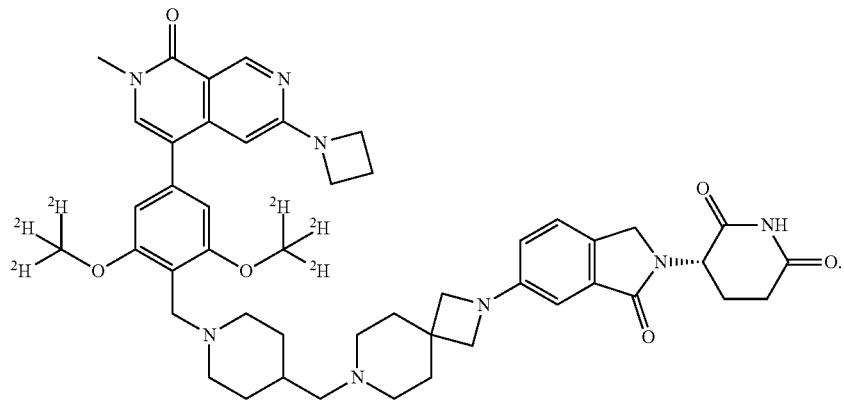

Formula Ia

The citrate salts may be included in a pharmaceutical composition (e.g., a liquid pharmaceutical composition). The pharmaceutical composition may include a buffer (e.g., a buffer sufficient to produce pH of 3.5 to 5.5, 3.5 to 5.0, 4.0 to 5.5, or 4.0 to 5.0, e.g., upon dissolution in water at pH 7, e.g., for solid pharmaceutical compositions). Suitable buffers are known in the art. A non-limiting example of the buffer is a citrate buffer, which is typically prepared from water, citric acid, and sodium citrate or sodium hydroxide. A liquid pharmaceutical composition may have pH of 3.5 to 5.5, 3.5 to 5.0, 4.0 to 5.5, or 4.0 to 5.0. The pharmaceutical composition may also include a cyclodextrin-based solubilizer (e.g., sulfobutylether-β-cyclodextrin). The pharmaceutical composition may also include saline (e.g., isotonic saline). When the pharmaceutical composition is a solid, the pharmaceutical composition may produce pH 3.5 to 5.5, 3.5 to 5.0, 4.0 to 5.5, or 4.0 to 5.0 upon dissolution in water at pH 7.

The invention also provides crystalline forms of the free-base solid form of the compound of Formula I:

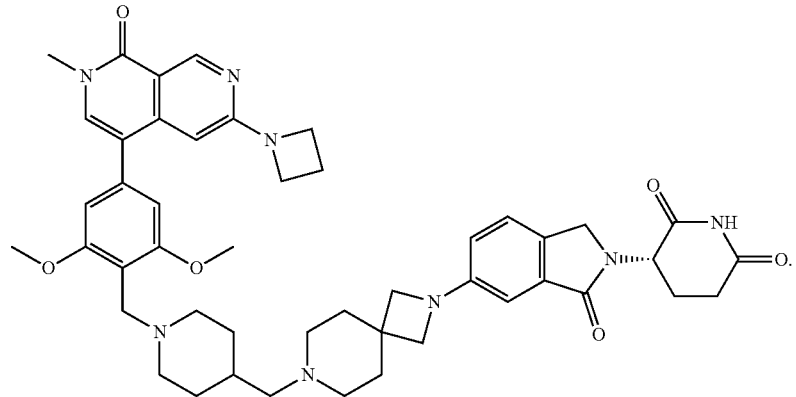

Formula I

The first of the crystalline forms is characterized by a powder x-ray diffraction pattern having peaks at 10.4±0.2 2θ and 26.9±0.2 2θ. In some embodiments, the x-ray diffraction pattern further includes peaks at 17.7±0.2 2θ and at 17.9±0.2 2θ. In some embodiments, the x-ray diffraction pattern further includes a peak at 20.8±0.2 2θ. In some embodiments, the x-ray diffraction pattern further includes a peak at 13.8±0.2 2θ. The second of the crystalline forms is characterized by a powder x-ray diffraction pattern having peaks at 13.4±0.2 2θ and 17.4±0.2 2θ. In some embodiments, the x-ray diffraction pattern further includes a peak at 26.3±0.2 2θ. In some embodiments, the x-ray diffraction pattern further includes a peak at 21.0±0.2 2θ. In some embodiments, the x-ray diffraction pattern further includes peaks at 13.6±0.2 2θ and 18.1±0.2 2θ. The crystalline form described herein may be provided in a pharmaceutical composition (e.g., a pharmaceutical composition described herein).

The invention further provides pharmaceutical compositions containing the free-base solid form of the compound of Formula I:

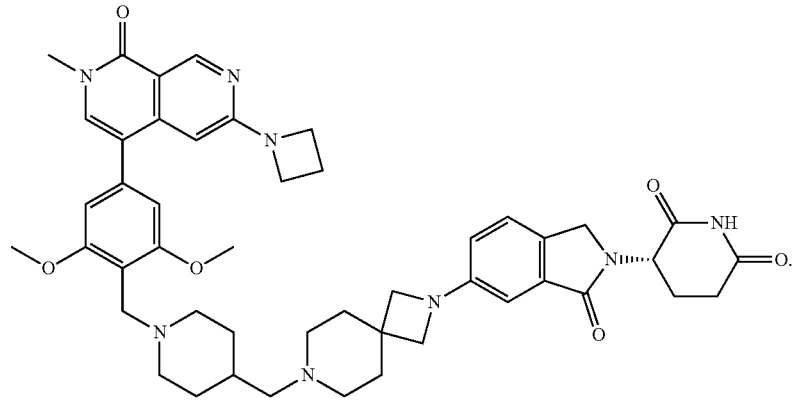

Formula I

The invention further provides pharmaceutical compositions containing the free-base solid form of the compound of Formula Ia:

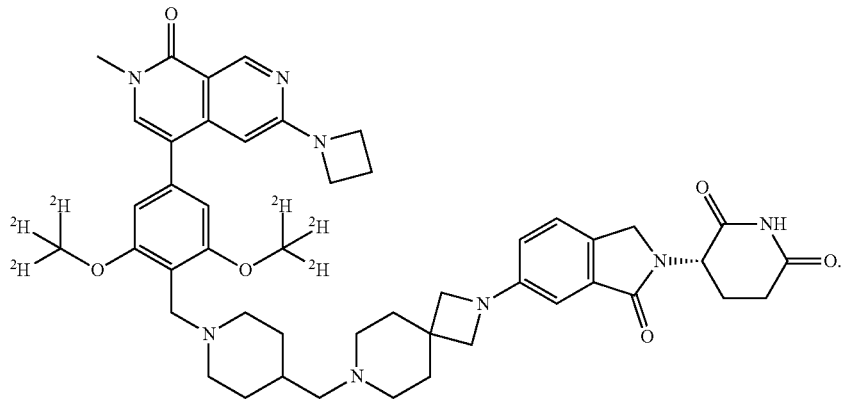

Formula Ia

The free-base solid form may be a lyophilizate. The pharmaceutical composition may contain a citrate buffer (e.g., citric acid and sodium citrate) in an amount sufficient produce a solution having pH of 3.5 to 5.5, 3.5 to 5.0, 4.0 to 5.5, or 4.0 to 5.0 upon dissolution in water at pH 7.

The invention provides a pharmaceutical composition comprising an aqueous solvent and the compound of Formula I:

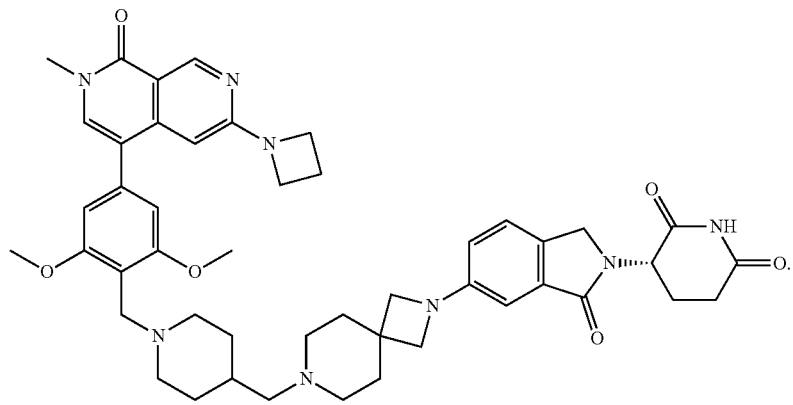

Formula I

The invention also provides a pharmaceutical composition comprising an aqueous solvent and the compound of Formula Ia:

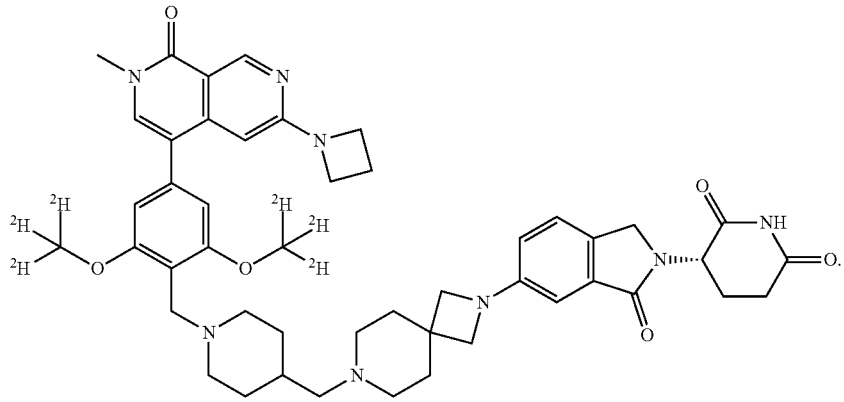

Formula Ia

The pharmaceutical composition may have pH of 3.5 to 5.5, 3.5 to 5.0, 4.0 to 5.5, or 4.0 to 5.0. The pharmaceutical composition may also include a cyclodextrin-based solubilizer (e.g., sulfobutylether-β-cyclodextrin). The pharmaceutical composition may also include saline (e.g., isotonic saline). The pharmaceutical composition may include a buffer (e.g., a citrate buffer).

The compounds of Formula I or Formula Ia may be administered to a subject according to a non-limiting method involving combining the compound of Formula I or Formula Ia in solid form with an aqueous solvent (e.g., a liquid composition containing water or saline (e.g., isotonic saline) and a buffer (e.g., a citrate buffer)) to produce an aqueous solution, and administering the aqueous solution to the subject intravenously.

Preparation of Compounds

Compounds disclosed herein may be prepared using methods disclosed herein. The methods disclosed herein may be advantageous by providing superior stereochemical purity of the end product, e.g., the compound of Formula I or the compound of Formula A. For example, the syntheses described herein can reduce the number of reactive steps involving stereochemically enriched piperidinedione moiety, thus reducing exposure of the stereochemical center therein to conditions capable of inducing racemization. For example, the reaction may produce a product with less than 15% erosion in the enantiomeric excess (e.g., less than 10% erosion in the enantiomeric excess). Additionally or alternatively, the use of reducing agents, e.g., borohydride agents, such as NHC—BH$_3$ adduct or NaBH$_3$CN, may also provide the desired product with a superior stereoretention. Additionally or alternatively, purification steps may be included in the preparation methods disclosed herein may. Advantageously, these purification steps may improve stereochemical enrichment of the desired product (e.g., compound of Formula I or Formula A) without requiring the use of other stereochemically enriched agents (other than the starting material) or chromatographic separation techniques. Thus, the compound of Formula I or Formula A may be obtained with less than 5% erosion in the enantiomeric excess (e.g., less than 4%, less than 3%, or less than 2% erosion in the enantiomeric excess).

The invention provides a method of preparing an enantioenriched compound of Formula I:

The method includes the step of reacting an enantioenriched compound of Formula Ib or a salt thereof and a compound of Formula Ic or a salt thereof under reductive amination reaction conditions, where the compound of Formula Ib is of the following structure:

Formula Ib

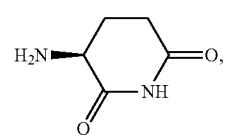

and the compound of formula of Formula Ic is of the following structure:

Formula Ic

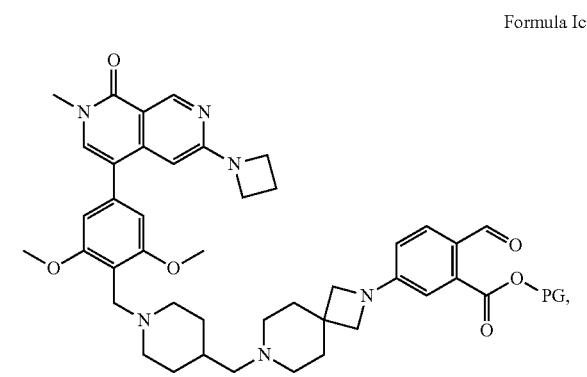

where PG is an O-protecting group.

In some embodiments, the reductive amination reaction conditions include the use of a borohydride agent as a reducing agent. In some embodiments, the borohydride agent is an NHC—BH$_3$ adduct, NaBH$_3$CN, or NaBH(OAc)$_3$. In some embodiments, the borohydride agent is the NHC—BH$_3$ adduct. In some embodiments, the borohydride agent is an adduct of N,N'-dimethylimidazolylidene and BH$_3$. In some embodiments, the reductive amination reaction conditions include the use of a Brønsted acid. In some embodiments, the Brønsted acid is acetic acid.

In some embodiments, the method includes the step of purifying the compound of Formula I.

Formula I

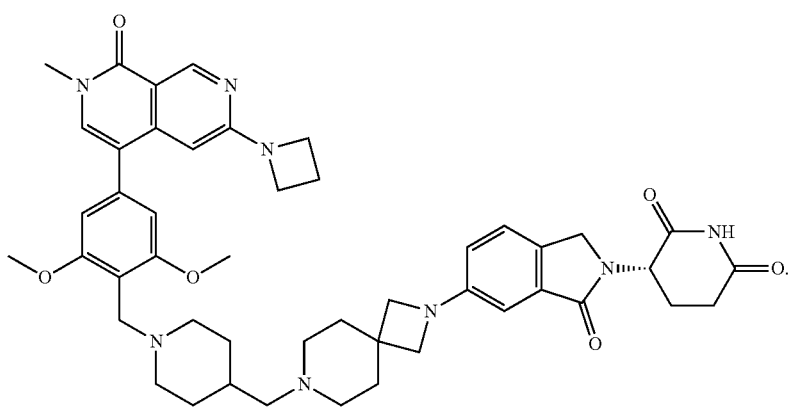

In some embodiments, the step of purifying the compound of Formula I includes:

(i) an aqueous work-up to produce an aqueous layer and an organic layer, (ii) separating the organic layer away from the aqueous layer, (iii) concentrating the organic layer to produce a residue, (iv) forming a slurry of the residue with dichloromethane/acetonitrile to produce a liquid phase and a solid phase, (v) isolating the liquid phase, and (vi) concentrating the liquid phase to produce the compound of Formula I in purified form.

In some embodiments, the method includes the step of further purifying the compound of Formula I, the step of further purifying the compound of Formula I including:

dissolving the compound of Formula I from step (vi) in dichloromethane/acetonitrile to produce a solution, adding water to the solution to form a wet cake slurry, and separating the solid away from the wet cake slurry to produce a purified compound of Formula I, and optionally subjecting one or more times the purified compound of Formula I to the steps of dissolving, adding water, and separating the solid to increase the purity of the compound of Formula I.

In some embodiments, the purified compound of Formula I is subjected to the steps of dissolving, adding water, and separating the solid once.

In an aspect, the invention provides a method of preparing an enantioenriched compound of Formula A:

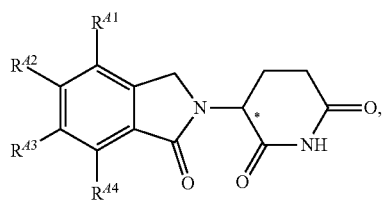

Formula A where

* designates an enantioenriched stereogenic center; and each of $R^{A1}$, $R^{A2}$, $R^{A3}$, and $R^{A4}$ is, independently, H, A-L-, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{A1}$ and $R^{A2}$, $R^{A2}$ and $R^{A3}$, or $R^{A3}$ and $R^{A4}$, together with the carbon atoms to which each is attached, combine to form

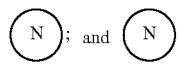

is optionally substituted $C_6$-$C_{10}$ aryl, optionally substituted $C_3$-$C_{10}$ carbocyclyl, optionally substituted $C_2$-$C_9$ heterocyclyl, or $C_2$-$C_9$ heterocyclyl, any of which is optionally substituted with A-L-, where one of $R^{A1}$, $R^{A2}$, $R^{A3}$, and $R^{A4}$ is A-L-, or

is substituted with A-L-;

L is a linker; and

A is a BRD9 binding moiety.

The method includes the step of reacting an enantioenriched compound of Formula A1 or a salt thereof and a compound of Formula A2 or a salt thereof under reductive amination reaction conditions, where the compound of Formula A1 is of the following structure:

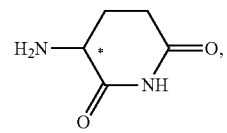

Formula A1 and the compound of formula of Formula A2 is of the following structure:

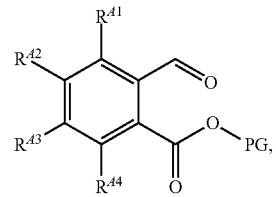

Formula A2 where PG is an O-protecting group.

In some embodiments, the reductive amination reaction conditions include the use of a borohydride agent as a reducing agent.

In some embodiments, the borohydride agent is an NHC—$BH_3$ adduct, $NaBH_3CN$, or $NaBH(OAc)_3$. In some embodiments, the borohydride agent is the NHC—$BH_3$ adduct. In some embodiments, the borohydride agent is an adduct of N,N'-dimethylimidazolylidene and $BH_3$.

In some embodiments, the reductive amination reaction conditions include the use of a Brønsted acid. In some embodiments, the Brønsted acid is acetic acid.

In some embodiments, the method includes the step of purifying the compound of Formula A.

In some embodiments, the step of purifying the compound of Formula A includes:

(i) an aqueous work-up to produce an aqueous layer and an organic layer, (ii) separating the organic layer away from the aqueous layer, (iii) concentrating the organic layer to produce a residue, (iv) forming a slurry of the residue with dichloromethane/acetonitrile to produce a liquid phase and a solid phase, (v) isolating the liquid phase, and (vi) concentrating the liquid phase to produce the compound of Formula A in purified form.

In some embodiments, the method includes the step of further purifying the compound of Formula A, the step of further purifying the compound of Formula A including:

dissolving the compound of Formula A from step (vi) in dichloromethane/acetonitrile to produce a solution, adding water to the solution to form a wet cake slurry, and
separating the solid away from the wet cake slurry to produce a purified compound of Formula A, and optionally subjecting one or more times the purified compound of Formula A to the steps of dissolving, adding water, and separating the solid to increase the purity of the compound of Formula A.

In some embodiments, the purified compound of Formula A is subjected to the steps of dissolving, adding water, and separating the solid once.

In some embodiments, PG is $C_{1-6}$ alkyl. In some embodiments, PG is methyl.

In the compounds of Formula A, the linkers and BRD9 binding moieties can be those described, e.g., in US 20220098190, US 20220048906, US 20210230190, US 20210009568, US 20190247509, US 20180044335, WO 2020051235, WO 2020160192, WO 2020160193, WO 2020160198, WO 2021055295, and WO 2021178920, the disclosures of which are incorporated herein by reference in their entirety.

The BRD binding moiety may be, e.g., a group of Formula III:

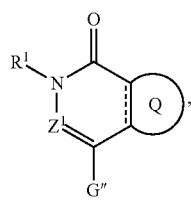

Formula III where
$R^1$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl;
$Z^1$ is $CR^2$ or N;
$R^2$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl;

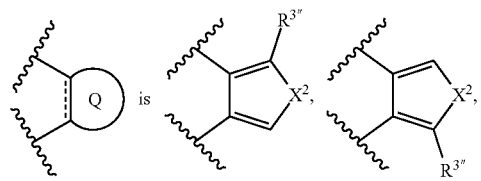

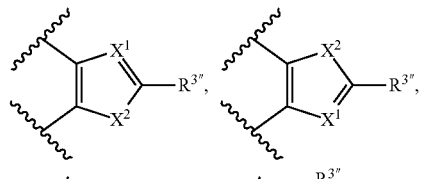

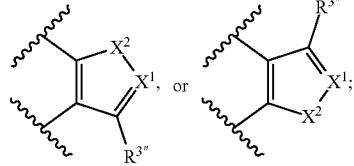

$X^1$ is $CR^{X1}$ or N;
$X^2$ is O or S;
$R^{X1}$ is H or optionally substituted $C_1$-$C_6$ alkyl;
$R^{3''}$ is H,

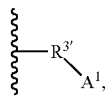

cyano, optionally substituted $C_1$-$C_6$ alkyl, optionally substituted $C_1$-$C_6$ heteroalkyl, optionally substituted $C_1$-$C_6$ alkoxy, optionally substituted amino, optionally substituted $C_3$-$C_{10}$ carbocyclyl, optionally substituted $C_6$-$C_{10}$ aryl, optionally substituted $C_3$-$C_{10}$ heterocyclyl, or optionally substituted $C_2$-$C_9$ heteroaryl;

$R^{3'}$ is absent, optionally substituted $C_1$-$C_6$ alkylene, optionally substituted $C_2$-$C_9$ heteroarylene, or optionally substituted $C_1$-$C_6$ heteroalkylene;

G'' is

optionally substituted $C_3$-$C_{10}$ carbocyclyl, $C_2$-$C_9$ heterocyclyl, optionally substituted $C_6$-$C_{10}$ aryl, or optionally substituted $C_2$-$C_9$ heteroaryl;

G' is optionally substituted $C_3$-$C_{10}$ carbocyclylene, $C_2$-$C_9$ heterocyclylene, optionally substituted $C_6$-$C_{10}$ arylene, or optionally substituted $C_2$-$C_9$ heteroarylene; and $A^1$ is a bond between A and the linker,
where G'' is

or $R^{3''}$ is

or a pharmaceutically acceptable salt thereof.

The BRD9 binding moiety may be, e.g., a group of Formula IV:

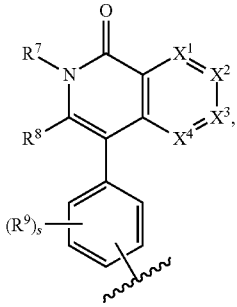

Formula IV where
R$^7$ is H, optionally substituted C$_1$-C$_6$ alkyl, optionally substituted C$_2$-C$_6$ alkenyl, optionally substituted C$_1$-C$_6$ heteroalkyl, or optionally substituted C$_3$-C$_{10}$ carbocyclyl;
R$^8$ is H, halogen, optionally substituted C$_1$-C$_6$ alkyl, optionally substituted C$_1$-C$_6$ heteroalkyl, optionally substituted C$_3$-C$_{10}$ carbocyclyl, or optionally substituted C$_6$-C$_{10}$ aryl;
s is 0, 1, 2, 3, or 4;
each R$^9$ is, independently, halogen, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxy, thiol, or optionally substituted amino;
X$^1$ is N or CR$^{10a}$;
X$^2$ is N or CR$^{10b}$;
X$^3$ is N or CR$^{10c}$;
X$^4$ is N or CR$^{10d}$; and
each of R$^{10a}$, R$^{10b}$, R$^{10c}$, and R$^{10d}$ is, independently, H, halogen, hydroxy, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxy, thiol, or optionally substituted amino,
or a pharmaceutically acceptable salt thereof.
The BRD9 binding moiety may be, e.g., a group of Formula V:

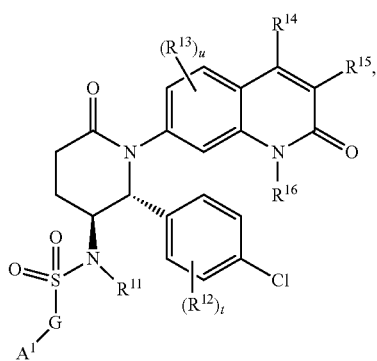

Formula V where
each R$^{11}$ and R$^{16}$ is, independently, H, optionally substituted C$_1$-C$_6$ alkyl, or optionally substituted C$_1$-C$_6$ heteroalkyl;
t is 0, 1, 2, 3, or 4;
each R$^{12}$ is, independently, halogen, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxy, thiol, or optionally substituted amino;
u is 0, 1, 2, 3, or 4;
each R$^{13}$ is, independently, halogen, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxy, thiol, or optionally substituted amino;
each R$^{14}$ and R$^{15}$ is, independently, selected form the group consisting of H, halogen, optionally substituted C$_1$-C$_6$ alkyl, or optionally substituted C$_6$-C$_{10}$ aryl;
A$^1$ is a bond between A and the linker; and
G is optionally substituted C$_1$-C$_6$ alkylene, optionally substituted C$_6$-C$_{10}$ arylene, or optionally substituted C$_3$-C$_6$ carbocyclylene;
or a pharmaceutically acceptable salt thereof.
The BRD9 binding moiety may be, e.g., a group of Formula VI:

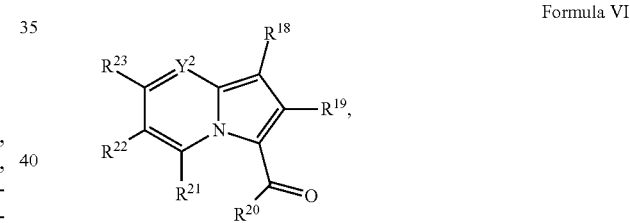

Formula VI where
Y$^2$ is CR$^{17}$ or N;
R$^{18}$ is a bond to the linker, optionally substituted C$_6$-C$_{10}$ aryl, or C$_2$-C$_9$ heteroaryl;
R$^{19}$ is H, halogen, optionally substituted C$_1$-C$_6$ alkyl, or optionally substituted C$_6$-C$_{10}$ aryl;
R$^{20}$ is H, optionally substituted C$_1$-C$_6$ alkyl, or optionally substituted C$_6$-C$_{10}$ aryl;
each R$^{17}$, R$^{21}$, and R$^{22}$ is, independently, H, halogen, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxy, thiol, or optionally substituted amino;
R$^{23}$ is H or —NR$^{24}$R$^{25}$; and
each of R$^{24}$ and R$^{25}$ is, independently, H, a bond to the linker, optionally substituted C$_1$-C$_6$ alkyl, or optionally substituted C$_1$-C$_6$ heteroalkyl, or R$^{24}$ and R$^{25}$ combine to form optionally substituted C$_2$-C$_9$ heterocyclyl,
where one of R$^{18}$, R$^{24}$, or R$^{25}$ is a bond to the linker,
or a pharmaceutically acceptable salt thereof.

The BRD9 binding moiety may be, e.g., a group of Formula VII:

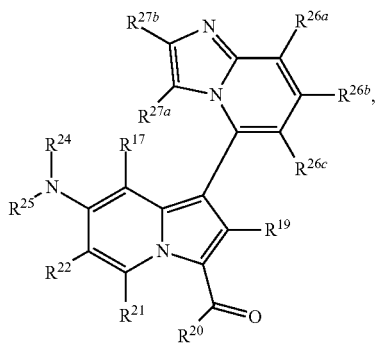

Formula VII where each $R^{26a}$, $R^{26b}$, and $R^{26c}$ is, independently, H, a bond to the linker, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

each $R^{27a}$ and $R^{27b}$ is, independently, H, halogen, optionally substituted $C_1$-$C_6$ alkyl, or optionally substituted $C_6$-$C_{10}$ aryl;

$R^{19}$ is H, halogen, optionally substituted $C_1$-$C_6$ alkyl, or optionally substituted $C_6$-$C_{10}$ aryl;

$R^{20}$ is H, optionally substituted $C_1$-$C_6$ alkyl, or optionally substituted $C_6$-$C_{10}$ aryl;

each $R^{17}$, $R^{21}$, and $R^{22}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and each of $R^{24}$ and $R^{25}$ is, independently, H, a bond to the linker, optionally substituted $C_1$-$C_6$ alkyl, or optionally substituted $C_1$-$C_6$ heteroalkyl, or $R^{24}$ and $R^{25}$ combine to form optionally substituted $C_2$-$C_9$ heterocyclyl, where one of $R^{26a}$, $R^{26b}$, $R^{26c}$, $R^{24}$ or $R^{25}$ is a bond to the linker, or a pharmaceutically acceptable salt thereof.

The BRD9 binding moiety may be, e.g., a group of Formula VIII:

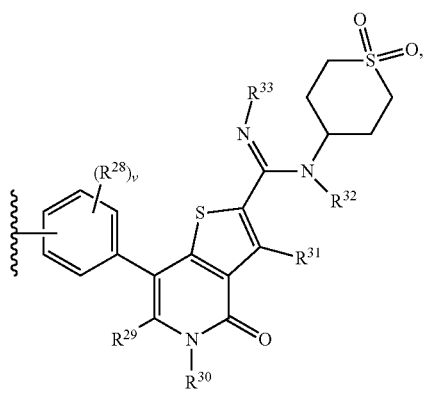

Formula VIII where v is 0, 1, 2, 3, or 4;

each $R^{28}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

$R^{29}$ is H, halogen, optionally substituted $C_1$-$C_6$ alkyl, or optionally substituted $C_6$-$C_{10}$ aryl;

$R^{31}$ is H, halogen, optionally substituted $C_1$-$C_6$ alkyl, or optionally substituted $C_6$-$C_{10}$ aryl; and each $R^{30}$, $R^{32}$, and $R^{33}$ is, independently, H, optionally substituted $C_1$-$C_6$ alkyl, or optionally substituted $C_1$-$C_6$ heteroalkyl, or a pharmaceutically acceptable salt thereof.

The BRD9 binding moiety may be, e.g., a group of Formula IX:

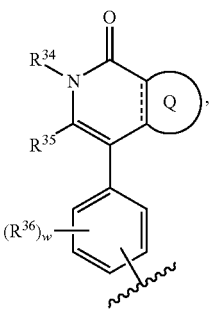

Formula IX where

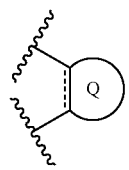

is

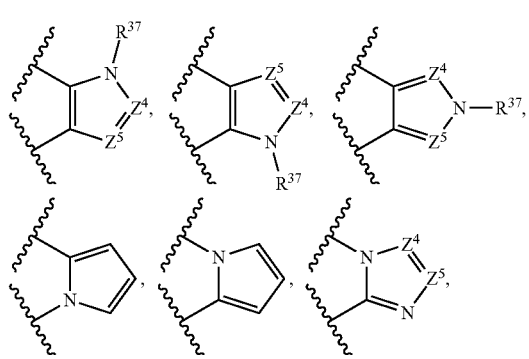

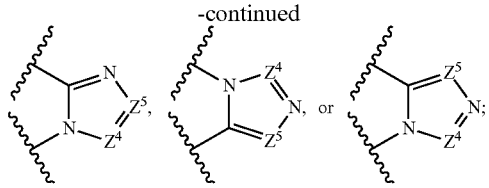

$Z^4$ is N or $CR^{38}$;

$Z^5$ is N or $CR^{39}$;

$R^{34}$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl;

$R^{35}$ is H, halogen, optionally substituted $C_1$-$C_6$ alkyl, optionally substituted $C_1$-$C_6$ heteroalkyl, optionally substituted $C_3$-$C_6$ carbocyclyl, or optionally substituted $C_6$-$C_{10}$ aryl;

$R^{37}$ is H, optionally substituted $C_1$-$C_6$ alkyl, or optionally substituted $C_1$-$C_6$ heteroalkyl;

$R^{38}$ is H, halogen, optionally substituted $C_1$-$C_6$ alkyl, or optionally substituted $C_6$-$C_{10}$ aryl;

$R^{39}$ is H, halogen, optionally substituted $C_1$-$C_6$ alkyl, or optionally substituted $C_6$-$C_{10}$ aryl;

w is 0, 1, 2, 3, or 4; and each $R^{36}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

The BRD9 binding moiety may be, e.g., a group of the following structure:

X2

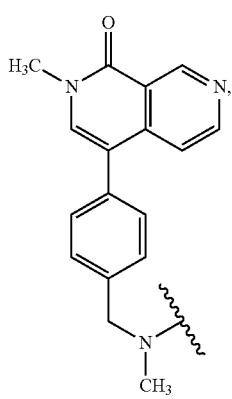

X3

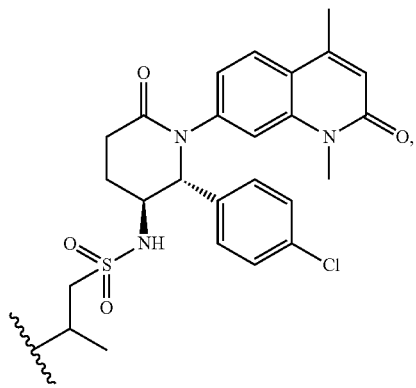

X4

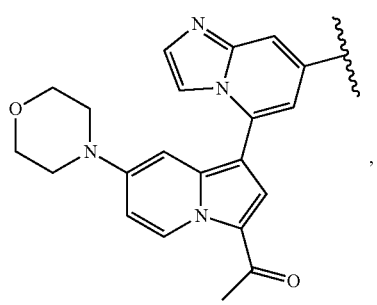

X5

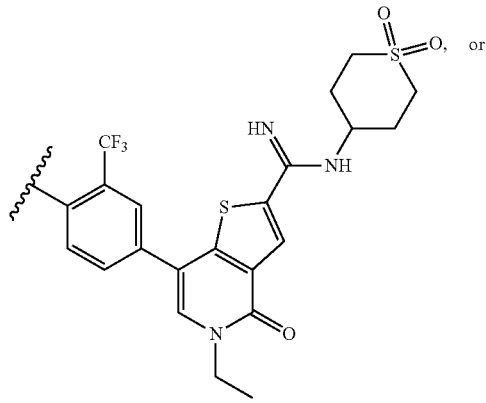

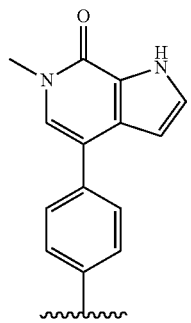

Linkers

A linker may be, e.g., as found in the BRD9 inhibitor of Formula II:

A-L-B      Formula II, where

A is a BRD9 binding moiety;

B is a degradation moiety; and

L has the structure of Formula II:

$A^1$-$(E^1)$-$(F^1)$—$(C^3)_m$-$(E^3)_n$—$(F^2)_{o1}$—$(F^3)_{o2}$-$(E^2)_p$-$A^2$,    Formula IIA where $A^1$ is a bond between the linker and A;

$A^2$ is a bond between B and the linker;

each of m, n, o1, o2, and p is, independently, 0 or 1;

each of $E^1$ and $E^2$ is, independently, O, S, $NR^N$, optionally substituted $C_1$-10 alkylene, optionally substituted $C_{2-10}$ alkenylene, optionally substituted $C_{2-10}$ alkynylene, optionally substituted $C_2$-$C_{10}$ polyethylene glycol, or optionally substituted $C_{1-10}$ heteroalkylene;

$E^3$ is optionally substituted $C_1$-$C_6$ alkylene, optionally substituted $C_1$-$C_6$ heteroalkylene, O, S, or $NR^N$;

each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;

$C^3$ is carbonyl, thiocarbonyl, sulphonyl, or phosphoryl; and each of $F^1$, $F^2$, and $F^3$ is, independently, optionally substituted $C_3$-$C_{10}$ carbocyclylene, optionally substituted $C_{2-10}$ heterocyclylene, optionally substituted $C_6$-$C_{10}$ arylene, or optionally substituted $C_2$-$C_9$ heteroarylene, or a pharmaceutically acceptable salt thereof.

In some embodiments, the linker has the structure of Formula IIA-a:

$A^1$-($E^1$)-($F^1$)—($C^3$)$_m$-($E^2$)$_p$-$A^2$.   Formula IIA-a In some embodiments, the linker has the structure of Formula IIA-b:

$A^1$-($E^1$)-($F^1$)-($E^2$)$_p$-$A^2$.   Formula IIA-b

In some embodiments, the linker has the structure of Formula IIA-c:

$A^1$-($E^1$)-($F^1$)-$A^2$.   Formula IIA-c

In some embodiments, the linker has the structure of Formula IIA-d:

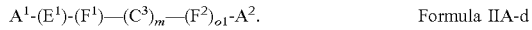
$A^1$-($E^1$)-($F^1$)—($C^3$)$_m$—($F^2$)$_{o1}$-$A^2$.   Formula IIA-d In some embodiments, the linker has the structure of Formula IIA-e:

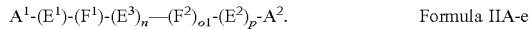
$A^1$-($E^1$)-($F^1$)-($E^3$)$_n$—($F^2$)$_{o1}$-($E^2$)$_p$-$A^2$.   Formula IIA-e In some embodiments, the linker has the structure of Formula IIA-f:

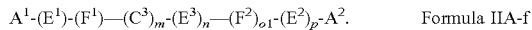
$A^1$-($E^1$)-($F^1$)—($C^3$)$_m$-($E^3$)$_n$—($F^2$)$_{o1}$-($E^2$)$_p$-$A^2$.   Formula IIA-f In some embodiments, the linker has the structure of Formula IIA-g:

$A^1$-($E^1$)-($F^1$)-($E^3$)$_n$—($F^2$)$_{o1}$-A,   Formula IIA-g

Pharmaceutical Uses

The compounds described herein are useful in the methods of the invention and, while not bound by theory, are believed to exert their desirable effects through their ability to modulate the level, status, and/or activity of a BAF complex, e.g., by inhibiting the activity or level of the BRD9 protein in a cell within the BAF complex in a mammal.

An aspect of the present invention relates to methods of treating disorders related to BRD9 such as cancer in a subject in need thereof. In some embodiments, the compound is administered in an amount and for a time effective to result in one of (or more, e.g., two or more, three or more, four or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of a subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound described herein. An increase in average survival time of a population may also be measured, for example, by calculating for a population the average length of survival following completion of a first round of treatment with a pharmaceutically acceptable salt of a compound described herein.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of a compound described herein. A decrease in the mortality rate of a population may also be measured, for example, by calculating for a population the average number of disease-related deaths per unit time following completion of a first round of treatment with a pharmaceutically acceptable salt of a compound described herein.

Combination Therapies

A method of the invention can be used alone or in combination with an additional therapeutic agent, e.g., other agents that treat cancer or symptoms associated therewith, or in combination with other types of therapies to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodophyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroids, progestins, estrogens, antiestrogen, androgens, antiandrogen, and gonadotropin-releasing hormone analog. Also included is 5-fluorouracil (5-FU), leucovorin (LV), irinotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredepa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, *Chem. Intl. Ed Engl.* 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE®, cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., *Proc. Am. Soc. Clin. Oncol.* 18:233a (1999), and Douillard et al., *Lancet* 355(9209):1041-1047 (2000).

In some embodiments, the second therapeutic agent is a DNA damaging agent (e.g., a platinum-based antineoplastic agent, topoisomerase inhibitors, PARP inhibitors, alkylating antineoplastic agents, and ionizing radiation).

Examples of platinum-based antineoplastic agent that may be used as a second therapeutic agent in the compositions and methods of the invention are cisplatin, carboplatin, oxaliplatin, dicycloplatin, eptaplatin, lobaplatin, miriplatin, nedaplatin, triplatin tetranitrate, phenanthrilplatin, picoplatin, and satraplatin. In some embodiments, the second therapeutic agent is cisplatin and the treated cancer is a testicular cancer, ovarian cancer, or a bladder cancer (e.g., advanced bladder cancer). In some embodiments, the second therapeutic agent is carboplatin and the treated cancer is an ovarian cancer, lung cancer, head and neck cancer, brain cancer, or neuroblastoma. In some embodiments, the second therapeutic agent is oxaliplatin and the treated cancer is a colorectal cancer. In some embodiments, the second therapeutic agent is dicycloplatin and the treated cancer is a non-small cell lung cancer or prostate cancer. In some embodiments, the second therapeutic agent is eptaplatin and the treated cancer is a gastric cancer. In some embodiments, the second therapeutic agent is lobaplatin and the treated cancer is a breast cancer. In some embodiments, the second therapeutic agent is miriplatin and the treated cancer is a hepatocellular carcinoma. In some embodiments, the second therapeutic agent is nedaplatin and the treated cancer is a nasopharyngeal carcinoma, esophageal cancer, squamous cell carcinoma, or cervical cancer. In some embodiments, the second therapeutic agent is triplatin tetranitrate and the treated cancer is a lung cancer (e.g., small cell lung cancer) or pancreatic cancer. In some embodiments, the second therapeutic agent is picoplatin and the treated cancer is a lung cancer (e.g., small cell lung cancer), prostate cancer, bladder cancer, or colorectal cancer. In some embodiments, the second therapeutic agent is satraplatin and the treated cancer is a prostate cancer, breast cancer, or lung cancer.

Examples of topoisomerase inhibitors that may be used as a second therapeutic agent in the compositions and methods of the invention are etoposide, teniposide, doxorubicin, daunorubicin, mitoxantrone, amsacrine, ellipticine, irinotecan, topotecan, camptothecin, and diflomotecan. In some embodiments, the second therapeutic agent is etoposide and the treated cancer is a lung cancer (e.g., small cell lung cancer) or testicular cancer. In some embodiments, the second therapeutic agent is teniposide and the treated cancer is an acute lymphoblastic leukemia (e.g., childhood acute lymphoblastic leukemia). In some embodiments, the second therapeutic agent is doxorubicin and the treated cancer is an acute lymphoblastic leukemia, acute myeloblastic leukemia, Hodgkin lymphoma, Non-Hodgkin lymphoma, breast cancer, Wilm's tumor, neuroblastoma, soft tissue sarcoma, bone sarcomas, ovarian carcinoma, transitional cell bladder carcinoma, thyroid carcinoma, gastric carcinoma, or bronchogenic carcinoma. In some embodiments, the second therapeutic agent is daunorubicin and the treated cancer is an acute lymphoblastic leukemia or acute myeloid leukemia. In some embodiments, the second therapeutic agent is mitoxantrone and the treated cancer is a prostate cancer or acute nonlymphocytic leukemia. In some embodiments, the second therapeutic agent is amsacrine and the treated cancer is a leukemia (e.g., acute adult leukemia). In some embodiments, the second therapeutic agent is irinotecan and the treated cancer is a colorectal cancer. In some embodiments, the second therapeutic agent is topotecan and the treated cancer is a lung cancer (e.g., small cell lung cancer). In some embodiments, the second therapeutic agent is diflomotecan and the treated cancer is a lung cancer (e.g., small cell lung cancer).

Examples of alkylating antineoplastic agents that may be used as a second therapeutic agent in the compositions and methods of the invention are cyclophosphamide, uramustine, melphalan, chlorambucil, ifosfamide, bendamustine, carmustine, lomustine, chlorozotocin, fotemustine, nimustine, ranimustine, busulfan, improsulfan, piposulfan, chlornaphazine, cholophosphamide, estramustine, mechlorethamine, mechlorethamine oxide hydrochloride, novembichin, phenesterine, prednimustine, trofosfamide, procarbazine, altretamine, dacarbazine, mitozolomide, and temozolomide. In some embodiments, the second therapeutic agent is cyclophosphamide and the treated cancer is a Non-Hodgkins lymphoma. In some embodiments, the second therapeutic agent is melphalan and the treated cancer is a multiple myeloma, ovarian cancer, or melanoma. In some embodiments, the second therapeutic agent is chlorambucil and the treated cancer is a chronic lymphatic leukemia, malignant lymphoma (e.g., lymphosarcoma, giant follicular lymphoma, or Hodgkin's lymphoma). In some embodiments, the second therapeutic agent is ifosfamide and the treated cancer is a testicular cancer. In some embodiments, the second therapeutic agent is bendamustine and the treated cancer is a chronic lymphocytic leukemia or non-Hodgkin lymphoma. In some embodiments, the second therapeutic agent is carmustine and the treated cancer is a brain cancer (e.g., glioblastoma, brainstem glioma, medulloblastoma, astrocytoma, ependymoma, or a metastatic brain tumor), multiple myeloma, Hodgkin's disease, or Non-Hodgkin's lymphoma. In some embodiments, the second therapeutic agent is lomustine and the treated cancer is a brain cancer or Hodgkin's lymphoma. In some embodiments, the second therapeutic agent is fotemustine and the treated cancer is a melanoma. In some embodiments, the second therapeutic agent is nimustine and the treated cancer is a brain cancer. In some embodiments, the second therapeutic agent is ranimustine and the treated cancer is a chronic myelogenous leukemia or polycythemia vera. In some embodiments, the second therapeutic agent is busulfan and the treated cancer is a chronic myelogenous leukemia. In some embodiments, the second therapeutic agent is improsulfan and the treated cancer is a sarcoma. In some embodiments, the second therapeutic agent is estramustine and the treated cancer is a prostate cancer (e.g., prostate carcinoma). In some embodiments, the second therapeutic agent is mechlorethamine and the treated cancer is a cutaneous T-cell lymphoma. In some embodiments, the second therapeutic agent is trofosfamide and the treated cancer is a sarcoma (e.g., soft tissue sarcoma). In some embodiments, the second therapeutic agent is procarbazine and the treated cancer is a Hodgkin's disease. In some embodiments, the second therapeutic agent is altretamine and the treated cancer is an ovarian cancer. In some embodiments, the second therapeutic agent is dacarbazine and the treated cancer is a melanoma, Hodgkin's lymphoma, or sarcoma. In some embodiments, the second therapeutic agent is temozolomide and the treated cancer is a brain cancer (e.g., astrocytoma or glioblastoma) or lung cancer (e.g., small cell lung cancer).

Examples of PARP inhibitors that may be used as a second therapeutic agent in the compositions and methods of the invention are niraparib, olaparib, rucaparib, talazoparib, veliparib, pamiparib, CK-102, or E7016. Advantageously, the compounds of the invention and a DNA damaging agent may act synergistically to treat cancer. In some embodiments, the second therapeutic agent is niraparib and the treated cancer is an ovarian cancer (e.g., BRCA mutated ovarian cancer), fallopian tube cancer (e.g., BRCA mutated fallopian tube cancer), or primary peritoneal cancer (e.g., BRCA mutated primary peritoneal cancer). In some embodiments, the second therapeutic agent is olaparib and the treated cancer is a lung cancer (e.g., small cell lung cancer), ovarian cancer (e.g., BRCA mutated ovarian cancer), breast cancer (e.g., BRCA mutated breast cancer), fallopian tube cancer (e.g., BRCA mutated fallopian tube cancer), primary peritoneal cancer (e.g., BRCA mutated primary peritoneal cancer), prostate cancer (e.g., castration-resistant prostate cancer), or pancreatic cancer (e.g., pancreatic adenocarcinoma). In some embodiments, the second therapeutic agent is rucaparib and the treated cancer is an ovarian cancer (e.g., BRCA mutated ovarian cancer), fallopian tube cancer (e.g., BRCA mutated fallopian tube cancer), or primary peritoneal cancer (e.g., BRCA mutated primary peritoneal cancer). In some embodiments, the second therapeutic agent is talazoparib and the treated cancer is a breast cancer (e.g., BRCA mutated breast cancer). In some embodiments, the second therapeutic agent is veliparib and the treated cancer is a lung cancer (e.g., non-small cell lung cancer), melanoma, breast cancer, ovarian cancer, prostate cancer, or brain cancer. In some embodiments, the second therapeutic agent is pamiparib and the treated cancer is an ovarian cancer. In some embodiments, the second therapeutic agent is CK-102 and the treated cancer is a lung cancer (e.g., non-small cell lung cancer). In some embodiments, the second therapeutic agent is E7016 and the treated cancer is a melanoma.

Without wishing to be bound by theory, the synergy between the compounds of the invention and DNA damaging agents may be attributed to the necessity of BRD9 for DNA repair; inhibition of BRD9 may sensitize cancer (e.g., cancer cell or cancer tissue) to DNA damaging agents.

In some embodiments, the second therapeutic agent is a JAK inhibitor (e.g., JAK1 inhibitor). Non-limiting examples of JAK inhibitors that may be used as a second therapeutic agent in the compositions and methods of the invention include tofacitinib, ruxolitinib, oclacitinib, baricitinib, peficitinib, fedratinib, upadacitinib, filgotinib, cerdulatinib, gandotinib, lestaurtinib, momelotinib, pacritinib, abrocitinib, solcitinib, itacitinib, or SHR0302. Without wishing to be bound by theory, the synergy between the compounds of the invention and JAK inhibitors may be inhibitor of SAGA complex to their combined effect of downregulating Foxp3+ Treg cells. In some embodiments, the second therapeutic agent is ruxolitinib and the treated cancer is a myeloproliferative neoplasm (e.g., polycythemia or myelofibrosis), ovarian cancer, breast cancer, pancreatic cancer. In some embodiments, the second therapeutic agent is fedratinib and the treated cancer is a myeloproliferative neoplasm (e.g., myelofibrosis). In some embodiments, the second therapeutic agent is cerdulatinib and the treated cancer is a lymphoma (e.g., peripheral T-cell lymphoma). In some embodiments, the second therapeutic agent is gandotinib and the treated cancer is a myeloproliferative neoplasm (e.g., polycythemia or myelofibrosis). In some embodiments, the second therapeutic agent is lestaurtinib and the treated cancer is a myeloproliferative neoplasm (e.g., polycythemia or myelofibrosis), leukemia (e.g., acute myeloid leukemia), pancreatic cancer, prostate cancer, or neuroblastoma. In some embodiments, the second therapeutic agent is momelotinib and the treated cancer is a myeloproliferative neoplasm (e.g., polycythemia or myelofibrosis) or pancreatic cancer (e.g., pancreatic ductal adenocarcinoma). In some embodiments, the second therapeutic agent is momelotinib and the treated cancer is a myeloproliferative neoplasm (e.g., polycythemia or myelofibrosis). In some embodiments, the second therapeutic agent is momelotinib and the treated cancer is a myeloproliferative neoplasm (e.g., polycythemia or myelofibrosis) or pancreatic cancer (e.g., pancreatic ductal adenocarcinoma).

In some embodiments, the second therapeutic agent is an inhibitor of SAGA complex or a component thereof. A SAGA complex inhibitor may be, e.g., an inhibitory antibody or small molecule inhibitor, of CCDC101, Tada2B, Tada3, Usp22, Tada1, Taf6I, Supt5, Supt20, or a combination thereof. Without wishing to be bound by theory, the synergy between the compounds of the invention and inhibitors of SAGA complex may be attributed to their combined effect of downregulating Foxp3+ Treg cells. In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOLIRIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The second agent may be a therapeutic agent which is a non-drug treatment. For example, the second therapeutic agent is radiation therapy, cryotherapy, hyperthermia, and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody or fusion a protein such as ipilimumab/YERVOY® or tremelimumab). In some embodiments, the inhibitor of checkpoint is an inhibitor (e.g., an inhibitory antibody or small molecule inhibitor) of PD-1 (e.g., nivolumab/OPDIVO®; pembrolizumab/KEYTRUDA®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the second therapeutic agent is ipilimumab and the treated cancer is a melanoma, kidney cancer, lung cancer (e.g., non-small cell lung cancer or small cell lung cancer), or prostate cancer. In some embodiments, the second therapeutic agent is tremelimumab and the treated cancer is a melanoma, mesothelioma, or lung cancer (e.g., non-small cell lung cancer). In some embodiments, the second therapeutic agent is nivolumab and the treated cancer is a melanoma, lung cancer (e.g., non-small cell lung cancer or small cell lung cancer), kidney cancer, Hodgkin lymphoma, head and neck cancer (e.g., squamous cell carcinoma of the head and neck), urothelial carcinoma, hepatocellular carcinoma, or colorectal cancer. In some embodiments, the second therapeutic agent is pembrolizumab and the treated cancer is a melanoma, lung cancer (e.g., non-small cell lung cancer or small cell lung cancer), Hodgkin lymphoma, head and neck cancer (e.g., squamous cell carcinoma of the head and neck), primary mediastinal large B-cell lymphoma, urothelial carcinoma, hepatocellular carcinoma, microsatellite instability-high cancer, gastric cancer, esophageal cancer, cervical cancer, Merkel cell carcinoma, kidney carcinoma, or endometrial carcinoma. In some embodiments, the second therapeutic agent is MPDL3280A and the treated cancer is a lung cancer (e.g., non-small cell lung cancer or small cell lung cancer), urothelial carcinoma, hepatocellular carcinoma, or breast cancer. In some embodiments, the second therapeutic agent is MEDI4736 and the treated cancer is a lung cancer (e.g., non-small cell lung cancer or small cell lung cancer) or urothelial carcinoma. In some embodiments, the second therapeutic agent is MSB0010718C and the treated cancer is a urothelial carcinoma. In some embodiments, the second therapeutic agent is MSB0010718C and the treated cancer is a melanoma, lung cancer (e.g., non-small cell lung cancer), colorectal cancer, kidney cancer, ovarian cancer, pancreatic cancer, gastric cancer, and breast cancer.

Advantageously, the compounds of the invention and a checkpoint inhibitor may act synergistically to treat cancer. Without wishing to be bound by theory, the synergy between the compounds of the invention and checkpoint inhibitors may be attributed to the checkpoint inhibitor efficacy enhancement associated with the BRD9 inhibition-induced downregulation of Foxp3+ Treg cells.

In some embodiments, the anti-cancer therapy is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The pharmaceutical compositions described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound described herein may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds described herein, and/or compositions including a compound described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds described herein may be administered initially in a suitable dosage that may be adjusted as required, depending on the clinical response. In general, satisfactory results may be obtained when the compounds described herein are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-100 mg/kg.

Kits

The invention also features kits including (a) a pharmaceutical composition including an agent that reduces the level and/or activity of BRD9 in a cell or subject described herein, and (b) a package insert with instructions to perform any of the methods described herein. In some embodiments, the kit includes (a) a pharmaceutical composition including an agent that reduces the level and/or activity of BRD9 in a cell or subject described herein, (b) an additional therapeutic agent (e.g., an anti-cancer agent), and (c) a package insert with instructions to perform any of the methods described herein.

EXAMPLES

Throughout the Examples, compound numbers

TABLE 1

Compounds

| Compound No. | Structure |
| --- | --- |
| D1 | 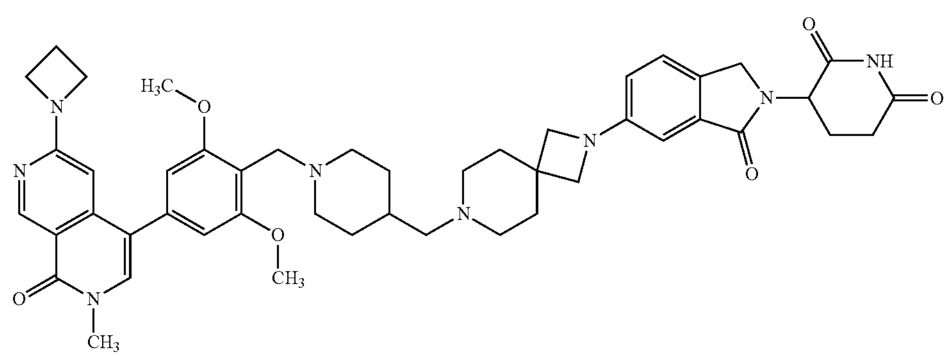 [SMILES: COc1cc(-c2cn(C)c(=O)c3cnc(N4CCC4)cc23)cc(OC)c1CN1CCC(CN2CCC3(CC2)CN(c2ccc4c(c2)C(=O)N(C2CCC(=O)NC2=O)C4)C3)CC1] |

TABLE 1-continued
Compounds
| Compound No. | Structure |
|---|---|
| S-D1 | 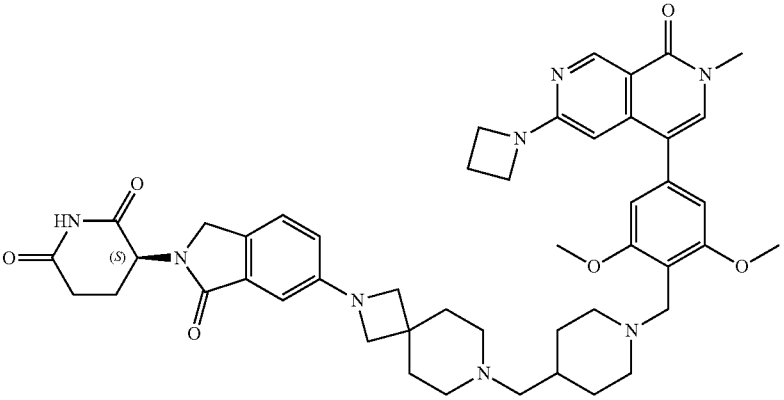 |
| R-D1 | 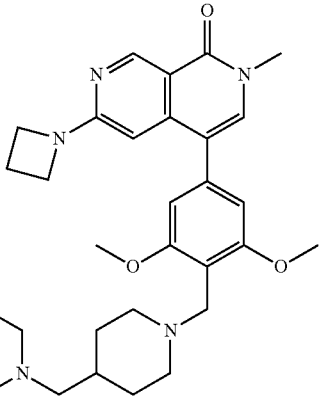 |
| D2 | 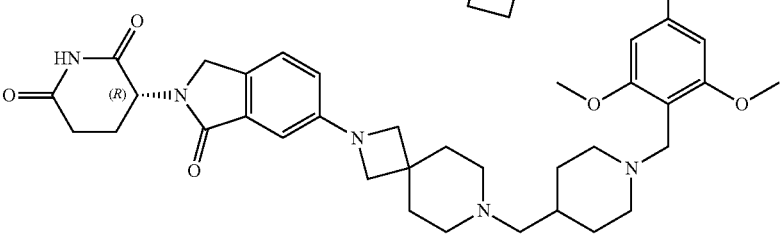 |

Example 1—BRD9 Degrader Depletes BRD9 Protein

The following example demonstrates the depletion of the BRD9 protein in synovial sarcoma cells treated with a BRD9 degrader.

Procedure: Cells were treated with DMSO or the BRD9 degrader, Compound 1 (also known as dBRD9, see Remillard et al, Angew. Chem. Int. Ed. Engl. 56(21):5738-5743 (2017); see structure of compound 1 below), for indicated doses and timepoints.

Figure 4:
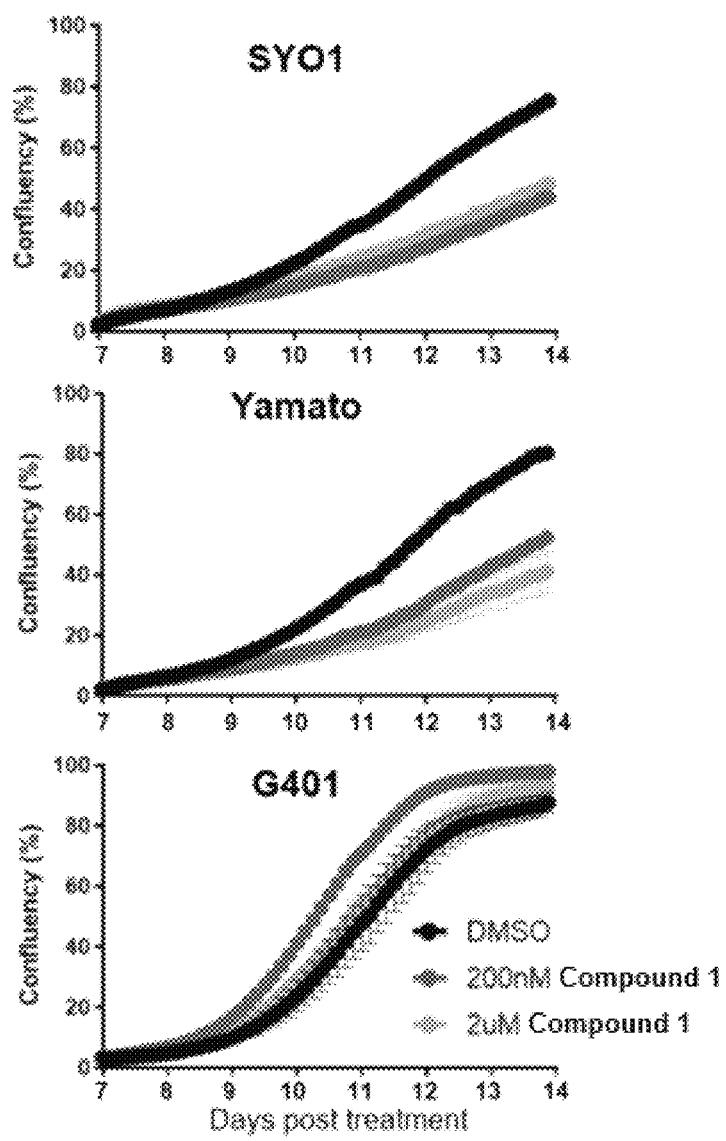
FIG. 4 is an image illustrating sustained suppression of BRD9 levels in synovial sarcoma cell lines (SYO1 and Yamato) in the presence of a BRD9 degrader over 7 days compared to the levels in cells treated with CRISPR reagents.

Procedures:
Cells were treated with DMSO or the BRD9 degrader, Compound 1, at indicated concentrations, and proliferation was monitored from day 7 to day 14 by measuring confluency overtime using an IncuCyte live cell analysis system (FIG. 4). Growth medium and compounds were refreshed every 3-4 days.

Cells were seeded into 12-well plates and treated with DMSO, 1 μM BRD9 inhibitor, Compound 2 (also known as BI-7273, see Martin et al, J Med Chem. 59(10):4462-4475 (2016); see structure of compound 2 below), or 1 μM BRD9 degrader, Compound 1.

(Compound 1)

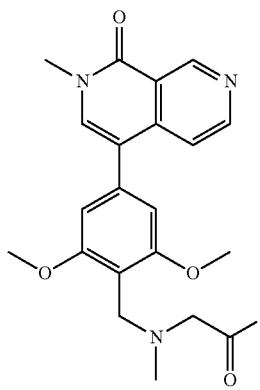

dBRD9

Whole cell extracts were fractionated by SDS-PAGE and transferred to a polyvinylidene difluoride membrane using a transfer apparatus according to the manufacturer's protocols (Bio-Rad). After incubation with 5% nonfat milk in TBST (10 mM Tris, pH 8.0, 150 mM NaCl, 0.5% Tween 20) for 60 min, the membrane was incubated with antibodies against BRD9 (1:1,000, Bethyl laboratory A303-781A), GAPDH (1:5,000, Cell Signaling Technology), and/or MBP (1:1,000, BioRad) overnight at 4° C. Membranes were washed three times for 10 min and incubated with anti-mouse or anti-rabbit antibodies conjugated with either horseradish peroxidase (HRP, FIGS. 2-3) or IRDye (FIG. 4, 1:20,000, LI-COR) for at least 1 h. Blots were washed with TBST three times and developed with either the ECL system according to the manufacturer's protocols (FIGS. 2-3) or scanned on an Odyssey CLx Imaging system (FIG. 4).

Figure 2:
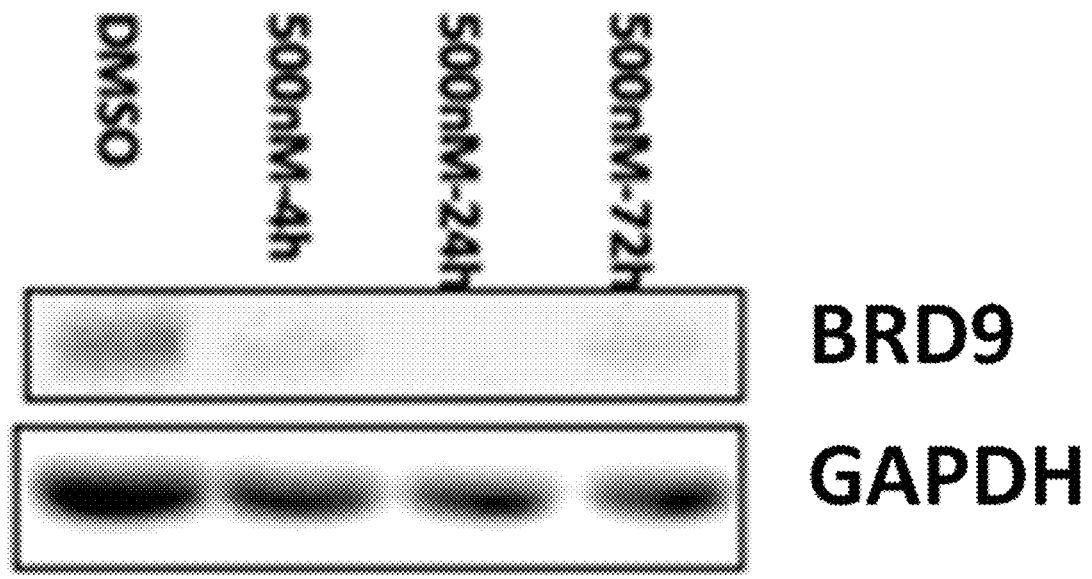
FIG. 2 is an image illustrating sustained suppression of BRD9 levels in a synovial sarcoma cell line (SYO1) in the presence of a BRD9 degrader over 72 hours.
Figure 3:
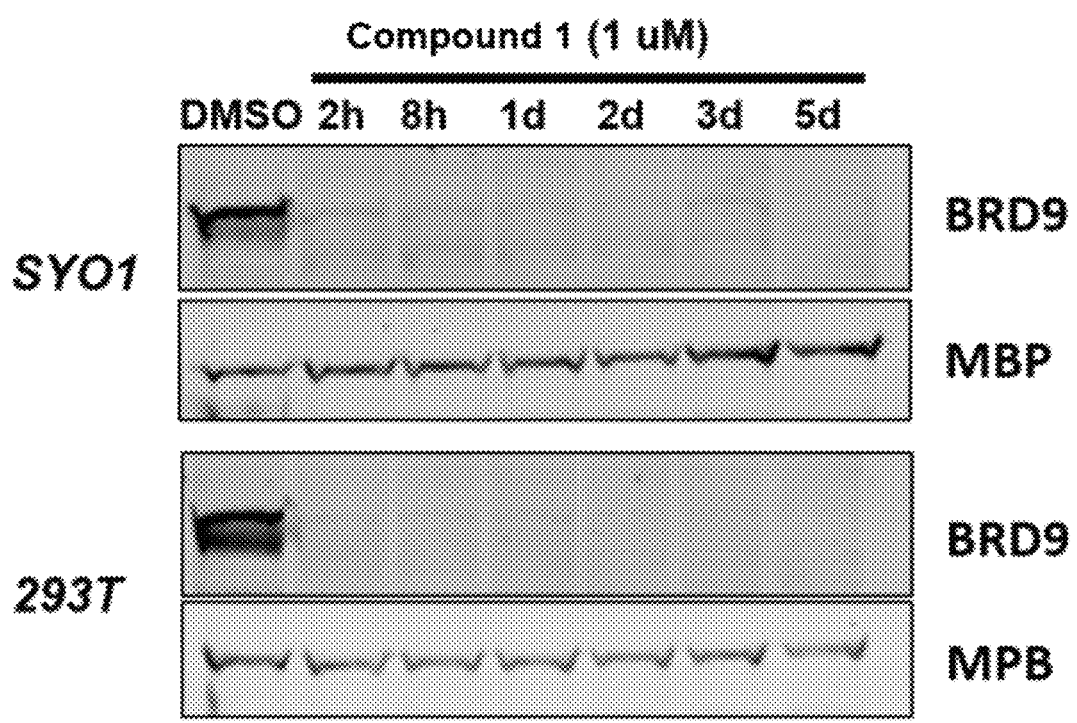
FIG. 3 is an image illustrating sustained suppression of BRD9 levels in two cell lines (293T and SYO1) in the presence of a BRD9 degrader over 5 days.

Results: Treatment of SYO1 synovial sarcoma cells with the BRD9 degrader Compound 1 results in dose dependent (FIG. 1) and time dependent (FIG. 2) depletion of BRD9 in the cells. Further, as shown in FIG. 3, the depletion of BRD9 by Compound 1 is replicated in a non-synovial sarcoma cell line (293T) and may be sustained for at least 5 days.

Example 2—Inhibition of Growth of Synovial Cell Lines by BRD9 Inhibitors and BRD9 Degraders The following example demonstrates that BRD9 degraders and inhibitors selectively inhibit growth of synovial sarcoma cells.

(Compound 2)

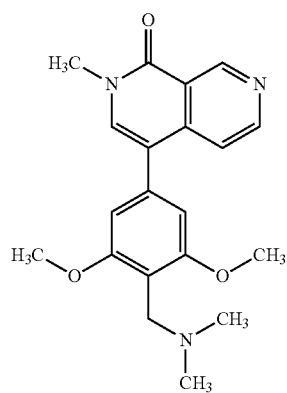

BI-7273

Figure 5:
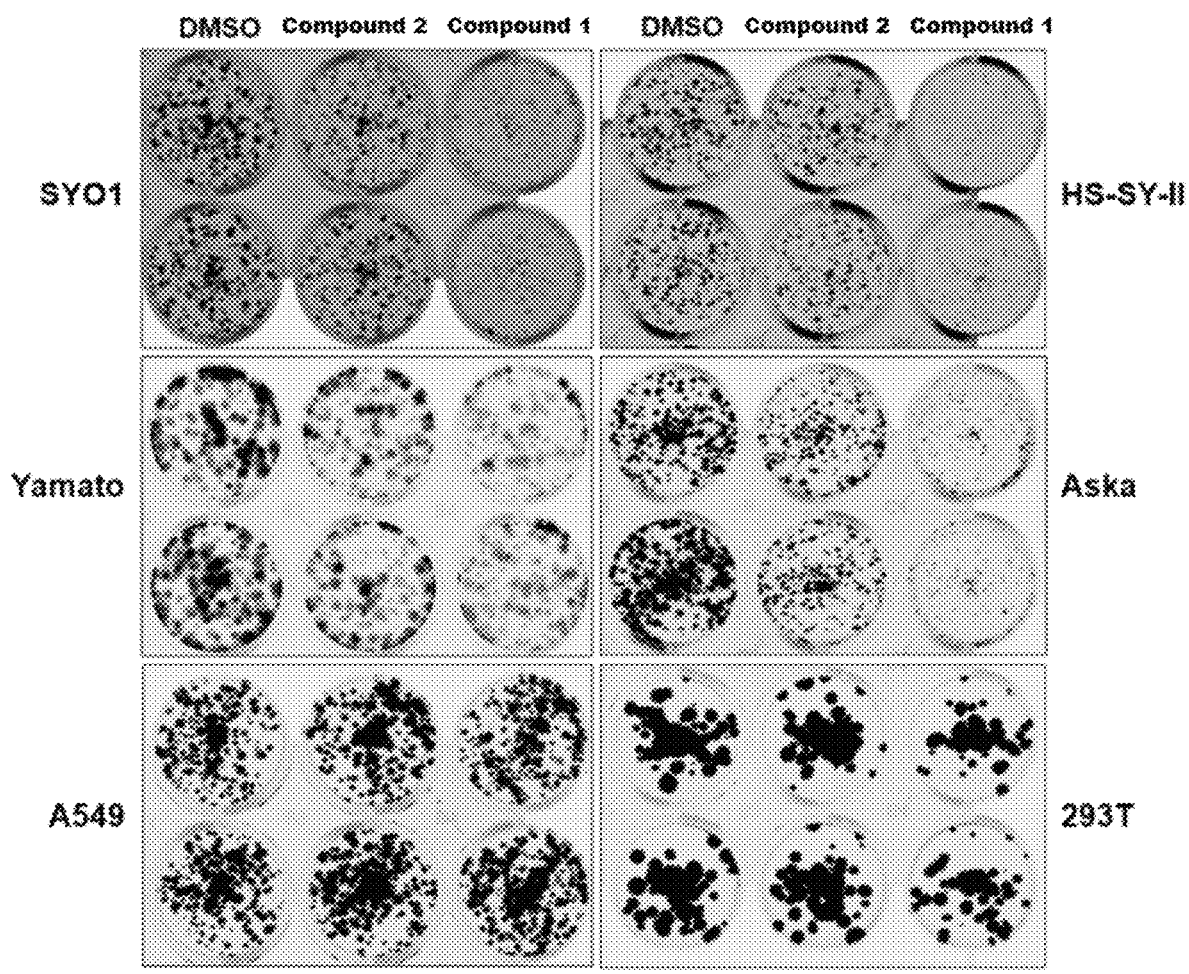
FIG. 5 is an image illustrating the effect on cell growth of six cell lines (SYO1, Yamato, A549, HS-SY-II, ASKA, and 293T) in the presence of a BRD9 degrader and a BRD9 inhibitor.

The number of cells was optimized for each cell line. Growth medium and compounds were refreshed every 3-5 days. SYO1, Yamato, A549, 293T and HS-SY-II cells were fixed and stained at day 11. ASKA cells were fixed and stained at day 23. Staining was done by incubation with crystal violet solution (0.5 g Crystal Violet, 27 ml 37% Formaldehyde, 100 mL 10×PBS, 10 mL Methanol, 863 dH20 to 1 L) for 30 min followed by 3× washes with water and drying the plates for at least 24 h at room temperature. Subsequently plates were scanned on an Odyssey CLx Imaging system (FIG. 5).

Cells were seeded into 96-well ultra-low cluster plate (Costar, #7007) in 200 μL complete media and treated at day 2 with DMSO, Staurosporin, or BRD9 degrader, Compound 1, at indicated doses (FIG. 2C). Media and compounds were changed every 5 d and cell colonies were imaged at day 14.

Figure 6:
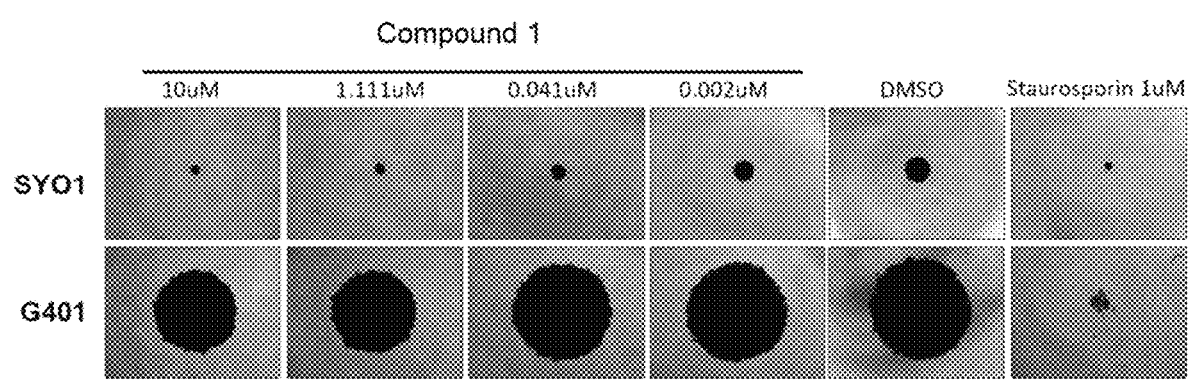
FIG. 6 is an image illustrating the effect on cell growth of two cell lines (SYO1 and G401) in the presence of a BRD9 degrader.

Results: As shown in FIGS. 4, 5, and 6, treatment of synovial sarcoma cell lines (SYO1, Yamato, HS-SY-II, and ASKA) with a BRD9 inhibitor, Compound 2, or a BRD9 degrader, Compound 1, results in inhibition of the growth of the cells, but does not result in inhibition of the growth of non-synovial control cancer cell lines (293T, A549, G401).

Example 3—Selective Inhibition of Growth of Synovial Cell Lines by BRD9 Degraders and BRD9 Binders The following example demonstrates that BRD9 degraders and binders selectively inhibit growth of synovial sarcoma cells.

Procedure: Cells were seeded into 6-well or 12-well plates and were treated daily with a BRD9 degrader (Compound 1), a bromo-domain BRD9 binder (Compound 2), E3 ligase binder (lenalidomide), DMSO, or staurosporin (positive control for cell killing), at indicated concentrations. The number of cells was optimized for each cell line. Growth media was refreshed every 5 days. By day 14, medium was removed, cells were washed with PBS, and stained using 500 μL of 0.005% (w/v) crystal violet solution in 25% (v/v) methanol for at least 1 hour at room temperature. Subsequently plates were scanned on an Odyssey CLx Imaging system.

Figure 7:
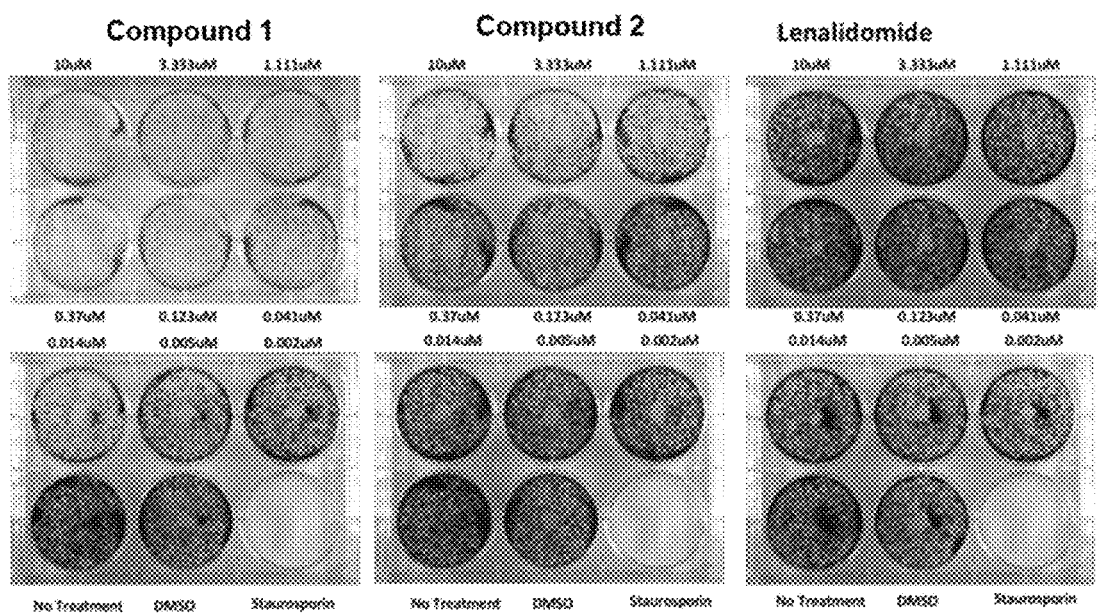
FIG. 7 is an image illustrating the effect on cell growth of three synovial sarcoma cell lines (SYO1, HS-SY-II, and ASKA) in the presence of a BRD9 degrader, BRD9 binder and E3 ligase binder.
Figure 7:
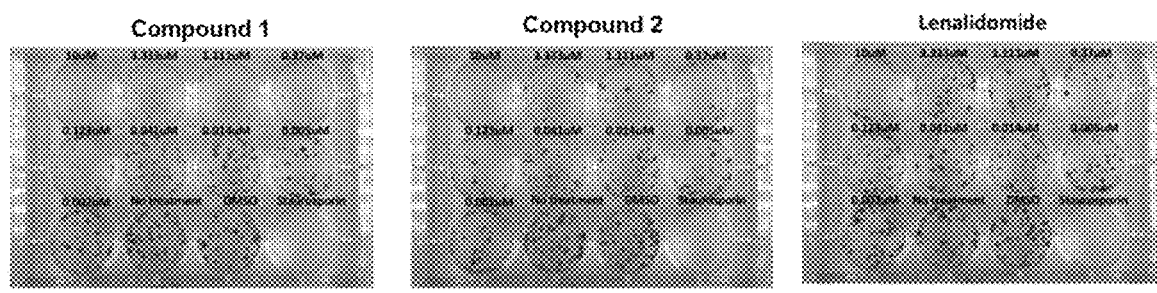
Figure 7:
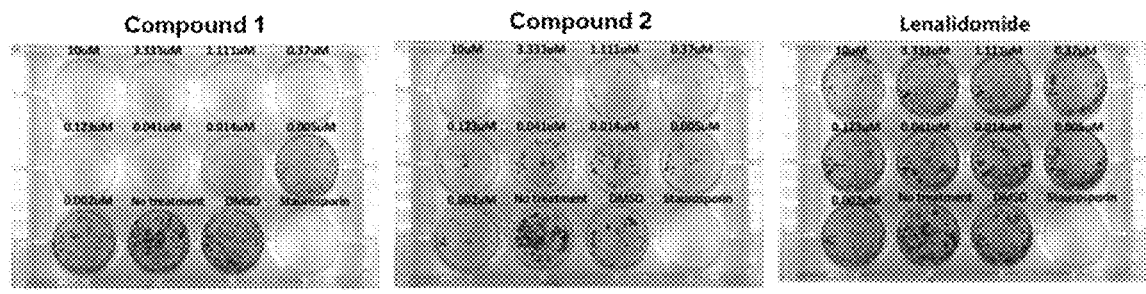
Figure 8:
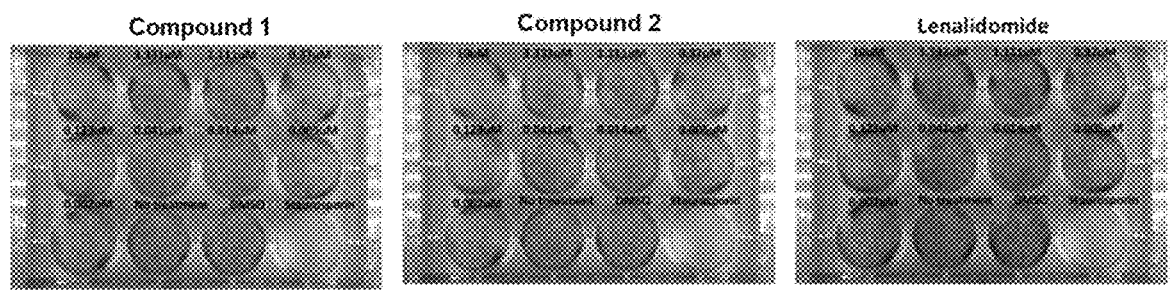
FIG. 8 is an image illustrating the effect on cell growth of three non-synovial sarcoma cell lines (RD, HCT116, and Calu6) in the presence of a BRD9 degrader, BRD9 binder and E3 ligase binder.
Figure 8:
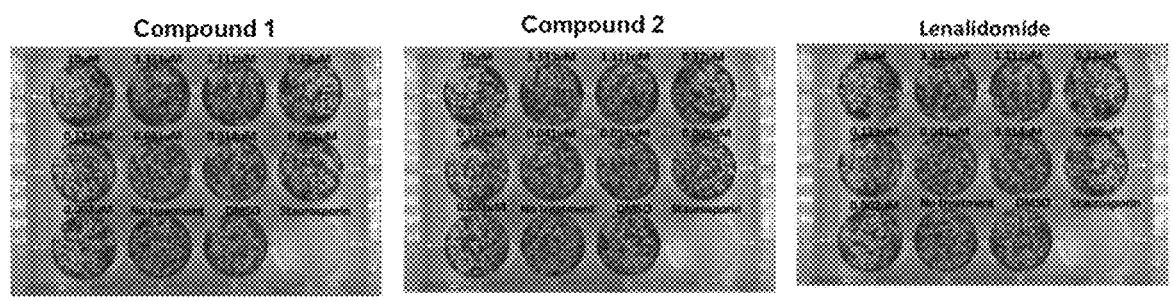
Figure 8:
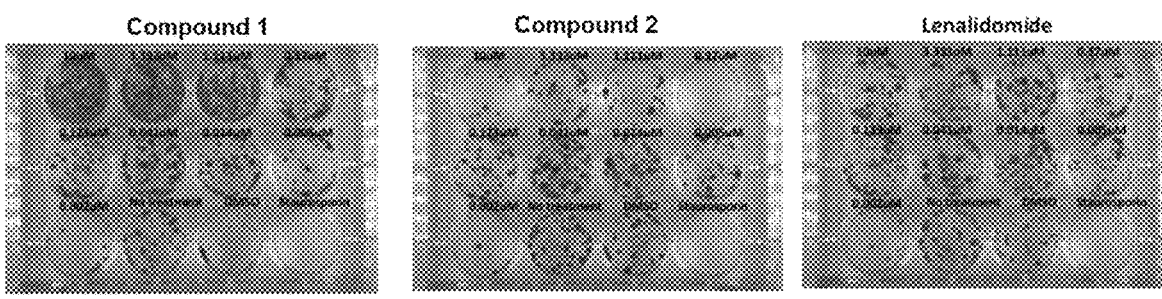
Figure 9:
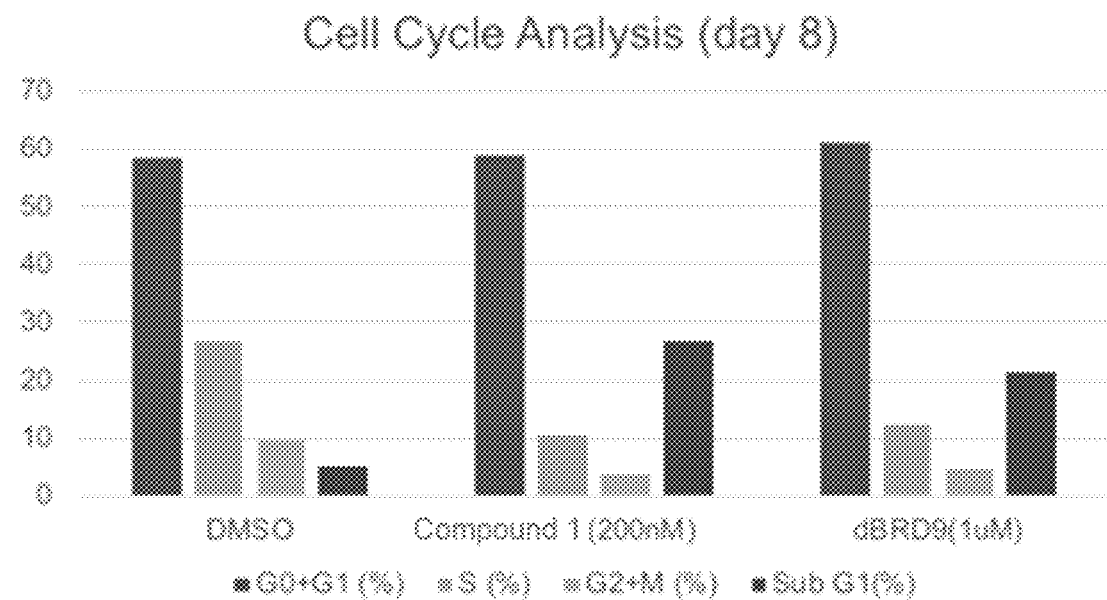
FIG. 9 is a graph illustrating the percentage of SYO1 in various cell cycle phases following treatment with DMSO, Compound 1 at 200 nM, or Compound 1 at 1 µM for 8 or 13 days.
Figure 9:
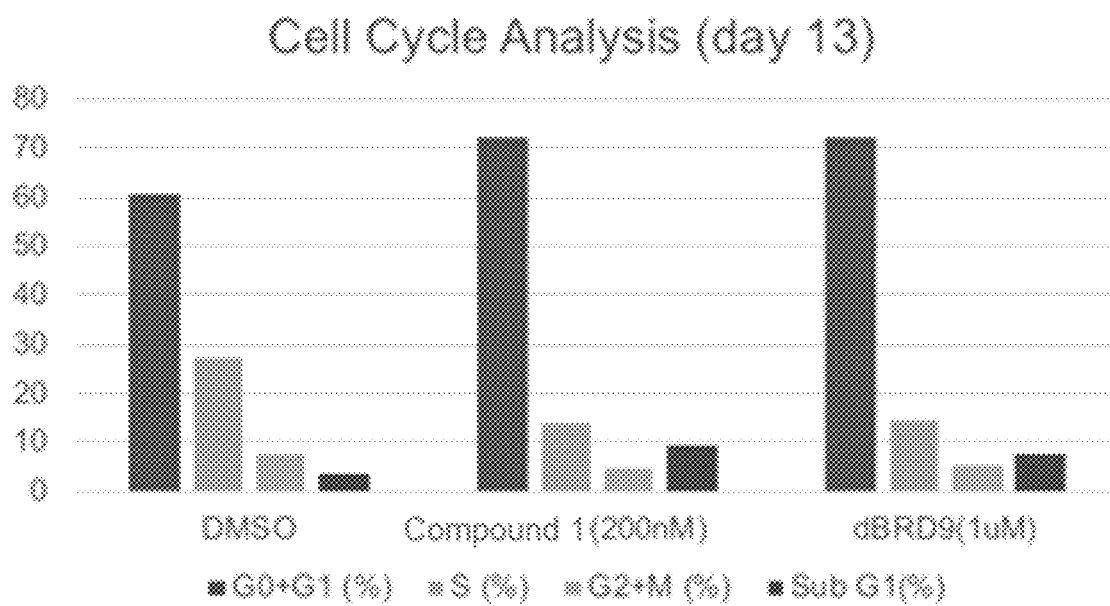
Figure 10:
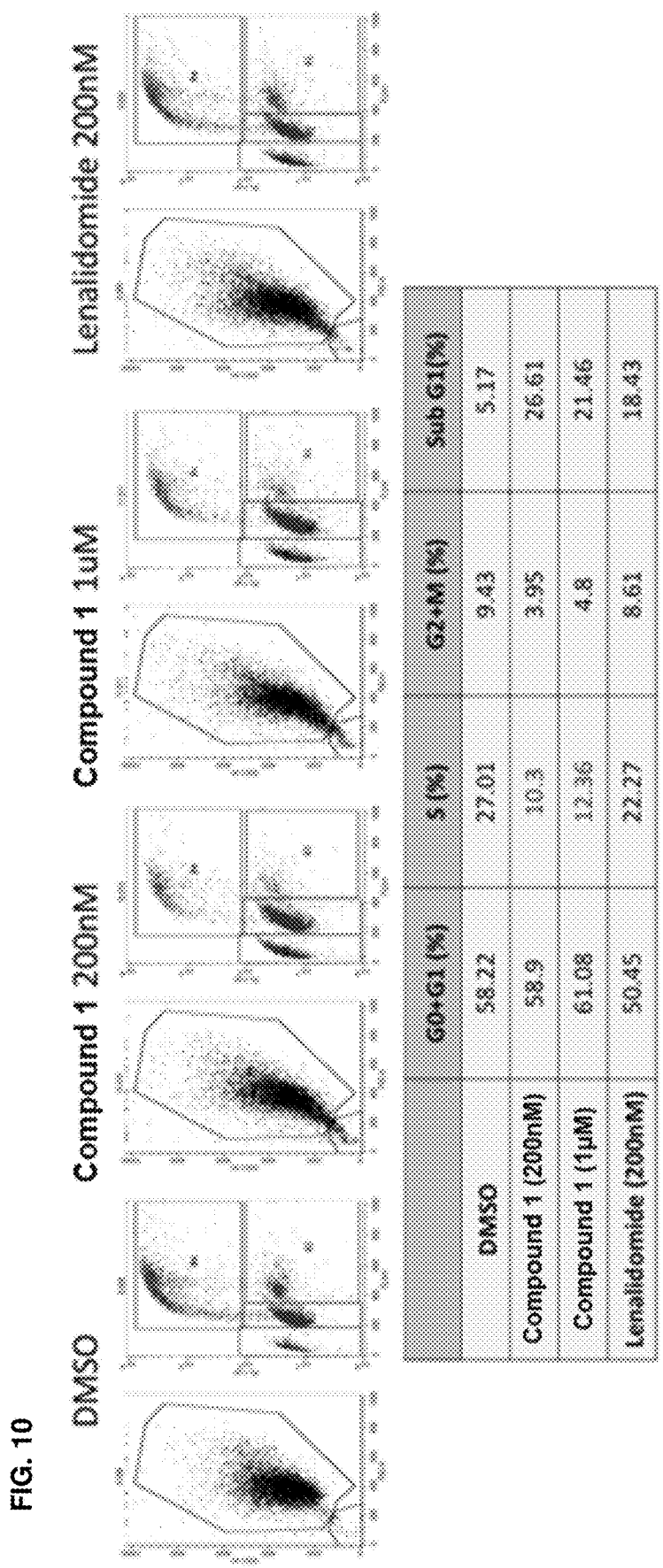
FIG. 10 is a series of contour plots illustrating the percentage of SYO1 cells in various cell cycle phases following treatment with DMSO, Compound 1 at 200 nM, Compound 1 at 1 µM, or lenalidomide at 200 nM for 8 days. Numerical values corresponding to each contour plot are found in the table below.
Figure 11:
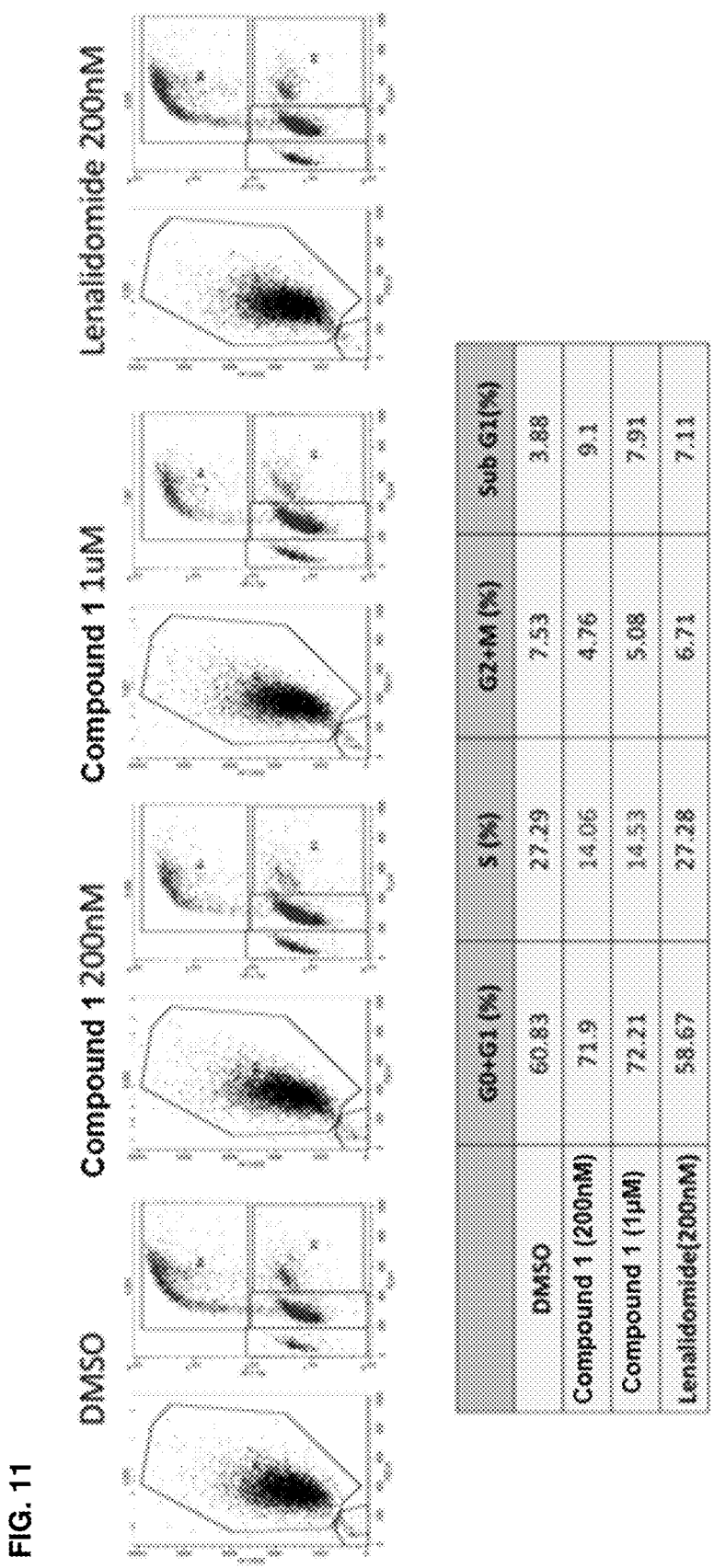
FIG. 11 is a series of contour plots illustrating the percentage of SYO1 cells in various cell cycle phases following treatment with DMSO, Compound 1 at 200 nM, Compound 1 at 1 µM, or lenalidomide at 200 nM for 13 days. Numerical values corresponding to each contour plot are found in the table below.
Figure 12:
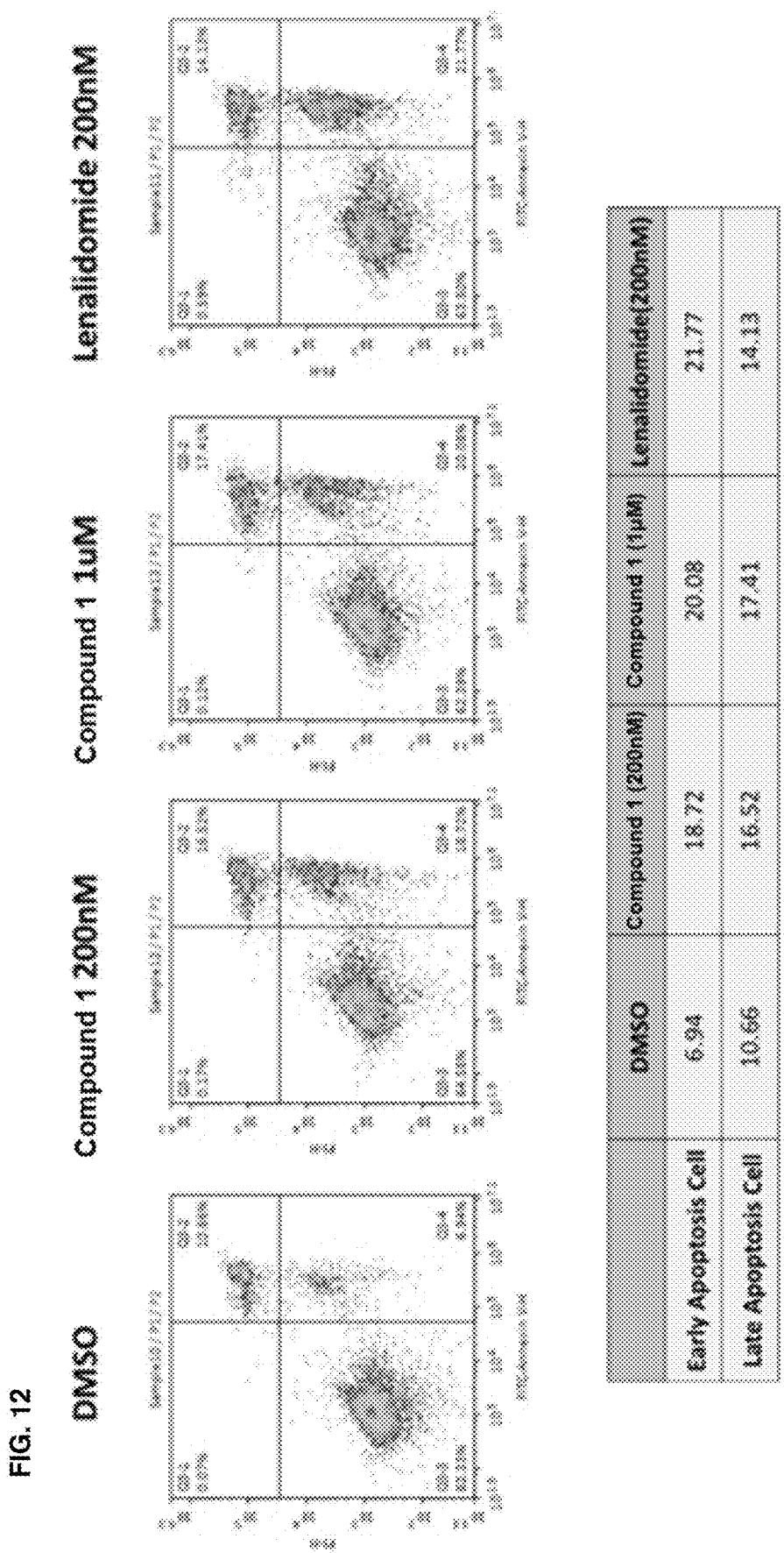
FIG. 12 is a series of contour plots illustrating the percentage of early- and late-apoptotic SYO1 cells following treatment with DMSO, Compound 1 at 200 nM, Compound 1 at 1 µM, or lenalidomide at 200 nM for 8 days. Numerical values corresponding to each contour plot are found in the table below.

Results: As shown in FIGS. 7 and 8, treatment of synovial sarcoma cell lines (SYO1, HS-SY-II, and ASKA) with Compound 1 or Compound 2 resulted in inhibition of the growth of the cells but did not result in inhibition of the growth of non-synovial control cancer cell lines (RD, HCT116, and Calu6). Overall, Compound 1 showed most significant growth inhibition in all synovial cell lines.

Example 4—Inhibition of Cell Growth in Synovial Sarcoma Cells

The following example shows that BRD9 degraders inhibit cell growth and induce apoptosis in synovial sarcoma cells.

Procedure: SYO1 cells were treated for 8 or 13 days with DMSO, a BRD9 degrader (Compound 1) at 200 nM or 1 μM, or an E3 ligase binder (lenalidomide) at 200 nM. Compounds were refreshed every 5 days. Cell cycle analysis was performed using the Click-iT™ Plus EdU Flow Cytometry Assay (Invitrogen). The apoptosis assay was performed using the Annexin V-FITC Apoptosis Detection Kit (Sigma A9210). Assays were performed according to the manufacturer's protocol.

Results: As shown in FIGS. 9-12, treatment with Compound 1 for 8 or 13 days resulted in reduced numbers of cells in the S-phase of the cell cycle as compared to DMSO and lenalidomide. Treatment with Compound 1 for 8 days also resulted in increased numbers of early- and late-apoptotic cells as compared to DMSO controls.

Example 5—Composition for SS18-SSX1-BAF

The following example shows the identification of BRD9 as a component of SS18-SSX containing BAF complexes.

Procedure: A stable 293T cell line expressing HA-SS18SSX1 was generated using lentiviral integration. SS18-SSX1 containing BAF complexes were subject to affinity purification and subsequent mass spectrometry analysis revealed SS18-SSX1 interacting proteins.

Figure 13:
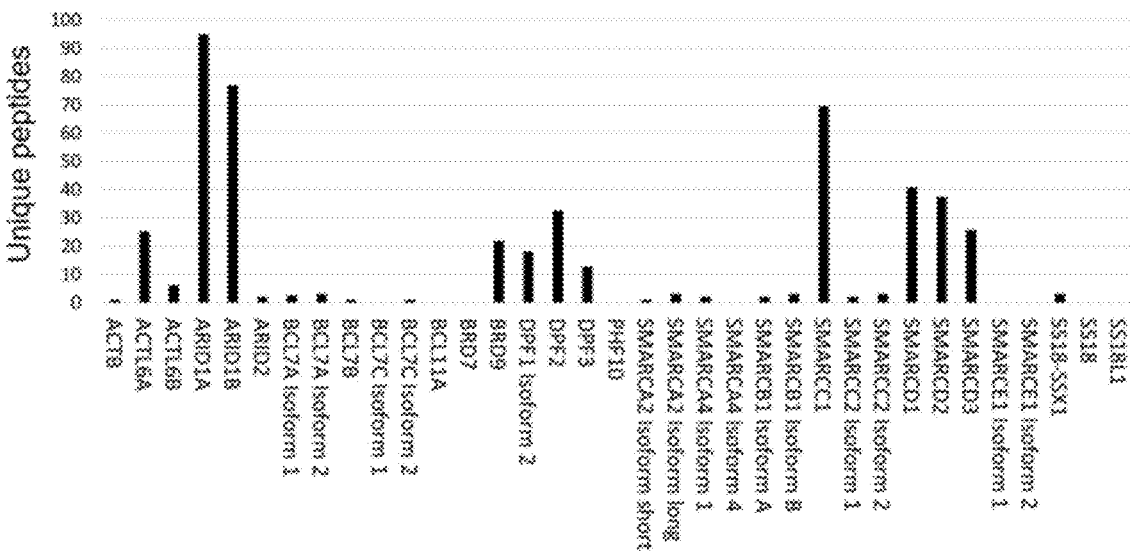
FIG. 13 is a graph illustrating the proteins present in BAF complexes including the SS18-SSX fusion protein.

Results: As shown in FIG. 13, BAF complexes including the SS18-SSX fusion protein also included BRD9. More than 5 unique peptides were identified for ARID1A (95 peptides), ARID1B (77 peptides), SMARCC1 (69 peptides), SMARCD1 (41 peptides), SMARCD2 (37 peptides), DPF2 (32 peptides), SMARCD3 (26 peptides), ACTL6A (25 peptides), BRD9 (22 peptides), DPF1 Isoform 2 (18 peptides), DPF3 (13 peptides), and ACTL6B (6 peptides).

Example 6—Preparation of 4-[6-(azetidin-1-yl)-2-methyl-1-oxo-2,7-naphthyridin-4-yl]-2,6-dimethoxybenzaldehyde (Intermediate H)

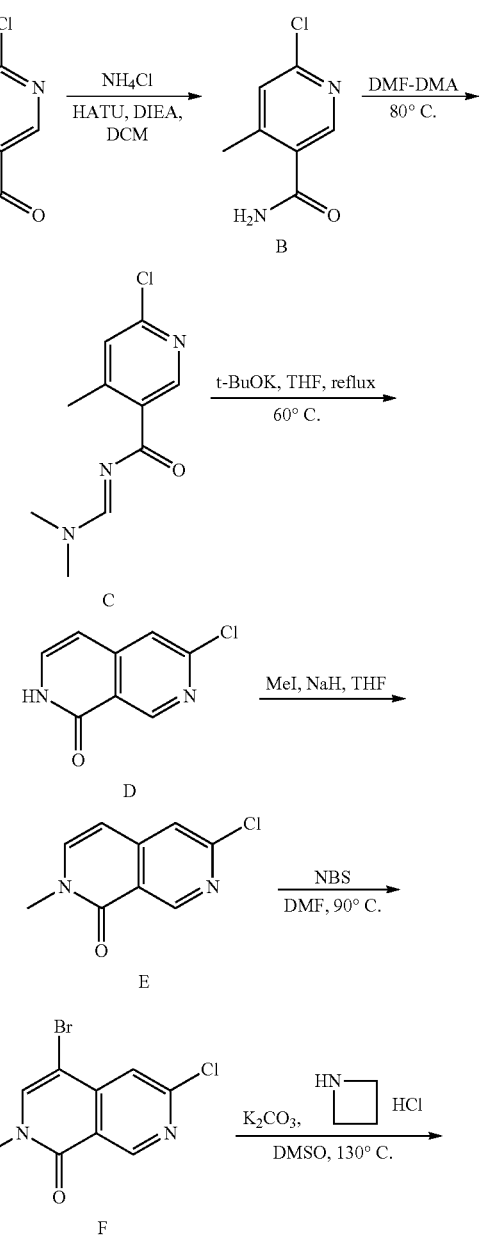

-continued

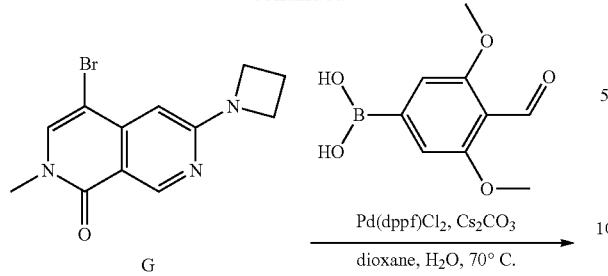

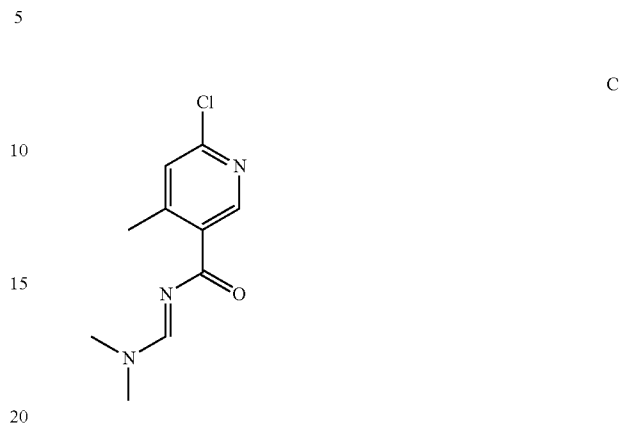

Step 2: Preparation of 6-chloro-N-[(1E)-(dimethylamino)methylene]-4-methylpyridine-3-carboxamide (Intermediate C)

To a stirred mixture of 6-chloro-4-methylpyridine-3-carboxamide (18.30 g, 107.268 mmol, 1.00 equiv) and in 2-methyltetrahydrofuran (100 mL) was added DMF-DMA (19.17 g, 160.903 mmol, 1.50 equiv) at 80° C. under nitrogen atmosphere, and stirred for additional 1 hour. Then the mixture was cooled and concentrated to afford 6-chloro-N-[(1E)-(dimethylamino)methylidene]-4-methylpyridine-3-carboxamide (26.3 g, 91.3%) as a yellow crude solid, which was used directly without further purification. LCMS (ESI) m/z: [M+H]$^+$=226.

Step 1: Preparation of 6-chloro-4-methylpyridine-3-carboxamide (Intermediate B)

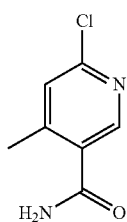

Step 3: Preparation of 6-chloro-2H-2,7-naphthyridin-1-one (Intermediate D)

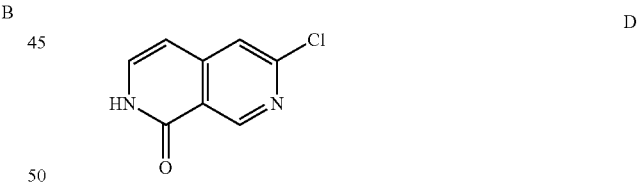

To a stirred mixture of 6-chloro-4-methylpyridine-3-carboxylic acid (20.00 g, 116.564 mmol, 1.00 equiv) and NH$_4$Cl (62.35 g, 1.17 mol, 10.00 equiv) in dichloromethane (DCM; 400 mL) was added DIEA (22.60 g, 174.846 mmol, 3.00 equiv). After stirring for 5 minutes, HATU (66.48 g, 174.846 mmol, 1.50 equiv) was added in portions. The resulting mixture was stirred for 3 hours at room temperature. The resulting mixture was concentrated under reduced pressure, and the residue was purified by silica gel column chromatography, eluted with petroleum ether/ethyl acetate (PE/EtOAc) from 1/1 to 3/2 to afford 6-chloro-4-methylpyridine-3-carboxamide (18.30 g, 61.3%) as a yellow solid. LCMS (ESI) m/z: [M+H]$^+$=171.

To a stirred mixture of 6-chloro-N-[(1E)-(dimethylamino)methylidene]-4-methylpyridine-3-carboxamide (26.30 g) in THF (170.00 mL) was added t-BuOK (174.00 mL, 1 mol/L in THF). The resulting solution was stirred at 60° C. under nitrogen atmosphere for 30 minutes. Then the mixture was cooled and concentrated under reduced pressure. The crude solid was washed with saturated NaHCO$_3$ solution (100 mL) and collected to give 6-chloro-2H-2,7-naphthyridin-1-one (14.1 g, 67.0%) as a pink solid, which was used directly without further purification. LCMS (ESI) m/z: [M+H]$^+$=181.

Step 4: Preparation of 6-chloro-2-methyl-2,7-naphthyridin-1-one (Intermediate E)

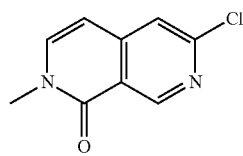

E

To a stirred mixture of 6-chloro-2H-2,7-naphthyridin-1-one (14.10 g, 78.077 mmol, 1.00 equiv) in anhydrous THF (280.00 mL) was added NaH (9.37 g, 234.232 mmol, 3.00 equiv, 60%) in portions at 0° C. After 10 minutes, MeI (33.25 g, 234.232 mmol, 3.00 equiv) was added at 0° C., and the mixture was allowed to stir for 10 minutes at 0° C., and then the mixture was allowed to stir for 12 hours at room temperature. The resulting mixture was concentrated under reduced pressure. The crude solid was slurried with water (100 mL), and the solid was filtered and collected to give the 6-chloro-2-methyl-2,7-naphthyridin-1-one (14.6 g, 94.1%) as a yellow solid, which was used directly without further purification. LCMS (ESI) m/z: [M+H]$^+$=195.

Step 5: Preparation of 4-bromo-6-chloro-2-methyl-2,7-naphthyridin-1-one (Intermediate F)

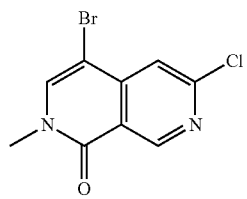

F

To a stirred mixture of 6-chloro-2-methyl-2,7-naphthyridin-1-one (8.00 g, 41.106 mmol, 1.00 equiv) in DMF (160.00 mL) was added NBS (8.78 g, 49.327 mmol, 1.20 equiv), and the resulting mixture was stirred for 2 hours at 90° C. The reaction mixture was cooled and diluted with DCM (150 mL) and washed with water (3×100 mL). The organic layers were dried and concentrated. Then the residue was slurried with EtOAc (20 mL), and the slurry was filtered. The filter cake was washed with EtOAc (20 mL) to give 4-bromo-6-chloro-2-methyl-2,7-naphthyridin-1-one (6.32 g, 55.7%) as a white solid, which was used directly without further purification. LCMS (ESI) m/z: [M+H]$^+$=273.

Step 6: Preparation of 6-(azetidin-1-yl)-4-bromo-2-methyl-2,7-naphthyridin-1-one (Intermediate G)

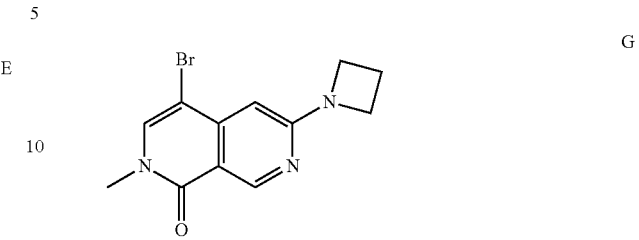

G

To a solution of 4-bromo-6-chloro-2-methyl-2,7-naphthyridin-1-one (5.00 g, 18.281 mmol, 1.00 equiv) and azetidine hydrochloride (3.2 g, 54.843 mmol, 3 equiv) in DMSO (50.00 mL) was added K$_2$CO$_3$ (12.6 g, 91.404 mmol, 5 equiv). The resulting solution was stirred at 130° C. for 2 hours. The resulting mixture was cooled and diluted with water (100 mL), and then extracted with EtOAc (3×100 mL). The combined organic layers were washed with saturated NaCl solution (3×50 mL), dried over anhydrous Na$_2$SO$_4$, and concentrated under reduced pressure to afford 6-(azetidin-1-yl)-4-bromo-2-methyl-2,7-naphthyridin-1-one (3.7 g, 68.8%) as a grey solid, which was used directly without further purification. LCMS (ESI) m/z: [M+H]$^+$=294.

Step 7: Preparation of 4-[6-(azetidin-1-yl)-2-methyl-1-oxo-2,7-naphthyridin-4-yl]-2,6-dimethoxybenzaldehyde (Intermediate H)

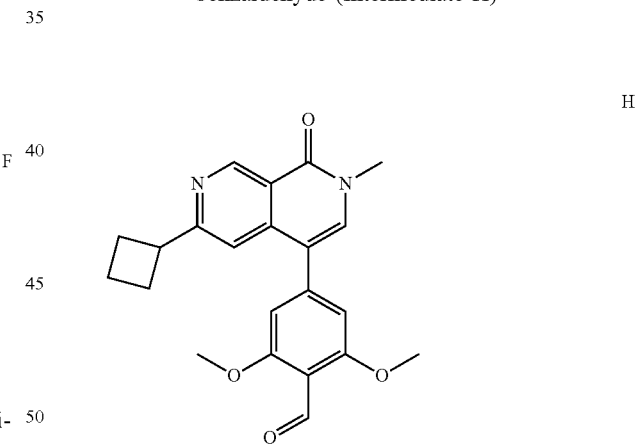

H

To a solution of 6-(azetidin-1-yl)-4-bromo-2-methyl-2,7-naphthyridin-1-one (1.42 g, 4.827 mmol, 1.00 equiv) and 4-formyl-3,5-dimethoxyphenylboronic acid (1.52 g, 7.241 mmol, 1.5 equiv) in dioxane (16.00 mL) and H$_2$O (4.00 mL) was added Pd(dppf)Cl$_2$ (353.2 mg, 0.483 mmol, 0.1 equiv) and Cs$_2$CO$_3$ (3.15 g, 9.655 mmol, 2 equiv), and the resulting solution was stirred at 70° C. for 2 hours. The resulting mixture was cooled and concentrated under reduced pressure. The residue was slurried with water (30 mL) and filtered, and the filter cake was collected. This solid was further slurried with MeOH (30 mL) and filtered. The solid was collected to afford 4-[6-(azetidin-1-yl)-2-methyl-1-oxo-2,7-naphthyridin-4-yl]-2,6-dimethoxybenzaldehyde (1.42 g, 77.5%) as a grey solid. LCMS (ESI) m/z: [M+H]$^+$=380.

Example 7—Preparation of 3-[1-oxo-6-[7-(piperidin-4-ylmethyl)-2,7-diazaspiro[3.5]nonan-2-yl]-3H-isoindol-2-yl]piperidine-2,6-dione (Intermediate P)
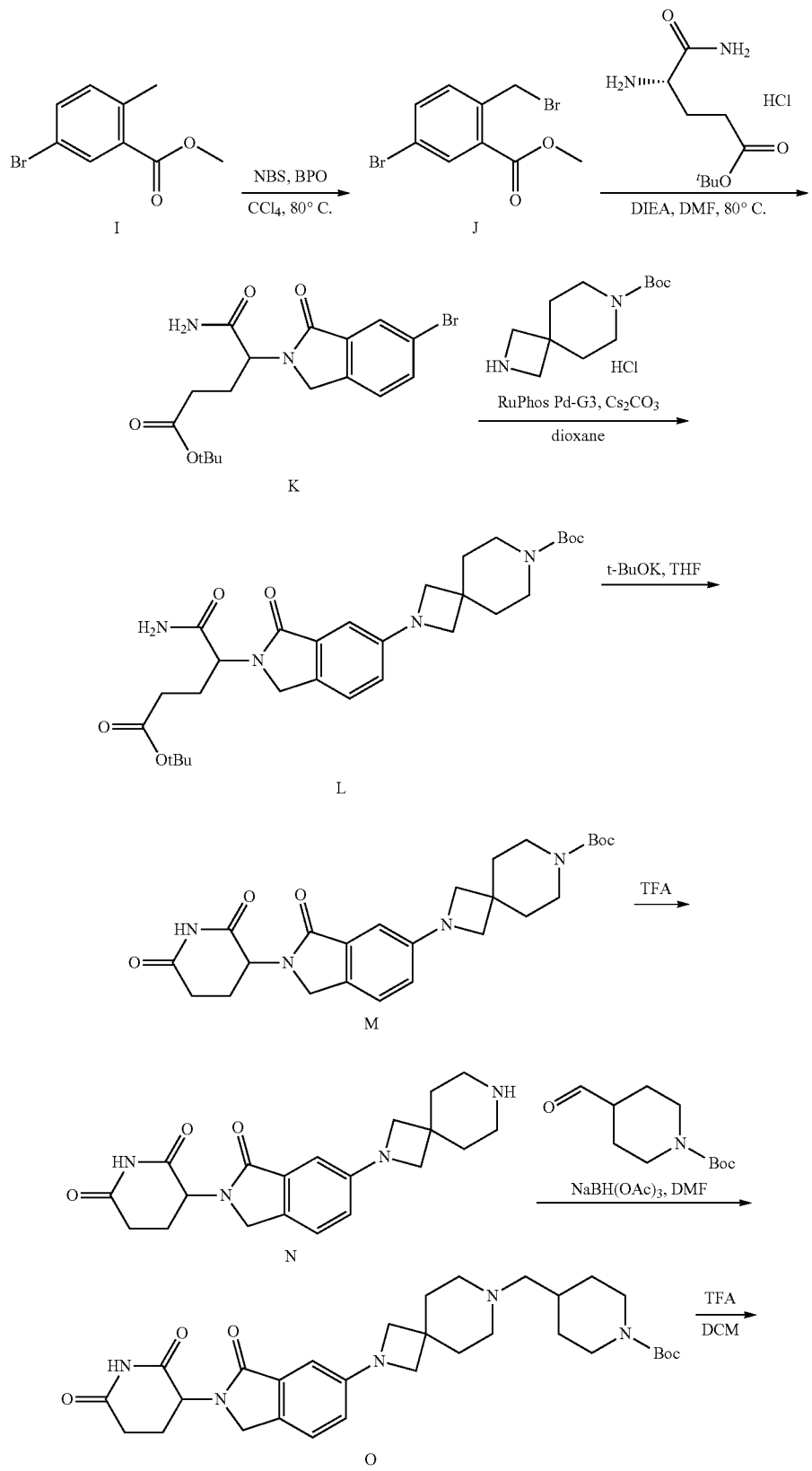

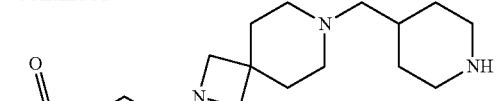

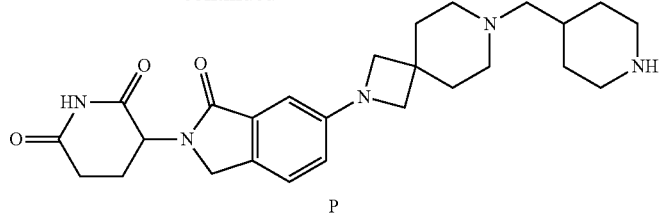

P

Step 1: Preparation of methyl 5-bromo-2-(bromomethyl)benzoate (Intermediate J)

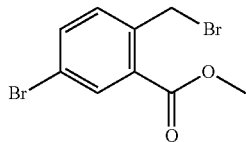

J

To a stirred mixture of methyl 5-bromo-2-methylbenzoate (50.00 g, 218.271 mmol, 1.00 equiv) in CCl$_4$ (500.00 mL) was added NBS (38.85 g, 218.271 mmol, 1.00 equiv) and BPO (5.59 g, 21.827 mmol, 0.10 equiv). After stirring for overnight at 80° C., the mixture was purified by silica gel column chromatography, eluted with PE/EtOAc (50:1) to afford methyl 5-bromo-2-(bromomethyl)benzoate (67 g, 74.75%) as a yellow oil. LCMS (ESI) m/z: [M+H]$^+$=307.

Step 2: Preparation of tert-butyl 4-(6-bromo-1-oxo-3H-isoindol-2-yl)-4-carbamoylbutanoate (Intermediate K)

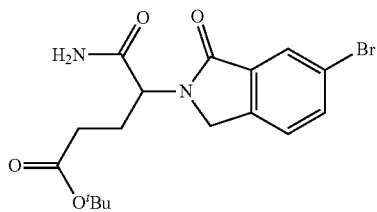

K

To a stirred mixture of methyl 5-bromo-2-(bromomethyl)benzoate (67.00 g, 217.554 mmol, 1.00 equiv) and tert-butyl (4S)-4-amino-4-carbamoylbutanoate hydrochloride (62.32 g, 261.070 mmol, 1.20 equiv) in DMF (100.00 mL) was added DIEA (112.47 g, 870.217 mmol, 4 equiv). After stirring for overnight at 80° C., the mixture was concentrated under reduced pressure. The residue was added water (200 mL) and stirred for 1 h at room temperature. The resulting mixture was filtered, the filter cake was added water (100 mL) and stirred. The precipitated solids were collected by filtration and washed with water (3×30 mL). This resulted in tert-butyl 4-(6-bromo-1-oxo-3H-isoindol-2-yl)-4-carbamoylbutanoate (55 g, 60.46%) as an off-white solid. LCMS (ESI) m/z: [M+H]$^+$=397.

Step 3: Preparation of tert-butyl 2-[2-[4-(tert-butoxy)-1-carbamoyl-4-oxobutyl]-3-oxo-1H-isoindol-5-yl]-2,7-diazaspiro[3.5]nonane-7-carboxylate (Intermediate L)

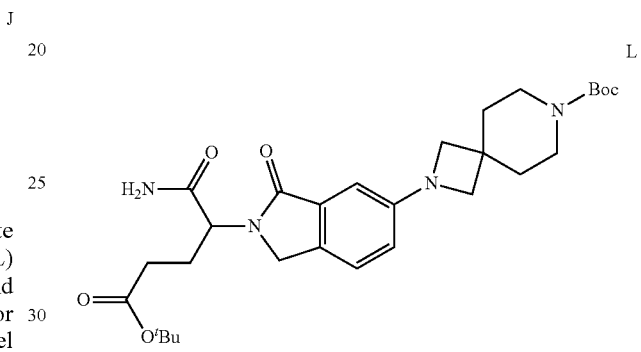

L

To a stirred solution of tert-butyl 4-(6-bromo-1-oxo-3H-isoindol-2-yl)-4-carbamoylbutanoate (10.00 g, 25.172 mmol, 1.00 equiv) and tert-butyl 2,7-diazaspiro[3.5]nonane-7-carboxylate hydrochloride (8.60 g, 32.723 mmol, 1.30 equiv) in dioxane (200.00 mL) was added Cs$_2$CO$_3$ (24.60 g, 75.516 mmol, 3.00 equiv) and RuPhos Palladacycle Gen. 3 (2.11 g, 2.517 mmol, 0.10 equiv). After stirring for overnight at 100° C. under nitrogen atmosphere, the resulting mixture was filtered while hot, and the filter cake was washed with 1,4-dioxane (3×50 mL). The filtrate was concentrated under reduced pressure to afford tert-butyl 2-[2-[4-(tert-butoxy)-1-carbamoyl-4-oxobutyl]-3-oxo-1H-isoindol-5-yl]-2,7-diazaspiro[3.5]nonane-7-carboxylate (21 g, crude) as a black solid. LCMS (ESI) m/z: [M+H]$^+$=543.

Step 4: Preparation of tert-butyl 2-[2-(2,6-dioxopiperidin-3-yl)-3-oxo-1H-isoindol-5-yl]-2,7-diazaspiro[3.5]nonane-7-carboxylate (Intermediate M)

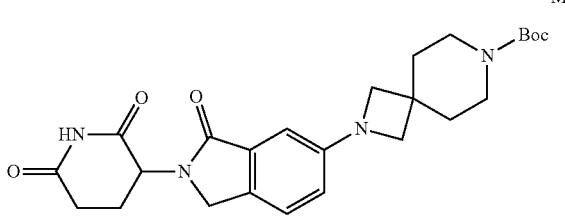

M

To a stirred mixture of tert-butyl 2-[2-[(1S)-4-(tert-butoxy)-1-carbamoyl-4-oxobutyl]-3-oxo-1H-isoindol-5-yl]-2,7-diazaspiro[3.5]nonane-7-carboxylate (13.68 g, 25.208 mmol, 1.00 equiv) in THF (100.00 mL) was added t-BuOK in THF (25.00 mL, 25.000 mmol, 0.99 equiv). The resulting mixture was stirred for 2 hours at room temperature. The mixture was acidified to pH 6 with 1 M HCl (aq.) and then neutralized to pH 7 with saturated NaHCO₃ (aq.). The resulting mixture was extracted with EtOAc (3×200 mL). The combined organic layers were concentrated under reduced pressure. This resulted in tert-butyl 2-[2-(2,6-dioxopiperidin-3-yl)-3-oxo-1H-isoindol-5-yl]-2,7-diazaspiro[3.5]nonane-7-carboxylate (7.8 g, 59.43%) as a yellow solid. LCMS (ESI) m/z: [M+H]⁺=469.

Step 5: Preparation of 3-(6-[2,7-diazaspiro[3.5]nonan-2-yl]-1-oxo-3H-isoindol-2-yl)piperidine-2,6-dione (Intermediate N)

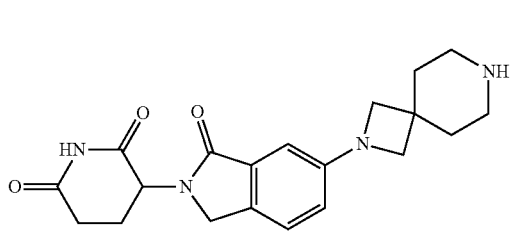

To a stirred mixture of tert-butyl 2-[2-(2,6-dioxopiperidin-3-yl)-3-oxo-1H-isoindol-5-yl]-2,7-diazaspiro[3.5]nonane-7-carboxylate (7.80 g, 16.647 mmol, 1.00 equiv) in DCM (10.00 mL) was added trifluoroacetic acid (TFA; 5.00 mL). After stirring for 2 hours at room temperature, the resulting mixture was concentrated under vacuum. This resulted in 3-(6-[2,7-diazaspiro[3.5]nonan-2-yl]-1-oxo-3H-isoindol-2-yl)piperidine-2,6-dione (6 g, 92.93%) as a light yellow solid. LCMS (ESI) m/z: [M+H]⁺=369.

Step 6: Preparation of tert-butyl 4-([2-[2-(2,6-dioxopiperidin-3-yl)-3-oxo-1H-isoindol-5-yl]-2,7-diazaspiro[3.5]nonan-7-yl]methyl)piperidine-1-carboxylate (Intermediate O)

To a stirred solution of 3-(6-[2,7-diazaspiro[3.5]nonan-2-yl]-1-oxo-3H-isoindol-2-yl) piperidine-2,6-dione (4.00 g, 8.685 mmol, 1.00 equiv, 80%) and tert-butyl 4-formylpiperidine-1-carboxylate (1.48 g, 6.939 mmol, 0.80 equiv) in DMF (20.00 mL) was added NaBH(OAc)₃ (3.68 g, 17.363 mmol, 2.00 equiv) at room temperature. The resulting mixture was stirred for 2 hours at room temperature. The reaction was quenched with water at room temperature. The resulting mixture was purified by reverse flash chromatography with the following conditions (column, C18 silica gel; mobile phase, CH₃CN in water (0.1% FA), 0 to 100% gradient in 40 minutes; detector, UV 254 nm). This resulted in tert-butyl 4-([2-[2-(2,6-dioxopiperidin-3-yl)-3-oxo-1H-isoindol-5-yl]-2,7-diazaspiro [3.5]nonan-7-yl]methyl)piperidine-1-carboxylate (2.8 g, 51.29%) as a dark yellow solid. LCMS (ESI) m/z: [M+H]⁺=566.

Step 7: Preparation of 3-[1-oxo-6-[7-(piperidin-4-ylmethyl)-2,7-diazaspiro[3.5]nonan-2-yl]-3H-isoindol-2-yl]piperidine-2,6-dione (Intermediate P)

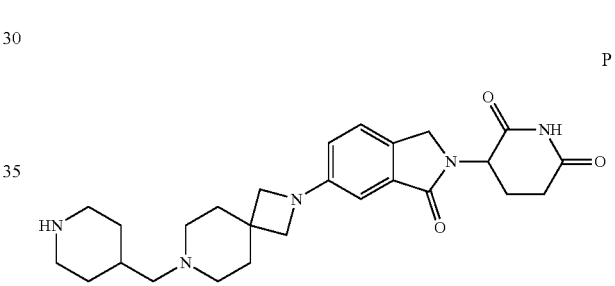

To a stirred mixture of tert-butyl 4-([2-[2-(2,6-dioxopiperidin-3-yl)-3-oxo-1H-isoindol-5-yl]-2,7-diazaspiro[3.5]nonan-7-yl]methyl)piperidine-1-carboxylate (2.80 g, 4.949 mmol, 1.00 equiv) in DCM (5.00 mL) was added TFA (2.00 mL). The mixture was stirred for 2 hours at room temperature. The resulting mixture was concentrated under reduced pressure to afford 3-[1-oxo-6-[7-(piperidin-4-ylmethyl)-2,7-diazaspiro[3.5]nonan-2-yl]-3H-isoindol-2-yl]piperidine-2,6-dione (3.9 g, crude) as a yellow solid. LCMS (ESI) m/z: [M+H]⁺=466.

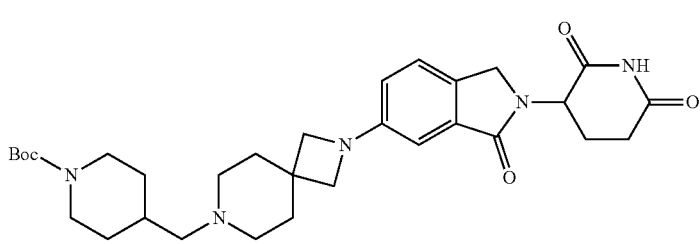

Example 8—Preparation of 3-[6-(7-[[1-([4-[6-(azetidin-1-yl)-2-methyl-1-oxo-2,7-naphthyridin-4-yl]-2,6-dimethoxyphenyl]methyl)piperidin-4-yl]methyl]-2,7-diazaspiro[3.5]nonan-2-yl)-1-oxo-3H-isoindol-2-yl]piperidine-2,6-dione TFA Salt (Compound D1 TFA Salt)

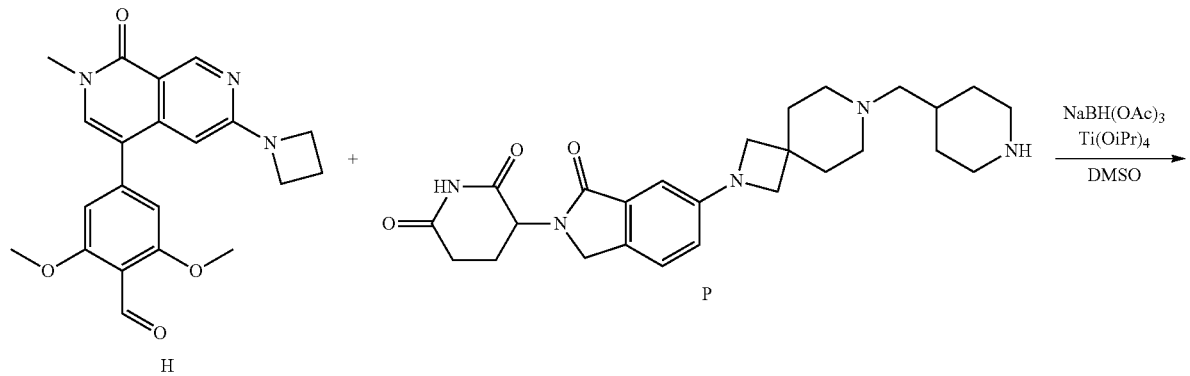

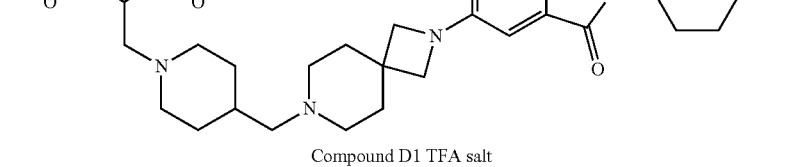

Compound D1 TFA salt

A solution of 3-[1-oxo-6-[7-(piperidin-4-ylmethyl)-2,7-diazaspiro[3.5]nonan-2-yl]-3H-isoindol-2-yl]piperidine-2,6-dione (4.5 g, 10.52 mmol, 1.00 equiv) and 4-[6-(azetidin-1-yl)-2-methyl-1-oxo-2,7-naphthyridin-4-yl]-2,6-dimethoxybenzaldehyde (4.0 g, 10.52 mmol, 1.00 equiv) and titanium(IV) isopropoxide (3.0 g, 10.52 mmol, 1.00 equiv) in DMSO (100 mL) was stirred at room temperature for 3 hours. Then NaBH(OAc)₃ (8.92 g, 42.08 mmol, 4.00 equiv) was added in batches to the above resulting solution, and the resulting mixture was stirred at room temperature overnight. The reaction was quenched by the addition of water (30 mL), and then the solution was filtered. The filter cake was wash by water and acetonitrile. Then the filtrate was concentrated in vacuo. The crude product was purified by reverse phase flash chromatography with the following conditions (Column: AQ C18 Column, 50×250 mm 10 µm; Mobile Phase A: Water (TFA 0.1%), Mobile Phase B: ACN; Flow rate: 100 mL/minute; Gradient: 5 B to 25 B in 35 minutes; 254/220 nm). Pure fractions were evaporated to dryness to afford 3-[6-(7-[[1-([4-[6-(azetidin-1-yl)-2-methyl-1-oxo-2,7-naphthyridin-4-yl]-2,6-dimethoxyphenyl]methyl)piperidin-4-yl]methyl]-2,7-diazaspiro[3.5]nonan-2-yl)-1-oxo-3H-isoindol-2-yl]piperidine-2,6-dione TFA salt (3.2 g, 32.3%) as a white solid. $^1$H NMR (400 MHz, DMSO-d6) δ 10.96 (s, 1H), 9.01 (s, 1H), 7.59 (s, 1H), 7.36 (d, J=8.0 Hz, 1H), 6.72 (s, 2H), 6.68 (d, J=8.1 Hz, 2H), 6.20 (s, 1H), 5.07 (dd, J=13.3, 5.1 Hz, 1H), 4.35-4.13 (m, 2H), 4.06-3.95 (m, 4H), 3.80 (s, 6H), 3.57 (s, 4H), 3.47 (s, 5H), 2.97-2.75 (m, 3H), 2.70-2.55 (m, 1H), 2.44-2.16 (m, 7H), 2.13-1.88 (m, 5H), 1.80-1.67 (m, 4H), 1.61 (d, J=12.4 Hz, 2H), 1.53-1.33 (m, 1H), 1.13-0.94 (m, 2H). LCMS (ESI) m/z: [M+H]⁺=829.55.

Enantiomers of compound D1 were separated by supercritical fluid chromatography on chiral support to produce compound S-D1 and compound R-D1.

Compound D1 is of the following structure:

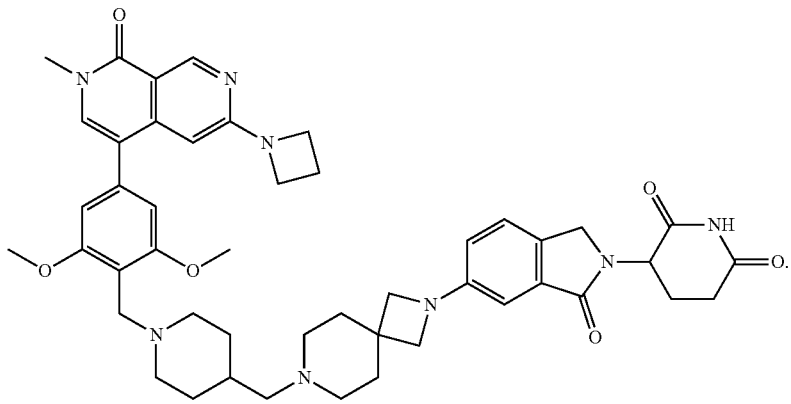 [SMILES: COc1cc(-c2cn(C)c(=O)c3cnc(N4CCC4)cc23)cc(OC)c1CN1CCC(CN2CCC3(CC2)CN(c2ccc4c(c2)C(=O)N(C2CCC(=O)NC2=O)C4)C3)CC1]

Compound S-D1 is of the following structure:

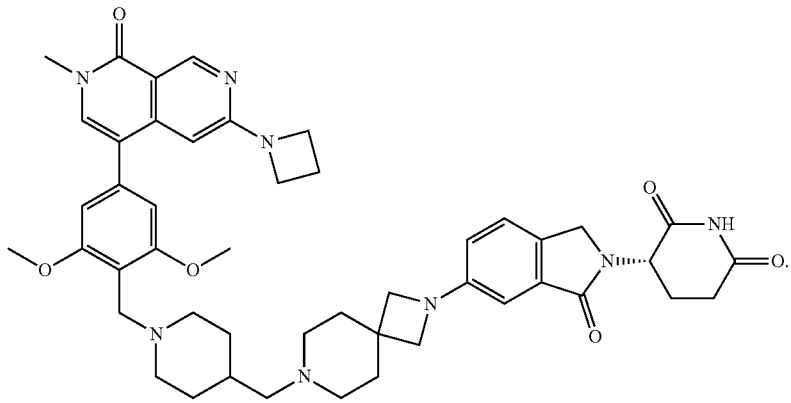

Compound R-D1 is of the following structure:

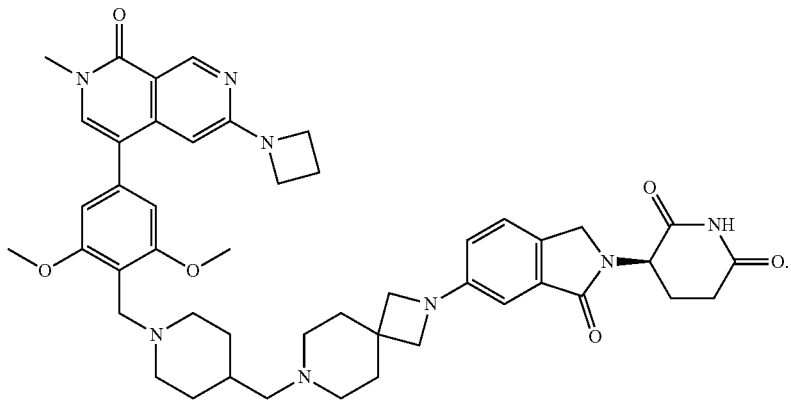 [SMILES: COc1cc(-c2cn(C)c(=O)c3cnc(N4CCC4)cc23)cc(OC)c1CN1CCC(CN2CCC3(CC2)CN(c2ccc4c(c2)C(=O)N([C@@H]2CCC(=O)NC2=O)C4)C3)CC1]

Example 9—Preparation of Compound D2

In analogy to the procedures described in the examples above, compound D2 was prepared using the appropriate starting materials.

Compound D2: $^1$H NMR (300 MHz, DMSO-d6) δ 10.98 (s, 1H), 9.02 (d, J=0.7 Hz, 1H), 7.63 (d, J=2.3 Hz, 1H), 7.41 (d, J=8.8 Hz, 1H), 6.88 (s, 2H), 6.70 (h, J=2.4 Hz, 2H), 6.24 (d, J=6.0 Hz, 1H), 5.08 (dd, J=13.2, 5.1 Hz, 1H), 4.41-4.14 (m, 4H), 4.04 (t, J=7.4 Hz, 4H), 3.91 (s, 1H), 3.70 (d, J=22.5 Hz, 4H), 3.50 (s, 3H), 3.45 (s, 1H), 3.22 (s, 1H), 3.14-2.82 (m, 6H), 2.60 (d, J=16.2 Hz, 1H), 2.55 (s, 2H), 2.44-2.28 (m, 3H), 2.18-2.05 (m, 3H), 1.97 (t, J=13.9 Hz, 5H), 1.51 (q, J=12.2, 11.1 Hz, 2H). LCMS (ESI) m/z: [M+H]$^+$=835.45.

Compound D2 is of the following structure:

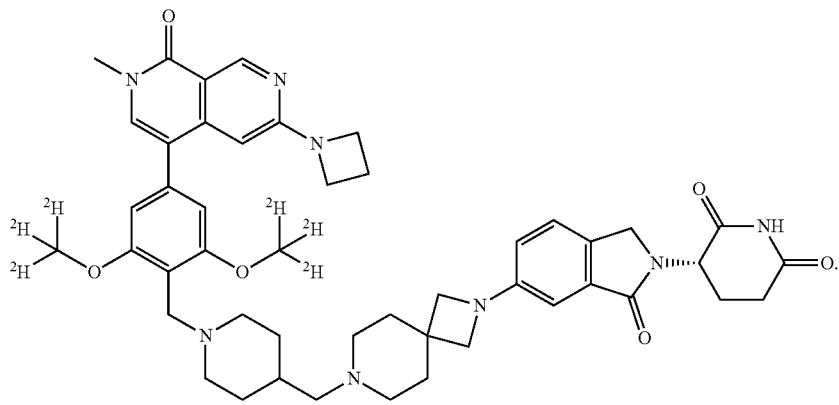 [SMILES: [2H]C([2H])([2H])Oc1cc(-c2cn(C)c(=O)c3cnc(N4CCC4)cc23)cc(OC([2H])([2H])[2H])c1CN1CCC(CN2CCC3(CC2)CN(c2ccc4c(c2)C(=O)N([C@H]2CCC(=O)NC2=O)C4)C3)CC1]

Example 10—SYO1 BRD9 NanoLuc Degradation Assay

This example demonstrates the ability of the compounds of the disclosure to degrade a Nanoluciferase-BRD9 fusion protein in a cell-based degradation assay.

Procedure: A stable SYO-1 cell line expressing 3×FLAG-NLuc-BRD9 was generated. On day 0 cells were seeded in 30 μL media into each well of 384-well cell culture plates. The seeding density was 8000 cells/well. On day 1, cells were treated with 30 nL DMSO or 30 nL of 3-fold serially DMSO-diluted compounds (10 points in duplicates with 1 μM as final top dose). Subsequently plates were incubated for 6 hours in a standard tissue culture incubator and equilibrated at room temperature for 15 minutes. Nanoluciferase activity was measured by adding 15 μL of freshly prepared Nano-Glo Luciferase Assay Reagent (Promega N1130), shaking the plates for 10 minutes and reading the bioluminescence using an EnVision reader.

Results: The Inhibition % was calculated using the following formula: % Inhibition=100×(Lum$_{HC}$−Lum$_{Sample}$)/(Lum$_{HC}$−Lum$_{LC}$). DMSO treated cells are employed as High Control (HC) and 1 μM of a known BRD9 degrader standard treated cells are employed as Low Control (LC). The data was fit to a four parameter, non-linear curve fit to calculate IC$_{50}$ (μM) values as shown in Table 2. As shown by the results in Table 2, a number of compounds of the present disclosure exhibit an IC$_{50}$ value of <1 μM for the degradation of BRD9, indicating their use as compounds for reducing the levels and/or activity of BRD9 and their potential for treating BRD9-related disorders.

TABLE 2

SYO1 BRD9-NanoLuc Degradation

| Compound No. | SYO1 BRD9-NanoLuc degradation IC$_{50}$ (nM) |
|---|---|
| D1 | 0.13 |
| D2 | 0.18 |

Example 11—Degradation of BRD9 Inhibits the Growth of Synovial Sarcoma Tumor In Vivo Method: NOD SCID mice (Beijing Anikeeper Biotech, Beijing) were inoculated subcutaneously on the right flank with the single cell suspension of SYO-1 human biphasic synovial sarcoma tumor cells (5×106) in 100 μL Dulbecco's Modified Eagle Medium (DMEM) with 10% fetal bovine serum (FBS). The mice were randomized into either control group [10% dimethyl sulfoxide (DMSO), 40% polyethylene glycol (PEG400) and 50% water], or treatment group D1 when the mean tumor size reached about 117 mm$^3$. Mice were dosed daily through intraperitoneal (i.p.) route over the course of 3 weeks. All dose volumes were adjusted by body weights in terms of mg/kg.

Figure 14:
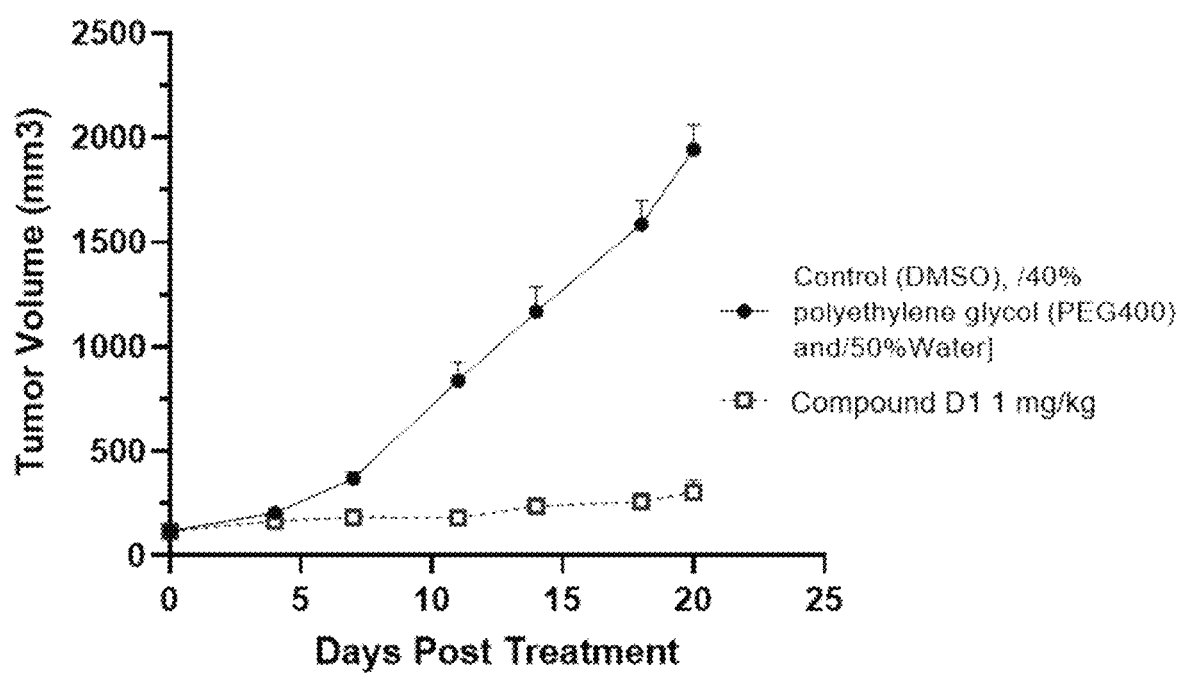
FIG. 14 is a graph showing efficacy of compound D1 in SOY-1 xenograft mouse model. Treatment with compound D1 led to tumor growth inhibition.

Results: As shown in FIG. 14, treatment with compound D1 at 1 mg/kg had led to tumor growth inhibition. All treatments were well tolerated based on % body weight change observed.

Example 12—Compound D1 Causes Degradation of BRD9 in Synovial Sarcoma Tumor In Vivo Method: Mice were treated with D1, 1 mg/kg, i.p. for 4 weeks. Mice were then euthanized, and tumors were collected at 8 hours, 72 hours, and 168 hours post last dose. Tumors were lysed with 1×RIPA lysis buffer (Boston Bio-Products, BP-115D) with protease and phosphatase protein inhibitor (Roche Applied Science #04906837001 & 05892791001). Equal amounts of lysate (30 μg) were loaded in in 4-12% Bis-Tris Midi Protein Gels in 1×MOPS buffer; samples ran at 120 V for 120 minutes. Protein was transferred to membrane with TransBlot at 250 mA for 150 minutes, and then membranes were blocked with Odyssey blocking buffer for 1 hour at room temperature. Membranes were hybridized overnight in cold room with primary antibodies. Images acquired using Li—COR imaging system (Li—COR Biotechnology, Lincoln, Nebr.).

Table 3 shows detection antibody information.

TABLE 3

| Antibody | Vendor | Cat# | Species | Dilution |
|---|---|---|---|---|
| BRD9 | Bethyl, (Montgomery, TX) | A303-781A | Rabbit | 1:1000 |
| GAPDH | CST, (Danvers, MA) | 97166 | Mouse | 1:2000 |

Figure 15:
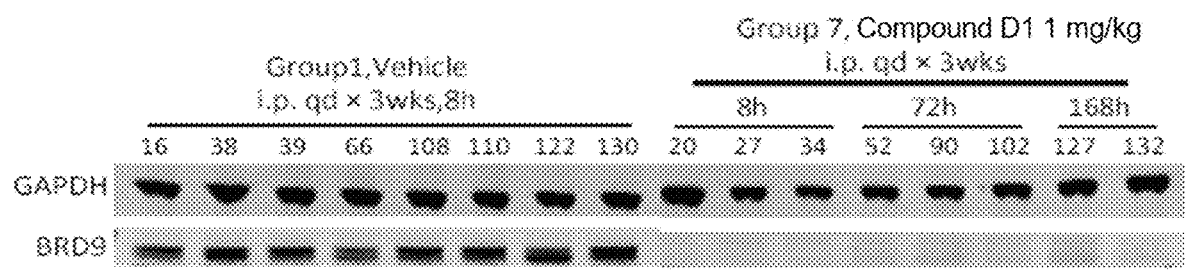
FIG. 15 is an image of a western blot showing BRD9 detection in the control group and the treatment group (compound D1). Treatment with compound D1 led to BRD9 inhibition.

Results: As shown in FIG. 15, treatment with compound D1 at 1 mg/kg led to complete degradation of BRD9 target up to 168 hours after dose.

Example 13—the Effect of Compounds S-D1 and R-D1 on Synovial Sarcoma Cells Method Synovial sarcoma cells were plated in 6-well plate at 500-100k cells/well and treated with serial concentrations of BRD9 degrader (10 nM top concentration, diluted 1:3) the next day for two time points at 37° C. Cells were then harvested, washed with cold PBS, and frozen in cell pellets at −80° C. Lysates were prepared by resuspending thawed pellets in 1×RIPA Lysis and Extraction buffer (Thermo Fisher, Cat #89900) with 1× Halt™ Protease and Phosphatase Inhibitor Cocktail, EDTA-free (Thermo Fisher, Cat #78441) and 1:1000 dilution Pierce™ Universal Nuclease for Cell Lysis 25 ku (Thermo Fisher, Cat #88700). Lysates were incubated on ice for 10 minutes and then centrifuged in 4° C. at maximum speed (15,000 rpm) for 10 minutes. Samples were then analyzed for total protein using BCA protein quantification assay and diluted to 1 µg/µL with lysis buffer and 1× NuPAGE™ LDS Sample Buffer (4×) (Thermo Fisher, Cat #NP0007) and 1×DTT from 30× stock (Cell Signaling Technologies, Cat #14265S). Samples with 20-25 ug of total protein were loaded into 4-12% Bis-Tris Mini-Gel with 1×MES Running buffer and run at 150V for 45 minutes. Gels were transferred using Trans-Blot® Turbo™ Transfer System (semi-dry) at 25V for 10 minutes (High MW setting) on nitrocellulose blots. Blots were blocked in 5% milk in TBST for 1 hour and probed with BRD9 antibody (Bethyl Labs, Cat #A303-781A, 1:750 for SYO1, and Cell Signaling Technologies, Cat #71232S for ASKA) and beta-Actin antibody (Cell Signaling Technologies, Cat #3700, 1:2,000) overnight at 4° C. The next day, blots were washed in TBST 3× and probed with 1:5,000 IRDye® 680LT Goat anti-Rabbit IgG Secondary Antibody (LiCOR, Cat #926-68021) and 1:10,000 IRDye® 800CW Goat anti-Mouse IgG Secondary Antibody (LiCOR, Cat #926-32210) in LiCOR Odyssey® Blocking Buffer (TBS) for 1 hour at room temperature. Blots were washed in TBST 3× and scanned at 700 nM and 800 nM wavelength using LiCOR Odyssey® CLx Imaging System. Western blot signal was quantified using same analyses program included in the same machine. BRD9 signal was quantified by normalizing to beta-actin signal and all samples were normalized to DMSO, set as 100% signal.

For the assessment of interconversion between Enantiomer 1 and Enantiomer 2 in cell medium, the following test was performed. Enantiomer 1 and Enantiomer 2 (each was 40 µM in DMSO) was spiked into cell medium (DMEM+Glutamax+10% FBS) at a final concentration of 0.2 µM and incubated at 37° C. and 5% $CO_2$ in duplicate. At designated time point, aliquot (50 µL) was taken and processed by the addition of 150 µL of acetonitrile containing 0.1% formic acid and internal standard for LC/MS-MS analysis. Peak areas of both Enantiomer 1 and Enantiomer 2 were determined for each sample using a chiral specific analytical method. The results are summarized in Table 5 below.

Figure 16:
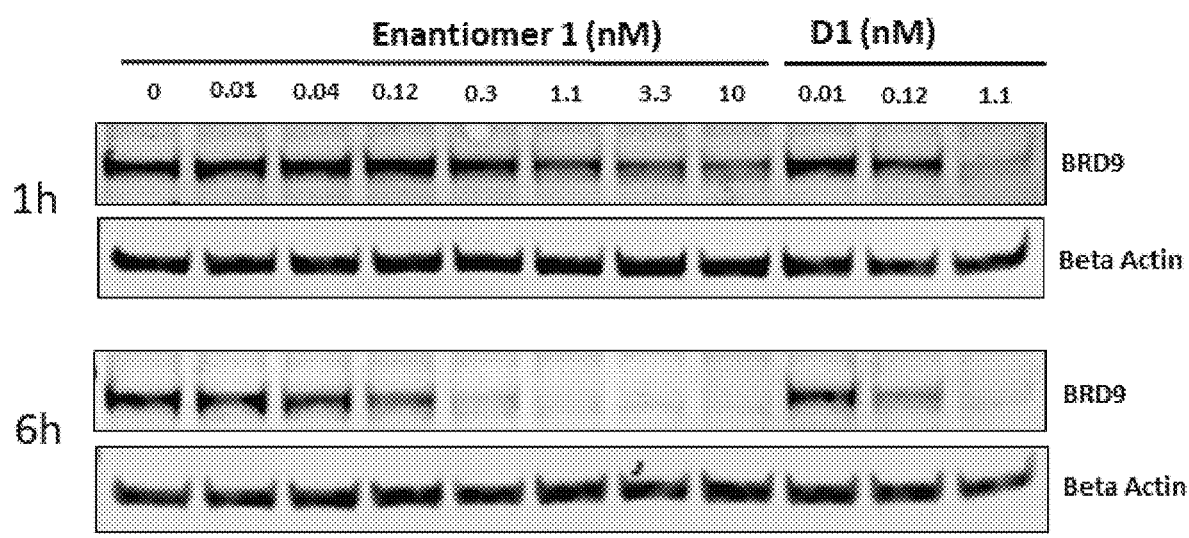
FIG. 16 is an image of western blots showing BRD9 detection in the SYO-1 cells treated with DMSO, Enantiomer 1, or racemic compound D1 for 1 or 6 hours.
Figure 17:
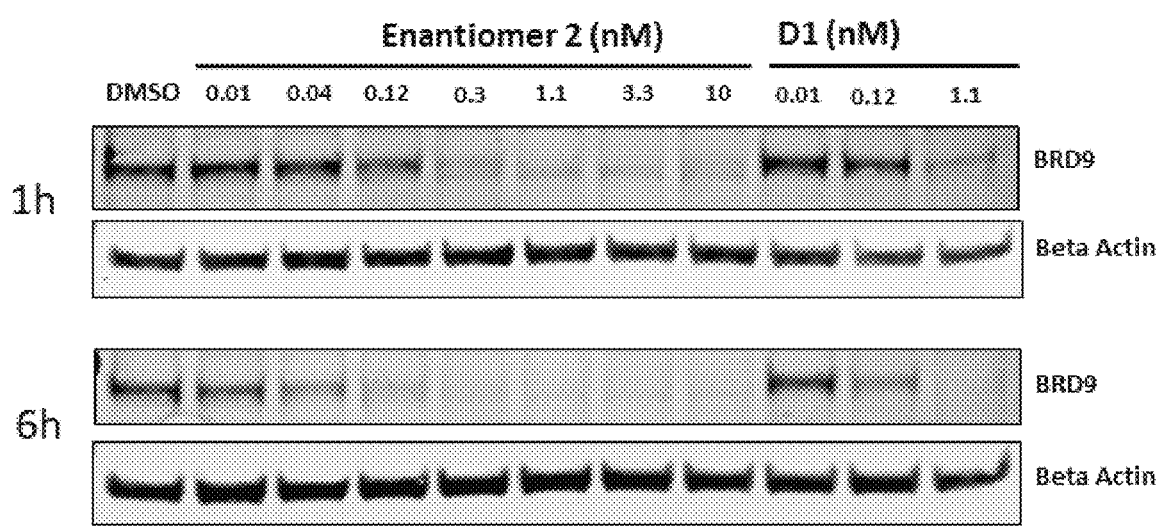
FIG. 17 is an image of western blots showing BRD9 detection in the SYO-1 cells treated with DMSO, Enantiomer 2, or racemic compound D1 for 1 or 6 hours.
Figure 18:
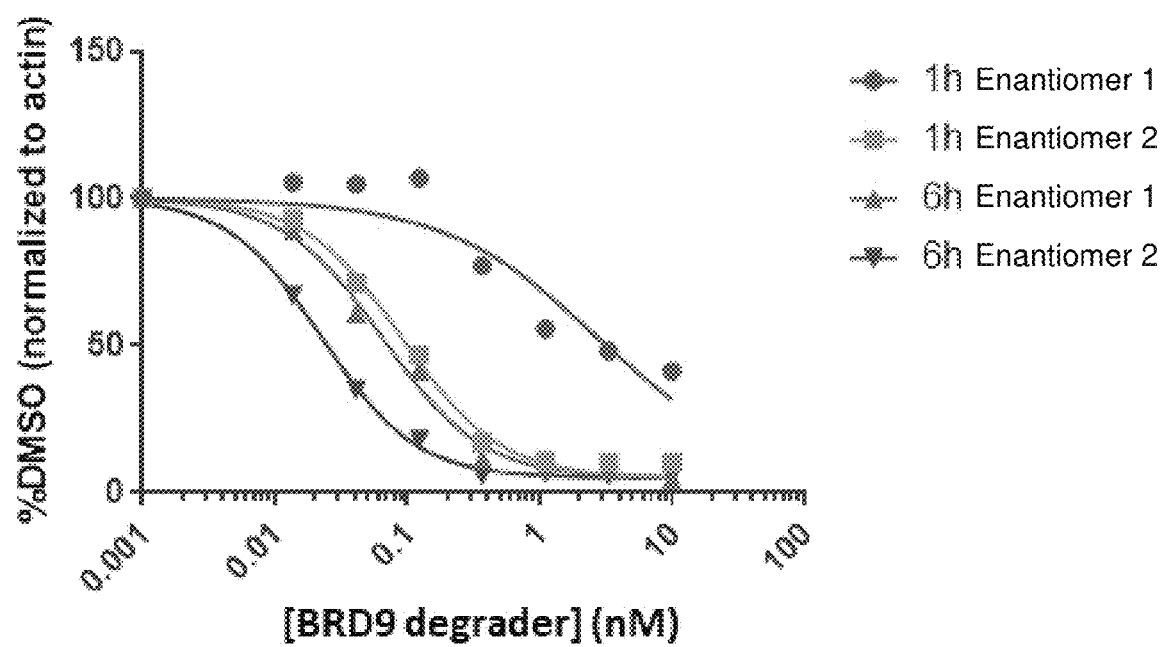
FIG. 18 is a graph showing dose response curves fitted to BRD9 band intensity data points from western blot images illustrated in FIGS. 16 and 17.
Figure 19:
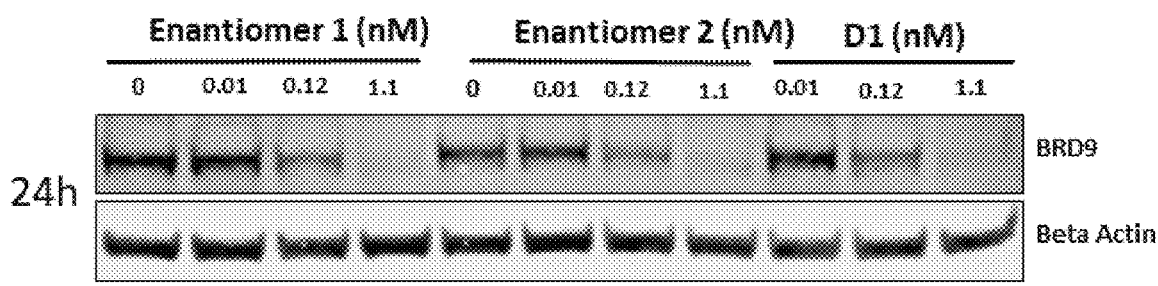
FIG. 19 is an image of western blots showing BRD9 detection in the SYO-1 cells treated with Enantiomer 1, Enantiomer 2, or racemic compound D1 for 24 hours.
Figure 20:
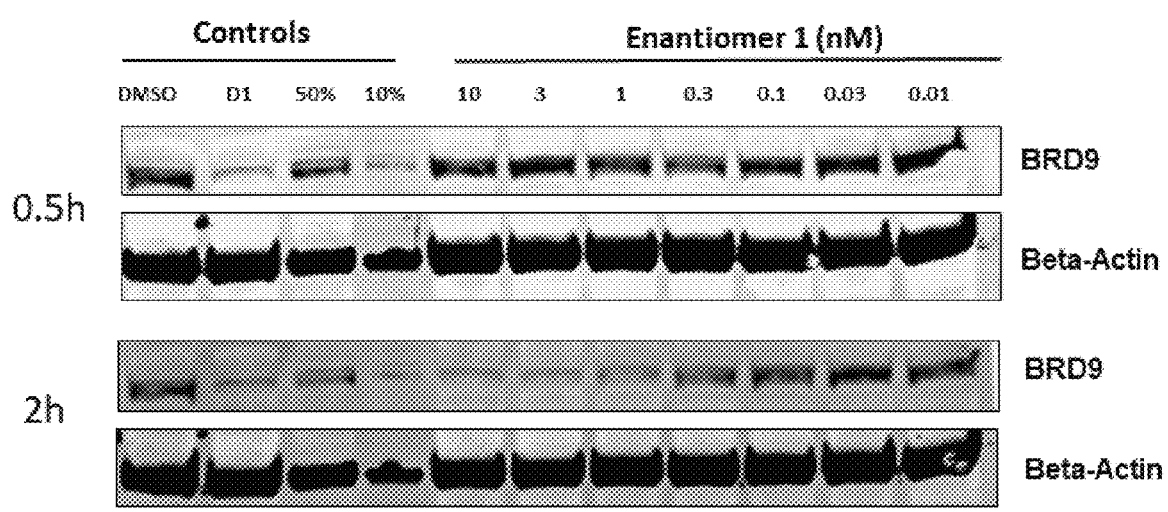
FIG. 20 is an image of western blots showing BRD9 detection in the ASKA cell controls and the ASKA cells treated with Enantiomer 1 or racemic compound D1 for 0.5 or 2 hours.
Figure 21:
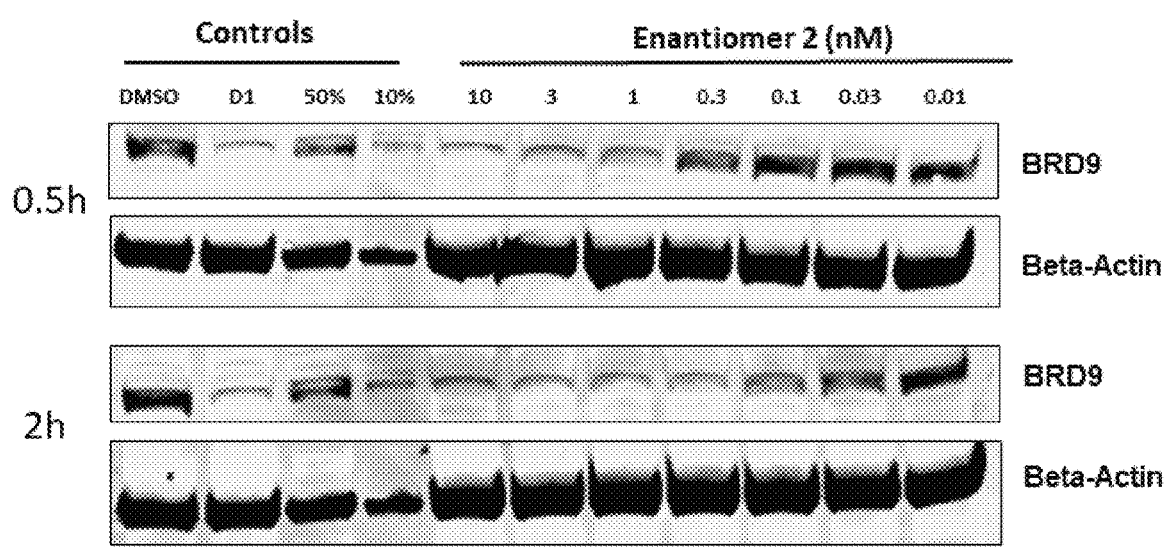
FIG. 21 is an image of western blots showing BRD9 detection in the ASKA cell controls and the ASKA cells treated with Enantiomer 2 or racemic compound D1 for 0.5 or 2 hours.
Figure 22:
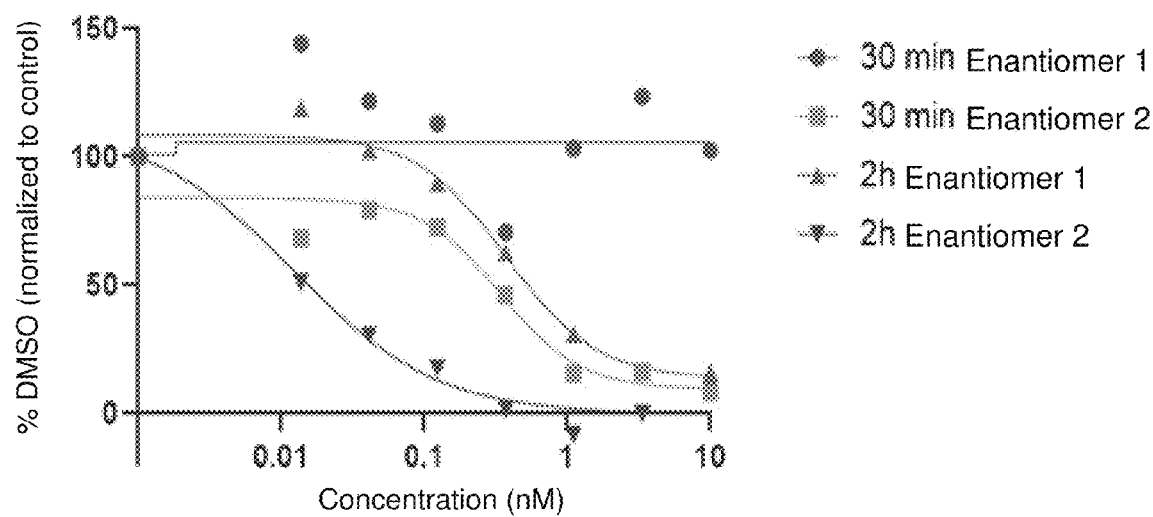
FIG. 22 is a graph showing dose response curves fitted to BRD9 band intensity data points from western blot images illustrated in FIGS. 20 and 21.

Results. To assess BRD9 degradation activity of two enantiomers, degrader treatment and subsequent western-blot experiments were carried out using two synovial sarcoma cell lines (SYO-1 and ASKA). Significant more potent BRD9 degradation activity was observed with Enantiomer 2, with a fitted $DC_{50}$ value of 0.092 nM, comparing to 2.8 nM for Enantiomer 1 in SYO-1 with 1 h treatment time (FIGS. 16, 17, and 18 and Table 4). Even more dramatic difference in ASKA cells is evident with a $DC_{50}$ of 0.34 nM for Enantiomer 2 at 30 minutes, but there is no discernable activity for Enantiomer 1 up to 10 µM at the same time point (FIGS. 20, 21, and 22 and Table 4). The difference is reduced to about 32-fold at 2 h in ASKA, with a fitted $DC_{50}$ value of 0.38 nM and 0.012 nM for Enantiomer 1 and Enantiomer 2, respectively (Table 4). The difference is further reduced to ca. 3-fold by 6 h in SYO1. Enantiomer 2 works slightly better than its racemic parent compound D1 in degrading BRD9 but overall comparable under the same study conditions (FIGS. 16 and 17). BRD9 degradation activity becomes highly similar for all three compounds at 24 h (FIG. 19). Taking together, Enantiomer 2 is much more potent in degradation endogenous BRD9 protein in two synovial sarcoma cell lines at early time point, whereas Enantiomer 1 is largely inactive or with much reduced degradation potency. However, the difference in potency is diminished over time and largely disappeared by 24 h.

TABLE 4

| Cell Line | Fitted $DC_{50}$ (nM) | Enantiomer 1 | Enantiomer 2 |
|---|---|---|---|
| ASKA | 0.5 h | >10 | 0.34 |
| SYO-1 | 1 h | 2.8 | 0.092 |
| ASKA | 2 h | 0.38 | 0.012 |
| SYO-1 | 6 h | 0.066 | 0.023 |

Epimerization of the chiral center in thalidomide or other IMiD drugs and their derivatives is reported. The acidic hydrogen in the chiral center can be scrambled under physical or neutral pH conditions. To investigate the chiral stability under cell assay conditions for these degraders, we performed a time course study for Enantiomer 1 and Enantiomer 2 in cell culture medium at 37° C. There is no detectable Enantiomer 2 in Enantiomer 1 samples at time 0 or 0.5 h. But substantial Enantiomer 2 was detected at later time points, accounting for 12% and 30% of the total at 2 h and 6 h, respectively (Table 5). Similarly, Enantiomer 2 is converted to Enantiomer 1 overtime and its effective concentration was reduced to 63% at 6 h (Table 5). These data indicate that epimerization rate is relatively fast under the cell assay conditions, and suggest that the time-dependent BRD9 degradation activity for Enantiomer 1 is likely due to the converted Enantiomer 2. Overall, these data indicate that Enantiomer 2 is the active enantiomer in degrading BRD9 in cells.

TABLE 5

| | Enantiomer 1 Dosing | | Enantiomer 2 Dosing | |
|---|---|---|---|---|
| Time (h) | Mean peak area ratio of Enantiomer 2 over Enantiomer 1 peak area ratio | % Enantiomer 2 | Mean peak area ratio of Enantiomer 1 over Enantiomer 2 peak area ratio | % Enantiomer 2 |
| 0 | 0.0 | 0.0 | 0.01 | 99 |
| 0.5 | 0.0 | 0.0 | 0.06 | 95 |
| 2 | 0.13 | 12 | 0.22 | 82 |
| 6 | 0.43 | 30 | 0.60 | 63 |

Example 14—the Effect of Compounds S-D1 and R-D1 on Synovial Sarcoma Cells

Method. The SYO-1 tumor cells were maintained in vitro as adherent cells in Dulbecco's Modified Eagle Medium (DMEM) supplemented with 10% fetal bovine serum at 37° C. in an atmosphere of 5% CO2 in air. The cells growing in an exponential growth phase were harvested and counted for tumor inoculation. BALB/c Nude mice (Shanghai Lingchang biological science) were inoculated subcutaneously on the right flank with (5×10$^6$) in 0.1 mL of phosphate buffered saline (PBS). The treatment—(described in the table below)—was started on day 19 after tumor inoculation, when the average tumor size reached 499 mm$^3$.

TABLE 6

Treatment information

| Antibody | Number of mice |
|---|---|
| Vehicle control, sulfobutylether-β-cyclodextrin (SBECD), Single Dose, 10 μL/g | 3 |
| Racemic D1, 0.5 mg/kg i.v., Single Dose, 10 μL/g (20% SBECD) | 12 |
| Enantiomer 1, 0.25 mg/kg i.v., Single Dose, 10 μL/g (20% SBECD) | 18 |
| Enantiomer 2, 0.25 mg/kg i.v., Single Dose, 10 μL/g (20% SBECD) | 18 |
| Enantiomer 2, 1 mg/kg i.v., Single Dose, 10 μL/g (20% SBECD) | 18 |

Mice were treated with racemic D1, 1 mg/kg, i.p. for 4 weeks, mice were euthanized, and tumors collected 1, 4, 8, 24, 48 and 72-hour post last dose. Tumors were lysed with 1×RIPA lysis buffer (Boston BioProducts, BP-115D) with protease and phosphatase protein inhibitor (Roche Applied Science #04906837001 & 05892791001). Equal amount of lysate (30 μg) were loaded in in 4-12% Bis-Tris Midi Protein Gels in 1×MOPS buffer; samples ran at 120 V for 120 min. Proteins was transferred to membrane (NC) with TransBlot at 250 mA for 150 minute, then membranes were blocked with Odyssey Blocking buffer for 1 hour at room temperature. Membranes were hybridized overnight in cold room with primary antibodies. Images acquired using Li—COR imaging system (Li—COR Biotechnology, Lincoln, Nebr.)

TABLE 7

Detection antibody information

| Antibody | Vendor | Cat# | Species | Dilution |
|---|---|---|---|---|
| BRD9 | Bethyl, (Montgomery, TX) | A303-781A | Rabbit | 1:1000 |
| GAPDH | CST, (Danvers, MA) | 97166 | Mouse | 1:2000 |

Figure 23:
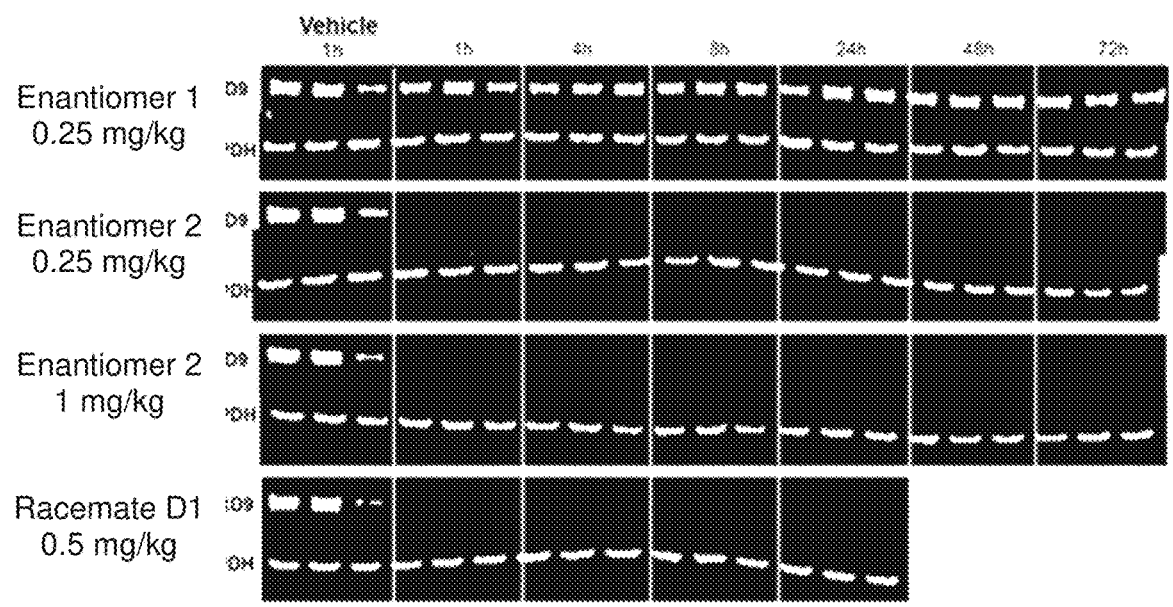
FIG. 23 are images showing a series of western blots for BRD9 detection in SYO-1 Zenograft model treated with Enantiomer 1, Enantiomer 2, or racemic compound D1.
Figure 24:
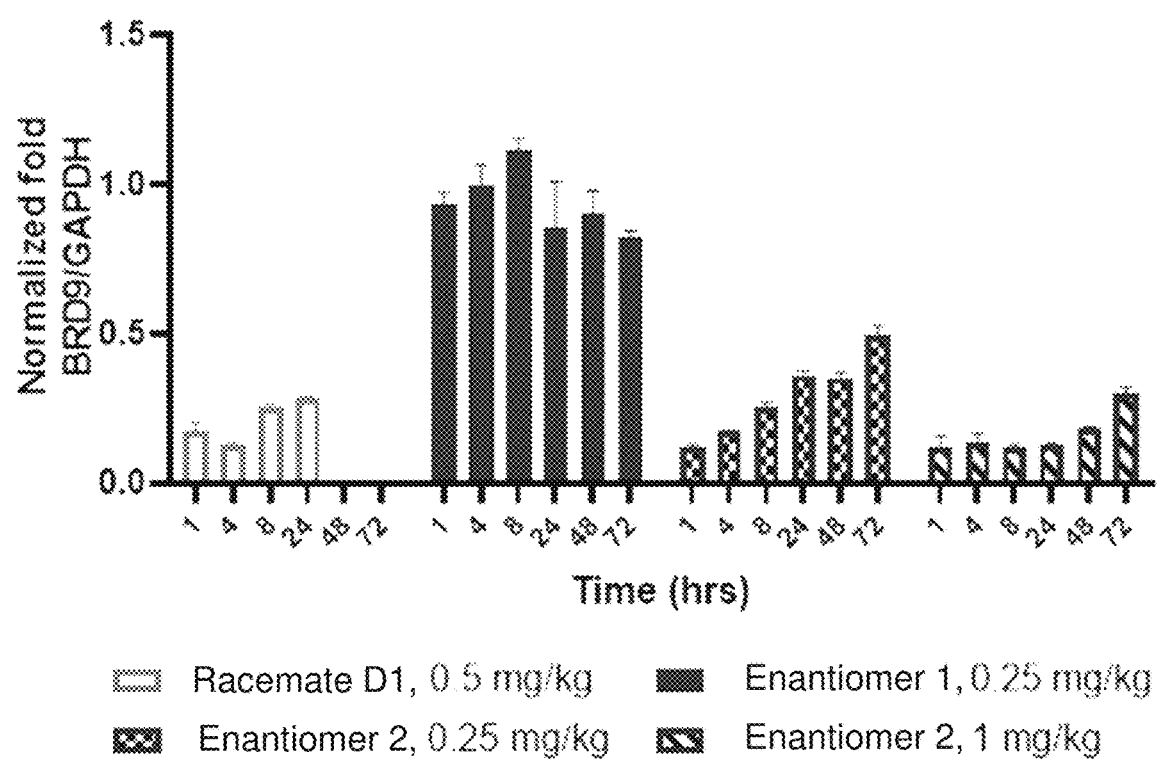
FIG. 24 is a bar graph quantifying the BRD9 level changes observed in western blots illustrated in FIG. 23.

Results. Pharmacodynamic activities of Enantiomer 1, Enantiomer 2, and racemic compound D1 were evaluated in SYO-1 Xenograft model. Enantiomer 2 demonstrated significant activity which was assessed by BRD9 protein level using western blot assay FIG. 23. Enantiomer 2 degraded BRD9 up to 72 hours after a single dose. Enantiomer 1 was inactive and did not degrade BRD9 protein. These results suggested Enantiomer 2 is equipotent to racemic compound D1.

Example 15—Forced Degradation Study of Compound D1

Solution Preparation
Diluent 1: H$_2$O
Diluent 2: dimethylsulfoxide (DMSO)
Diluent 3: [0.05% formic acid (FA) in acetonitrile (MeCN)]: H$_2$O=1:1 (v/v)
2N HCl was prepared by weighing 19.7076 g concentrated aq. HCl (37%) into a 100 mL volumetric flask containing approximately 20 mL diluent 1, diluting to volume with diluent 1, and mixing well.

0.002N HCl was prepared as follows. 1 mL of 2N HCl into was transferred into a 100 mL volumetric flask containing approximately 20 mL diluent 1, diluted to volume with diluent 1, and mixed well. Then, 1 mL of this solution was pipetted into a 10 mL volumetric flask, diluted to volume with diluent 1, and mixed well.

Diluent 4: 0.001N HCl was prepared as follows. 1 mL of the 2N HCl was transferred into a 100 mL volumetric flask containing approximately 20 mL diluent 1, diluted to volume with diluent 1, and mixed well. Then, 5 mL of this solution were pipetted into a 100 mL volumetric flask, made up to volume with diluent 1 and mixed well.

2N NaOH was prepared as follows. 8.0248 g of NaOH were weighed into a 100 mL volumetric flask, diluted to volume with diluent 1, and mixed well.

0.1N NaOH was prepared as follows. 5 mL of the 2N NaOH were transferred into a 100 mL volumetric flask containing approximately 5 mL diluent 1, diluted to volume with diluent 1, and mixed well.

0.002N NaOH was prepared as follows. 1 mL of the 2N NaOH was transferred into a 100 mL volumetric flask containing approximately 20 mL diluent 1, diluted to volume with diluent 1, and mixed well. Then, 10 mL of this solution were pipetted into a 100 mL volumetric flask, diluted to volume with diluent 1, and mixed well.

6% Hydrogen peroxide was prepared as follows. 20 mL of concentrated H$_2$O$_2$ (30%) were transferred to a 100 mL volumetric flask, diluted to volume with diluent 1, and mixed well.

92% relative humidity control was achieved using a dryer containing a saturated potassium nitrate solution.

1N Citric acid was prepared as follows. 19.2032 g of citric acid were weighed into a 100 mL volumetric flask, diluted to volume with diluent 1, and mixed well.

pH=4.0 50 mM Sodium citrate buffer was prepared as follows. 1.4814 g of sodium citrate were weighed into a 100 mL volumetric flask, diluted up to volume with diluent 1, and mixed well. pH was adjusted to 4.0 by 1N citric acid.

pH=5.0 50 mM Sodium citrate buffer was prepared as follows. 1.4815 g of sodium citrate were weighed into a 100 mL volumetric flask, diluted to volume with diluent 1, and mixed well. pH was adjusted to 5.0 by 1N citric acid.

pH=7.0 Phosphate buffer was prepared as follows. 0.6963 g of KH$_2$PO$_4$ were weighed into a 100 mL volumetric flask, 29.1 mL of the 0.1N NaOH were transferred into the same volumetric flask, diluted to volume with diluent 1, and mixed well.

Sample Preparation

Sample stock solution was prepared by weighing 60.74 mg of compound D1 to a 100 mL volumetric flask, dissolving by ultrasonic in 50 mL of diluent 2, diluting to volume with diluent 2, and mixing well.

Unstressed sample solution was prepared by weighing 21.32 mg of compound D1 into a 100 mL volumetric flask, dissolving by ultrasonic in 50 mL of diluent 3, diluting to volume with diluent 3, and mixing well.

Sensitivity solution (LOQ) was prepared as follows. 1.0 mL of unstressed sample solution was pipetted into a 100 mL volumetric flask, diluted to volume with diluent 3, and mixed well. Then, 5 mL of this sample solution were pipetted into a 100 mL volumetric flask, diluted to volume with diluent 3, and mixed well.

Sample solution for pH=4.0 solution stability was prepared as follows. 20.96 mg of compound D1 were weighed into a 100 mL volumetric flask, dissolved by ultrasonic in 50 mL of pH=4.0 50 mM sodium citrate buffer, diluted to volume with pH=4.0 50 mM sodium citrate buffer, and mixed well.

Sample solution for pH=5.0 solution stability was prepared as follows. 20.75 mg of compound D were weighed into a 100 mL volumetric flask, dissolved by ultrasonic in 50 mL of pH=5.0 50 mM sodium citrate buffer, diluted to volume with pH=5.0 50 mM sodium citrate buffer, and mixed well.

Sample solution for pH=7.0 solution stability was prepared as follows. 19.91 mg of compound D1 and 684.71 mg $KH_2PO_4$ were weighed into a 100 mL volumetric flask, dissolved by ultrasonic in 50 mL of diluent 1, transferred 29.1 mL of 0.1N NaOH into the same volumetric flask, diluted to volume with diluent 1, and mixed well.

Forced Degradation
Stress Conditions

TABLE 8

Stress Conditions and Sampling time points

| Degradation type | Stress Solvent/Conditions | Time Point |
|---|---|---|
| Acid Hydrolysis | 1N HCl at RT | 0 h, 1 d, 2 d, 3 d |
| Basic Hydrolysis | 0.001N NaOH at RT | 0 h, 1 h |
| Oxidation | 3% Hydrogen Peroxide at RT | 0 h, 8 h |
| Photolysis | 1.10 $W/m^2$/25° C. for solid (1.10 $W/m^2$/25° C. with 13 hours equal to visible 1.2M lux hrs and UV 647 $Wh/m^2$) | 13 h, 26 h, 39 h |
| Thermal | 80° C. for solid | 1 d, 3 d, 7 d |
|  | 80° C. for solution | 1 d, 7 d |
| Humidity | 92% RH | 1 d, 3 d, 7 d |
| Solution Stability | pH = 4.0, 50 mM Sodium citrate buffer at RT | 0 h, 1 d, 3 d, 7 d |
|  | pH = 5.0, 50 mM Sodium citrate buffer at RT | 0 h, 1 d, 3 d, 7 d |
|  | pH = 7.0 Phosphate buffer at RT | 0 h, 1 d, 3 d, 7 d |

Notes:
1. The target endpoint of a stress study was to form approximately 5-15% of total degradation product. 2. Based on actual degradation of the sample, the stress conditions including concentration of sample and reagent, and temperature, humidity, light may be adjusted. 3. After stressing samples in acid and base, neutralize them before placing into freezer. 4. All degradable samples before analysis must be placed into the 2° C. to 8° C. condition.

Acid degradation (1N HCl at RT). 3 mL of the sample stock solution (see above) were transferred into an 8 mL vial, 3 mL of 2N HCl solution were added, and the resulting mixture was mixed well. Samples were prepared in quadruplicate and kept at RT. At the sampling point, 2 mL of the sample were transferred into an 8 mL vial and neutralized with 1 mL of 2N NaOH.

Blank: a blank has been prepared following the same procedure as described above, only without the inclusion of compound D1.

Basic degradation (0.001N NaOH at RT). 3 mL of the sample stock solution (see above) were transferred into an 8 mL vial, 3 mL of 0.002N NaOH solution were added, and the resulting mixture was mixed well. Samples were prepared in triplicate and kept at RT. At the sampling point, 2 mL of the solution were transferred into an 8 mL vial and neutralized with 1 mL of 0.002N HCl.

Blank: a blank has been prepared following the same procedure as described above, only without the inclusion of compound D1.

Oxidation degradation (3% $H_2O_2$ at RT). 3 mL of the sample stock solution (see above) were transferred into an 8 mL vial, 3 mL of 6% $H_2O_2$ solution were added, and the resulting mixture was mixed well. Samples were prepared in quadruplicate and kept at RT. At the sampling time point, 2 mL of the solution were transferred into an 8 mL vial, neutralized with 1 mL of diluent 3, and mixed well.

Blank: a blank has been prepared following the same procedure as described above, only without the inclusion of compound D1.

Photolysis degradation (solid). About 60 mg of compound D1 were placed onto a watch glass. Samples were prepared in triplicate and placed in a photo chamber (see Table 8). At the sampling time point, the sample was placed in a vial for analysis. About 20.0±2.0 mg of the sample into a 100 mL volumetric flask, dissolved by ultrasonic in 50 mL of diluent 3, diluted to volume with diluent 3, and mixed well.

TABLE 9

Photolysis degradation of samples' mass weight

| Sampling Name* | Weight (mg) |
|---|---|
| PSD-13h | 20.44 |
| PSD-26h | 19.93 |
| PSD-39h | 19.43 |

*PSD-13h, PSD-26h and PSD-39h in category mean the compound is degradation product under photolysis solid stress condition in 13 h, 26 h, and 39 h, respectively.

Dark control sample: one sample was prepared as described above for this test, but the watch glass was covered with aluminum foil, and processed as described above.

Thermal Stress Degradation (80° C. for Solid and Solution).

Solid: about 60 mg of compound D1 were weighted into an 8 mL vial. Samples were prepared in triplicate and placed in an oven at 80° C. At the sampling time point, about 20.0±2.0 mg of the sample were weighed into a 100 mL volumetric flask, dissolved by ultrasonic in 50 mL of diluent 3, diluted to volume with diluent 3, and mixed well.

TABLE 10

Thermal degradation of samples' mass weight

| Sample Name* | Weight (mg) |
|---|---|
| T-1d | 19.82 |
| T-3d | 22.07 |
| T-7d | 21.68 |

*T-1d, T-3d and T-7d in category mean the compound is degradation product under thermal solid stress condition in 1 d, 3 d and 7 d, respectively.

Solution: 3 mL of the sample stock solution (see above) were transferred into an 8 mL vial. Samples were prepared in triplicate and placed them in an oven at 80° C. At the sampling time point, 1 mL of the solution was transferred into an 8 mL vial, neutralized with 2 mL of diluent 3, and mixed well.

Blank: a blank has been prepared following the same procedure as described above, only without the inclusion of compound D1.

Humidity degradation (92% RH for solid). About 60 mg of compound D1 were transferred into a 20 mL vial (without cap). Samples were prepared in triplicate and placed in a desiccator at 92% RH. At the sampling time point, about 20.0±2.0 mg of the sample were transferred into a 100 mL volumetric flask, dissolved by ultrasonic in 50 mL of diluent 3, diluted to volume with diluent 3, and mixed well.

TABLE 11

Humidity degradation of samples' mass weight

| Sample Name* | Weight (mg) |
|---|---|
| H-1d | 21.02 |
| H-3d | 21.41 |
| H-7d | 20.11 |

*H-1d, H-3d and H-7d in category mean the compound is degradation product under humidity solid stress condition in 1 d, 3 d and 7 d, respectively.

Solution Stability. Samples were prepared tested under the solution stability conditions noted in Table 8. The sampling time points were as noted in Table 8.

Blank: a blank has been prepared following the same procedure as described above, only without the inclusion of compound D1.

Sample Analysis

TABLE 12

| HPLC Method 1 | |
|---|---|
| Mobile Phase A | $H_2O$ + 0.1% TFA |
| Mobile Phase B | MeCN + 0.1% TFA |
| Column | Poroshell 120 SB-AQ (3.0*150 mm, 2.7 μm) |
| Needle Wash | MeCN:$H_2O$ = 1:1 |
| Injection volume | 3 μL |
| Column Temperature | 40° C. |
| Flow Rate | 0.8 mL/min |
| Detection | 210 nm |

| | Time (min) | % A | % B |
|---|---|---|---|
| Gradient | 0.0 | 98 | 2 |
| | 7.0 | 70 | 30 |
| | 12.0 | 50 | 40 |
| | 15.0 | 5 | 95 |
| | 17.0 | 5 | 95 |

| Post time | 5 min |
|---|---|
| Run time | 17 min |

TABLE 13

Summary

| Degradation Type | Stress Solvent/ Conditions | Sample Name | Sample Number | Time | Area % | % Degradation | % Mass Balance |
|---|---|---|---|---|---|---|---|
| Unstressed | N/A | N/A | 0 | N/A | 94.172 | N/A | N/A |
| Acid Hydrolysis | 1N HCl RT | A 0 | 1 | 0 h | 93.734 | 0.438 | 108.2 |
| | | A 1 | 2 | 1 d | 89.391 | 4.781 | 106.5 |
| | | A 2 | 3 | 2 d | 85.180 | 8.992 | 107.6 |
| | | A 3 | 4 | 3 d | 82.047 | 12.125 | 106.9 |
| Base Hydrolysis | 1N NaOH RT | B 0 | 5 | 0 h | 68.962 | 25.210 | 104.0 |
| | | B 1 | 6 | 1 h | 17.331 | 76.841 | 98.0 |
| Oxidation | 3% $H_2O_2$ RT | O 0 | 7 | 0 h | 77.988 | 16.184 | 106.8 |
| | | O 8 | 8 | 8 h | 33.755 | 60.417 | 105.2 |
| Photolysis | 1.10 W/m²/25° C. for solid with 13 hours equal to visible 1.2 M lux hrs and UV 647 Wh/m² | P 1 | 9 | 13 h | 91.084 | 3.088 | 101.0 |
| | | P 2 | 10 | 26 h | 90.916 | 3.256 | 92.1 |
| | | P 3 | 11 | 39 h | 90.736 | 3.436 | 105.7 |
| Thermal | 80° C. Solid | TSD 1 | 12 | 1 d | 93.448 | 0.724 | 105.7 |
| | | TSD 3 | 13 | 3 d | 93.194 | 0.978 | 97.6 |
| | | TSD 7 | 14 | 7 d | 82.192 | 11.980 | 92.7 |
| | 80° C. Solution | TSN 1 | 15 | 1 d | 94.053 | 0.119 | 100.5 |
| | | TSN 7 | 16 | 7 d | 31.937 | 62.235 | 104.2 |
| Humidity | 92% RH | H 1 | 17 | 1 d | 92.927 | 1.245 | 98.8 |
| | | H 3 | 18 | 3 d | 92.081 | 2.091 | 99.5 |
| | | H 7 | 19 | 7 d | 90.890 | 3.282 | 99.8 |
| Solution Stability | pH = 4.0, 50 mM Sodium citrate buffer at RT | pH4 0 | 20 | 0 h | 93.516 | 0.656 | 90.1 |
| | | pH4 1 | 21 | 1 d | 93.331 | 0.841 | 93.7 |
| | | pH4 3 | 22 | 3 d | 92.873 | 1.299 | 93.9 |
| | | pH4 7 | 23 | 7 d | 92.130 | 2.042 | 93.7 |
| | pH = 5.0 50 mM Sodium citrate buffer at RT | pH5 0 | 24 | 0 h | 92.498 | 1.674 | 95.3 |
| | | pH5 1 | 25 | 1 d | 92.250 | 1.922 | 103.1 |
| | | pH5 3 | 26 | 3 d | 92.039 | 2.133 | 100.0 |
| | | pH5 7 | 27 | 7 d | 89.514 | 4.658 | 100.8 |
| | pH = 7.0 Phosphate buffer at RT | pH7 0 | 28 | 0 h | 92.638 | 1.534 | 97.1 |
| | | pH7 1 | 29 | 1 d | 85.252 | 8.920 | 102.6 |
| | | pH7 2 | 30 | 2 d | 79.002 | 15.170 | 100.6 |

TABLE 14

Summary result of mass balance, resolution and purity factor

| Sample Number | Purity % | Mass Balance | | | *Resolution | | | Purity Factor | | |
|---|---|---|---|---|---|---|---|---|---|---|
| | | Result | Criteria | Pass/Fail | Result | Criteria | Pass/Fail | Result | Criteria | Pass/Fail |
| 4 | 82.047 | 106.9 | 90%-110% | Pass | 2.0 | ≥1.2 | Pass | 999.943 | >990 | Pass |
| 6 | 17.331 | 98.0 | | | 1.8 | | | 996.409 | | |
| 8 | 33.755 | 105.2 | | | 1.0 | | Fail | 998.510 | | |
| 11 | 90.736 | 105.7 | | | 1.8 | | Pass | 999.780 | | |
| 14 | 82.192 | 92.7 | | | 1.8 | | | 999.941 | | |
| 16 | 31.937 | 104.2 | | | 1.8 | | | 999.708 | | |
| 19 | 90.890 | 99.8 | | | 1.9 | | | 999.438 | | |
| 23 | 92.130 | 93.7 | | | 2.0 | | | 999.830 | | |
| 27 | 89.514 | 100.8 | | | 2.0 | | | 999.639 | | |
| 30 | 79.002 | 100.6 | | | 2.0 | | | 998.160 | | |

*Resolution was the adjacent impurity with the main peak.
According to the result above, samples 6 and 8 were used to method optimized.

Example 16—Forced Degradation Study of Compound S-D1

Solutions Preparation

Mobile phase: methanol (MeOH): acetonitrile (MeCN)=3:7 (v/v)+25 mM formic acid (FA)+25 mM $NH_3$. Prepared by transferring 300 mL MeOH, 700 mL MeCN, 970 µL FA, and 12.5 mL Ammonia in to 1 L bottle, mixed well.

Needle wash solution: MeOH

Diluent 1: $H_2O$

Diluent 2: 0.05% FA in MeCN:THF=1:1 (v/v)

2N HCl was prepared by weighing 19709.02 mg concentrated aq. HCl (37%) into a 100 mL volumetric flask containing approximately 20 mL diluent 1, diluting to volume with diluent 1, and mixing well.

0.3N HCl was prepared by transferring 15 mL of the 2N HCl (see above) into a 100 mL volumetric flask containing approximately 20 mL diluent 1, diluting to volume with diluent 1, and mixing well.

2N NaOH was prepared by weighing 7996.77 mg NaOH into a 100 mL volumetric flask, made up to volume with diluent 1 and mixed well.

0.3N NaOH was prepared by transferring 15 mL of the 2N NaOH (see above) into a 100 mL volumetric flask containing approximately 5 mL diluent 1, diluting to volume with diluent 1, and mixing well.

0.1N NaOH was prepared by transferring 5 mL of the 2N NaOH (see above) into a 100 mL volumetric flask containing approximately 5 mL diluent 1, diluting to volume with diluent 1, and mixing well.

1N Citric acid was prepared by weighing 19193.47 mg citric acid into a 100 mL volumetric flask, diluting to volume with diluent 1, and mixing well.

pH=4.0 50 mM Sodium citrate buffer was prepared by weighing 1474.25 mg sodium citrate into a 100 mL volumetric flask, diluting to volume with diluent 1, and mixing well. pH was adjusted pH to 4.0 by 1N citric acid.

pH=5.0 50 mM Sodium citrate buffer was prepared by weighing 1474.11 mg sodium citrate into a 100 mL volumetric flask, diluting to volume with diluent 1, and mixing well. pH was adjusted to 5.0 by 1N citric acid.

Sample solution stock was prepared by weighing 501.53 mg of compound S-D1 to a 100 mL volumetric flask, dissolving by ultrasonic in 50 mL of diluent 2, diluting to volume with diluent 2, and mixing well.

Unstressed sample solution was prepared by weighing 50.83 mg of compound S-D1 into a 100 mL volumetric flask, dissolving by ultrasonic in 50 mL of diluent 2, diluting to volume with diluent 2, and mixing well.

Sensitivity solution (LOQ) was prepared as follows. 1.0 mL of unstressed sample solution were pipetted into a 100 mL volumetric flask, diluted to volume with diluent 2, and mixed well. Then 2 mL of this sample solution were pipetted into a 10 mL volumetric flask, diluted to volume with diluent 2, and mixed well.

Sample solution for pH=4.0 solution stability was prepared as follows. 50.79 mg of compound S-D1 were weighed into a 100 mL volumetric flask, dissolved by ultrasonic in 50 mL of pH=4.0 50 mM sodium citrate buffer (see above), diluted to volume with pH=4.0 50 mM sodium citrate buffer, and mixed well.

Sample solution for pH=5.0 solution stability was prepared as follows. 50.66 mg of the compound of Formula I were weighed into a 100 mL volumetric flask, dissolved by ultrasonic in 50 mL of pH=5.0 50 mM sodium citrate buffer (see above), diluted to volume with 50 mL of pH=5.0 50 mM sodium citrate buffer and mixed well.

Sample solution for pH=7.0 solution stability was prepared as follows. 50.78 mg of compound S-D1 and 680.42 mg $KH_2PO_4$ were weighed into a 100 mL volumetric flask, dissolved by ultrasonic in 50 mL of diluent 1, transferred 29.1 mL of the 0.1N NaOH (see above), diluted to volume with diluent 1, and mixed well.

TABLE 15

Stress Conditions and Sampling Time Points

| Degradation type | Stress Solutions/Conditions | Sampling Time Point |
|---|---|---|
| Acid Hydrolysis | 1N HCl at RT | 0 h, 1 d, 2 d, 3 d |
| Basic Hydrolysis | 0.15N NaOH at RT | 0 h, 1 h |
| Thermal | 50° C. for solid | 1 d, 3 d, 7 d |
| Solution Stability | pH = 4.0, 50 mM Sodium citrate buffer at RT | 0 h, 1 d, 2 d, 3 d |
| | pH = 5.0, 50 mM Sodium citrate buffer at RT | 0 h, 1 d, 2 d, 3 d |
| | pH = 7.0 Phosphate buffer at RT | 0 h, 1 d, 2 d, 3 d |

Note:
After stressing samples in acid or base, the samples were neutralized before placing into freezer.

Acid degradation (1N HCl at RT). 3 mL of the sample stock solution (see above) into an 8 mL vial, added 3 mL of 2N HCl solution, and mixed well. Samples were prepared in quadruplicate and kept at room temperature (RT). At the sampling time point, 1 mL of the sample was transferred into a 5 mL volumetric flask, neutralized with 0.5 mL of 2N NaOH, diluted to volume with diluent 2, and mixed well.

Blank: a blank has been prepared following the same procedure as described above, only without the inclusion of compound S-D1.

Basic degradation (0.15N NaOH at RT). 3 mL of the sample stock solution (see above) into an 8 mL vial, added 3 mL of 0.3N NaOH solution, and mixed well. Samples were prepared in quadruplicate and kept at room temperature (RT). At the sampling time point, 1 mL of the sample was transferred into a 5 mL volumetric flask, neutralized with 0.5 mL of 2N NaOH, diluted to volume with diluent 2, and mixed well.

Blank: a blank has been prepared following the same procedure as described above, only without the inclusion of compound S-D1.

Thermal stress degradation (50° C. for solid). Approximately 150 mg of compound S-D1 were weighed into an 8 mL vial. Multiple samples were prepared and placed in an oven at 50° C. At the sampling time points, each of the 50.57 mg, 50.84 mg, and 50.84 mg samples were transferred into their respective 100 mL volumetric flasks, dissolved by ultrasonic in 50 mL of diluent 2, diluted to volume with diluent 2, and mixed well.

Solution Stability. The study was performed according to the conditions outlined in Table 15 using sample solution for pH=4.0 solution stability, sample solution for pH=5.0 solution stability, and sample solution for pH=7.0 solution stability (see above).

Blank: a blank has been prepared following the same procedure as described above, only without the inclusion of sample.

Sample Analysis

TABLE 16

| HPLC Method | |
| --- | --- |
| Mobile Phase | MeOH:MeCN = 3:7 (v/v) + 25 mM FA + 25 mM $NH_3$ |
| Column | Cellulose SB, 100*4.6 mm, 3.0 μm |
| Needle Wash | MeOH |
| Injection volume | 1 μL |
| Column Temperature | 30° C. |
| Flow Rate | 0.8 mL/min |

TABLE 16-continued

| HPLC Method | |
| --- | --- |
| Diluent | 0.05% FA in MeCN:THF = 1:1 (v/v) |
| Autosampler Temperature | RT |
| Detection | 280 nm |

| | Time (minute) | Mobile Phase (%) |
| --- | --- | --- |
| Isocratic | 0.0 | 100 |
| | 8.0 | 100 |
| Data Record Time | 8 minutes | |

TABLE 17

| Summary | | | | | | |
| --- | --- | --- | --- | --- | --- | --- |
| Degradation Type | Stress Solvent/ Conditions | Time | Sample Number | Area % (R-D1) | Area % (S-D1) | % Degradation |
| Unstressed | N/A | N/A | 0 | 0.823 | 99.177 | N/A |
| Acid Hydrolysis | 1N HCl RT | 0 h | 1 | 0.825 | 99.176 | 0.002 |
| | | 1 d | 2 | 0.828 | 99.172 | 0.005 |
| | | 2 d | 3 | 0.834 | 99.166 | 0.011 |
| | | 3 d | 4 | 0.839 | 99.161 | 0.016 |
| Base Hydrolysis | 0.15 N NaOH RT | 0 h | 5 | 19.083 | 80.917 | 18.260 |
| | | 1 h | 6 | 53.033 | 46.967 | 52.210 |
| Thermal | 50° C. | 1 d | 7 | 1.001 | 98.999 | 0.178 |
| | | 3 d | 8 | 1.154 | 98.847 | 0.331 |
| | | 7 d | 9 | 1.203 | 98.797 | 0.380 |
| Solution Stability | pH = 4.0, 50 mM Sodium citrate buffer at RT | 0 h | 10 | 0.921 | 99.079 | 0.098 |
| | | 1 d | 11 | 0.962 | 99.038 | 0.139 |
| | | 2 d | 12 | 1.124 | 98.876 | 0.301 |
| | | 3 d | 13 | 1.305 | 98.695 | 0.482 |
| | pH = 5.0 50 mM Sodium citrate buffer at RT | 0 h | 14 | 1.471 | 98.529 | 0.648 |
| | | 1 d | 15 | 1.861 | 98.139 | 1.038 |
| | | 2 d | 16 | 2.230 | 97.770 | 1.407 |
| | | 3 d | 17 | 2.825 | 97.175 | 2.002 |
| | pH = 7.0 Phosphate buffer at RT | 0 h | 18 | 11.555 | 88.445 | 10.732 |
| | | 1 d | 19 | 19.745 | 80.255 | 18.922 |
| | | 2 d | 20 | 28.374 | 71.626 | 27.551 |
| | | 3 d | 21 | 35.926 | 64.074 | 35.103 |

TABLE 18

| Summary result of resolution | | | | | | | | |
| --- | --- | --- | --- | --- | --- | --- | --- | --- |
| | Resolution between compound R-D1 peak and its adjacent peak | | | Resolution between compound S-D1 peak and its adjacent peak | | | Purity Factor | | |
| Sample Number | Result | Criteria | Pass/ Fail | Result | Criteria | Pass/ Fail | Result | Criteria | Pass/ Fail |
| 4 | 1.3 | ≥1.2 | Pass | 2.0 | ≥1.2 | Pass | 999.917 | >990 | Pass |
| 6 | 1.8 | | | 4.4 | | | 996.140 | | |
| 9 | 1.8 | | | 2.3 | | | 999.152 | | |
| 13 | 1.7 | | | 3.7 | | | 999.947 | | |
| 17 | 1.9 | | | 4.1 | | | 999.616 | | |
| 21 | 2.1 | | | 3.9 | | | 999.728 | | |

Example 17—Stability Studies of the Intravenous Formulations of the Compound of Formula I The data obtained in this study indicate that superior stability may be obtained at lower temperature 2-5° C. vs 2500 vs 4000, lower pH ~5 vs ~6, and higher concentration of sulfobutylether-β-cyclodextrin (SBECD) 20% vs 10% vs 0%. Samples stored at 2-5° C., pH ~5 containing 20% SBECD showed the lowest amount of degradation. SBECD percentages in this Example are (w/w).

HPLC Method. Key method parameters are listed in Table 19.

TABLE 19

Key Method Parameters

| HPLC Column | Waters RP Shield C18, 4.6 × 250 mm, 5 mm | | |
|---|---|---|---|
| | Time (min) | % A 10 mM ammonium bicarbonate, adjusted to pH 6.5 with formic acid | % B Acetonitrile |
| Mobile Phase | 0 | 90 | 10 |
| | 25 | 20 | 80 |
| | 30 | 20 | 80 |
| | 30.1 | 90 | 10 |
| | 35 | 90 | 10 |
| Column Temp. | 40° C. | | |
| Autosampler Temp. | Room Temperature | | |
| Flow Rate | 1.0 mL/min | | |
| Injection Volume | 5 μL | | |
| Detection | UV 254 nm | | |
| Run Time | 35 min | | |
| Target Conc. | 0.5 mg/mL | | |
| Standard Prep | Dissolved in $H_2O$ (1 drop of 0.1N HCl added to solubilize if needed) | | |
| Sample Prep | Dilute 20 mg/mL solution 40 folds in DI water to obtain 0.5 mg/mL concentration | | |

The chromatogram of the racemate of the free base of the compound of Formula I is described below. The retention time of the parent compound peak is approximately 18 min (Peak #11 below). The two major degradant peaks have retention times of 12.2 and 12.4 min (RRT's 0.67 and 0.68, respectively). The HPLC purity of the racemate of the free base of the compound of Formula I as provided was found to 97.1 %

| | Peak # | RT | RRT | Area % |
|---|---|---|---|---|
| Typical Chromatograms | 1 | 12.172 | 0.67 | 0.02 |
| | 2 | 12.407 | 0.69 | 0.04 |
| | 3 | 13.545 | 0.75 | 0.67 |
| | 4 | 14.391 | 0.80 | 0.19 |
| | 5 | 14.558 | 0.81 | 0.44 |
| | 6 | 14.784 | 0.82 | 0.25 |
| | 7 | 15.6 | 0.86 | 0.17 |
| | 8 | 15.758 | 0.87 | 1.05 |
| | 9 | 16.32 | 0.90 | 0.07 |
| | 10 | 16.904 | 0.94 | 0.04 |
| | 11 | 18.066 | 1.00 | 97.06 |
| Total | | | | 100 |

Stability Studies

Summary of Experiments. It was found that complete dissolution of the racemate of the free base of the compound of Formula I may be achieved at pH 3 (e.g., by lowering the pH with a hydrochloric acid solution). The pH of the compounding solution would later be adjusted by sodium hydroxide solution to the target pH. It was found that formulations containing 0% or 10% SBECD showed diminished solubility at both pH 5 and pH 6 compared (less than 20 mg/mL). Only samples containing 20% SBECD (samples S-1.1 and S-2.1) were fully soluble at the desired pH. While the free-base of the compound of Formula I had high solubility at pH 3 in all formulations, significant precipitation was observed upon adjusting the pH when the formulation contained <20% SBECD. Formulations containing 0% SBECD or 10% SBECD showed significant decomposition at both pH 5 and pH 6 over 1 week ranging from ~10-43% at 40° C. In general, decomposition was found to be lower at lower temperatures.

Sample Preparation. To a 20 mL scintillation vial was added 60 mg of the racemate of the free base of the compound of Formula I and a magnetic stir bar. 3 mL of formulation solution (either 0%, 10% or 20% w/w SBECD in $H_2O$) was added. The pH of the mixture was adjusted to approximately pH 3 by the addition of 1N HCl. Upon full dissolution (with magnetic stirring, sonication if necessary), the IV formulation was adjusted to the final pH by the addition of 1N NaOH solution. The IV formulation was filtered through a syringe filter, separated into 3 samples of approximately equal volume, and the samples were transferred to a stability chamber at 2-5° C., 25° C., or 40° C. At the specified time point the sample was removed from the stability chamber, an aliquot of the IV formulation was removed and diluted to 0.5 mg/mL with $H_2O$ for HPLC analysis.

Stability Data. IV formulations of free-base compound D1 were prepared at different concentrations of SBECD and different pH levels as shown in Table 20.

TABLE 20

| Sample ID | API | pH | SBECD w/w |
|---|---|---|---|
| C-1 | 20 mg/mL | 5.23 | — |
| S-1.1 | 20 mg/mL | 5.04 | 20% |
| S-1.2 | 20 mg/mL | 5.33 | 10% |
| C-2 | 20 mg/mL | 6.33 | — |
| S-2.1 | 20 mg/mL | 6.19 | 20% |
| S-2.2 | 20 mg/mL | 6.40 | 10% |

As noted above, significant precipitation of compound D1 occurred upon adjusting the IV formulation to the final pH level of 5 or 6 for IV formulations containing <20% SBECD. IV formulations containing %20 SBECD showed no precipitation. IV formulations were filtered prior to conducting the stability studies.

The stability data (in Area % of main API HPLC peak relative to total Area %) at 2-5° C., 25° C., and 40° C. are included in Table 21.

TABLE 21

| | | 2-5° C. | | | | 25° C. | | | | 40° C. | | |
|---|---|---|---|---|---|---|---|---|---|---|---|---|
| | t = 0 | t = 24 h | t = 48 h | t = 1 week | Area % of API lost | t = 24 h | t = 48 h | t = 1 week | Area % of API lost | t = 24 h | t = 48 h | t = 1 week | Area % of API lost |
| C-1 | 97.06 | 69.33 | 69.01 | 52.04 | 45.02 | 87.23 | 74.64 | 65.71 | 31.35 | 83.28 | 83.10 | 80.88 | 16.18 |
| S-1.1 | | 96.05 | 95.94 | 95.93 | 1.14 | 95.44 | 95.16 | 94.93 | 2.13 | 93.72 | 94.32 | 93.46 | 3.60 |
| S-1.2 | | 92.52 | 92.28 | 92.21 | 4.85 | 91.17 | 90.14 | 91.03 | 6.03 | 88.98 | 88.85 | 85.17 | 11.89 |
| C-2 | | 79.02 | 78.822 | 63.91 | 33.15 | 86.99 | 85.85 | 75.73 | 21.33 | 81.01 | 80.79 | 77.04 | 20.02 |
| S-2.1 | | 95.45 | 95.27 | 95.50 | 1.56 | 94.27 | 93.90 | 93.30 | 3.76 | 92.73 | 92.43 | 88.69 | 8.37 |
| S-2.2 | | 89.52 | 89.19 | 87.04 | 10.02 | 83.05 | 78.58 | 68.16 | 28.90 | 71.26 | 64.91 | 54.85 | 42.21 |

The stability data (in Area % of main API HPLC peak relative to Area % of major degradants only) at 2-5° C., 25° C., and 40° C. are included in Table 22.

TABLE 22

| | | | 2-5° C. | | | | 25° C. | | | | 40° C. | | |
|---|---|---|---|---|---|---|---|---|---|---|---|---|---|
| C-1 | Peak # | RRT | t = 24 h | t = 48 h | t = 1 week | Area % of API lost | t = 24 h | t = 48 h | t = 1 week | Area % of API lost | t = 24 h | t = 48 h | t = 1 week | Area % of API lost |
| | 1 | 0.67 | 0.54 | 2.37 | * | — | 0.81 | 3.35 | 3.93 | 11.38 | 1.92 | 2.92 | 4.09 | 12.17 |
| | 2 | 0.68 | 1.25 | 5.89 | * | | 1.79 | 7.85 | 7.46 | | 3.98 | 6.95 | 8.08 | |
| | 3 | 1.00 | 98.21 | 91.74 | * | | 97.41 | 88.81 | 88.62 | | 94.09 | 90.13 | 87.83 | |
| | Total | | 100 | 100 | | | 100 | 100 | 100 | | 100 | 100 | 100 | |
| S-1.1 | Peak # | RRT | t = 24 h | t = 48 h | t = 1 week | Area % of API lost | t = 24 h | t = 48 h | t = 1 week | Area % of API lost | t = 24 h | t = 48 h | t = 1 week | Area % of API lost |
| | 1 | 0.67 | 0.10 | 0.10 | 0.10 | <0.5% | 0.14 | 0.23 | 0.30 | 0.95 | 0.35 | 0.46 | 1.06 | 3.31 |
| | 2 | 0.68 | 0.23 | 0.31 | 0.22 | | 0.27 | 0.59 | 0.65 | | 0.7 | 91.15 | 2.25 | |
| | 3 | 1.00 | 99.67 | 99.59 | 99.68 | | 99.59 | 99.19 | 99.05 | | 98.87 | 98.39 | 96.69 | |
| | Total | | 100 | 100 | 100 | | 100 | 100 | 100 | | 100 | 100 | 100 | |
| S-1.2 | Peak # | RRT | t = 24 h | t = 48 h | t = 1 week | Area % of API lost | t = 24 h | t = 48 h | t = 1 week | Area % of API lost | t = 24 h | t = 48 h | t = 1 week | Area % of API lost |
| | 1 | 0.67 | 0.18 | 0.28 | 0.23 | 0.85 | 0.38 | 0.56 | 1.08 | 3.73 | 0.94 | 1.56 | 3.09 | 9.94 |
| | 2 | 0.68 | 0.47 | 0.80 | 0.62 | | 0.90 | 1.60 | 2.65 | | 2.22 | 4.07 | 6.85 | |
| | 3 | 1.00 | 99.35 | 98.92 | 99.15 | | 98.72 | 97.84 | 96.27 | | 96.84 | 94.37 | 90.06 | |
| | Total | | 100 | 100 | 100 | | 100 | 100 | 100 | | 100 | 100 | 100 | |
| C-2 | Peak # | RRT | t = 24 h | t = 48 h | t = 1 week | Area % of API lost | t = 24 h | t = 48 h | t = 1 week | Area % of API lost | t = 24 h | t = 48 h | t = 1 week | Area % of API lost |
| | 1 | 0.67 | 1.80 | 1.258 | * | — | 2.18 | 2.09 | 5.06 | 15.08 | 3.49 | 4.26 | 6.19 | 18.32 |
| | 2 | 0.68 | 4.04 | 3.223 | * | | 4.85 | 5.26 | 10.01 | | 7.25 | 10.40 | 12.13 | |
| | 3 | 1.00 | 94.17 | 95.52 | * | | 92.98 | 92.65 | 84.93 | | 89.26 | 85.35 | 81.69 | |
| | Total | | 100 | 100 | | | 100 | 100 | 100 | | 100 | 100 | 100 | |

TABLE 22-continued

| S-2.1 | Peak # | RRT | t = 24 h | t = 48 h | t = 1 week | Area % of API lost | t = 24 h | t = 48 h | t = 1 week | Area % of API lost | t = 24 h | t = 48 h | t = 1 week | Area % of API lost |
|---|---|---|---|---|---|---|---|---|---|---|---|---|---|---|
| | 1 | 0.67 | 0.16 | 0.25 | 0.20 | 0.70 | 0.27 | 0.45 | 0.81 | 2.88 | 0.63 | 1.11 | 2.34 | 7.78 |
| | 2 | 0.68 | 0.36 | 0.64 | 0.50 | | 0.65 | 1.29 | 2.07 | | 1.47 | 3.02 | 5.44 | |
| | 3 | 1.00 | 99.49 | 99.11 | 99.30 | | 99.07 | 98.27 | 97.12 | | 97.90 | 95.88 | 92.22 | |
| | Total | | 100 | 100 | 100 | | 100 | 100 | 100 | | 100 | 100 | 100 | |

| S-2.2 | Peak # | RRT | t = 24 h | t = 48 h | t = 1 week | Area % of API lost | t = 24 h | t = 48 h | t = 1 week | Area % of API lost | t = 24 h | t = 48 h | t = 1 week | Area % of API lost |
|---|---|---|---|---|---|---|---|---|---|---|---|---|---|---|
| | 1 | 0.67 | 0.99 | 1.51 | 2.04 | 8.02 | 2.92 | 4.40 | 8.22 | 28.98 | 7.16 | 8.73 | 13.18 | 43.55 |
| | 2 | 0.68 | 2.61 | 4.52 | 5.98 | | 7.35 | 12.67 | 20.77 | | 16.75 | 23.08 | 30.36 | |
| | 3 | 1.00 | 96.40 | 93.97 | 91.98 | | 89.74 | 82.93 | 71.02 | | 76.09 | 68.19 | 56.46 | |
| | Total | | 100 | 100 | 100 | | 100 | 100 | 100 | | 100 | 100 | 100 | |

*Sample for analysis contained minimal API due to precipitation of sample overtime In the data table above only the Area % values for the API and the major degradation products (RRT's 0.67 and 0.68) are provided. It is important to note that the initial ~3% impurity in the initially provided sample of free-base compound D1 is present in the sample throughout the stability studies and in some cases (particularly at 40° C.) these initial impurities are further degraded to a variety of new peaks with ~3% combined area in overall intensity.

As an example, the HPLC trace of IV formulation S-1.1 after 1 week at 40° C. is included below. With consideration to only the 2 major degradants (RRT's 0.67 and 0.68) the Area % of the API in the sample is approximately 96.7% (as reported in the full data table above). With consideration of the additional impurities present in the initial sample the Area % of the API in the sample is approximately 93.5%

In Vitro Dissolution Test of IV Formulation. The in vitro dissolution test method on IV formulation samples has been completed in accordance with the method as provided by Foghorn. IV formulation samples were prepared as above. Both IV formulations C-1 and C-2 showed initial precipitation upon dilution of the IV formulation with diluent (step 1 in procedure provided, left-most vial in pictures below) but eventually became fully homogenous with full dilution (step 4 in procedure provided; right-most vial in pictures below). All other IV formulations did not show any precipitate throughout the test or become cloudy.

Example 18—Lyophilized Formulations of the Compound of Formula I

General Procedure

1) An appropriately sized beaker and stir bar was obtained for drug product formulation.

2) An 80% charge of WFI was dispensed into the formulation beaker, which was then placed on a stir plate and mixing was initiated.

3) A 20 mM citrate buffer at pH 4.5 was compounded by adding citric acid, monohydrate and sodium citrate, dihydrate at proper concentrations and dissolving them.

4) The required amount of SBECD (Captisol) was added to the formulation vessel, and mixed until fully dissolved.

5) The formulation vessel, DS, and magnetic stir plate was moved inside an isolator.

6) The required amount of compound S-D1 was measured, added to the formulation vessel, and mixed until fully dissolved. The solution and stir bar were then removed from the isolator.

7) The pH of the solution was determined, and adjusted to 4.5±0.1, if necessary.

8) The solution was then QSed with WFI using an appropriately sized volumetric flask or graduated cylinder. The solution was then dispensed back into the vessel and mixed for an additional five minutes.

9) The solution was then filtered with a 0.22 µm PES/PVDF filter.

10) A sample post-filter for density was removed. The fill weight and fill range were calculated based on a 5 mL fill volume.

11) A 3.2 mm tubing set was installed onto a peristaltic pump, and the pump was set to dispense the required mass per vial of product. Three consecutive passing weight checks were performed before continuing.

12) The filtered solution was dosed into vials and a fill check performed every 50 vials.

13) Once filling was complete, the vials were stoppered with 20 mm stoppers in the lyophilization position. Thermocouples were added to vials as necessary.

14) Vials were unloaded onto a lyophilizer shelf. The lyophilizer door was then sealed and the cycle initiated.

15) Once the cycle was complete, vials were backfilled with filtered nitrogen to 600,000 mTorr and stoppered. Once stoppered, the vacuum was broken to atmospheric pressure the vials were removed from the lyophilizer.

16) Vials were capped with 20 mm caps and visually inspected for any defects.

17) Acceptable finished product samples were then sampled for finished product testing, including appearance, reconstitution time, pH, osmolality, residual moisture, assay/related substances, X-Ray diffraction, and particulate matter.

18) Vials were then packaged and stored at 2-8° C.

Experiment 1

The pH screening study formulations are summarized in Table 23.

TABLE 23

| | Formulation ID | | | |
|---|---|---|---|---|
| | R1 | R2 | R3 | R4 |
| Buffer | N/A | Citrate 20 mM | Citrate 20 mM | Citrate 20 mM |

TABLE 23-continued

| | Formulation ID | | | |
|---|---|---|---|---|
| | R1 | R2 | R3 | R4 |
| SBECD | 200 mg/mL | 200 mg/mL | 200 mg/mL | 200 mg/mL |
| pH | 4.0 | 4.0 | 4.5 | 4.5 |
| Compound S-D1 | 5 mg/mL | 5 mg/mL | 5 mg/mL | 10 mg/mL |

Formulation, Filtration, and Filling. The formulation was performed as described in the General Procedure section above. Excipients were added based on their proposed concentration for each sublot. The density of each sublot was taken to determine the fill volume on a mass basis, and a sample from Sublot R1 was taken for thermal analysis (see Section 13.0). Each solution was then filtered with a 0.22 μm PVDF Stericup filter into a HEPA-filtered hood. Filtration was slow, taking approximately 15 to 20 minutes for each sublot. Each sublot was filled into respectively labelled 20R vials at 5 mL/vial for sublots R1 to R3 while sublot R4 was filled at 2.5 mL per vial. Thermocouples were inserted into a vial in each sublot and subsequently loaded into the lyophilizer. The product was lyophilized using a conservative cycle to ensure lyophilized product quality.

Figure 25:
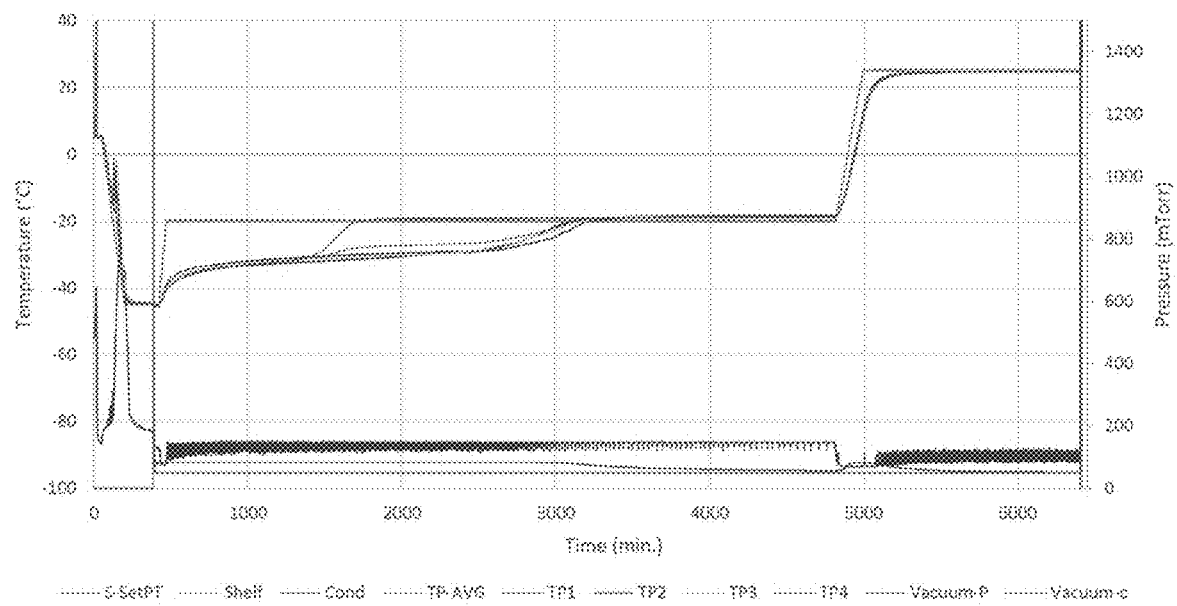
FIG. 25 is a chart outlining the lyophilization run for a lyophilized formulation of compound S-D1. Temperature is shown on the first y-axis. Vacuum is shown on the second y-axis. Time is shown on the x-axis. Shelf inlet temperature, shelf set point, condenser temperature, product average temperature, individual product temperatures (TP1-TP4), Pirani gauge vacuum level, and capacitance manometer vacuum level are shown.

Lyophilization. Vials were loaded onto a shelf controlled at 5.0° C. Once thermocouples were inserted, a slight vacuum was applied to the system to seal the door from the external environment. The loading temperature was held at 5.0° C. for 30 minutes to allow all vials to reach equilibrium. The shelf temperature was ramped to −45.0° C. over 150 minutes and held for 180 minutes to ensure all vials were thoroughly frozen. The lyophilizer condenser was then chilled, and vacuum was pulled to 50 mTorr. Once the vacuum set-point was achieved, the shelf temperature was ramped to −20.0° C. over 50 minutes and held constant for 4,350 minutes. Completion of primary drying was indicated by the convergence of the Pirani gauge with the capacitance manometer, as shown in FIG. 2. The vacuum gauges converged within at approximately 3,800 minutes of primary drying. Following completion of primary drying, the shelf temperature was ramped to 25.0° C. over 180 minutes and held for 1,410 minutes. At the completion of secondary drying, the system was backfilled with nitrogen to ~600,000 mTorr and vials were fully stoppered. The programmed lyophilization cycle is shown in Table 24 and the run chart is shown in FIG. 25.

TABLE 24

| Step # | Operation | Temperature (° C.) |
|---|---|---|
| 1 | Load Set Point | 5.0 |

| | Door Seal | |
|---|---|---|
| Step # | Operation | Pressure (mTorr) |
| 2 | Seal Door | ~550,000 |

| | Thermal Treatmen | | |
|---|---|---|---|
| Step # | Operation | Shelf Temperature (° C.) | Duration (min) |
| 3 | Hold | 5.0 | 30 |
| 4 | Ramp | −45.0 | 150 |
| 5 | Hold | −45.0 | 180 |

TABLE 24-continued

| Step # | Operation | Shelf Temperature (° C.) | Vacuum (mTorr) | Duration (min) |
|---|---|---|---|---|
| | Primary Drying | | | |
| 10 | Hold | −45.0 | 50 | 30 |
| 11 | Ramp | −20.0 | 50 | 50 |
| 12 | Hold | −20.0 | 50 | 4,350 |
| | Secondary Drying | | | |
| 13 | Ramp | 25.0 | 50 | 180 |
| 14 | Hold | 25.0 | 50 | 1,410 |

| Step # | Operation | Shelf Temperature (° C.) |
|---|---|---|
| | Shut Down | |
| 15 | Backfill with nitrogen gas to 11.6 PSIA = ~600,000 mTorr | 25.0 |
| 16 | Stopper vials. | 25.0 |
| | Unloading | |
| 17 | Unload | 20.0 |
| | Total Time | 6,380 minutes (106.3 hrs)[1] |

Packaging and Storage. Lyophilized vials were capped with flip-off 20 mm caps and inspected. Thermocouple vials were rejected. A total of 701 vials were acceptable (approximately 175 per sublot). Vials were sampled for t=0 testing, which included appearance, reconstitution time, pH, osmolality, residual moisture, assay/related substances, X-Ray diffraction, and particulate matter. Once samples were taken, each sublot was stored at 2-8° C. until a final sublot was chosen to be placed on accelerated stability.

Lyophilization Cycle Analysis. Analysis of the run chart demonstrates that shelf temperature was controlled to within 1.4° C. of the set point during all stages of the cycle. The condenser was maintained at low temperatures throughout the drying portion, and vacuum was controlled within less than 1 mTorr of the set-point.

In the lyophilization process, sublimation occurs when the vapor pressure of the frozen solvent at a certain temperature is higher than the pressure of the environment. The difference between the vapor pressure of ice at a corresponding temperature and the subsequent vacuum level of the product chamber is the driving force behind sublimation. The product temperature during primary drying is also dictated by the shelf temperature and vacuum of the shelf chamber; higher product temperatures result in a higher vapor pressure of ice, and will provide more efficient sublimation at the same vacuum level. Care must be taken, however, that the product temperature does not exceed a critical temperature (glass transition temperature, eutectic melt, etc.) that will result in a collapsed product.

Product temperatures were maintained below −24° C. during primary drying when the shelf temperature was held at −20.0° C. As the critical temperatures for each sublot were observed to be very low (see DSC and FDM Results, Section 11.0), the lyophilizer setpoints remained conservative throughout primary drying.

Figure 26:
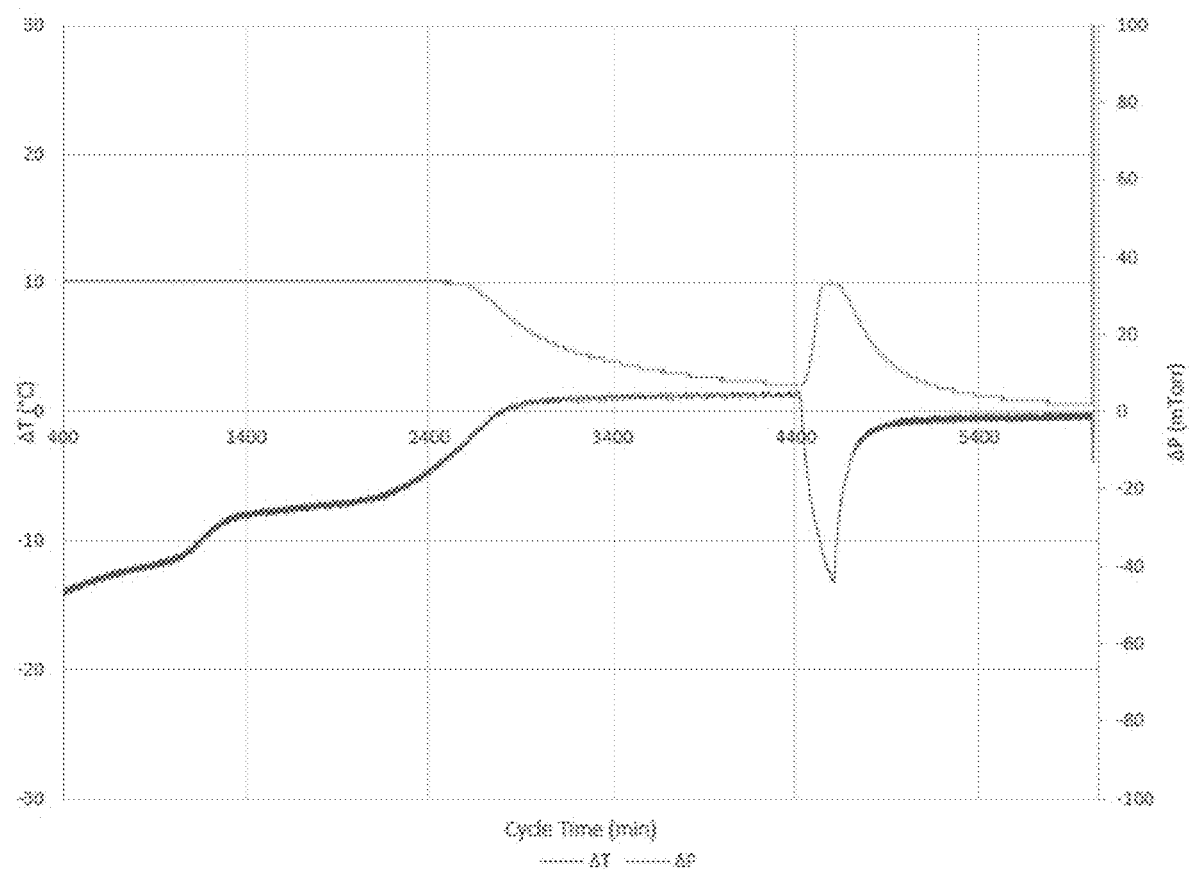
FIG. 26 is a chart showing the primary and secondary drying. The ΔP (Pirani-Capacitance) is the lower curve, and the ΔT (Product Avg-Shelf) is the upper curve.

Product temperatures were observed to converge with the shelf temperature at approximately the same time (except for Sublot R1) compared to the convergence of the Pirani vacuum gauge and the capacitance manometer. The vacuum gauge convergence is considered in the industry as the principal method for determining the end-point of primary drying. The difference in conversion times between vacuum gauges and thermocouples can be attributed to faster drying rates observed within vials containing thermocouple probes and the location of the probe within the cake. Therefore, for the purposes of future cycle development, the convergence of the vacuum gauges was used as the primary indicator for the completion of primary drying, and product temperature convergence acted as a secondary confirmation (FIG. 26). Vacuum gauge convergence for this cycle occurred at 3,800 minutes from the start of the primary drying ramp. The full convergence is determined as the point where the Pirani gauge begins to plateau close to the capacitance reading within 5 mTorr of the vacuum setpoint.

When the cycle was advanced to secondary drying, an increase in the Pirani gauge reading was observed. This indicated additional moisture being removed from vials as bound water via desorption. This is consistent with amorphous products, which tend to bind or trap water molecules. Product temperatures followed closely with the shelf temperature through the ramp to secondary drying and throughout the secondary drying hold. This is consistent with a dried cake with no residual bound or un-bound water.

Finished Product Testing Results. Acceptable finished product vials were analyzed by LSNE for t=0 finished product testing. Vials for HPLC and particulate matter were performed by LSNE QC Analytical, and X-Ray diffraction was performed at a third-party lab. The HPLC method was in development at the time this report was written; THE and 0.9% NaCl were used for dilution due to the method still being under development. The t=0 finished product results are shown in Tables 26-28.

TABLE 26

| Test | Specification | Sublots | | | |
|---|---|---|---|---|---|
| | | R1 | R2 | R3 | R4 |
| Appearance (Lyophilized) | Report | Acceptable | Acceptable | Acceptable | Acceptable |
| Appearance (Reconstituted) | Report | Acceptable | Acceptable | Acceptable | Acceptable |
| Reconstitution Time | Report | 34 sec | 39 sec | 38 sec | 24 sec |
| pH | Report | 4.15 | 3.94 | 4.43 | 4.44 |
| Osmolality | Report | 576 | 600 | 606 | 448 |
| Residual Moisture via KF | NMT 3.0% | 0.527% | 0.557% | 0.533% | 0.469% |

Note:
all vials were tested in duplicate - the average between the two runs is reported.
Diluent used for reconstitution was 0.9% NaCl.

TABLE 27

| | | Sublots | | | | | |
|---|---|---|---|---|---|---|---|
| | | R1 | R2 | | R3 | | R4 | |
| Test | Specification | THF | THF | 0.9% NaCl | THF | 0.9% NaCl | THF | 0.9% NaCl |
| Assay (mg/mL) | 93%-110% or 23.25 mg/mL-27.5 mg/mL | 2.30 | 18.01 | 21.60 | 19.01 | 21.62 | 21.51 | 24.22 |
| Related Substances | Purity-Report | 25.71 | 96.96 | 97.69 | 97.69 | 97.79 | 97.44 | 97.72 |
| | RRT 0.65 | 55.87 | 0.42 | 0.31 | 0.28 | 0.24 | 0.37 | 0.31 |
| | RRT 0.83 | 18.42 | 1.95 | 1.33 | 1.28 | 1.22 | 1.80 | 1.69 |
| | RRT 0.89 | ND | ND | ND | 0.09 | 0.08 | ND | ND |
| | RRT 1.23 | ND | 0.42 | 0.41 | 0.42 | 0.41 | 0.39 | 0.28 |
| | RRT 1.69 | ND | 0.24 | 0.26 | 0.25 | 0.27 | ND | ND |
| Particulate Matter | NMT 6 K Particles ≥ 10 μm | 284 | 357 | | 397 | | 401 | |
| | NMT 600 Particles ≥ 25 μm | 15 | 19 | | 53 | | 28 | |

Note:
all vials were tested in duplicate-the average between the two runs is reported.
The HPLC method was performed twice with THF and 0.9% NaCl as the diluents.
ND = Not Detected.

TABLE 28

| Test | Specification | Sublots | | | |
|---|---|---|---|---|---|
| | | R1 | R2 | R3 | R4 |
| Assay (mg/mL) | 90%-110% or 23.25 mg/mL-27.5 mg/mL | 11.3 | 24.0 | 24.6 | 24.1 |

Note:
all vials were tested in duplicate - the average between the two runs is reported.
ND = Not Detected.

Critical Temperature Determination

Figure 27:
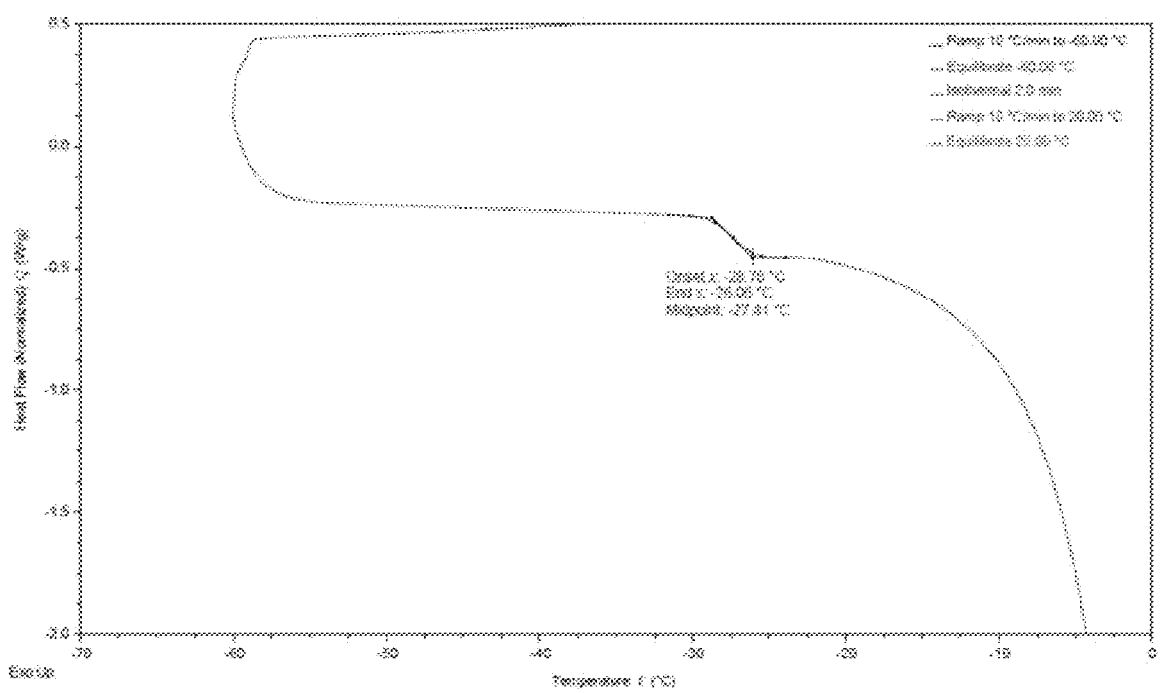
FIG. 27 is a chart showing a DSC thermogram for Sublot R3 of a formulation of compound S-D1.

Differential Scanning Calorimetry. Each sample was tested by DSC to determine if any glass transition temperatures (Tg'), eutectic melt temperatures (Teu), or re-crystallization temperatures (Tcry) were present. Standard 10° C./min and 2° C./min heat cycles were performed. The results from DSC analysis are described in Table 29, and a representative figure of a thermogram is described in FIG. 27.

TABLE 29

| | Sublot R3 | | | |
|---|---|---|---|---|
| | Tnuc (° C.) | Tg (° C.) | Tcry (° C.) | Tmelt (° C.) |
| Method 1, Run 1 (10° C./min) | −21.4 | −27.41 | N/A | −6.06 |
| Method 1, Run 2 (10° C./min) | −19.66 | −27.49 | N/A | −5.61 |
| Method 2, Run 1 (2° C./min) | −23.16 | −28.95 | N/A | −5.47 |
| Method 2, Run 2 (2° C./min) | −20.30 | −29.08 | N/A | −5.27 |
| Average: | −21.13 | −28.23 | N/A | −5.60 |

DSC testing consisted of running two different methods. The methods consisted of standard freeze/heat DSC cycles, employing a heating rate of 10° C./min and 2° C./min, respectively. The higher heating rate method (Method 1, 10° C./min) is used to increase the amplitude of critical temperatures at the expense of temperature accuracy, while the lower ramp rate (Method 2) is used to define critical temperatures more accurately at the expense of the larger amplitude.

Figure 28:
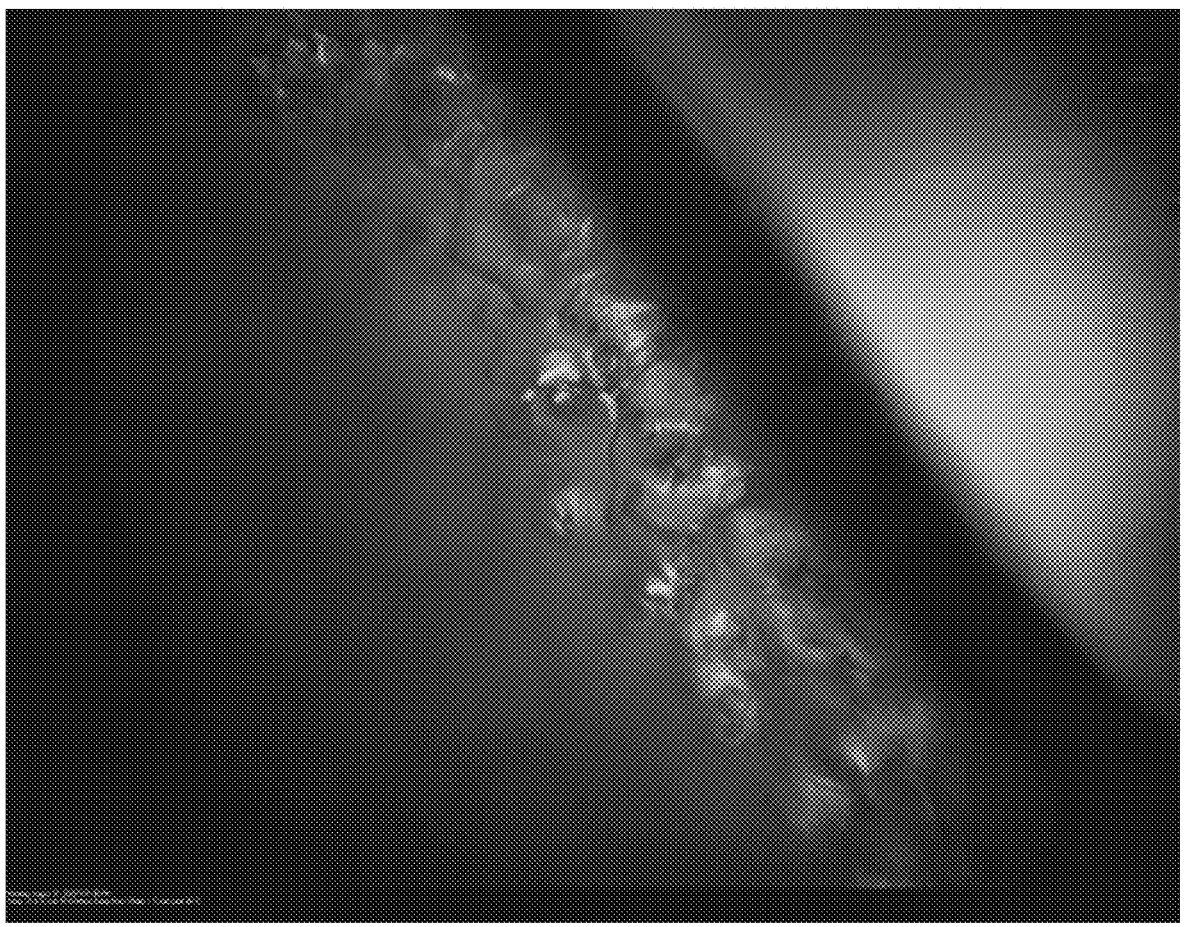
FIG. 28 is an image of the formulation of compound S-D1 obtained using freeze-drying microscopy.

Freeze-Drying Microscopy. A sample was retained and thermally characterized via freeze-drying microscopy (FDM). Additionally, an annealing FDM cycle was run to determine the effect of annealing on the collapse temperature. The annealing temperature was set above the glass transition temperature to drive crystallization during annealing. The results are described in Table 30, and a representative photo of the FDM process is shown in FIG. 28.

TABLE 30

| Method | Run # | Collapse Onset (° C.) | Average Collapse Onset (° C.) | Total Collapse (° C.) |
|---|---|---|---|---|
| 1 | 1 | −23.7 | −23.6 | −22.6 |
| | 2 | −24.2 | | −20.1 |
| | 3 | −22.9 | | −21.6 |
| 2 | 1 | −24.0 | −24.0 | −21.1 |

Low Robustness

Formulation, Filtration. Filling. The formulation was performed as described in the General Procedure above, and a total batch size of 1,000 mL was compounded. An excipient solution was generated using the proposed concentrations. The solution was pH adjusted with 1N HCl to a post-QS pH of 4.52 and a 5 mL sample was taken for density in order to determine the fill volume on a mass basis. A pre and post filtration sample was taken for HPLC analysis; results can be seen in Table 32. Filtration was performed using a PES filter into the HEPA-filtered hood. Flow visibly slowed overtime. Upon completion of filtration it was noted that the filter membrane appeared yellow. One full tray of 20R vials were assembled, and the formulation was filled to a weight of 5.43 grams per vial. All fill weights were within specification. Thermocouples were inserted as required, and the trays were loaded into the lyophilizer. The cycle was initiated according to Table 31.

Lyophilization. Vials were loaded onto a shelf controlled at 5.0° C. Once thermocouples were inserted, a slight vacuum was applied to the system to seal the door from the external environment. The loading temperature was held at 5.0° C. for 30 minutes to allow all vials to reach equilibrium. The shelf temperature was ramped to −45.0° C. over 100 minutes and held for 840 minutes to ensure all vials were thoroughly frozen. The shelves were then ramped to −50° C. over 10 minutes and held for an additional 60 minutes. The lyophilizer condenser was then chilled, and vacuum was pulled to 70 mTorr. Once the vacuum set-point was achieved (approximately 30 minutes), the shelf temperature was ramped to −20.0° C. over 60 minutes and held for 3,930 minutes. Completion of primary drying was indicated by the convergence of the Pirani gauge with the capacitance manometer. The vacuum gauges plateaued after approximately 3,600 minutes of primary drying time. Following completion of primary drying, the shelf temperature was ramped to 25.0° C. over 180 minutes and held for 1,450 minutes. Samples were taken over the course of secondary drying in order to map the residual moisture overtime (See Table 15). At the completion of secondary drying, the system was backfilled with nitrogen to ~600,000 mTorr and vials were fully stoppered. The programmed lyophilization cycle is shown in Table 31.

TABLE 31

| Step # | Operation | Temperature (° C.) | | |
|---|---|---|---|---|
| 1 | Load Set Point | 5.0 | | |

Door Seal

| Step # | Operation | Pressure (mTorr) | | |
|---|---|---|---|---|
| 2 | Seal Door | ~550,000 | | |

Thermal Treatment

| Step # | Operation | Shelf Temperature (° C.) | Duration (min) | |
|---|---|---|---|---|
| 3 | Hold | 5.0 | 30 | |
| 4 | Ramp | −45.0 | 100 | |
| 5 | Hold | −45.0 | 840 | |
| 6 | Ramp | −50.0 | 10 | |
| 7 | Hold | −50.0 | 60 | |

| Step # | Operation | Shelf Temperature (° C.) | Vacuum (mTorr) | Duration (min) |
|---|---|---|---|---|

Primary Drying

| | | | | |
|---|---|---|---|---|
| 8 | Hold | −50.0 | 70 | 30 |
| 9 | Ramp | −20.0 | 70 | 60 |
| 10 | Hold | −20.0 | 70 | 3,930 |

Secondary Drying

| | | | | |
|---|---|---|---|---|
| 11 | Ramp | 25.0 | 70 | 180 |
| 12 | Hold | 25.0 | 70 | 1,450 |

TABLE 31-continued

| Step # | Operation | Shelf Temperature (° C.) |
|---|---|---|
| | Shut Down | |
| 13 | Backfill with nitrogen gas to ~600,000 mTorr | 25.0 |
| 14 | Stopper vials. | 25.0 |
| | Unloading | |
| 15 | Unload | 25.0 |
| | Total Time | 6,690 minutes (111.5 hrs)[1] |

[1]total cycle time does not account for the time required to reach vacuum or unloading.

Lyophilization Cycle Analysis. During thermal treatment, the shelf temperature was lowered to −45° C. and held for several hours before being lowered to −50° C., which was held for 60 minutes. This ensures that the ramp rate matches the extended time it takes to get to the primary drying temperature. After thermal treatment of the product, run chart demonstrates that shelf temperature was controlled to within ±2° C. of the set point during all stages of the cycle. The condenser was maintained at low temperatures throughout the drying portion, and vacuum was controlled within ±2 mTorr of the set-point.

Product temperatures were observed to reach a temperature of approximately −35.0° C. at the beginning of the primary drying hold. The product temperatures then increase until thermocouple break point at approximately 2,700 minutes of primary drying.

The convergence of the Pirani vacuum gauge and the capacitance manometer occurred after the thermocouple gauge convergence. Vacuum gauge convergence for this cycle was allowed to fully complete to ensure that primary drying was completed since this cycle is used to set the primary drying time of the nominal cycle. Vacuum gauge convergence (±5 mTorr) occurred at 4,800 minutes from the start of the primary drying hold. The Pirani vacuum gradually dropped throughout primary drying. After convergence, the shelf temperature was ramped into secondary drying.

When the cycle was advanced to secondary drying, an increase in the Pirani gauge reading was observed, indicating additional moisture being removed from vials as bound water via desorption. Product temperatures followed closely with the shelf temperature through the ramp to secondary drying and throughout the secondary drying hold. The secondary drying time was determined by leveraging the moisture content results from this run. Since the moisture results were passing after t=240 minutes of secondary drying, it was recommended that the secondary drying time be lengthened to further drive the moisture from 1.0% to 0.50%. At t=12 hours during secondary drying, this condition was met; the average residual moisture was 0.8216% as seen in Table 32 below.

Intentional Collapse. Vials filled for the first cycle development study were subjected to an intentional collapse experiment to verify that product would not collapse, experience ablation or cake lift, and to detect any degradation of DS. Vials were loaded at 5.0° C., which was held for 5 minutes. The shelf was then ramped to −45.0° C. over 50 minutes and held for 30 minutes before a vacuum was applied at 250 mTorr. Once the vacuum was pulled, the shelf temperature was raised to 35.0° C. over 80 minutes and held for 795 minutes. FIG. 13 shows the freeze-drying cycle for the intentional collapse study.

The lyophilized cakes were dense, pale yellow cakes with no cracks and a porous surface with significant shrinkage; mild collapse was present. After reconstituting the cakes with 10 mL of 0.9% NaCl, the solution was a pale yellow, clear solution. Representative photos can be found in FIG. 12 and finished product testing results can be seen in Table 32. The intentional collapse run showed that the product does not blow out, or experience cake lift.

TABLE 32

| Test | Specification | t = 0 | t = 2 Hours | t = 4 Hours | t = 12 Hours | Pre-Filtration | Post-Filtration | FP | IC |
|---|---|---|---|---|---|---|---|---|---|
| Appearance (Lyophilized) | Conforms | | | N/A | | | | Acceptable | Porous surface with minor collapse. |
| Appearance (Reconstituted) | Conforms | | | | | | | Acceptable | Acceptable |
| Reconstitution Time (Average) | Report | | | | | | | 41 Seconds | 23 Seconds |
| pH (Average) | Report | | | | | | | 4.41 | 4.43 |
| Osmolality (Average) | Report | | | | | | | 609 | 571 |
| Residual Moisture via KF (Average) | In Process: Report Finished Product: NMT 3.0% | 3.0180 | 1.5204 | 1.3091 | 0.8216 | N/A | | 0.5580 | 1.6424 |
| Assay | 90.0%-110.0% (Label Claim) | | N/A | | | 98.9 | 98.9 | 99.1 | 98.8 |
| Related Substances | RRT 0.543 | | | | | 0.63 | 0.60 | 0.56 | 0.56 |
| | RRT 0.954 | | | | | 0.94 | 0.87 | 0.85 | 0.84 |
| Particulate Matter | NMT 6 K Particles ≥ 10 μm | | | | | N/A | | 772 | 667 |
| | NMT 600 Particles ≥ 25 μm | | | | | | | 199 | 149 |

Nominal Cycle and High Robustness

Formulation, Filtration, Filling. The formulation was performed as described in the General Procedure above, and a total batch size of 2,000 mL was formulated to be split between both the nominal and high robustness cycles. All fill weight checks were within specification. Vials were stoppered in the lyophilization position, and thermocouples were inserted as needed.

Lyophilization—Nominal Cycle. Vials were loaded onto a shelf controlled at 20.000. Once thermocouples were inserted, a slight vacuum was applied to the system to seal the door from the external environment. The loading temperature was held at 20.0° C. for 30 minutes to allow all vials to reach equilibrium. The shelf temperature was ramped to −45.0° C. over 130 minutes and held for 180 minutes to ensure all vials were thoroughly frozen. The lyophilizer condenser was then chilled, and vacuum was pulled to 95 mTorr. Once the vacuum set-point was achieved the shelf temperature was ramped to −15.0° C. over 60 minutes and held constant for 4,770 minutes. Completion of primary drying was indicated by the convergence of the Pirani gauge with the capacitance manometer. Because of the need to pull samples during secondary drying, primary drying was extended an additional 840 minutes. Since the Low Robustness cycle showed that primary drying completed at 3,930 minutes, it was acceptable to extend primary drying to extend the cycle. The vacuum gauges converged at approximately 2,400 minutes. Following completion of primary drying, the shelf temperature was ramped to 30.0° C. over 180 minutes and held for 720 minutes. At the completion of secondary drying, the system was backfilled with nitrogen to ~600,000 mTorr and vials were fully stoppered. The programmed lyophilization cycle is shown in Table 33.

TABLE 33

| Step # | Operation | Temperature (° C.) | | |
|---|---|---|---|---|
| 1 | Load Set Point | 20.0 | | |
| Door Seal | | | | |
| Step # | Operation | Pressure (mTorr) | | |
| 2 | Seal Door | ~550,000 | | |
| Thermal Treatmen | | | | |
| Step # | Operation | Shelf Temperature (° C.) | Duration (min) | |
| 3 | Hold | 20.0 | 30 | |
| 4 | Ramp | −45.0 | 130 | |
| 5 | Hold | −45.0 | 180 | |
| Step # | Operation | Shelf Temperature (° C.) | Vacuum (mTorr) | Duration (min) |
| Primary Drying | | | | |
| 6 | Hold | −45.0 | 95 | 30 |
| 7 | Ramp | −15.0 | 95 | 60 |
| 8 | Hold | −15.0 | 95 | 4,770 |
| Secondary Drying | | | | |
| 9 | Ramp | 30.0 | 95 | 180 |
| 10 | Hold | 30.0 | 95 | 720 |

TABLE 33-continued

| Step # | Operation | Shelf Temperature (° C.) |
|---|---|---|
| Shut Down | | |
| 15 | Backfill with nitrogen gas to ~600,000 mTorr | 30.0 |
| 16 | Stopper vials. | 30.0 |
| Unloading | | |
| 17 | Unload | 30.0 |
| | Total Time | 6,100 minutes (101.7 hrs)[1] |

[1]total cycle time does not account for the time required to reach vacuum or unloading.

Lyophilization Cycle Analysis—Nominal Cycle. Analysis of the run chart demonstrates that shelf temperature was controlled to within 1.700 of the set point during all stages of the cycle. The condenser was maintained at low temperatures throughout the drying portion, and vacuum was controlled within ±1 mTorr of the set-point.

Product temperatures were observed to reach a maximum temperature of −26.0° C. during primary drying when the shelf temperature was held at −20.0° C., which is within the 3° C. safe zone that was applied to the collapse onset temperature as described in section 11. This was expected, as the low robustness run demonstrates the worst-case sublimation rate and lowest temperature/vacuum combination.

Product temperatures were observed to converge with the shelf temperature at a relatively similar time compared to the convergence of the Pirani vacuum gauge and the capacitance manometer. Vacuum gauge convergence occurred at approximately 2,400 minutes from the start of the primary drying hold as seen in FIG. 16. As stated above, a portion of the cycle was not recorded due to a computer malfunction therefore a portion of the convergence chart is not available and is reflected on the chart. The primary drying time was also extended in order to allow for sampling over secondary drying for high robustness. Since both cycles were running in tandem, it was decided to extend both cycles. Primary drying was already determined by the low robustness run, therefore, there is low risk associated with extending the primary drying time. The product in both cycles is thermodynamically static after convergence.

When the cycle was advanced to secondary drying, an increase in the Pirani gauge reading was observed, indicating additional moisture being removed from vials as bound water was removed from the product via desorption. Product temperatures followed closely with the shelf temperature through the ramp to secondary drying and throughout the secondary drying hold.

Packaging and Storage—Nominal Cycle. Lyophilized vials were capped with flip-off/tear-off 20 mm caps and inspected. Thermocouple vials were rejected. A total of 190 vials were acceptable. Vials were sampled for analytical testing and stored at 2-8° C.

TABLE 34

| Test | Specification | Results (Average n = 2 vials) |
|---|---|---|
| Appearance (Lyophilized) | Conforms | Acceptable |
| Appearance (Reconstituted) | Conforms | Acceptable |
| Reconstitution Time (Average) | Report | 34 Seconds |

TABLE 34-continued

| Test | Specification | Results (Average n = 2 vials) |
|---|---|---|
| pH (Average) | Report | 4.38 |
| Osmolality (Average) | Report | 588 |
| Residual Moisture via KF (Average) | NMT 3.0% | 0.6269 |
| Assay | 93.0%-107.0% (Label Claim) | 23.85 mg/mL |
| Related Substances | RRT (0.54) | 0.52 |
| | RRT (0.96) | 0.59 |
| | RRT (0.98) | ND |
| Particulate Matter | NMT 6K Particles ≥10 μm | 583 |
| | NMT 600 Particles ≥25 μm | 19 |

Lyophilization—High Robustness. Vials were loaded onto a shelf controlled at 25.0° C. Once thermocouples were inserted, a slight vacuum was applied to the system to seal the door from the external environment. The loading temperature was held at 25.0° C. for 30 minutes to allow all vials to reach equilibrium. The shelf temperature was ramped to −40.0° C. over 130 minutes and held for 180 minutes to ensure all vials were thoroughly frozen. The lyophilizer condenser was then chilled, and vacuum was pulled to 120 mTorr. Once the vacuum set-point was achieved, the shelf temperature was held at −40.0° C. for 30 minutes to allow all vials to equilibrate. The shelf was then ramped to −10.0° C. over 60 minutes and held constant for 4,770 minutes. Completion of primary drying was indicated by the convergence of the Pirani gauge with the capacitance manometer. The primary shelf temperature was held for an additional 840 minutes due to time constraints. This cycle was the high robustness condition for primary drying, the vacuum gauges were allowed to fully converge to set the timepoint for primary drying. The vacuum gauges converged at approximately 1,930 minutes of total drying. Following completion of primary drying, the shelf temperature was ramped to 35.0° C. over 180 minutes and held for 720 minutes. At the completion of secondary drying, the system was backfilled with nitrogen to ~600,000 mTorr and vials were fully stoppered. The programmed lyophilization cycle is shown in Table 35.

TABLE 35

| Step # | Operation | Temperature (° C.) |
|---|---|---|
| 1 | Load Set Point | 25.0 |

Door Seal

| Step # | Operation | Pressure (mTorr) |
|---|---|---|
| 2 | Seal Door | ~550,000 |

Thermal Treatmen

| Step # | Operation | Shelf Temperature (° C.) | Duration (min) |
|---|---|---|---|
| 3 | Hold | 25.0 | 30 |
| 4 | Ramp | −40.0 | 130 |
| 5 | Hold | −40.0 | 180 |

TABLE 35-continued

| Step # | Operation | Shelf Temperature (° C.) | Vacuum (mTorr) | Duration (min) |
|---|---|---|---|---|
| Primary Drying | | | | |
| 6 | Hold | −40.0 | 120 | 120 |
| 7 | Ramp | 25.0 | 120 | 60 |
| 8 | Hold | 25.0 | 120 | 4,770 |
| Secondary Drying | | | | |
| 9 | Ramp | 35.0 | 120 | 180 |
| 10 | Hold | 35.0 | 120 | 720 |

| Step # | Operation | Shelf Temperature (° C.) |
|---|---|---|
| Shut Down | | |
| 15 | Backfill with nitrogen gas to 11.6 PSIA = ~600,000 mTorr | 35.0 |
| 16 | Stopper vials. | 35.0 |
| Unloading | | |
| 17 | Unload | 35.0 |
| | Total Time | 6,190 minutes (103.2 hrs)[1] |

[1]Total cycle time does not account for the time required to reach vacuum or unloading.

Lyophilization Cycle Analysis. Analysis of the run chart demonstrates that shelf temperature was controlled to within 10OC of the set point during all stages of the cycle. The condenser was maintained at low temperatures throughout the drying portion, and vacuum was controlled within ±1 mTorr of the set-point.

Product temperatures were observed to reach a maximum temperature of −24.2° C. during primary drying when the shelf temperature was held at −10.0° C., which is within the safe zone of the collapse temperature of the product. This was expected, as the low robustness run demonstrates the worst-case sublimation rate and lowest temperature/vacuum combination.

Due to issues with obtaining the individual product traces, it is unknown when, or at what time the product temperatures converged with the shelf set point. However, an estimate can be made with the thermocouple average temperature trace of approximately 1,700 minutes. Vacuum gauge convergence for this cycle was allowed to fully complete to ensure that primary drying was completed. Vacuum gauge convergence occurred at 2,885 minutes from the start of the primary drying hold.

When the cycle was advanced to secondary drying, an increase in the Pirani gauge reading was observed, indicating additional moisture being removed from vials as bound water was removed from the product via desorption. Product temperatures followed closely with the shelf temperature through the ramp to secondary drying and throughout the secondary drying hold.

In order to trace potential degradation during secondary drying, samples were taken at t=60 minutes, and t=360 minutes into secondary drying. The results can be seen in Table 36.

TABLE 36

| Test | Specification | t = 60 min at 35° C. | t = 360 min at 35° C. | FP |
|---|---|---|---|---|
| Appearance (Lyophilized) | Conforms | N/A | | Acceptable |
| Appearance (Reconstituted) | Conforms | | | Acceptable |
| Reconstitution Time (Average) | Report | | | 30 Seconds |
| pH (Average) | Report | | | 4.38 |
| Osmolality (mOsm/kg) | Report | | | 600 |
| Residual Moisture via KF (Average) | NMT 3.0% | | | 0.5544 |
| Assay | 93.0%-107.0% (Label Claim) | 23.3 mg/mL | 23.7 mg/mL | 23.7 mg/mL |
| Related Substances | RRT (0.54) | 0.55 | 0.55 | 0.54 |
| | RRT (0.96) | 0.62 | 0.55 | 0.56 |
| | RRT (0.98) | ND | ND | 0.12 |
| Particulate Matter | NMT 6K Particles ≥10 μm | | N/A | 542 |
| | NMT 600 Particles ≥25 μm | | N/A | 23 |

The final lyophilization cycle is outlined in Table 37 below.

TABLE 37

| Step # | Operation | Temperature (° C.) |
|---|---|---|
| 1 | Load Set Point | 20.0 ± 5.0 |

Door Seal

| Step # | Operation | Pressure (mTorr) |
|---|---|---|
| 2 | Seal Door | ~550,000 |

Thermal Treatmen

| Step # | Operation | Shelf Temperature (° C.) | Duration (min) |
|---|---|---|---|
| 3 | Hold | 20.0 ± 5.0 | 30 |
| 4 | Ramp | −45.0 ± 5.0 | 130 |
| 5 | Hold | −45.0 ± 5.0 | 180 |

| Step # | Operation | Shelf Temperature (° C.) | Vacuum (mTorr) | Duration (min) |
|---|---|---|---|---|

Primary Drying

| 6 | Hold | −45.0 ± 5.0 | 95 ± 25 | 30 |
| 7 | Ramp | −15.0 ± 5.0 | 95 ± 25 | 60 |
| 8 | Hold | −15.0 ± 5.0 | 95 ± 25 | 3930 |

Secondary Drying

| 9 | Ramp | 30.0 ± 5.0 | 95 ± 25 | 180 |
| 10 | Hold | 30.0 ± 5.0 | 95 ± 25 | 720 |

| Step # | Operation | Shelf Temperature (° C.) |
|---|---|---|

Shut Down

| 15 | Backfill with nitrogen gas to 11.6 PSIA = ~600,000 mTorr | 30.0 ± 5.0 |
| 16 | Stopper vials. | 30.0 ± 5.0 |

Unloading

| 17 | Unload | 30.0 ± 5.0 |
| | Total Time | 5,260 minutes (87.7 hrs)[1] |

[1]Total cycle time does not account for the time required to reach vacuum or unloading.

Example 19—Crystalline Feasibility Study of an Enantiomer of Compound D1

Crystalline feasibility assessment of the citrate salt of compound R-D1 and salt screening were performed as follows.

Crystalline feasibility assessment of citrate

Freebasing and salt screening using 19 counter ions

Crystalline feasibility of freebase

Since properties described in this Example are same for enantiomers, the observations described in this Example for compound R-D1 are also applicable to compound S-D1.

Crystalline feasibility studies of the citrate included long-term slurries in a wide range of solvents, vapor diffusion onto solid, antisolvent vapor diffusion, and slow evaporation. Most experiments did not yield crystalline patterns. However, after stirring for the duration of the project, a crystalline pattern was observed from MeOH slurry as wet cake. The solid became amorphous upon drying at 50° C. under vacuum and therefore was not characterized further.

To generate material for salt screening, freebasing of the amorphous citrate was carried out in dichloromethane (DCM) with the slow addition of a solution of ammonium bicarbonate (5 wt. %) and subsequent washes with brine and water. The resulting amorphous freebase was fully characterized and used for salt screening. The salt screening was performed using 15 counterions and different solvents. The freebase did not produce salts with any of the counterions in the initial sampling. The experiments were left to stir for a few weeks and a salt was formed with toluenesulfonic acid (TSA) in acetonitrile (ACN). Although the salt was stable upon drying at 50° C., it resulted in an amorphous solid after exposure to >95% relative humidity (RH). Therefore, the salt was not considered a viable form.

On the other hand, it was observed that the amorphous freebase converted to a crystalline form upon mixing in various solvents with the aid of sonication. The freebase formed crystalline Pattern FF-A in methanol (MeOH), while Pattern FF-B was produced in ethanol (EtOH) and acetone. Both patterns showed hygroscopicity and slight decrease in crystallinity upon drying and exposure to humidity, although Pattern FF-B regained some crystallinity after re-exposure to humidity. Slurries of crystalline FF-A were prepared in EtOH:water (95:5 vol) and MeOH at room temperature and after ~1 h and both showed Pattern FF-B by XRPD. A selective salt formation using Pattern FF-A was performed using three counterions and two solvents. However, no new patterns were observed from these experiments.

Based on the data collected (summarized in Table 38) the salts obtained in this work do not represent preferred forms of the compound R-D1 due to their instability upon humidification.

TABLE 38

| XRPD pattern | XRPD pattern Wet | XRPD pattern Dry | XRPD pattern Humid | DSC onsets (° C.) [enthalpy (J/g)] | Purity by HPLC (%) chemical [chiral] | Residual solvents by $^1$H-NMR (wt. %) | Hygro-scopicity by DVS (up to 95% RH) | Purity by HPLC (%) After 1 week 75% RH chemical and [chiral] |
|---|---|---|---|---|---|---|---|---|
| FF-A | FF-A | FF-A | FF-A | 190.4 [3.07] | 98.50 [97.11] | BDL | >10.70 | 98.28 [94.55] |
| FF-B | FF-B | FF-B | FF-B | 191.4 [20.57] 225.2 [9.38] | 98.85 [96.56] | BDL | >8.80 | 98.56 [96.13] |
| citrate (amorphous) | Am | Am | Am | 154.11 [47.65] 171.44 [45.43] | 99.46 [99.05] | 2.68 (IPA) | >25.55 | 99.12 NA |

Note:
Am, amorphous;
BDL, below detection limit;
NA, not applicable.

XRPD Patterns for XPRD Patterns FF-A and FF-B are in Tables 39 and 40, respectively.

TABLE 39

| 2θ (deg.) | d-spacing (ang.) | Rel. Intensity |
|---|---|---|
| 5.26 | 16.79 | 57 |
| 9.04 | 9.77 | 38 |
| 10.41 | 8.49 | 40 |
| 13.41 | 6.60 | 14 |
| 13.80 | 6.41 | 100 |
| 14.82 | 5.97 | 16 |
| 15.26 | 5.80 | 15 |
| 15.54 | 5.70 | 9 |
| 16.12 | 5.49 | 14 |
| 17.32 | 5.11 | 11 |
| 17.71 | 5.00 | 71 |
| 17.91 | 4.95 | 99 |
| 18.45 | 4.80 | 21 |
| 18.71 | 4.74 | 10 |
| 20.54 | 4.32 | 11 |
| 20.82 | 4.26 | 45 |
| 21.48 | 4.13 | 13 |
| 22.57 | 3.94 | 10 |
| 22.78 | 3.90 | 4 |
| 23.74 | 3.75 | 10 |
| 24.12 | 3.69 | 11 |
| 26.34 | 3.38 | 10 |
| 26.85 | 3.32 | 24 |
| 27.91 | 3.19 | 6 |
| 28.34 | 3.15 | 5 |

Note.
Only peaks with relative intensity ≥ 5 were reported.

TABLE 40

| 2θ (deg.) | d-spacing (ang.) | Rel. Intensity |
|---|---|---|
| 5.11 | 17.29 | 26 |
| 5.39 | 16.37 | 46 |
| 8.81 | 10.03 | 28 |
| 9.05 | 9.77 | 39 |
| 10.15 | 8.71 | 4 |
| 10.47 | 8.44 | 8 |
| 10.74 | 8.23 | 11 |
| 13.10 | 6.75 | 10 |
| 13.38 | 6.61 | 53 |
| 13.58 | 6.52 | 100 |
| 13.97 | 6.33 | 8 |
| 14.59 | 6.07 | 9 |
| 15.19 | 5.83 | 31 |
| 15.76 | 5.62 | 33 |
| 17.41 | 5.09 | 93 |
| 18.10 | 4.90 | 78 |
| 18.62 | 4.76 | 31 |
| 19.37 | 4.58 | 6 |
| 20.36 | 4.36 | 7 |
| 21.00 | 4.23 | 69 |
| 21.59 | 4.11 | 4 |
| 22.30 | 3.98 | 4 |
| 22.65 | 3.92 | 6 |
| 23.06 | 3.85 | 8 |
| 23.51 | 3.78 | 10 |
| 24.25 | 3.67 | 11 |
| 24.76 | 3.59 | 5 |
| 25.80 | 3.45 | 15 |
| 26.33 | 3.38 | 32 |
| 27.47 | 3.24 | 8 |
| 28.09 | 3.17 | 7 |

Note. Only peaks with relative intensity ≥ 4 were reported.

Analytical Techniques

Differential Scanning Calorimetry (DSC). DSC was performed using a Mettler Toledo DSC$^{3+}$. The sample (1-5 mg) was weighed directly in a 40 μL hermetic aluminum pan with a pinhole and analyzed according to the parameters in Tables 41 and 42.

TABLE 41

| Parameters | |
|---|---|
| Method | Ramp |
| Sample size | 3-5 mg |
| Heating rate | 10.0° C./min |
| Temperature range | 30 to 300° C. |
| Method gas | $N_2$ at 60.00 mL/min |

TABLE 42

| Parameters | |
|---|---|
| Method | Modulation |
| Sample size | 5-10 mg |
| Amplitude | 1° C. |
| Period | 60 s |
| Heating rate | 2.0° C./min |
| Temperature range | 30 to 300° C. |
| Method gas | $N_2$ at 60.00 mL/min |

Dynamic Vapor Sorption (DVS). DVS was performed using a Q5000SA. The sample (5-15 mg) was loaded into a metallic quartz sample pan, suspended from a microbalance, and exposed to a humidified stream of nitrogen gas. Weight changes were relative to a matching empty reference pan opposite the sample, suspended from the microbalance. One of two methods was used:

Method 1: The sample was held for a minimum of 10 min at each level and only progressed to the next humidity level if there was <0.002% change in weight between measurements (interval: 5 s) or 60 min had elapsed. The following program was used:

1—Equilibration at 50% RH
2—50% to 2%. (50%, 40%, 30%, 20%, 10%, and 2%)
3—2% to 95% (2%, 10%, 20%, 30%, 40%, 50%, 60%, 70%, 80%, 90%, and 95%)
4—95% to 2% (95%, 80%, 70%, 60%, 50%, 40%, 30%, 20%, 10%, and 2%)
5—2% to 50% (2%, 10%, 20%, 30%, 40%, and 50%)

Method 2: The sample was held for a minimum of 10 min at each level and only progressed to the next humidity level if there was <0.002% change in weight between measurements (interval: 5 s) or 45 min had elapsed. The following program was used:

1—Equilibration at 50% RH
2—50% to 5%. (50%, 35%, 20%, and 5%)
3—5% to 95% (5%, 20%, 35%, 50%, 65%, 80%, and 95%)
4—95% to 5% (95%, 80%, 65%, 50%, 35%, 20%, and 5%)
5—5% to 50% (5%, 20%, 35%, and 50%)

High Performance Liquid Chromatography (HPLC). HPLC was conducted using an Agilent 1220 Infinity LC or Agilent 1220 Infinity 2 LC equipped with diode array detector (DAD). Flow rate range of the instrument is 0.2-5.0 mL/min, operating pressure range is 0-600 bar, temperature range is 5° C. above ambient to 60° C., and wavelength range is 190-600 nm.

The HPLC methods used in this study are shown in Tables 43 and 44.

TABLE 43

| Parameters for chemical purity | | | |
|---|---|---|---|
| Mobile phase A | 10 mM $NH_4FA$ in distilled water (pH 4.0) | | |
| Mobile phase B | 0.02% formic acid (FA) acid in ACN:MeOH (3:2 vol.) | | |
| Diluent | 0.05% FA in ACN:water (1:1 vol.) | | |
| Injection volume | 5 µL | | |
| Monitoring wavelength | 210 nm | | |
| Column | Waters C-18, 4.6 × 150 mm, 3.5 µm | | |
| Column temperature | 45° C. | | |
| | Time (min) | % A | Flow rate (mL/min) |
| Gradient method | 0 | 95 | 1.0 |
| | 10 | 60 | 1.0 |
| | 14 | 15 | 1.0 |
| | 17 | 15 | 1.0 |
| | 17.10 | 95 | 1.0 |
| | 26.00 | 95 | 1.0 |

TABLE 44

| Parameters for chiral purity | | |
|---|---|---|
| Mobile phase A | 25 mM FA and 25 mM $NH_3$ in ACN: MeOH (7:3 vol.) | |
| Diluent | 0.05% FA in ACN:THF (1:1 vol.) | |
| Injection volume | 0.80 µL | |
| Monitoring wavelength | 280 nm | |
| Column | ChiralPak IB, 150 × 4.6 mm, 5 µm, chiral | |
| Column temperature | 30° C. | |
| | Time (min) % A | Flow rate (mL/min) |
| Gradient method | 0 | 1.0 |
| | 20 | 1.0 |

Infrared (IR) Spectroscopy.

Smart iTX. IR spectroscopy was performed using a Thermo Scientific Nicolet iS10 FTIR Spectrometer with a helium-neon laser. The beam splitter was potassium bromide/germanium optimized for mid IR. The source type was Ever-Glo and tungsten/halogen. The spectral range was 7800-350 $cm^{-1}$ and spectral resolution was ≤0.4 $cm^{-1}$. The detector type was deuterated triglycine sulfate. Data was analyzed using Thermo Scientific OMNIC software (Version 9.8). Samples were analyzed as solids on the Smart iTX accessory with high-efficiency optic reflectors and diamond ATR crystal attenuator.

TGA-IR. IR spectroscopy was performed using a Thermo Scientific Nicolet iS10 FTIR Spectrometer with a helium-neon laser. The beam splitter was potassium bromide/germanium optimized for mid IR. The source type was Ever-Glo and tungsten/halogen. The spectral range was 7800-350 $cm^{-1}$ and spectral resolution was ≤0.4 $cm^{-1}$. The detector type was deuterated triglycine sulfate. Data was analyzed using Thermo Scientific OMNIC software (Version 9.8).

The evolved gas emitted from samples upon TGA using the Mettler Toledo TGA/$DSC^{3+}$ was analyzed with IR spectroscopy via a TGA-IR Module for Nicolet FTIR Spectrometers. The TGA-IR accessory facilitated time-based correlation of evolved gas emissions in IR analysis. The accessory was connected directly to the furnace of the TGA/DSC unit with 5 feet insulated, glass-lined, stainless steel transfer line (⅛" O.D.) and compression fittings. The transfer line temperature was maintained at 250° C. with a digital controller. The flow cell was nickel-plated aluminum, with a volume of 22 mL and an optical path length of 10 cm.

Karl Fischer (KF) Titration. KF titration for water determination was performed using a Mettler Toledo C20S Coulometric KF Titrator equipped with a current generator cell with a diaphragm, and a double-platinum-pin electrode. The range of detection of the instrument is 1 ppm to 5% water. Aquastar™

CombiCoulomat fritless reagent was used in both the anode and cathode compartments. Samples of approximately 0.03-0.10 g were dissolved in the anode compartment and titrated until the solution potential dropped below 100 mV. Hydranal 1 wt. % water standard was used for validation prior to sample analysis.

Microscopy. Optical microscopy was performed using a Zeiss AxioScope A1 digital imaging microscope equipped with 2.5×, 10×, 20×, and 40× objectives and polarizer. Images were captured through a built-in Axiocam 105 digital camera and processed using ZEN 2 (blue edition) software provided by Zeiss.

Proton Nuclear Magnetic Resonance ($^1$H NMR).

Bruker. $^1$H NMR was performed on a Bruker Avance 300 or 500 MHz spectrometer. Solids were dissolved in 0.75 mL deuterated solvent in a 4 mL vial, transferred to an NMR tube (Wilmad 5 mm thin wall 8" 200 MHz, 506-PP-8) and analyzed according to the parameters in Tables 45 and 46.

TABLE 45

| Parameters - Bruker Avance 300 | |
|---|---|
| Instrument | Bruker Avance 300 MHz spectrometer |
| Temperature | 300K |
| Probe | 5 mm PABBO BB-1H/DZ-GRD Z104275/0170 |
| Number of scans | 16 |
| Relaxation delay | 1.000 s |
| Pulse width | 14.2500 μs |
| Acquisition time | 2.9999 s |
| Spectrometer frequency | 300.15 MHz |
| Nucleus | $^1$H |

TABLE 46

| Parameters - Bruker Avance 500 | |
|---|---|
| Instrument | Bruker Avance 500 MHz spectrometer |
| Temperature | 300K |
| Probe | 5 mm PABBO BB-1H/D Z-GRD Z113652/0159 |
| Number of scans | 32 |
| Relaxation delay | 1.000 s |
| Pulse width | 14.0000 μs |
| Acquisition time | 3.2506 s |
| Spectrometer frequency | 500.13 MHz |
| Nucleus | $^1$H |

Nanalysis. $^1$H NMR was performed on an Nanalysis 60e NMReady 60 MHz spectrometer. Solids were dissolved in 0.75 mL deuterated solvent in a 4 mL vial, transferred to an NMR tube (New Era NE-BT5-7, 4.95 mm+/−0.03 mm OD, 0.43 mm+/−0.02 mm wall, 7" long, Type 1 Class B borosilicate glass) and analyzed according to the parameters in Table 47.

TABLE 47

| Parameters | |
|---|---|
| Instrument | Nanalysis 60e NMReady 60 MHz spectrometer |
| Temperature | 33.00° C. |

TABLE 47-continued

| Parameters | |
|---|---|
| Number of scans | 256 |
| Relaxation delay | 1.0 s |
| Pulse angle | 78.88 |
| Pulse width | 14.45 μs |
| Acquisition time | 3.7 s |
| Digital Resolution | 0.04 Hz |
| Spectrometer frequency | 60 MHz |
| Nucleus | $^1$H | pH Measurement. InLab Expert NTC30 pH electrode. The electrode has two open junctions and U-glass membrane resistance of <250 MΩ. The electrode uses the ARGENTHAL™ reference system and XEROLYT® polymer reference electrolyte. The operating range is 0-14 pH units at 0-100° C.

Simultaneous Thermogravimetric Analysis and Differential Scanning Calorimetry (TGA and DSC). TGA and DSC were performed on the same sample simultaneously using a Mettler Toledo TGA/DSC$^{3+}$. Protective and purge gas was nitrogen at a flowrate of 20-30 mL/min and 50-100 mL/min, respectively. The desired amount of sample (5-10 mg) was weighed directly in a hermetic aluminum pan with pinhole and analyzed according to the parameters below:

TABLE 48

| Parameters | |
|---|---|
| Method | Ramp |
| Sample size | 5-10 mg |
| Heating rate | 10.0° C./min |
| Temperature range | 30 to 300° C. |

X-Ray Powder Diffraction (XRPD). XRPD was performed using a Rigaku MiniFlex 600 in reflection mode (i.e., Bragg-Brentano geometry). Samples were prepared on Si zero-return wafers. The parameters for XRPD methods used are listed in Table 49.

TABLE 49

| Parameter | Regular scan | High resolution scan |
|---|---|---|
| X-ray wavelength | Cu Kα1, 1.540598 Å | Cu Kα1, 1.540598 Å |
| X-ray tube setting | 40 kV, 15 mA | 40 kV, 15 mA |
| Slit condition | 1.25° div., Ni kβ filter, 0.3 mm rec. | 1.25° div., Ni kβ filter, 0.3 mm rec. |
| Scan mode | Continuous | Continuous |
| Scan range (°2θ) | 4-30 | 4-40 |
| Step size (°2θ) | 0.05 | 0.05 |
| Scan speed (°/min) | 5 | 1.25 |
| Spin | No | No |

XRPD was performed using a Bruker D8 Advance equipped with LYNXEYE detector in reflection mode (i.e., Bragg-Brentano geometry). Samples were prepared on Si zero-return wafers. The parameters for XRPD methods used are listed in Table 50.

TABLE 50

| Parameter | Regular scan | High resolution scan |
|---|---|---|
| X-ray wavelength | Cu Kα1, 1.540598 Å | Cu Kα1, 1.540598 Å |
| X-ray tube setting | 40 kV, 40 mA | 40 kV, 40 mA |
| Slit condition | 0.6 mm div. + 2.5° soller | 0.6 mm div. + 2.5° soller |

TABLE 50-continued

| Parameter | Regular scan | High resolution scan |
| --- | --- | --- |
| Scan mode | Step | Step |
| Scan range (°2θ) | 4-30 | 4-40 |
| Step size (°2θ) | 0.03 | 0.02 |
| Dwell time (s/step) | 0.23 | 0.9 |
| Spin | Yes (0.5 Hz) | Yes (0.5 Hz) |

Citrate of Compound R-D1

Figure 29:
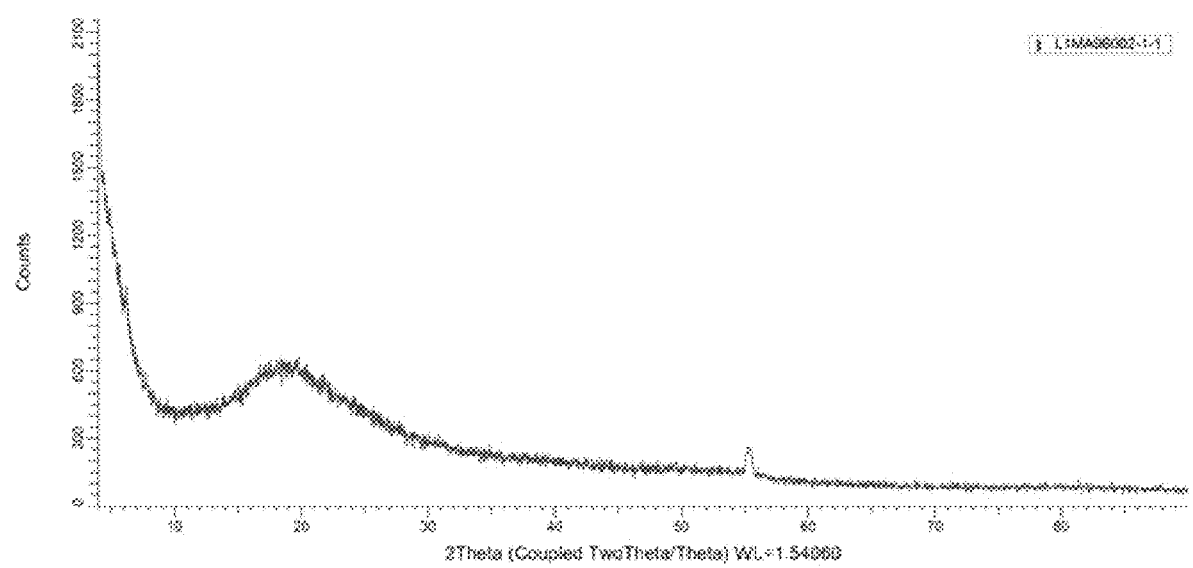
FIG. 29 is a chart showing the X-ray powder diffraction (XRPD) for the citrate salt of compound R-D1.
Figure 30:
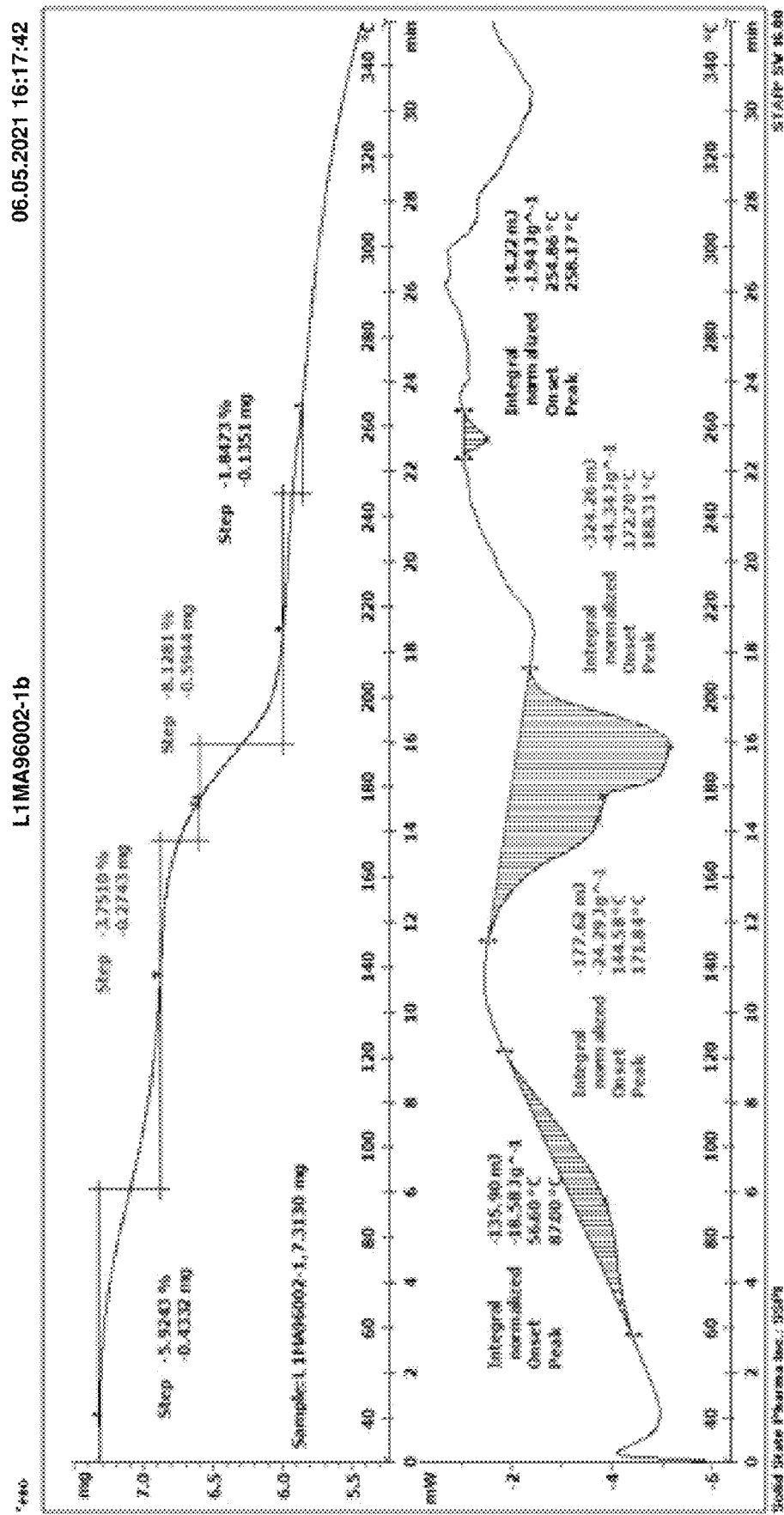
FIG. 30 is a chart showing the simultaneous thermogravimetric analysis (TGA)/differential scanning calorimetry (DSC) thermograms for the citrate salt of compound R-D1. The TGA thermogram is an upper thermogram, and the DVS thermogram is the lower thermogram.
Figure 31:
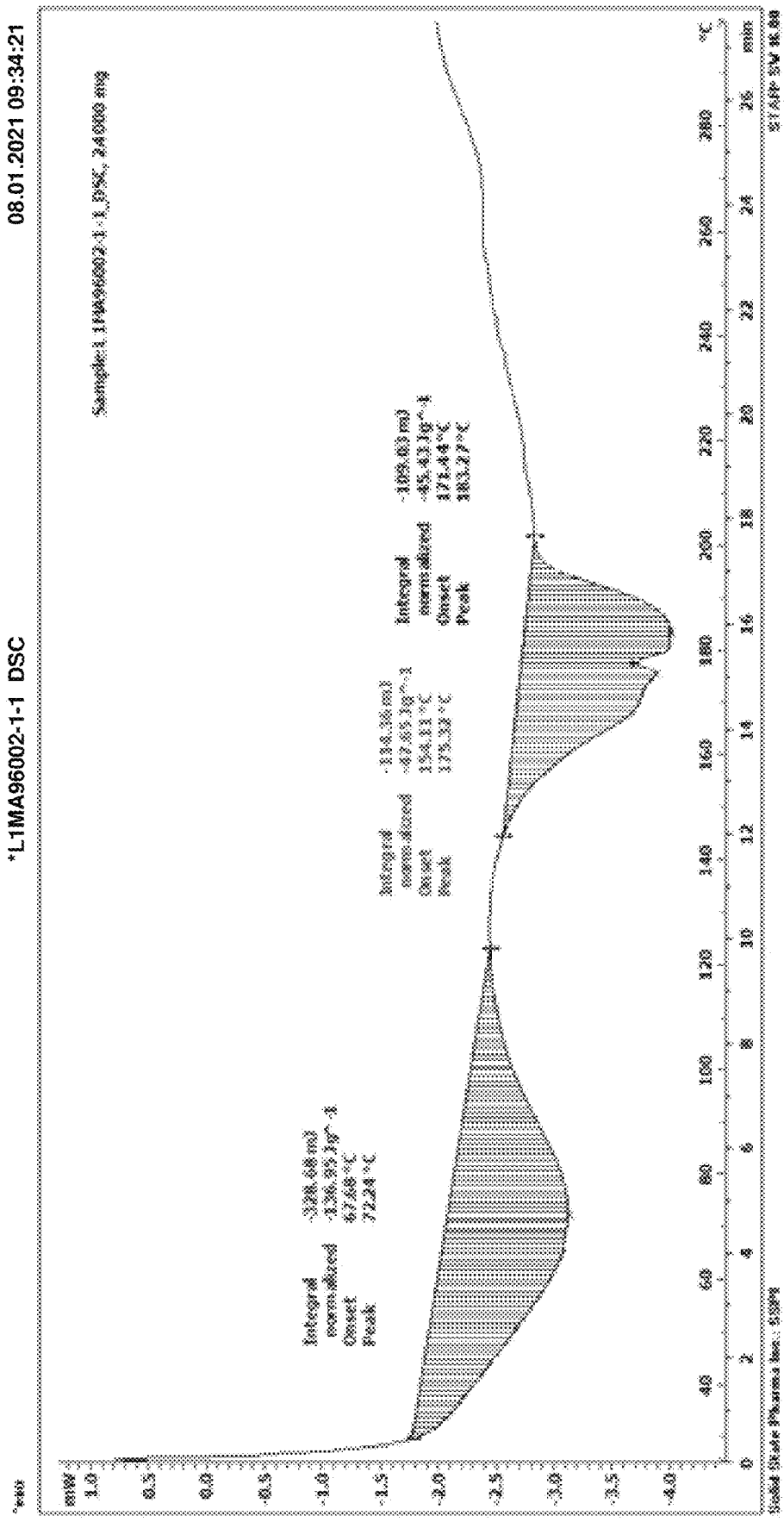
FIG. 31 is a chart showing the stand-alone DSC thermogram for the citrate salt of compound R-D1.
Figure 32A:
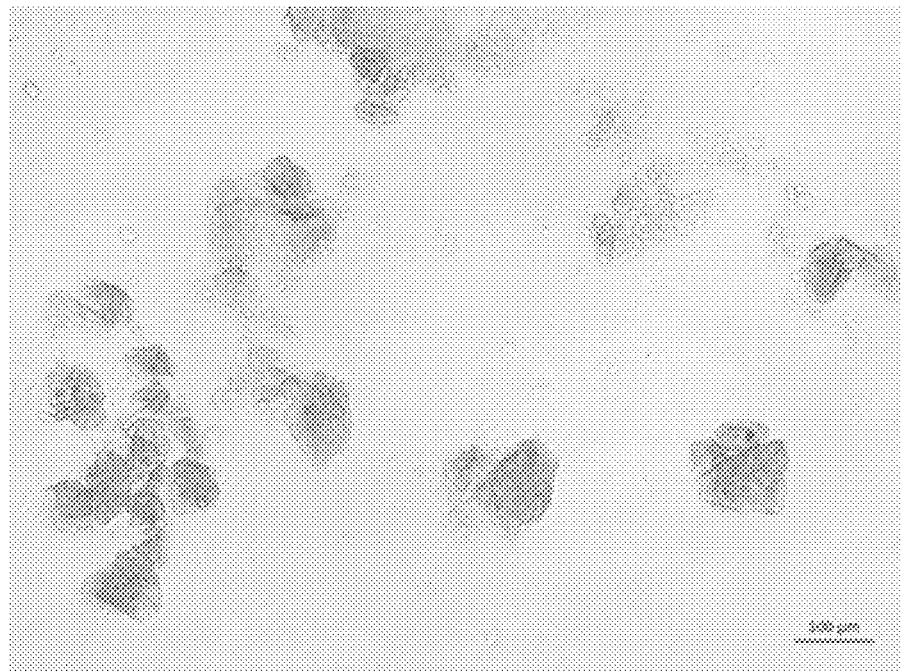
FIGS. 32A, 32B, and 32C are microscopy images of the citrate of compound R-D1.
Figure 32B:
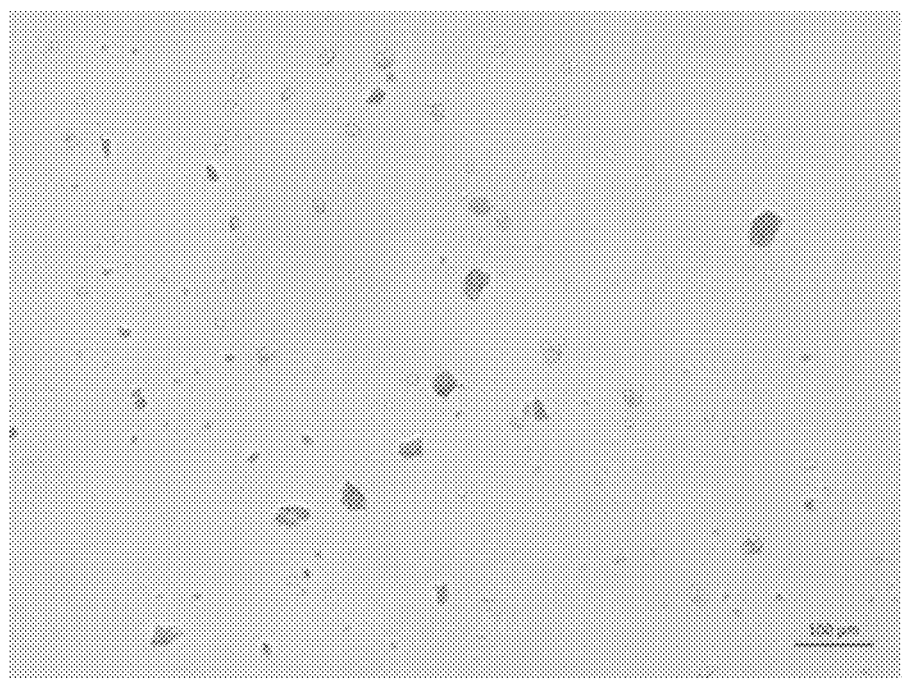
Figure 32C:
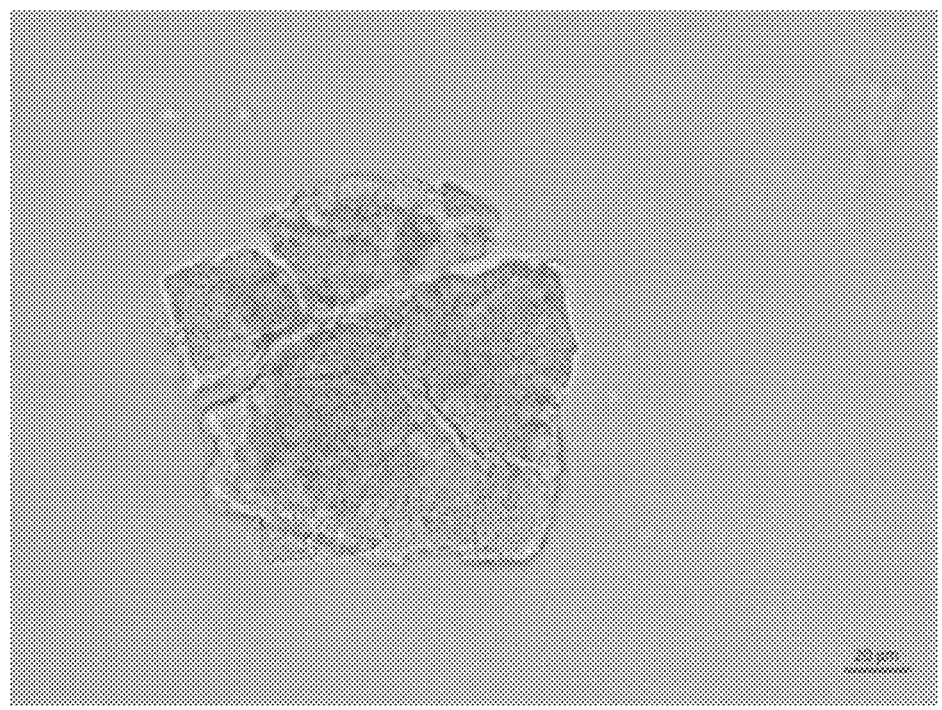
Figure 33:
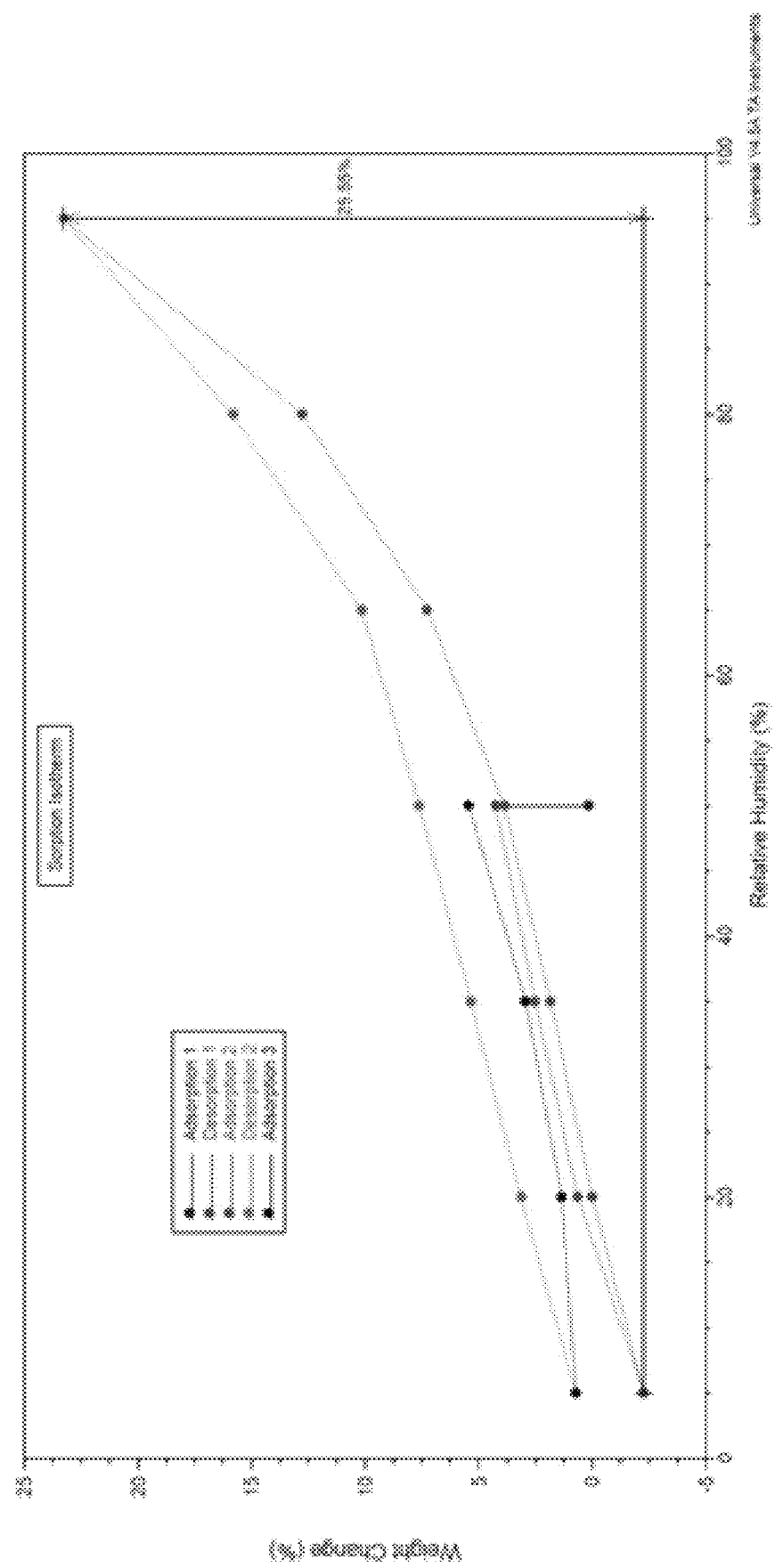
FIG. 33 is a DVS isotherm plot for the citrate salt of compound R-D1.
Figure 34:
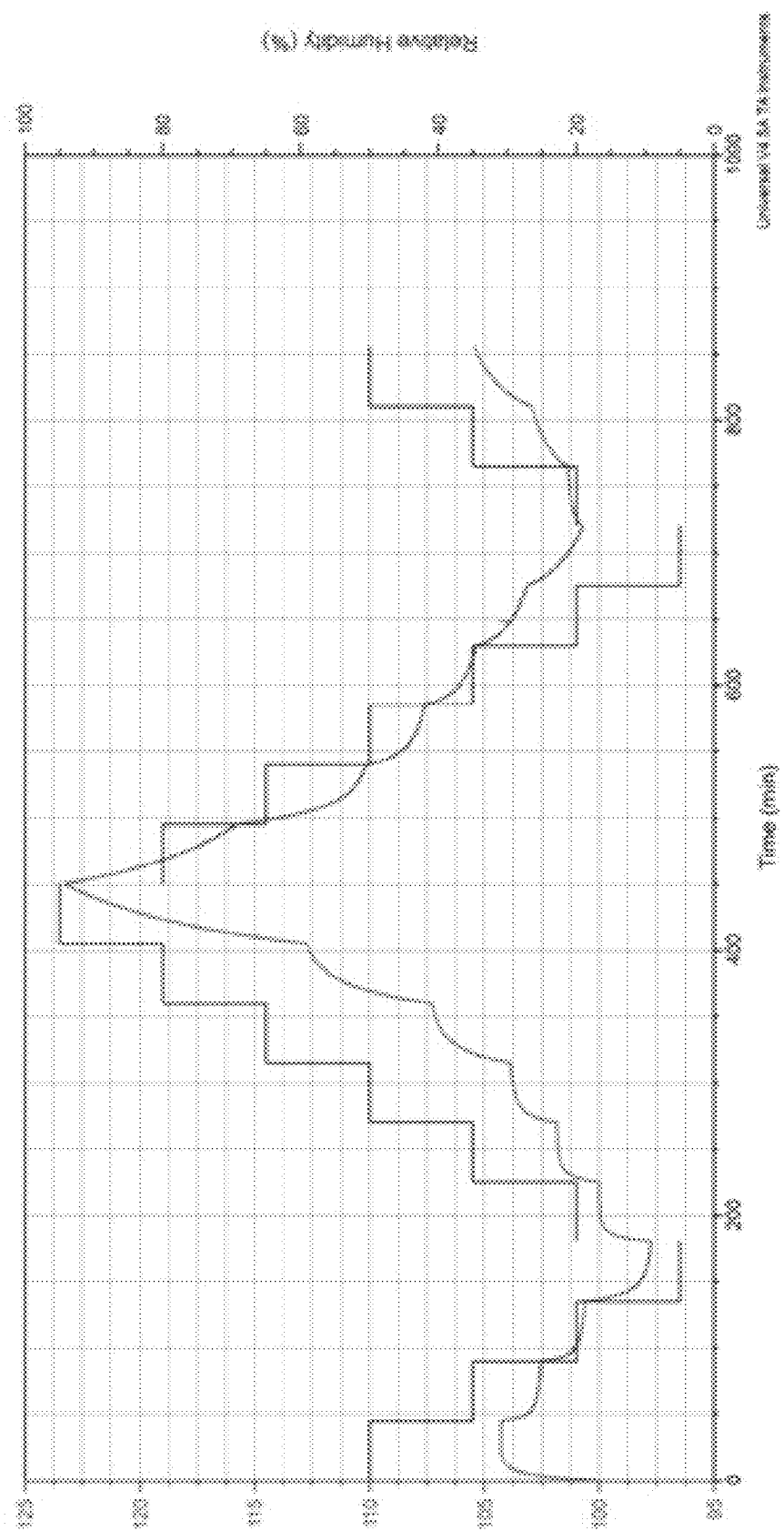
FIG. 34 is a DVS mass plot for the citrate salt of compound R-D1.
Figure 35:
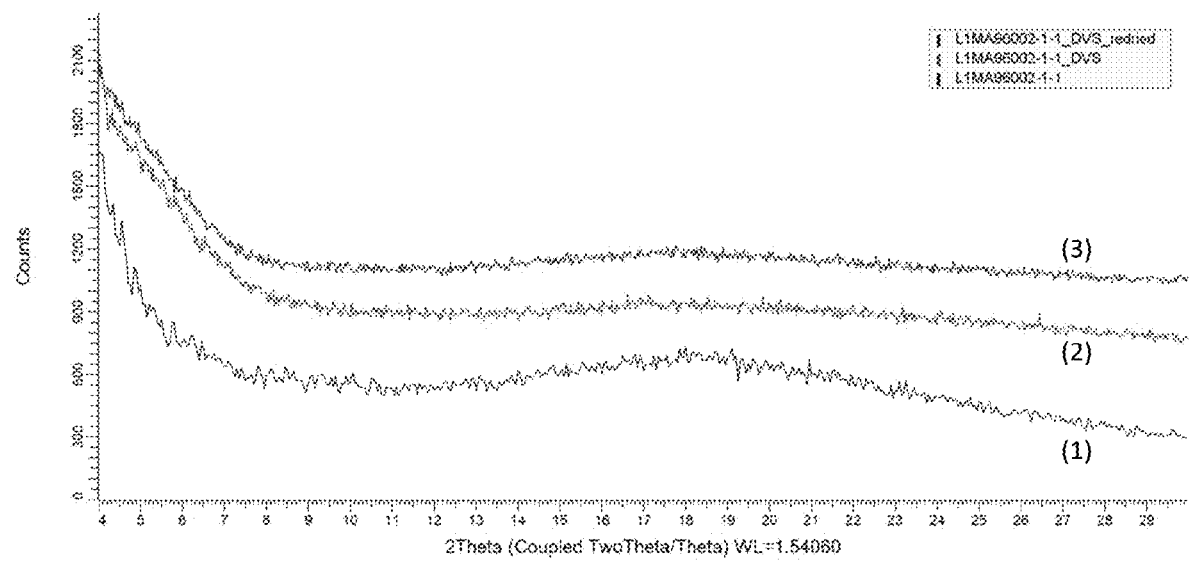
FIG. 35 is an overlay of three XRPD traces. Trace (1) corresponds to the citrate salt of compound R-D1 prior to the DVS study. Trace (2) corresponds to the citrate salt of compound R-D1 after the DVS study. Trace (3) corresponds to the post-DVS analysis citrate salt of compound R-D1 after redrying the sample under vacuum at room temperature.

The X-ray powder diffraction (XRPD) revealed an amorphous pattern, as shown in FIG. 29. The simultaneous thermogravimetric analysis (TGA)/differential scanning calorimetry (DSC) thermograms showed a mass loss event of 5.92 wt. % over the course of a broad low temperature endotherm (FIG. 30). The water content measured by Karl Fischer titration (KF) was 2.20 wt. %, which is indicative of additional residual solvent present in the material when compared to the TGA result. Two subsequent endotherms at 171.6 and 188.3° C. were also observed with associated mass losses of 3.75 and 8.04 wt. %, respectively. The temperature of these thermal transitions was corroborated with stand-alone DSC analysis (FIG. 31). Proton nuclear magnetic resonance ($^1$H NMR) in deuterated chloroform (chloroform-d) and dimethyl sulfoxide (DMSOd$_6$) showed the presence of 2.68 wt. % isopropanol (IPA) as residual solvent, which can be partially removed to 1.63 wt. % by drying at room temperature (RT) under vacuum (~−29 inHg) for 2 days and 6 h. Microscopy revealed the morphology to be irregular particles of various sizes (FIGS. 32A, 32B, and 32C). The high-performance liquid chromatography (HPLC) assessment of the chemical and chiral purity revealed 99.46 and 99.05% of purity, respectively. Finally, the dynamic vapor sorption (DVS) isotherm plot revealed that the compound is very hygroscopic, according to the European Pharmacopeia standards. This was indicated by the high humidity absorption (25.55 wt. %, 15.8 eq.) over a 5-95% humidity range (FIGS. 33 and 34). Equilibrium was not reached during the measurement. Therefore, the water uptake is likely to be higher if left for a prolonged time. The sample presented a yellow discoloration and a change in texture after the analysis, i.e., the compound initially appeared off-white and fluffy, in contrast to yellow hard particles by the end of the analysis. The XRPD did not show conversion to a crystalline pattern after performing the DVS analysis (FIG. 35, trace (2)), or upon redrying the collected solids at RT under vacuum for 2 h (FIG. 35, trace (3)). The HPLC chemical purity of the compound after DVS analysis resulted in 99.55% purity.

Solubility in Process Solvents

Qualitative solubility of the citrate salt of compound R-D1 at RT (22-24° C.) was assessed in 12 solvents having diverse properties. A summary of the results is shown in Table 51.

Figure 36:
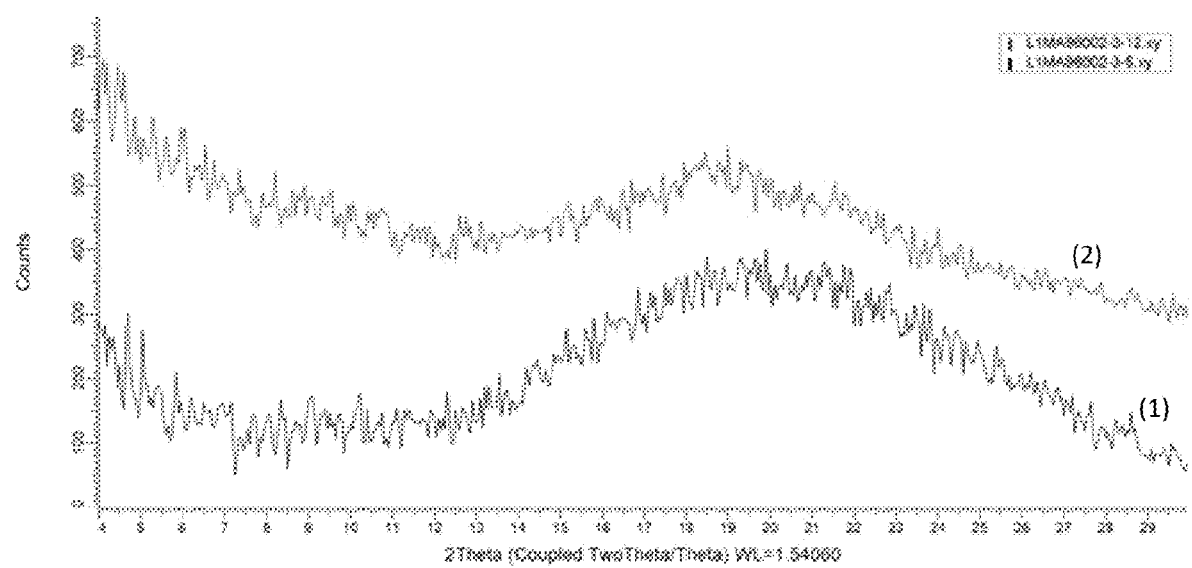
FIG. 36 is an overlay of two XRPD traces. Trace (1) corresponds to the wet cake of the citrate salt of compound R-D1 from dichloromethane. Trace (2) corresponds to the dried cake of the citrate salt of compound R-D1 from dioxane:ethanol (1:1 vol).

In this procedure, the material was weighed in 2 mL vials, then a 6.3 mm stir bar was added to each vial. Three volumes (vol.) of solvent were added at first, followed by the addition in 1 vol. increments up until 12 vol., then 2 vol. increments up to 26 vol., followed by 5 vol. increments up to 44 vol., and finally 10 vol. increments until the solids dissolved. In the samples where solubility was low, the solvent was added until the vial filled. The slurries formed in CM and in dioxane:EtOH (1:1 vol.) thinned and formed a gel. However, they did not yield crystalline solids, as shown in FIG. 36. All the samples were left to stir at RT for approximately 2 months to assess possible crystallization.

Figure 37:
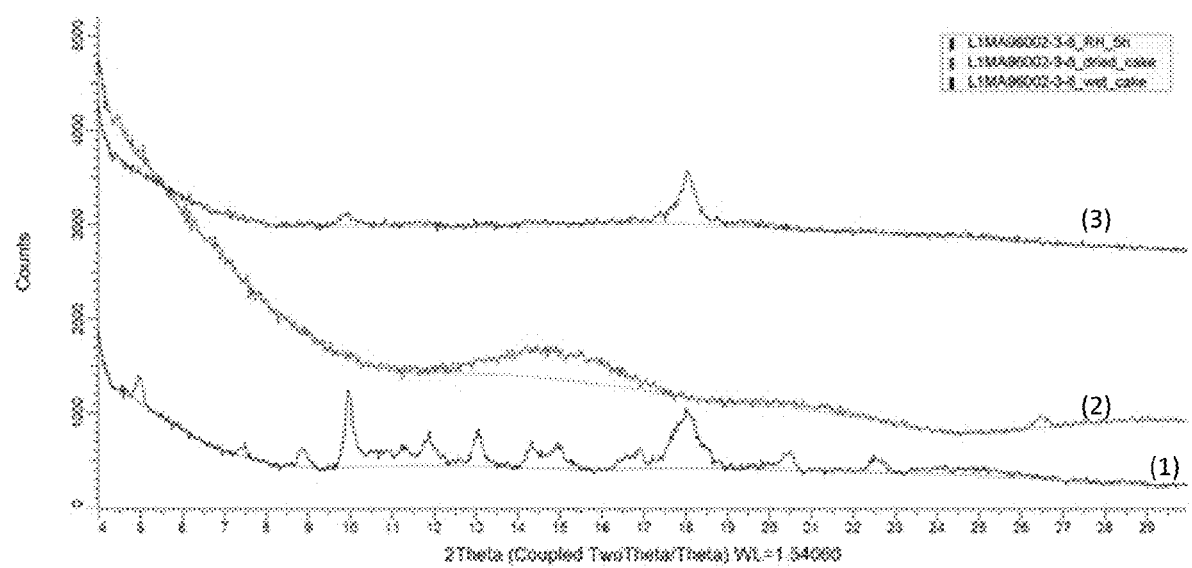
FIG. 37 is an overlay of three XRPD traces. Trace (1) corresponds to the wet cake of the citrate salt of compound R-D1. Trace (2) corresponds to the dried cake of the citrate salt of compound R-D1. Trace (3) corresponds to the citrate salt of compound R-D1 after >95% RH for 5 hours at RT.

The vials were monitored until the end of the project and it was noted that the yellow gum initially produced in MeOH turned into an off-white thick after about six weeks slurry that was filtered and analyzed. The solids collected from this sample produced a low crystalline Pattern, citrate-A. The material was dried at 50° C. for 3 h, followed by exposure to >95% RH for 5 h. The sample became amorphous after drying and exposure to RH, as shown in FIG. 37. This material was not characterized further.

TABLE 51

| Solvent | Solubility (mg/mL) | Observations |
| --- | --- | --- |
| TFE | >333 | Yellow clear solution. |
| THF | <16 | White slurry. |
| 1,4-Dioxane | <16 | White slurry, flowable but tended to settle partially. |
| DMSO | >333 | Yellow clear solution. |
| DCM | <15 | White slurry that thinned and formed a gel. |
| EtOH | <15 | White slurry, flowable but tended to settle partially. |
| IPA | <14 | White slurry, flowable but tended to settle partially. |
| MeOH | <42 | Insoluble yellow gum. Turned into a white slurry overtime (~6 weeks) |
| 2-MeTHF | <14 | White slurry. |
| EtOAc | <14 | White slurry. |
| Acetone | <14 | White slurry, flowable but tended to settle partially. |
| Dioxane:EtOH (1:1 vol.) | <14 | White slurry that thinned and formed a gel. |
| DMAC | >333 | Yellow clear solution. |
| Benzyl alcohol | 200-333 | Yellow clear solution. |

Stability at 40° C./75% RH

The stability at high RH was assessed for the citrate salt of compound R-D1. In this experiment, 30 mg of the citrate salt of compound R-D1 were weighed in a 4 mL vial and placed in a 20 mL vial set at 40° C. and 75% RH, with no stirring, for 1 week. The humid environment was generated with saturated sodium chloride in water in a sealed container. After one week, the sample appeared pale-yellow upon inspection. The XRPD analysis of this sample did not show conversion to a crystalline form.

Amorphous to Crystalline Studies of Citrate

Thermal Treatment of Amorphous Salt. Thermal treatment of the citrate salt of compound R-D1 was evaluated by subjecting the sample to high temperature, mainly 130, 175, and 205° C., followed by cooling down to RT. The thermal events were measured by TGA/DSC and XRPD was used to study the resulting materials. None of these experiments resulted in crystalline solids, as observed by XRPD and TGA/DSC.

Long-Term Slurries. Long-term slurries were carried out for the purpose of producing crystalline forms. Slurries of the citrate salt of compound R-D1 were produced in 15 solvents (Chlorobenzene, Anisole, MEK, Methyl acetate, ACN, THF:DMSO (9:1 vol.), EtOH:DMSO (9:1 vol.), IPA:DMSO (9:1 vol.), 2-MeTHF:DMSO, (9:1 vol.), Acetone:DMSO, (9:1 vol.), IPAc:DMSO (9:1 vol.), ACN:DMSO (9:1 vol.), EtOH:water (95:5 vol.), n-Propanol, Toluene, THF, 1,4-Dioxane, DCM, EtOH, IPA, MeOH, 2-MeTHF, EtOAc, Acetone, Dioxane:EtOH, (1:1 vol.), Chlorobenzene:MeOH (8:2 vol.), Anisole:MeOH (8:2 vol.), MEK:MeOH (8:2 vol.), MeOAc:MeOH (8:2 vol.), ACN:MeOH (8:2 vol.), Acetone:MeOH (8:2 vol.), Toluene:MeOH (8:2 vol.), THF:MeOH (8:2 vol.), 1,4-Dioxane:MeOH (8:2 vol.), DCM:MeOH (8:2 vol.), 2-MeTHF:MeOH (8:2 vol.), EtOAc:MeOH (8:2 vol.), MtBE:MeOH (8:2 vol.), Chloroform:MeOH (8:2 vol.), and DMF:MeOH (8:2 vol.)) at RT in addition to the slurries continued from solubility experiments. In this procedure, 30 mg of solid was added to a 2 mL vial containing a 6.3 mm stir bar. Then, 3 vol. of solvent was added, followed by the addition of more solvent in 5 vol. increments until it formed a flowable slurry. After 10 days, the solids were filtered and transferred to an XRPD plate for further analysis on the wet cake. Overall, crystalline patterns were not observed after one week. However, a crystalline solid was observed after stirring in MeOH for about six weeks.

Vapor-Diffusion Crystallization onto Solution and Solids. The vapor diffusion onto antisolvent solution was carried out by weighing 20 mg of the citrate salt of compound R-D1 in a 4 mL vial. A suitable solvent was added to completely dissolve the solid, while producing a solution of slightly undersaturated concentration. The open vial was placed inside a 20 mL scintillation vial and 3 mL of antisolvent was added to the 20 mL vial to diffuse into the solution. The 20 mL vial was capped, sealed with parafilm, and kept undisturbed at RT. A summary of the solvent systems used in this experiment is presented in Table 52.

TABLE 52

| Solvent added | Antisolvent added | Observations | Pattern |
| --- | --- | --- | --- |
| DMAC | ACN | Yellow-white solids | Am |
| | Chlorobenzene | Clear solution | — |
| | Acetone | Yellow-white solids | Am |
| | EtOAc | Yellow-white solids | Am |
| | MEK | Yellow-white solids | Am |
| | IPA | Yellow-white solids | Am |
| | DCM | Yellow-white solids | Am |
| DMSO | 2-MeTHF | Clear solution | — |
| | Chlorobenzene | Clear solution | — |
| | Acetone | Yellow-white solids | Am |
| | MeOAc | Yellow-white solids | Am |
| | MEK | Yellow-white solids | Am |
| | EtOH | Yellow-white solids | Am |
| | DCM | Yellow-white solids | Am |
| Benzyl alcohol | can | Clear solution | — |
| | Chlorobenzene | Clear solution | — |
| | Acetone | Yellow-white solids | Am |
| | MeOAc | Yellow-white solids | Am |
| | THF | Clear solution | — |
| | EtOH | Yellow-white solids | Am |

Note. Am, amorphous.

Vapor diffusion onto solids was also started. The procedure is very similar, with the only difference that the active pharmaceutical ingredient (API) is not dissolved in a solvent; the vapor diffused directly onto the solid. The samples were monitored for visual changes in the solid (color, texture, size, etc.) over 2 months. The samples that did not present a significant change were not analyzed further by XRPD. A summary of this experiment set up is presented in Table 53.

TABLE 53

| Antisolvent added | Observations | Pattern |
| --- | --- | --- |
| ACN | — | — |
| Chlorobenzene | — | — |
| Acetone | — | — |
| EtOAc | — | — |
| MeOAc | — | — |
| MEK | — | — |
| IPA | — | — |
| EtOH | — | — |
| MeOH | Clear yellow gum | Am |

TABLE 53-continued

| Antisolvent added | Observations | Pattern |
| --- | --- | --- |
| DCM | Clear yellow solids | Am |
| MeTHF | — | — |
| THF | — | — |
| MtBE | White-yellow powder | Am |
| Hexanes | White-yellow powder | Am |
| Diethyl ether | White-yellow powder | Am |
| Methyl cyclohexane | White-yellow powder | Am |
| Cyclohexane | White-yellow powder | Am |
| Dioxane | — | — |
| Toluene | — | — |
| Chloroform | Yellow hardened particles | Am |

Note. Am, amorphous.

Slow Evaporation. Approximately 5-10 mg of the citrate salt of compound R-D1 was weighed in a vial, and the solvent was added until the sample dissolved or up to 1.7 mL in total. The samples that did not dissolve were split up by half its volume, and a cosolvent was added to each part until the sample dissolved or thinned out. The samples that were thin slurries were filtered with a 45 µm syringe filter to obtain a clear solution. In some cases, cosolvent was added to obtain a solution. A needle was inserted in the cap septa to allow the solvents to evaporate slowly. The solutions were monitored frequently for precipitation. The experiments did not yield crystalline solids.

Freebasing

The freebasing of compound R-D1 from its citrate salt was carried out to produce a freeform of the compound. In this procedure, 250 mg of the citrate salt of compound R-D1 was weighed in a 20 mL vial. Twenty volumes of DCM were added with stirring on a chiller block set at 10° C. Then, 30 vol. of a base, either $NH_4HCO_3$ or $NaHCO_3$ (5 wt. %), was added dropwise and the suspension was stirred for a few minutes. A yellow gum formed during this procedure; the suspension was vortexed vigorously. The undissolved gum was brought down to the DCM phase with the aid of a spatula and the suspension was left to stir in the chiller block for an additional 20 min. Subsequently, the stirring was stopped, and the suspension was left undisturbed to allow the separation of the phases. The aqueous phase was removed carefully, and 30 vol. of the basic solution was added dropwise to the DCM layer with stirring, at 10° C. The aqueous phase was removed again after allowing the suspension to stand undisturbed for a few minutes. The DCM phase was transferred to a clean vial, and 20 vol. of a saturated solution of NaCl (brine) was added. The suspension was stirred for 10 min. After this time, the aqueous phase was removed carefully with a pipette, and 20 vol. of distilled water was added to remove any residual salt. The suspension was left to stir for 5 min on the chiller block, and the water was removed carefully with a pipette. More water was added (20 vol.), and the suspension was left to stir for another 5 min, followed by the removal of the aqueous phase. Finally, the DCM phase was transferred to a clean vial and the solution was dried at RT overnight, followed by drying in a rotatory evaporator for 10 min.

Figure 38:
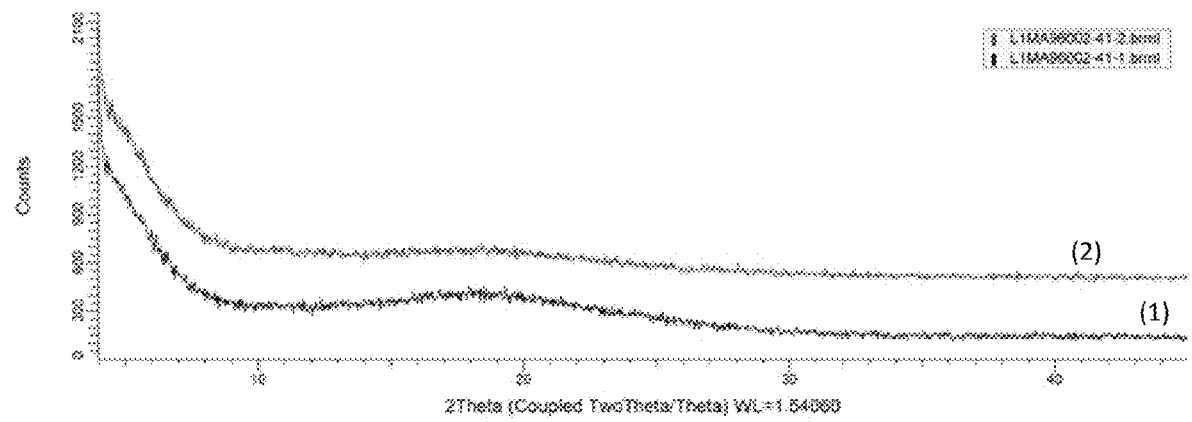
FIG. 38 is an overlay of XRPD traces. Trace (1) corresponds to the wet cake of free-base compound R-D1 isolated from the freebasing procedure utilizing ammonium bicarbonate. Trace (2) corresponds to the wet cake of free-base compound R-D1 isolated from the freebasing procedure utilizing sodium bicarbonate.

The resulting freebase was a yellow solid with glassy appearance. The XRPD analysis showed an amorphous material for the samples obtained in ammonium bicarbonate and sodium bicarbonate, as shown in FIG. 38. The chemical purity assessed by HPLC for both compounds resulted in 97.20 and 98.72% for the freebase prepared in ammonium bicarbonate and sodium bicarbonate, respectively, as measured by HPLC. The amorphous freebase obtained using ammonium bicarbonate showed a chiral purity of 98.88%, while the compound prepared in sodium bicarbonate was 99.31%, as measured by HPLC.

Figure 39A:
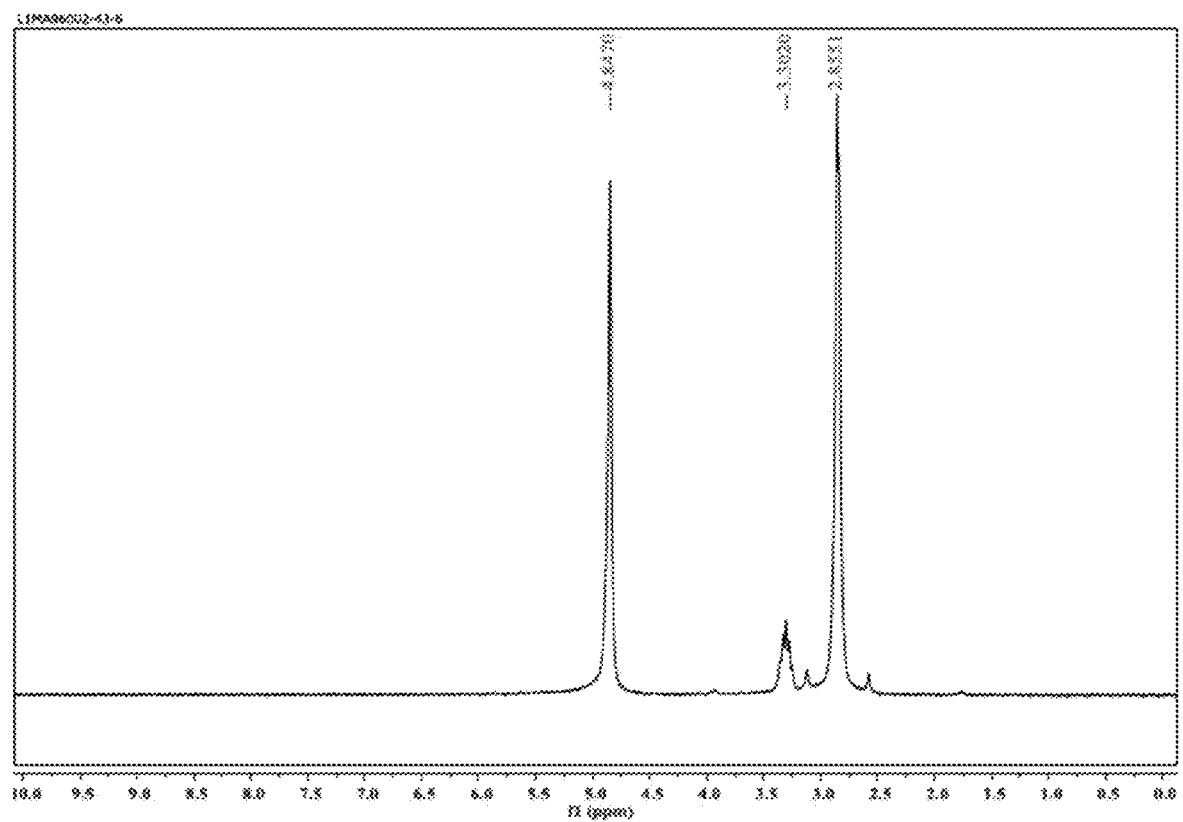
FIG. 39A is a $^1$H NMR spectrum of citric acid in MeOH-$d_4$.
Figure 39B:
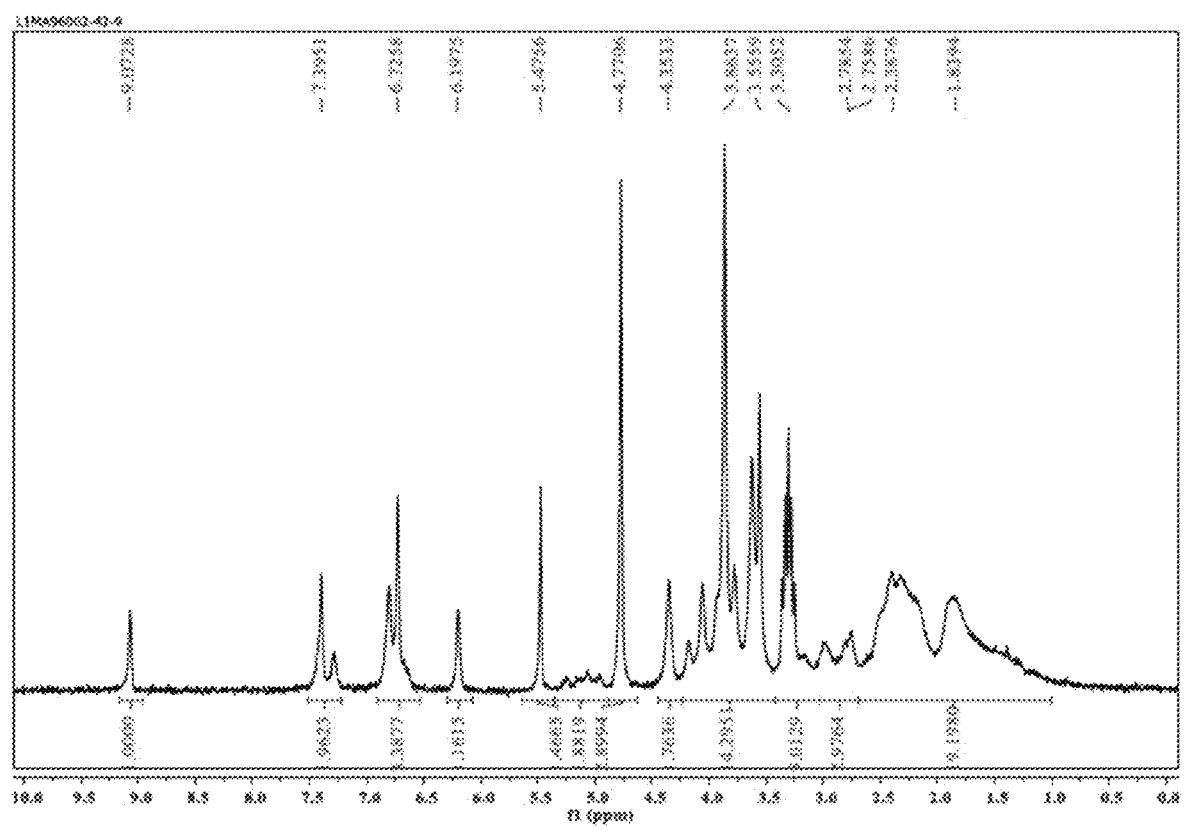
FIG. 39B is a $^1$H NMR spectrum of free-base compound R-D1 in MeOH-$d_4$.

To corroborate the removal of the citric acid, this compound was analyzed by $^1$H NMR in deuterated methanol (MeOH-$d_4$) (FIG. 39A), and the signals were compared to those in the freebase acquired in the same solvent (FIG. 39B). The lack of signals at 2.85 in the spectrum of the freebase showed that the citrate anion was removed.

The amorphous freebase also showed the presence of residual DCM in 4.76 and 5.32 wt. %, for the solids prepared with ammonium bicarbonate and sodium bicarbonate, respectively, as measured by $^1$H NMR in chloroform-d (300 MHz).

Freebasing Scale Up. The scale-up of the amorphous freebase of compound R-D1 was performed using 5.0152 g of its citrate salt. About 5 g of the citrate salt were weighed in a 400 mL EasyMax vessel. Twenty vol. of DCM were added with stirring at 300 rpm (0.39 Watts/kg) at 10° C. A solution of ammonium bicarbonate (30 vol.) (5 wt. %) was added in volumes of 10 mL dropwise and the suspension was allowed to stir for a few minutes. A yellow gum formed after the addition of 20 mL; the suspension was left to stir vigorously to aid dissolving it. The undissolved gum was brought down to the DCM phase with the aid of a spatula. Subsequently, 40 mL of the base was added in vol. of 10 mL in a period of 30 min with stirring, followed by the addition of 1 mL of MeOH used as co-solvent. After this time, 90 mL of the base was added slowly during the period of 2.5 h to bring the volume of the base to a total of 30 vol. with respect to the weight of the citrate salt used. The suspension was left to stir for an additional 2 h. The gum was transferred to an amber vial, along with a portion of the DCM and the base used in the reaction in an approximately 2:3 vol. ratio. The gum was sonicated for 30 min in an ice bath to avoid heating up the mixture. After the amount of gum was brought to a minimum, the sonicated suspension was incorporated to the original bi-phasic solution, and it was stirred for additional 5 min at 300 rpm (0.16 Watts/kg). The suspension was left undisturbed to allow the separation of the phases. The aqueous phase was removed with the aid of a pipette. Additional 150 mL (30 vol.) of the ammonium bicarbonate solution (5 wt. %) was added in 10 mL vol., dropwise, over 50 min, with stirring at 0.16 Watts/kg at 10° C. After adding the base, the mixture was stirred for an additional 5 min, followed by the careful removal of the aqueous solution. The DCM layer was transferred to a clean 400 mL vessel. 100 mL (20 vol.) of a saturated solution of NaCl (brine) was added. The suspension was stirred for 10 min. Then, the aqueous phase was removed carefully with a pipette. 100 mL (20 vol.) of distilled water was added to remove any residual salt. The suspension was left to stir at 300 rpm (0.20 Watts/kg) for 5 min, and the water was removed carefully with a pipette. Distilled water was added again (20 vol.), and the suspension was left to stir for another 5 min, followed by the removal of the aqueous phase. The DCM phase was transferred to six clean scintillation vials, and the solution was dried at RT overnight. The residual DCM was dried using a direct flux of nitrogen until most of the solvent was evaporated. The vials were dried under vacuum (~−29 inHg) at RT for 3 days. The yield of the reaction calculated after removing the residual solvent and water was 32%.

Figure 40:
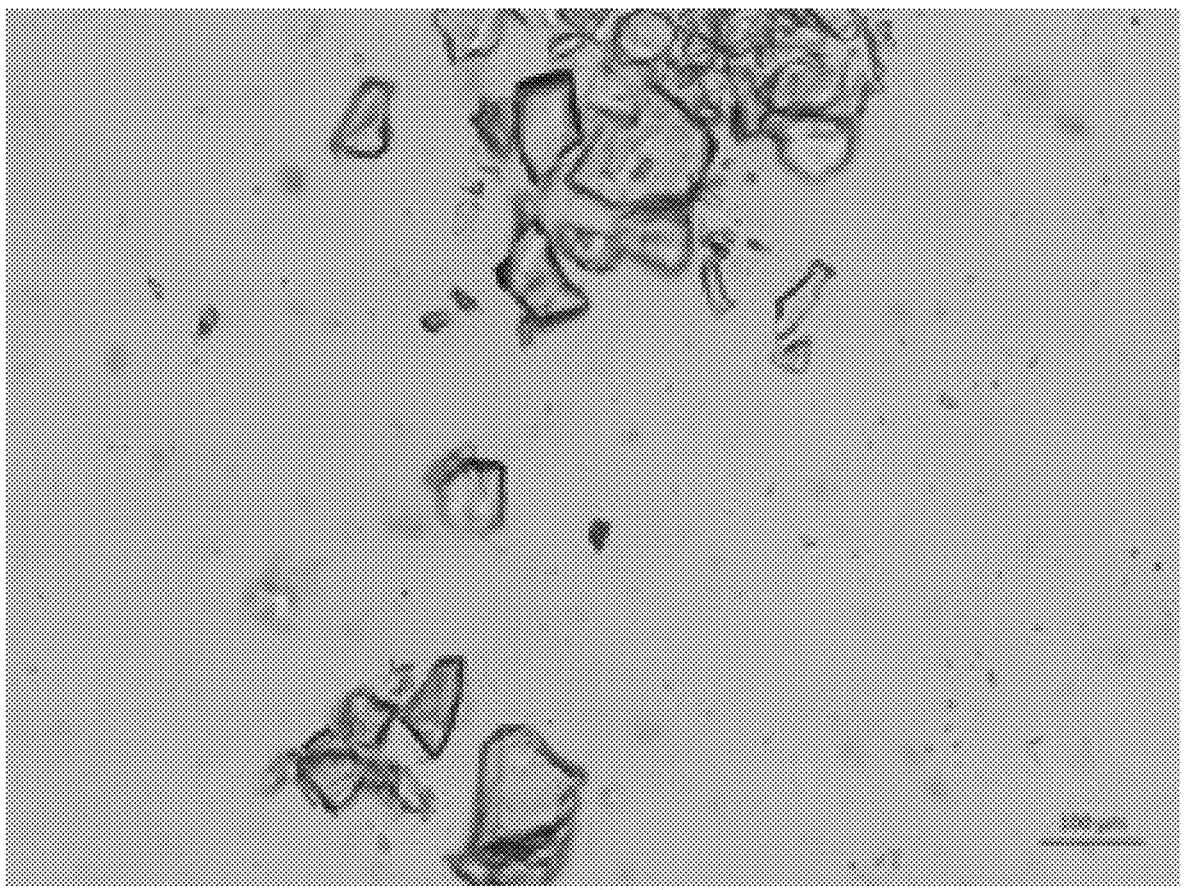
FIG. 40 is a microscopy image of free-base compound R-D1.
Figure 41:
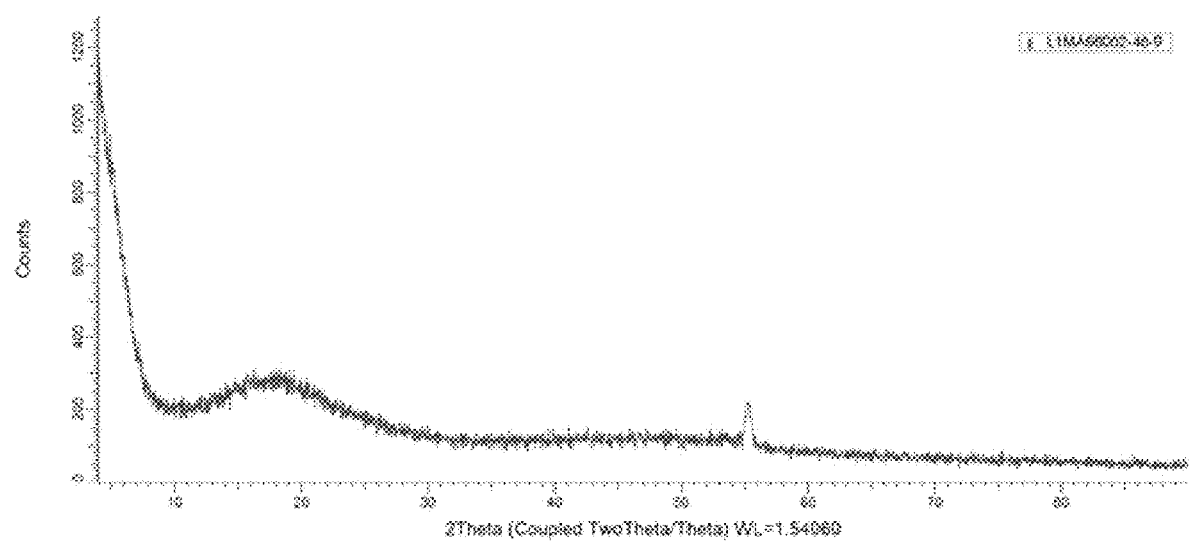
FIG. 41 is a chart showing the XRPD for amorphous free-base compound R-D1.

The resulting freebase was a yellow solid with powdery appearance and irregular particles as shown in FIG. 40. The XRPD analysis showed that the material consisted of an amorphous compound (FIG. 41), with a chemical and chiral purity of 97.09% and 97.57%, as measured by HPLC.

The analysis by $^1$H NMR in MeOH-$d_4$ corroborated the removal of the citric acid, as indicated by the lack of signals at 2.85 ppm in the spectrum. The sample also showed residual DCM (8.01 wt. %) after drying the sample for 1 h at RT under vacuum (~29 inHg), as evidenced by $^1$H NMR. The amount of solvent was partially removed to 4.48 wt. % after further drying for 3 h at RT under vacuum (~29 inHg).

Simultaneous TGA/DSC was also carried out to evaluate the residual content of DCM and water in the amorphous freebase after drying for 3 h under vacuum at RT. The simultaneous TGA/DSC thermogram showed two mass losses over the course of a broad temperature endotherm. The first weight loss of 2.93 wt. % corresponded to residual DCM, while the loss of 5.21 wt. % was related to water. After drying the amorphous freebase for over 3 days, the thermogram showed a partial removal of both the DCM and water, as indicated by the weight losses of 1.63 and 2.90 wt. %, respectively.

Salt Screening Using the Amorphous Free-Base Compound R-D1

The salt screening was initially set up with 15 counter ions (acetic acid, benzoic acid, citric acid, fumaric acid, gentisic acid, gluconic acid, glucuronic acid, malic acid, maleic acid, malonic acid, oxalic acid, sulfuric acid, succinic acid, phosphoric acid, and toluenesulfonic acid) in 3 solvents, using 1.1 eq. of counter ion to freebase; sulfuric acid was also set up using 0.55 eq.

Fifty-one experiments were initially set up for the salt screening process in 2 mL vials containing 6.3 mm stir bars, including experiments involving the amorphous freebase in the absence of counter ions. A stock solution of the freebase obtained in DCM and ammonium bicarbonate was prepared in TFE at a concentration of 60.51 mg/mL. Stock solutions of the counter ions were prepared in EtOH at a concentration of 20 mg/mL. Each vial contained 495.8 μL of the freebase solution (30 mg in total), and 1.1 eq. of the counter ion stock solution was added. Three vials contained the freebase dissolved in TFE, only, with no counter ion used. The vials were heated at 45° C. with stirring at 540 rpm for 2 h, followed by evaporation at RT overnight.

EtOH, THF, and IPAc, were chosen for the first round of solvent screening. The experiments produced solids in 40/51 vials. To sample these experiments, the vials were left to stand undisturbed for 30 min and an aliquot of the slurry was then filtered and analyzed. Crystalline salts were not observed for the first round of solvents. After sampling all the slurries, the vials were left uncapped to evaporate to be used in a second round of solvents using ACN, dioxane, and 2-methyltetrahydrofuran (2-MeTHF). The second round of solvents yielded 42/51 slurries that were analyzed following the same procedure mentioned above. Crystalline salts were initially not observed. The experiments were left to stir at 45° C. for 2 days and then at RT for approximately 3 weeks to be sampled again after this time.

These screens afforded one crystalline compound, which did not correspond to either the counter ion or the crystalline freebase used for the screening. The compound was stable upon drying. However, it converted to an amorphous solid after exposure to high RH overnight.

Crystalline Feasibility of Free-Base Compound R-D1

Figure 42:
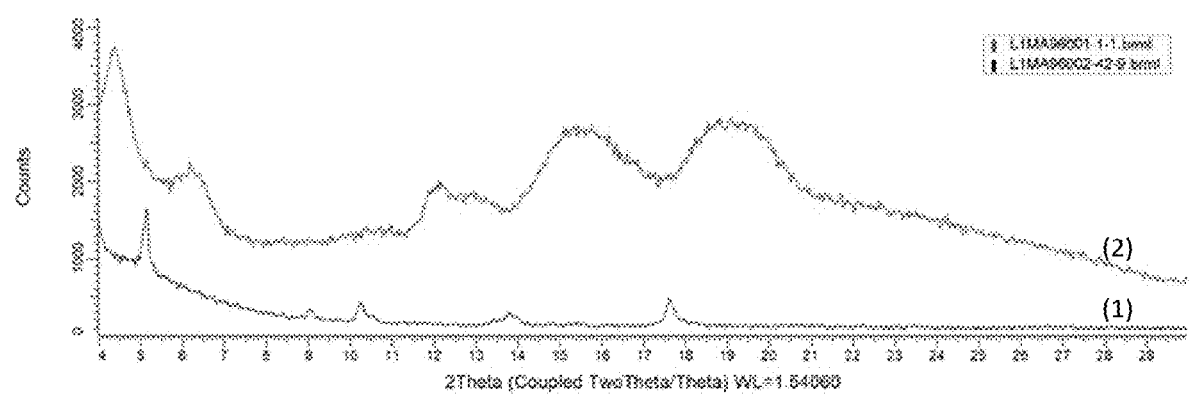
FIG. 42 is an overlay of two XRPD traces. Trace (1) corresponds to the wet cake of crystal pattern FF-A of free-base compound R-D1. Trace (2) corresponds to the citrate salt of racemic compound D1.
Figure 43:
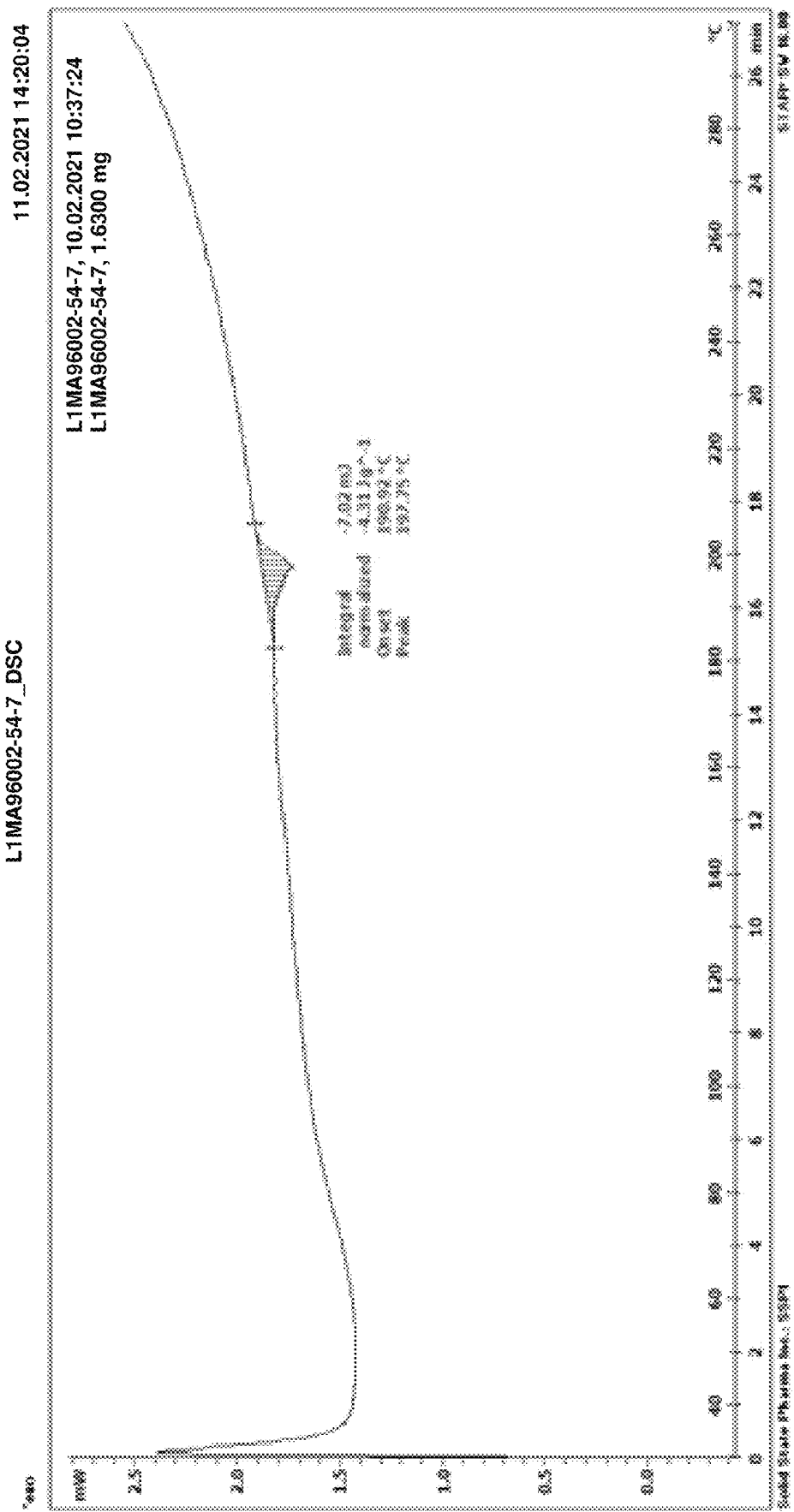
FIG. 43 is a DSC thermogram for crystal pattern FF-A of free-base compound R-D1.

For this experiment, 7.2 mg of the amorphous freebase prepared from DCM and ammonium bicarbonate were weighed in a 4 mL vial, and 0.75 mL of MeOH-$d_4$ was added. The suspension was sonicated for thorough dissolution, and it was transferred to an NMR tube for $^1$H NMR analysis. After approximately 1 h, the clear yellow solution became hazy pink, and white solids precipitated out of the solution. The solids showed crystallinity, as demonstrated by XRPD analysis (FIG. 42, crystal pattern FF-A). The crystalline material obtained from was different than the low crystalline racemic mixture pattern, as shown by XRPD. This was also confirmed by evaluating the chiral purity with HPLC, which confirmed the presence of the R-enantiomer in a 94.01% purity (compared to 99.05% purity for the citrate salt of compound R-D1 and 98.99% purity of free-base compound R-D1 prior to the study. The chemical purity of this compound resulted in 84.40%. The analysis by attenuated total reflectance-infrared (ATR-IR) spectroscopy was in good agreement with the citrate salt of compound R-D1 and freebase compound R-D1. The DSC thermogram indicated that the solid had low crystallinity (FIG. 43).

Crystalline Patterns Observed from Free-Base Compound R-D1 in MeOH and EtOH

The amorphous freebase prepared in DCM and ammonium bicarbonate was weighed (15.5 mg) in a 2 mL vial, and 20 vol. of MeOH (ACS grade) or EtOH were added. The suspension was sonicated for thorough dissolution, which resulted in a yellow gum that dissolved in the solvent quickly, yielding a clear solution. After approximately 10 min under constant sonication, white solids formed in the solution, and the suspension was left to sonicate for some additional minutes. An aliquot of the sample was filtered for further XRPD analysis, while the remaining suspension was transferred to a stirring plate set at 500 rpm at RT. The resulting slurries were filtered to collect the solids for XRPD analysis on the wet cakes.

XRPD analysis was done in three stages. XRPD of the wet cake was done for all samples where solids were observed. The samples that showed unique patterns were further dried on the XRPD plates at 50° C., under vacuum for 3 h, and were characterized with XRPD analysis.

The solids were then exposed to >95% RH overnight. This humid environment was produced by placing a beaker of saturated potassium sulfate in water in a sealed container at RT. The materials exposed to these conditions were evaluated by XRPD, and their patterns were compared to those produced before.

Figure 44:
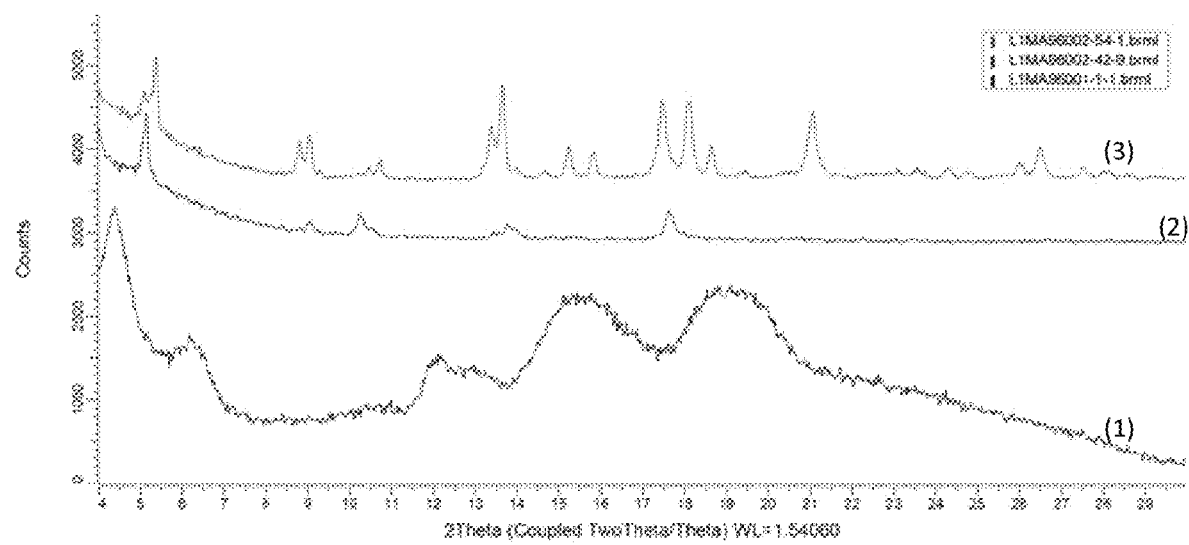
FIG. 44 is an overlay of three XRPD traces. Trace (1) corresponds to the citrate salt of racemic compound D1. Trace (2) is an XRPD trace for the wet cake of free-base compound R-D1, crystal pattern FF-A. Trace (3) is an XRPD trace for the wet cake of free-base compound R-D1, crystal pattern FF-B.
Figure 45:
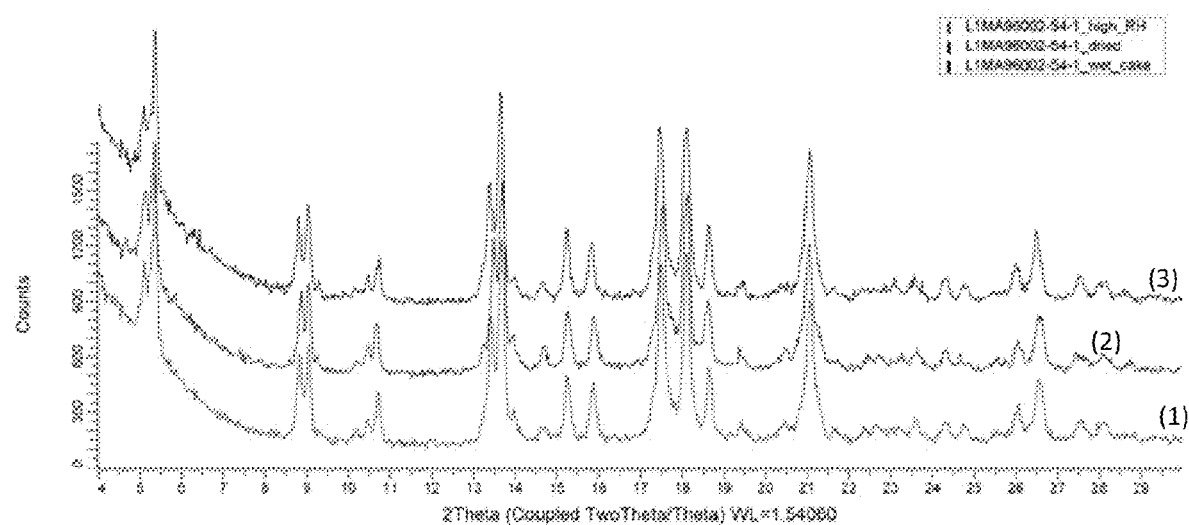
FIG. 45 is an overlay of three XRPD traces. Trace (1) is an XRPD trace for the wet cake of free-base compound R-D1, crystal pattern FF-A. Trace (2) is an XRPD trace for the dried cake of free-base compound R-D1, crystal pattern FF-B. Trace (3) is an XRPD trace for the wet cake of free-base compound R-D1, crystal pattern FF-B, after humidity exposure at >95% RH.
Figure 46A:
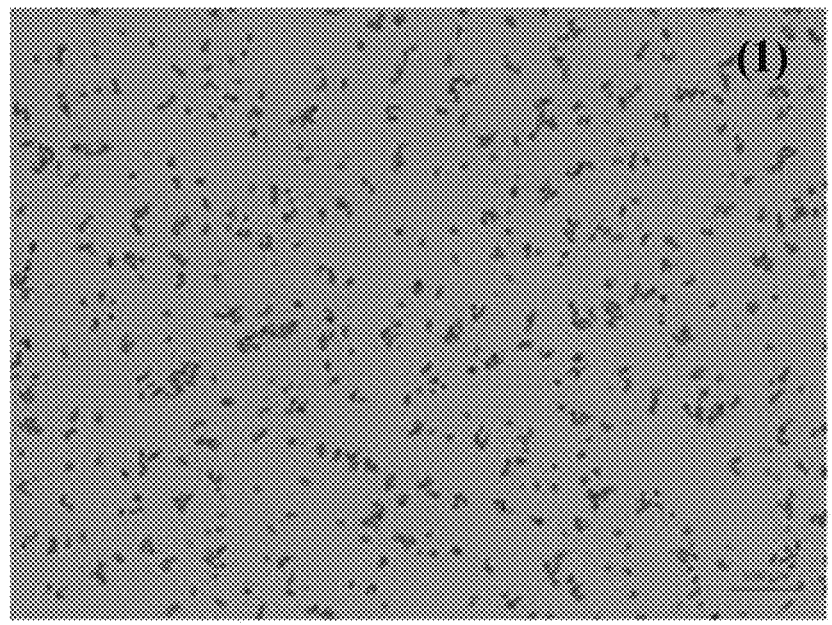
FIGS. 46A and 46B are microscopy images of the free-base compound R-D1 solids precipitated from MeOH.
Figure 46B:
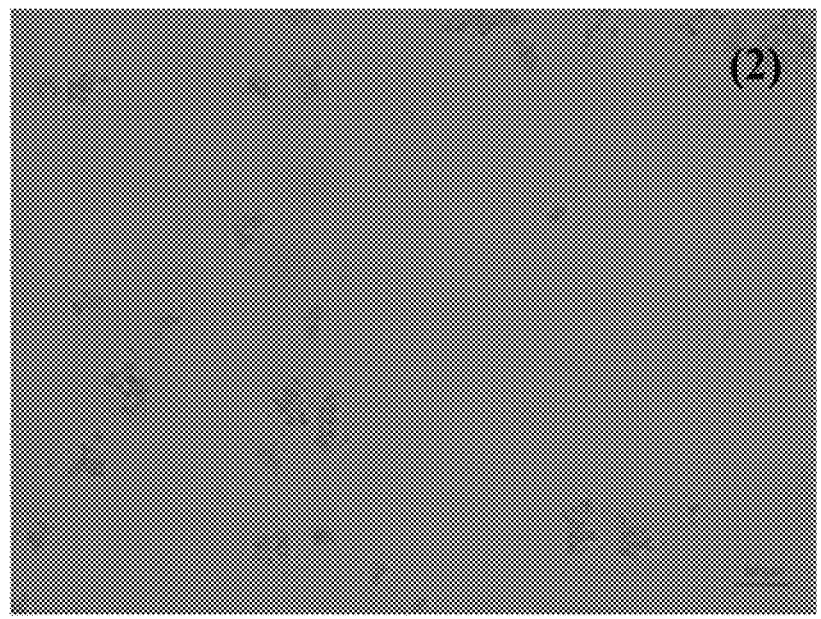

The solids collected from MeOH showed high crystallinity, the patterns did not agree with the low crystalline racemic mixture (FIG. 44). Overall, these solids were physically stable upon drying and high humidity exposure, as shown in FIG. 45. The microscopy images showed fines (FIGS. 46A and 46B).

Figure 47:
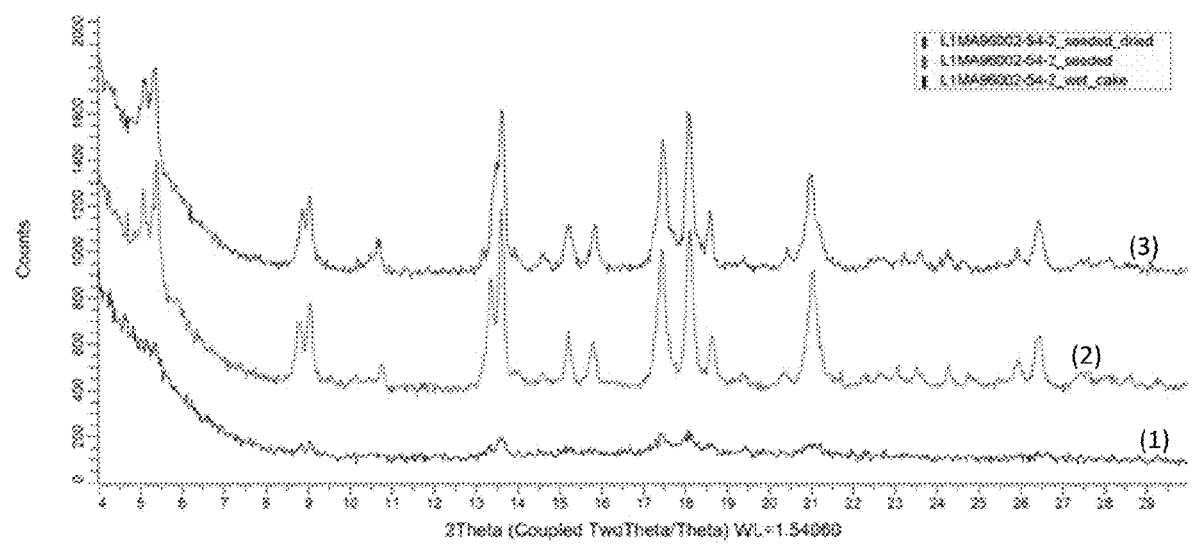
FIG. 47 is an overlay of three XRPD traces. Trace (1) is an XRPD trace for the wet cake of free-base compound R-D1, crystal pattern FF-B. Trace (2) is an XRPD trace for the wet cake of free-base compound R-D1, crystal pattern FF-B, after seeding and stirring overnight. Trace (3) is an XRPD trace for the wet cake of free-base compound R-D1, crystal pattern FF-B, after humidity exposure at >95% RH.

The solids collected from EtOH showed low crystallinity (FIG. 47, trace (1)). The remaining suspension was seeded using 30 μL of a suspension containing the crystals formed in MeOH, to help promote the conversion to a more crystalline material. The mixture was left to stir overnight at 540 rpm at RT. An aliquot of the suspension was filtered for XRPD analysis of the wet cake, and its patterns were compared to those obtained before the seeding (FIG. 47). After seeding and stirring overnight, the solids showed higher crystallinity.

Preparation of Pattern FF-A in MeOH

To produce crystalline freebase, 50 mg of the amorphous freebase of compound R-D1 were weighed in a 4 mL vial, and 20 vol. of MeOH was added. The amorphous freebase formed a yellow gum upon contact with the solvent. The mixture was vortexed vigorously to dissolve the gum, followed by sonication until the yellow clear solution turned into a white immobile slurry. More solvent was added (13 vol.) to produce a flowable slurry. A sample of the slurry was filtered, and analyzed by XRPD on the wet cake, which showed that the compound was initially low crystalline (by XRPD). The sample was seeded using 50 μL of a seed in acetone (Pattern FF-B) and it was left to stir at 540 rpm at RT using a 10 mm stir bar. An aliquot of the slurry was filtered for further XRPD analysis after 6, 18, and 24 h of seeding and slurring in MeOH. The analysis showed increased crystallinity after 6 h (by XRPD), showing the Pattern FF-A. The whole sample was filtered in a pre-weighed vial and filter paper. The solids collected were washed 3 times using 2 vol. of MeOH each time. The white solids were left to dry at RT in a vacuum oven (~−29 inHg) for 24 h.

The XRPD diffractogram of the dried sample revealed a crystalline Pattern FF-A. The HPLC analysis showed a chemical purity of 97.85% and a chiral purity of 96.80%, as compared to the chemical purities of 99.46% and 96.62% for the citrate salt of compound R-D1 and free-base compound R-D1, respectively, and to the chiral purities of 99.05% and 98.95% for the citrate salt of compound R-D1 and free-base compound R-D1, respectively.

Preparation of Pattern FF-A has also been scaled up. HPLC showed a chemical and chiral purity of 98.50 and 97.11%, respectively. The wet cake of Pattern FF-A was dried at 50° C. under vacuum for 3 h. It was then exposed to >95% RH overnight. Reduction in the crystallinity of Pattern FF-A was observed, as indicated by a decrease in the intensity and broadening of some features in the XRPD trace.

The one-week stability at 75% RH was also tested. In this experiment, 12 mg of the dried crystalline freebase from MeOH were weighted in a 4 mL vial and placed in a 20 mL vial set at 40° C. and 75% RH for 1 week. The humid environment was generated with saturated sodium chloride in water in a sealed container. The chemical and chiral purities of the resulting material, as measured by HPLC after this experiment, resulted in 98.27 and 94.55%, respectively.

Finally, the DVS isotherm plot revealed that the compound is hygroscopic, according to the European Pharmacopeia standards. This was indicated by the high humidity absorption (10.70 wt. %, 5.5 eq.) over a 5-95% humidity range. However, equilibrium was not reached at high RH therefore the mass change was representative of kinetics and may be higher with longer time. The adsorption/desorption profile also showed that this process is reversible. The XRPD analysis of the compound collected after the DVS analysis showed a new signal at 2θ=5.8°. This signal was consistent upon subjecting the same sample to drying under vacuum at RT for 2 h. The chemical purity measured by HPLC for the compound after the DVS analysis resulted in 98.68%.

To study the effect of the temperature, the compound was subjected to a thermal treatment consisting of heating up the sample from RT up to 100° C. at a 10° C./min, and holding this temperature for 5 min to subsequently cool down to RT. The sample was collected and further analyzed with XRPD. The resulting patterns from this sample showed loss of some crystallinity.

Overall, these analyses showed that the crystalline freebase, Pattern FF-A, produced in MeOH loses some crystallinity upon drying and exposure to humidity. Additionally, an extra peak by XRPD was observed after humidity exposure in DVS.

Preparation of Pattern FF-B

Figure 48:
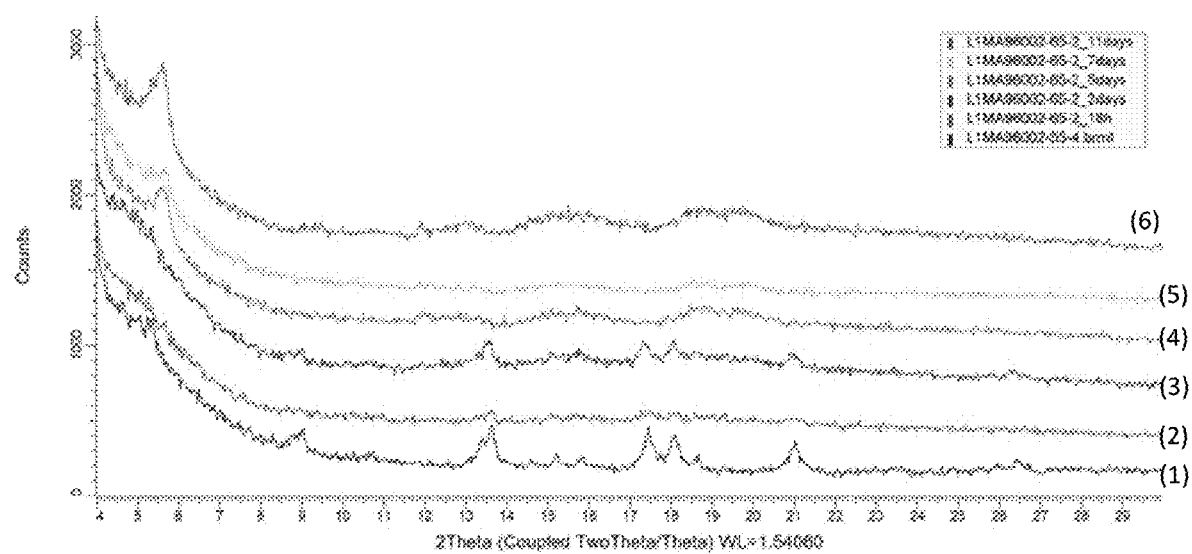
FIG. 48 is an overlay of six XRPD traces. Trace (1) is an XRPD trace of free-base compound R-D1, crystal pattern FF-B, from acetone. Trace (2) is an XRPD trace for the wet cake of free-base compound R-D1, 18 h after seeding. Trace (3) is an XRPD trace for the wet cake of free-base compound R-D1, after heating up to 45° C. and adding more seed. Trace (4) is an XRPD trace for the wet cake of free-base compound R-D1, after adding DCM and more seed. Trace (5) is an XRPD trace for the wet cake of free-base compound R-D1, after 7 days of slurring. Trace (6) is an XRPD trace for the wet cake of free-base compound R-D1, after 11 days of slurring.

Approximately 150 mg of the amorphous freebase were weighed in a 4 mL vial. EtOH (15 vol.) was added, resulting in a yellow gum that was dispersed by vigorous vortex, followed by sonication Preparation of Pattern FF-B in EtOH. for a prolonged time until producing a hazy yellow slurry. The suspension was seeded with 100 μL of the crystalline freebase obtained in acetone (Pattern FF-B). The slurry was left to stir overnight at 540 rpm, at RT using a 10 mm bar. The next day, the slurry appeared thicker with off-white color. The XRPD pattern on the wet cake showed an amorphous compound (FIG. 48, trace (2)). After approximately 48 h, the slurry was brought to 45° C. After reaching this temperature, the slurry was seeded one more time with the dried solids of the crystals isolated from MeOH (Pattern FF-A). The XRPD pattern of the wet cake showed an amorphous compound, with some conversion to Pattern FF-B, as shown in FIG. 48, trace (3). After 3 days, 20 μL of DCM were added to the sample to enhance the crystalline conversion. After 15 min, the sample was seeded by adding dried seeds isolated from acetone (Pattern FF-B). The experiment was left to stir overnight at 45° C. An aliquot was filtered for XRPD analysis, which showed an amorphous pattern FIG. 48, trace (4)). The slurry was monitored for visual changes and sampled frequently with XRPD analysis over the course of 1 week. The compound revealed an amorphous pattern (FIG. 48, trace (5)). The slurry was monitored daily up to 11 days. After 11 days of stirring, an aliquot of the slurry was filtered and sampled for XRPD analysis. The material showed an amorphous pattern (FIG. 48, trace (6)).

Figure 49:
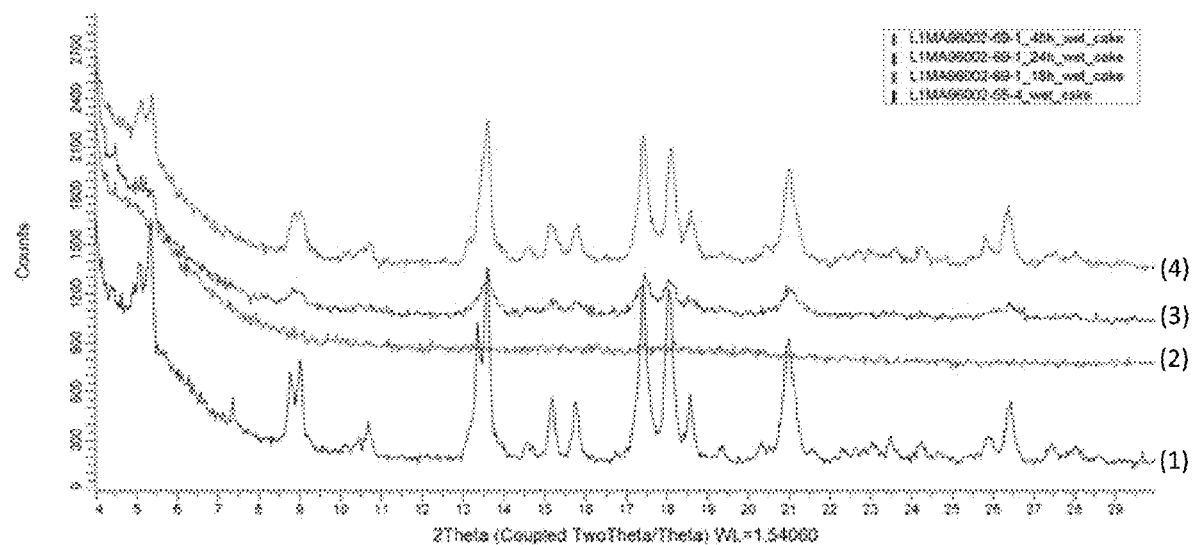
FIG. 49 is an overlay of four XRPD traces. Trace (1) is an XRPD trace of free-base compound R-D1, crystal pattern FF-B, from acetone. Trace (2) is an XRPD trace for the wet cake of free-base compound R-D1, 18 h after seeding. Trace (3) is an XRPD trace for the wet cake of free-base compound R-D1, after heating up to 45° C. Trace (4) is an XRPD trace for the wet cake of free-base compound R-D1, 5 h after adding DCM and more seed.

Preparation of Pattern FF-B in Acetone. Approximately 200 mg of the amorphous freebase were weighed in a 20 mL vial. Acetone (20 vol.) was added, and the mixture was sonicated to produce a hazy yellow slurry mixed with a clear yellow solution, with off-white particles when left to stand. The suspension was seeded with dried solids of the crystalline freebase previously obtained in acetone (Pattern FF-B, FIG. 49, trace (1)). The slurry was left to stir overnight at 540 rpm, at RT using a 10 mm thick bar. After approximately 18 h, the slurry appeared thicker with an off-white color. The XRPD pattern on the wet cake showed an amorphous compound (FIG. 49, trace (2)). The slurry was brought to 45° C. After reaching this temperature, 20 μL of DMC was added and the slurry was seeded with dried solids of the crystals isolated from acetone (Pattern FF-B). After 7 h of seeding, the XRPD pattern of the wet cake showed some conversion to Pattern FF-B, as shown in FIG. 49, trace (3). The slurry was left to stir at RT overnight. On day 2, the slurry appeared thicker and a yellow-white color. An aliquot was filtered for XRPD analysis, which showed crystalline Pattern FF-B (FIG. 49, trace (4)). The slurry was filtered and washed twice using 2 vol. of acetone. The resulting solids were transferred to a prepared 4 mL vial and dried overnight at RT under vacuum (~−29 inHg) for further analysis. The yield of the experiment was 52%.

Characterization of Pattern FF-B. The TGA/DSC thermograms showed a mass loss event of 3.9 wt. % over the course of a broad temperature endotherm. The analysis by KF showed a water content of 3.36 wt. % (1.6 eq.), in good agreement with the TGA/DSC result. In addition, the $^1$H NMR in chloroform-d did not show the presence of additional solvent. Two subsequent melts with an onset at 195.7 and 226.7° C. were also observed without associated mass losses. The temperature of these thermal transitions was corroborated with stand-alone DSC analysis. Microscopy images revealed the morphology to be irregular particles of yellow color that showed birefringence under polarized light. The chemical and chiral purities evaluated by HPLC were 98.85 and 96.56%, respectively.

Figure 50:
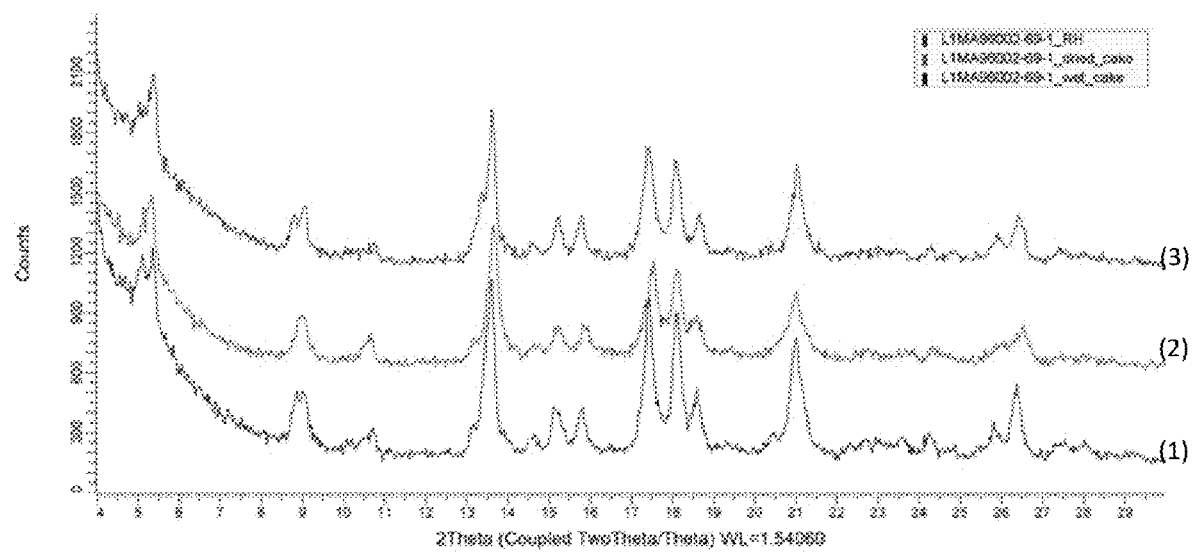
FIG. 50 is an overlay of three XRPD traces. Trace (1) is an XRPD trace of the wet cake of free-base compound R-D1, crystal pattern FF-B. Trace (2) is an XRPD trace for the dried cake of free-base compound R-D1. Trace (3) is an XRPD trace for the free-base compound R-D1, after exposure to >95% RH overnight at room temperature.

The pattern FF-B was dried at 50° C. under vacuum for 3 h after filtration for further XRPD analysis. The solids were then exposed to >95% RH overnight. This humid environment was produced by placing a beaker of saturated potassium sulfate in water in a sealed container at RT. The materials exposed to these conditions were evaluated by XRPD, and their patterns were compared to those of the crystalline freebase along each step. This experiment showed that the crystallinity of the compound decreased after drying the sample under vacuum, as indicated by the loss of intensity and broadening of some features in the diffractogram (FIG. 50, trace (2)). Some of the crystallinity was regained after exposing the sample to high RH overnight, as shown in FIG. 50, trace (3).

Figure 51:
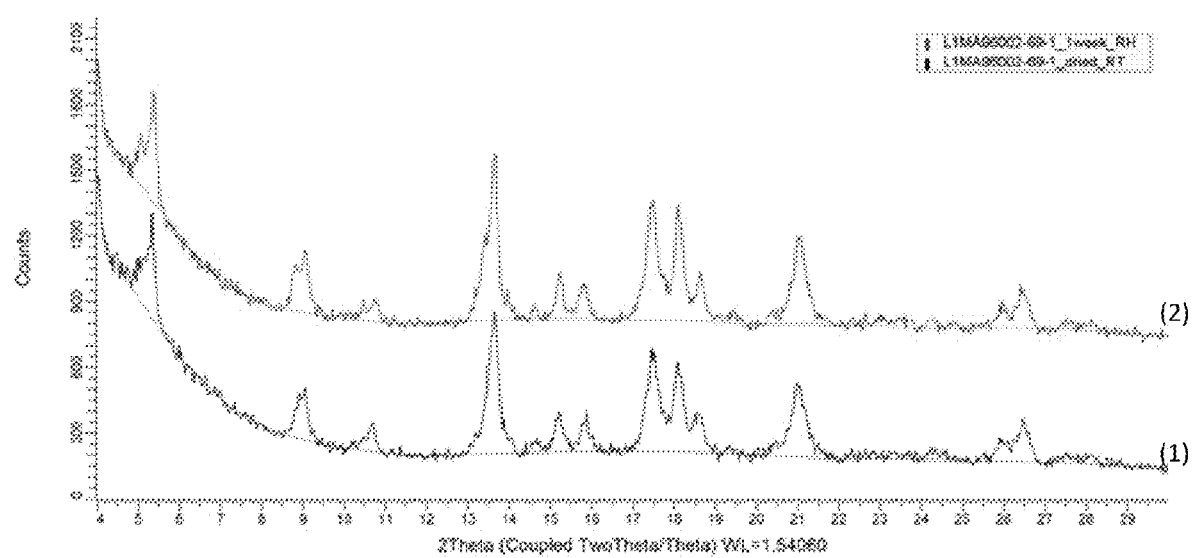
FIG. 51 is an overlay of two XRPD traces. Trace (1) is an XRPD trace of the dried cake of free-base compound R-D1, crystal pattern FF-B. Trace (2) demonstrates that compound R-D1, crystal pattern FF-A, converted to compound R-D1, crystal pattern FF-B, after 1 week of storage at 40° C. at 75% RH.

The one-week stability at 75% RH was also tested. In this experiment, 12 mg of the crystalline freebase from MeOH was weighted in a 4 mL vial and placed in a 20 mL vial set at 40° C. and 75% RH for 1 week. The humid environment was generated with saturated sodium chloride in water in a sealed container. The XRPD analysis showed the splitting of the signal at 5.3 and 13.7°, as shown in FIG. 51. The HPLC analysis showed a chemical and chiral purity of 98.56% and 96.13%, respectively.

Figure 52:
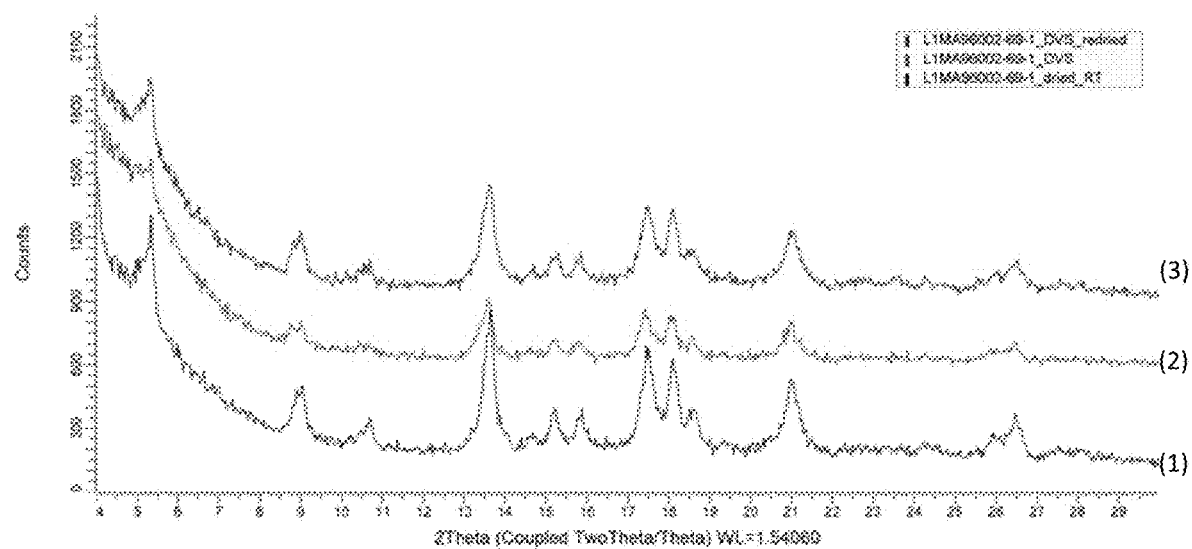
FIG. 52 is an overlay of three XRPD traces. Trace (1) is an XRPD trace of dried solids of free-base compound R-D1, crystal pattern FF-B. Trace (2) is an XRPD trace of the solids collected after the DVS analysis of free-base compound R-D1, crystal pattern FF-B. Trace (3) is an XRPD trace of the solids collected after the DVS analysis of free-base compound R-D1, crystal pattern FF-B, and dried under vacuum at room temperature for 2 h.

The DVS isotherm plot revealed that the compound is hygroscopic, according to the European Pharmacopeia standards. This was indicated by the high humidity absorption (8.80 wt. %, 4.0 eq.) over a 5-95% humidity range. However, equilibrium was not reached at high RH. Therefore, the mass change was representative of kinetics and may be higher with longer time. The adsorption/desorption profile also showed that this process is reversible. The XRPD analysis of the compound collected after the DVS analysis showed a slight loss in crystallinity, indicated by the decreased intensity of some signals (FIG. 52, trace (2)). This process was slightly reversible, as indicated by the patterns acquired on the same sample after drying for 2 h under vacuum, as shown in FIG. 52, trace (3). The chemical purity evaluated with HPLC resulted in 99.06%.

The sample was subjected to a thermal treatment consisting of heating the sample gradually (10° C./min) up to the first two thermal events shown by TGA/DSC analysis, i.e., 130 and 225° C. In each case, the temperature was held for 5 min, followed by cooling down to RT. The sample was collected and further analyzed with XRPD. The patterns of the collected sample showed decreased crystallinity after exposure to 130° C., possibly by releasing water. Overall, the crystalline freebase Pattern FF-B obtained from acetone lost some crystallinity upon drying and exposure to humidity and heat.

Example 20—Preparation of the Compounds of Formula A

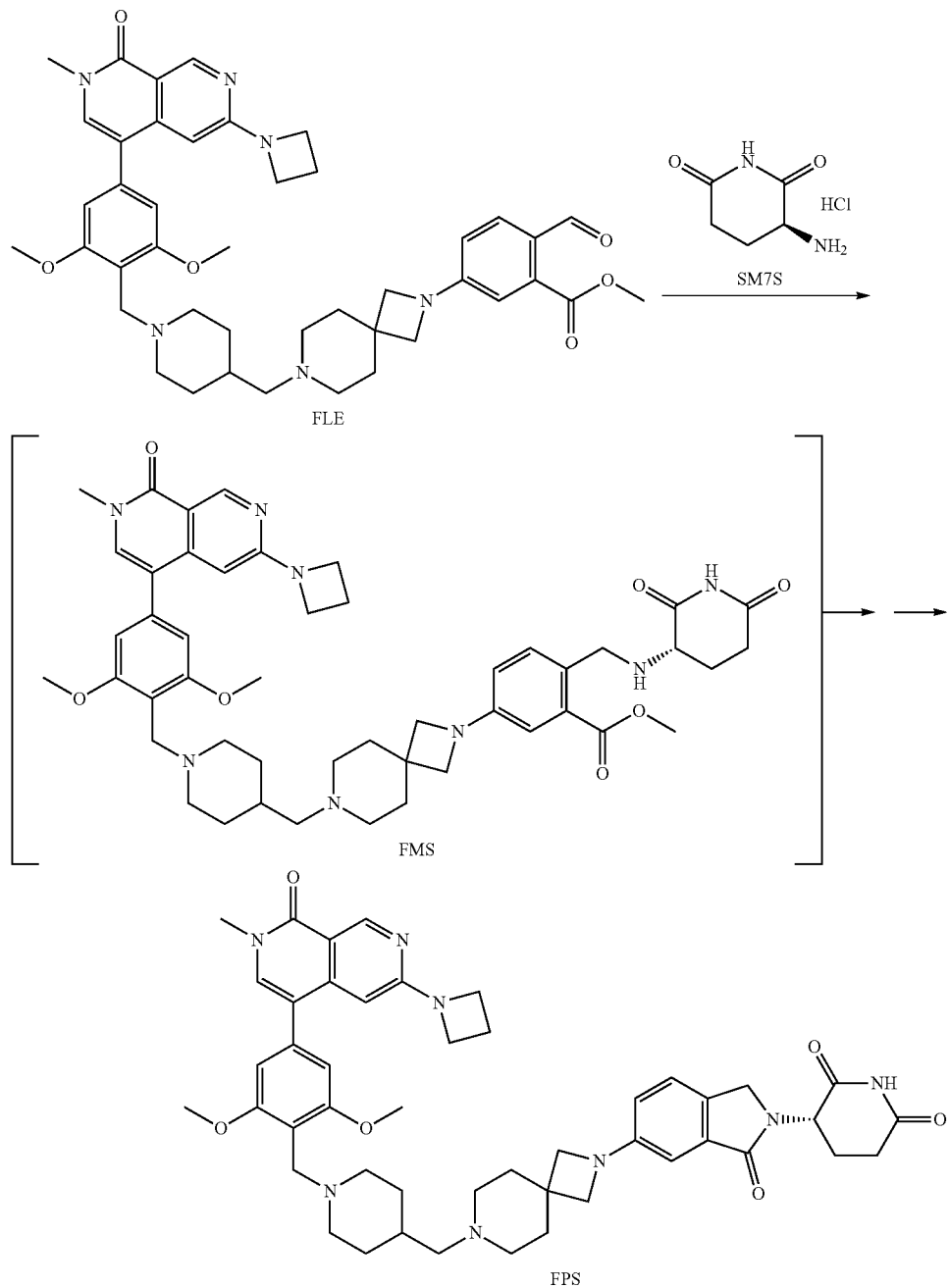

A solution of FLE (5.0 g, 6.68 mmol, 1.00 equiv) and SM7S (2.2 g, 13.41 mmol, 2.00 equiv) in THF (90 ml) and MeOH (10 mL) was cooled to 0-10° C. and AcOH (0.5 g, 8.33 mmol, 1.25 equiv) was added. The reaction mixture was stirred at 0-10° C. for 0.5-6 hrs. Then NaCNBH$_3$ (1.25 g, 19.89 mmol, 3.00 equiv) was added as solution (10 ml of THF:MeOH 9:1) to the above resulting solution, and the resulting mixture was stirred at 0-10° C. for 2 h and then warmed to room temperature overnight. The solution was cooled 0-15° C. reaction and was quenched by the addition of DCM (37.5V), DMSO (12.5V), and 5% Na$_2$CO$_3$ aqueous solution (30V), and then the solution was warmed to room temperature. The phases were separated and to the organic phase was added 5% Na$_2$CO$_3$ aqueous solution (30V). The phases were separated and to the organic phase was added a brine solution (25V). The phases were separated and to the organic phase was added 5% Na$_2$CO$_3$ aqueous solution (30V). The phases were separated and to the organic phase was added a brine solution (25V). The organic phase is concentrated to 7.5 V and MeCN (10V) is added. The reaction mixture is then filtered to remove solids and the filter cake is washed with DCM/MeCN (1:10). The filtrate is then concentrated to 7.5V and DMF (7V) is added. The solution is concentrated to 8V and cooled to room temperature. To the concentrated is added water (3V) and the reaction mixture is stirred. The reaction mixture is then filtered and the filter cake was wash by water. The filtrate was dried in vacuo. This provided 3-[6-(7-[[1-([4-[6-(azetidin-1-yl)-2-methyl-1-oxo-2,7-naphthyridin-4-yl]-2,6-dimethoxyphenyl]methyl)piperidin-4-yl]methyl]-2,7-diazaspiro[3.5]nonan-2-yl)-1-oxo-3H-isoindol-2-yl]piperidine-2,6-dione (2.77 g, 50%) as a yellow solid.

TABLE 54

| Type | $\delta_C^b$ (ppm) | $\delta_H^c$ (ppm) | Relative Intensity |
|---|---|---|---|
| C | 173.4 | N/A | N/A |
| CH2 | 31.7 | 2.91(o), 2.54(o) | 2H |
| CH2 | 23.0 | 2.38(o), 1.98(m) | 2H |
| CH | 52.2 | 5.07(dd, J = 13.20 Hz, 5.00 Hz) | 1H |
| C | 171.6 | N/A | N/A |
| NH | N/A | 10.96(s) | 1H |
| C | 169.0 | N/A | N/A |
| C | 132.9 | N/A | N/A |
| C | 130.7 | N/A | N/A |
| CH2 | 47.2 | 4.25(o) | 2H |
| CH | 104.7 | 6.67(o) | 1H |
| C | 152.4 | N/A | N/A |
| CH | 115.9 | 6.69(o) | 1H |
| CH | 124.2 | 7.37(d, J = 8.80 Hz) | 1H |
| CH2 | 62.1 | 3.60(br) | 4H |

TABLE 54-continued

| Type | $\delta_C^b$ (ppm) | $\delta_H^c$ (ppm) | Relative Intensity |
|---|---|---|---|
| C | 34.4 | N/A | N/A |
| CH2 | 34.9 | 1.77(o) | 4H |
| C | 106.3 | N/A | N/A |
| C | 159.7 | N/A | N/A |
| CH3 | 56.8 | 3.89(s) | 6H |
| CH | 105.6 | 6.85(s) | 2H |
| C | 139.4 | N/A | N/A |
| C | 115.3 | N/A | N/A |
| CH | 138.0 | 7.60(s) | 1H |
| C | 161.3 or 161.4 | N/A | N/A |
| C | 111.9 | N/A | N/A |
| C | 142.3 | N/A | N/A |
| CH3 | 36.3 | 3.48(s) | 3H |
| CH | 151.7 | 9.01(s) | 1H |
| C | 161.4 or 161.3 | N/A | N/A |
| CH | 94.2 | 6.20(s) | 1H |
| CH2 | 50.7 | 4.00(m) | 4H |
| CH2 | 16.5 | 2.34(o) | 2H |
| C | 177.1 | N/A | N/A |
| C | 72.0 | N/A | N/A |
| C | 171.9 | N/A | N/A |
| CH2 | 44.5 | 2.54(o) | 4H |

LCMS (ESI) m/z: [M + H]⁺ = 829.55.

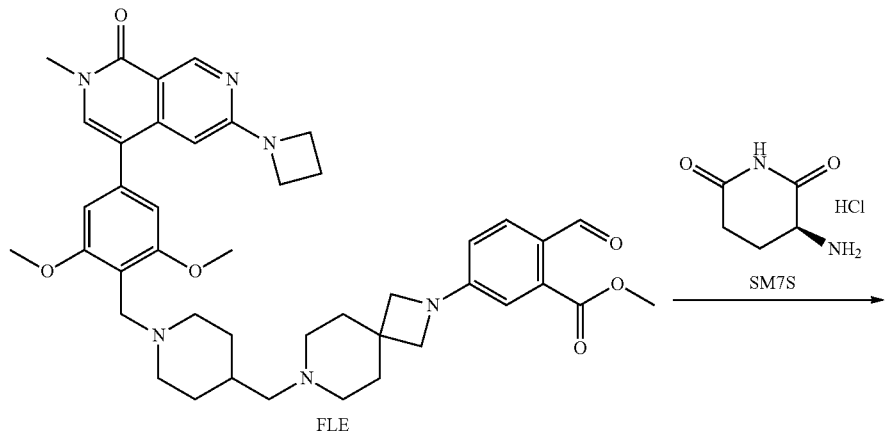

FLE

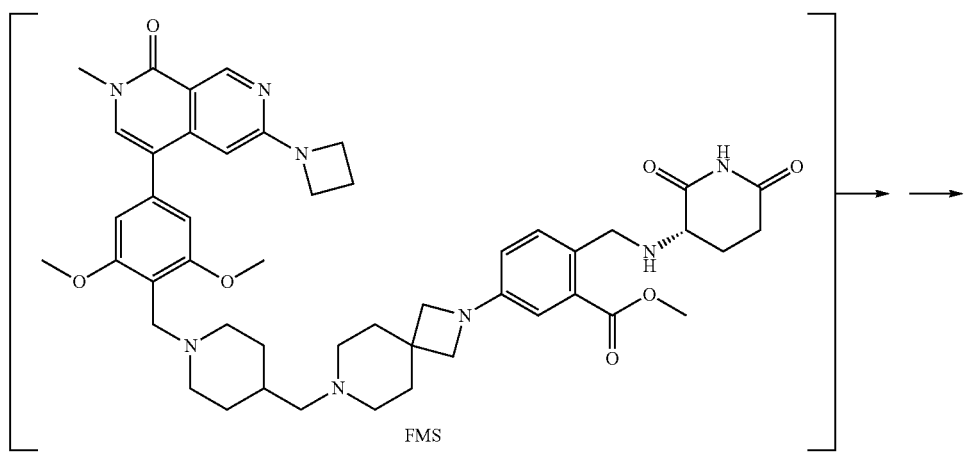

FMS

-continued

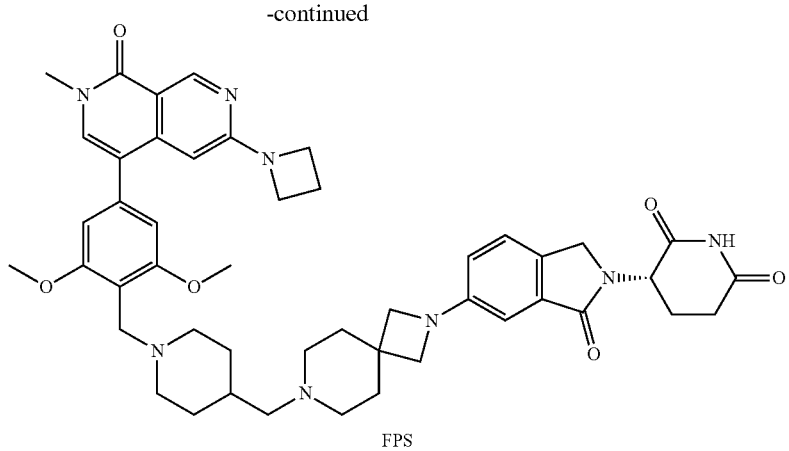

FPS

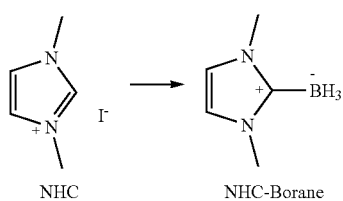

NHC → NHC-Borane

Compound FPS has also been prepared with NHC-borane as described above in example 20, with the exception that NHC-borane was used instead of NaCNBH$_3$. The chiral purity of FPS was assessed at each stage of the purification, and the results are summarized in Table 55.

TABLE 55

| Starting Material | | | Crude NHC-Borane (~45% assay) | Reaction Conditions (temp/time) | | | IPC (%) FPS | Result Chiral purity of FPS |
|---|---|---|---|---|---|---|---|---|
| FLE | SM7S | AcOH | | Solvent | Temp (° C.) | Time (h) | | |
| 4.7 g net | 3.0 eq. | 5% | 1.5 eq. | THF/MeOH 9:0.5 (v/v) | 20-30 | 12 | 50.7% | 89.1% |
| Charge 30 V DCM and 10 V DMSO into the reaction mixture | | | | | | Organic layer | 69.7% | 87.1% |
| Charge 30 V 5% NaHCO$_3$ into R1 | | | | | | | | |
| Separated to obtain organic layer | | | | | | | | |
| Wash the organic layer with another 5% NH$_4$HCO$_3$ twice | | | | | | | | |
| Concentrated and slurry the residual in DCM/MeCN to improve chiral purity Filter to obtain mother solution | | | | | | Wet cake Mother solution | 91.7% 59.0% | 65.6% 99.8% |
| Concentrate the mother solution to dryness | | | | | | supernatant | 7.2% | 81.6% |
| Dissolved the dryness in 7 V DMF and 3 V MeCN | | | | | | Wet cake | 77.0% | |
| Charge ~3 V water slowly into the solution, and charge seed into the solution | | | | | | | | |
| Stir the reaction mixture for 16 hrs | | | | | | | | |
| Slurry the wet cake in DMF/MeCN/Water (7 V/3 V/3 V) Dry to obtain 2.6 g crude FPS | | | | | | Wet cake2 product | 77.3% 79.2% | 98.4% chiral |

227

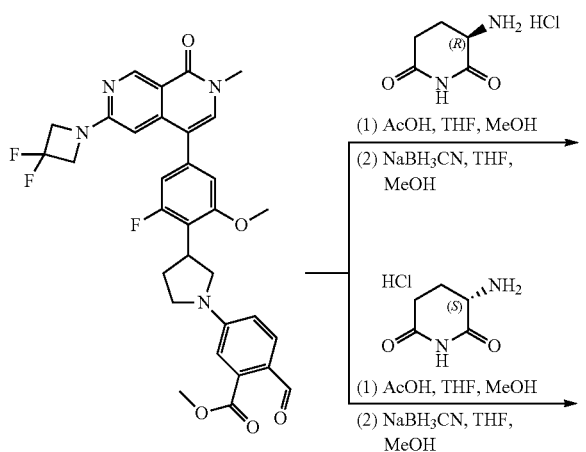

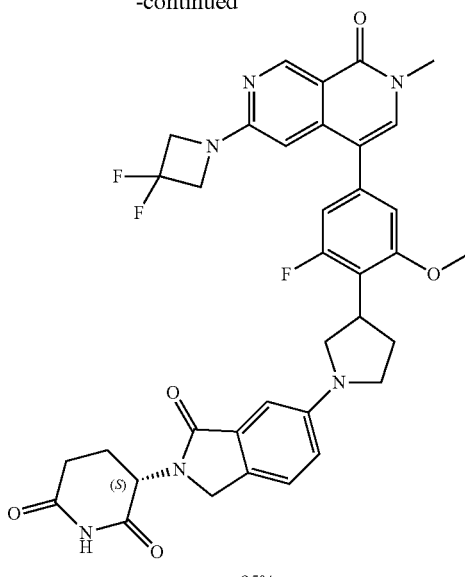

228

-continued

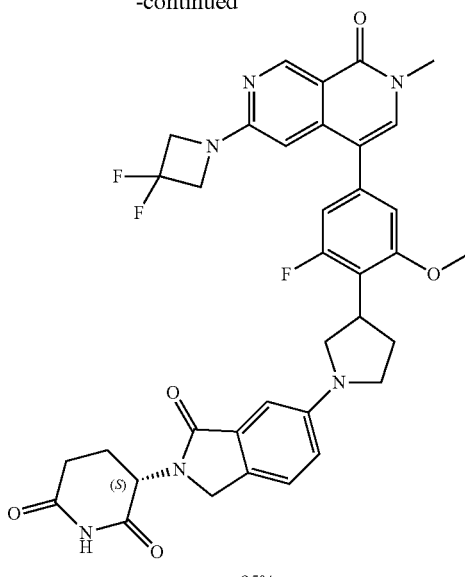

ee: >95%

Preparation of (3R)-3-{6-[(3R)-3-{4-[6-(3,3-difluoroazetidin-1-yl)-2-methyl-1-oxo-2,7-naphthyridin-4-yl]-2-fluoro-6-methoxyphenyl}pyrrolidin-1-yl]-1-oxo-3H-isoindol-2-yl}piperidine-2,6-dione To a stirred solution of acetic acid; methyl methyl 5-[(3R)-3-{4-[6-(3,3-difluoroazetidin-1-yl)-2-methyl-1-oxo-2,7-naphthyridin-4-yl]-2-fluoro-6-methoxyphenyl} pyrrolidin-1-yl]-2-formylbenzoate (100 mg, 0.150 mmol, 1 equiv) and (3R)-3-aminopiperidine-2,6-dione hydrochloride (49.38 mg, 0.300 mmol, 2 equiv) in MeOH (0.5 mL) and THF (5 mL) were added AcOH (11.71 mg, 0.195 mmol, 1.3 equiv) in THF (1 mL) dropwise at room temperature under nitrogen atmosphere, The mixture was stirred for 0.5 h at 0° C., then the mixture was added NaBH₃CN (28.28 mg, 0.450 mmol, 3 equiv) in MeOH (0.1 mL) and THF (1 mL) dropwise at 0° C. under nitrogen atmosphere. The resulting mixture was stirred for overnight at room temperature under nitrogen atmosphere. The residue was purified by reverse flash chromatography with the following conditions: column, C18 silica gel; mobile phase, MeCN in Water (0.1% TFA), 10% to 50% gradient in 10 min; detector, UV 254 nm. to afford (3R)-3-{6-[(3R)-3-{4-[6-(3,3-difluoroazetidin-1-yl)-2-methyl-1-oxo-2,7-naphthyridin-4-yl]-2-fluoro-6-methoxyphenyl}pyrrolidin-1-yl]-1-oxo-3H-isoindol-2-yl}piperidine-2,6-dione (38.5 mg) as a white solid. LCMS (ESI) m/z: [M+H]⁺=687. 1H NMR (300 MHz, DMSO-d6) δ 10.98 (s, 1H), 9.09 (d, J=0.7 Hz, 1H), 7.70 (s, 1H), 7.40 (d, J=8.3 Hz, 1H), 7.04-6.93 (m, 2H), 6.88 (dd, J=8.4, 2.3 Hz, 1H), 6.82 (d, J=2.2 Hz, 1H), 6.45 (s, 1H), 5.10 (dd, J=13.2, 5.1 Hz, 1H), 4.51 (t, J=12.4 Hz, 4H), 4.39-4.16 (m, 2H), 4.12-3.94 (m, 1H), 3.89 (s, 3H), 3.66-3.38 (m, 7H), 2.92 (ddd, J=17.7, 13.4, 5.3 Hz, 1H), 2.60 (d, J=16.8 Hz, 1H), 2.50-2.20 (m, 3H), 2.07-1.94 (m, 1H).

A modified version of the procedure described above has also been used in the stereoretentive preparation shown below.

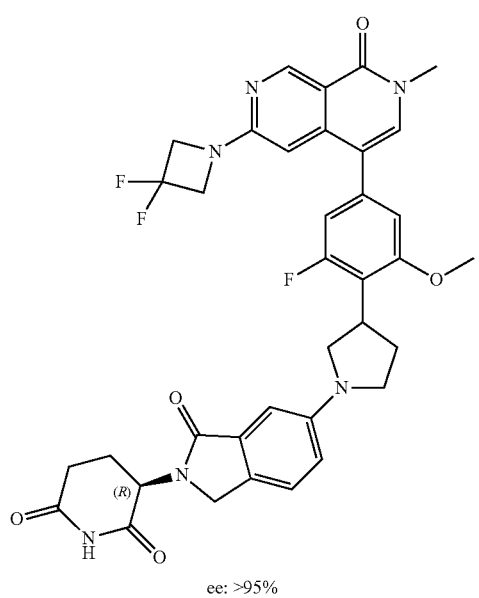

ee: >95%

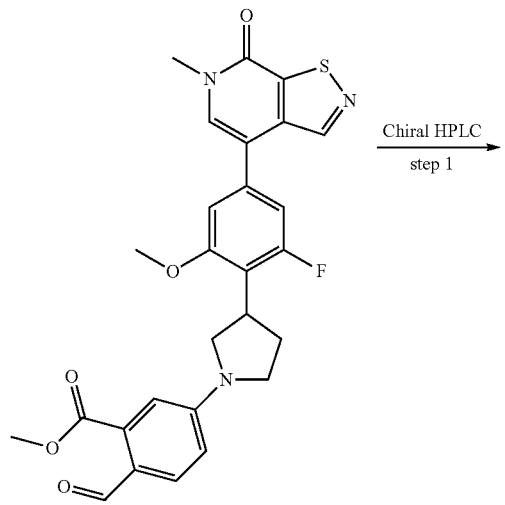
Chiral HPLC
step 1
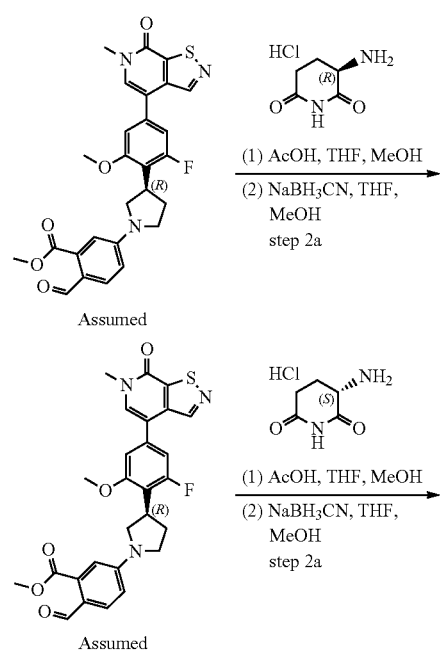

231
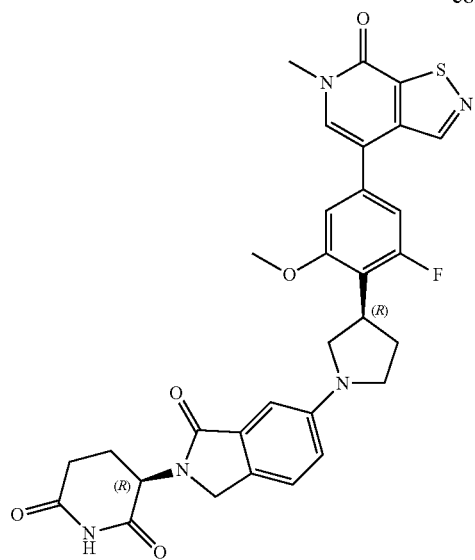
Assumed (R,R)
232
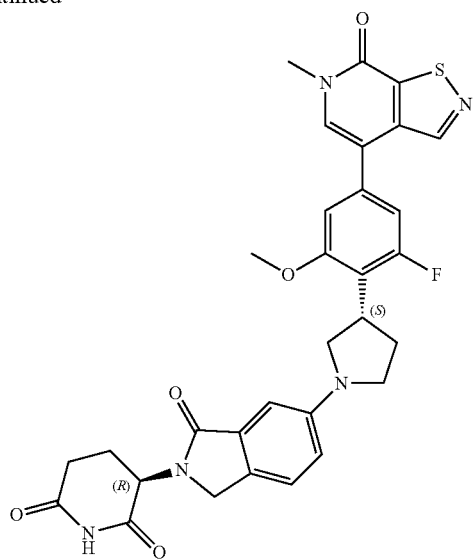
Assumed (S,R)
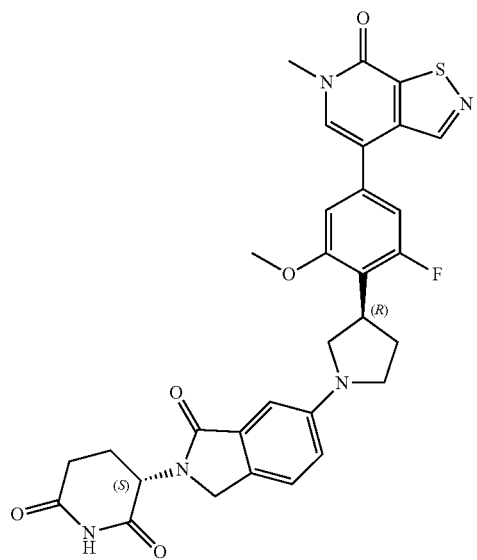
Assumed (R,S)
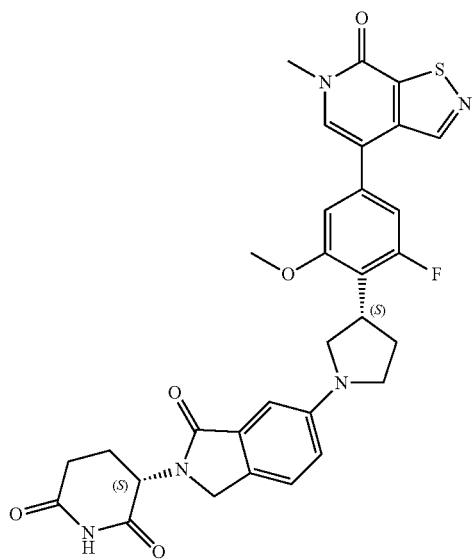
Assumed (S,S)

Other Embodiments

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A citrate salt of the compound of Formula I:

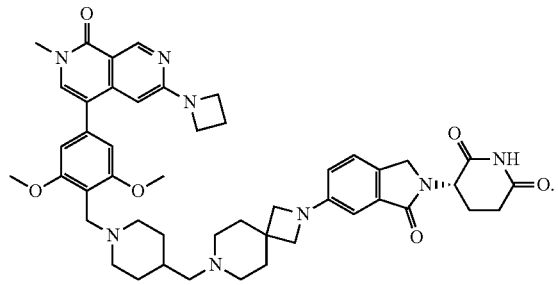

Formula I

2. A pharmaceutical composition comprising the citrate salt of claim 1.

3. The pharmaceutical composition of claim 2, wherein the pharmaceutical composition is liquid.

4. The pharmaceutical composition of claim 2, further comprising a buffer.

5. The pharmaceutical composition of claim 4, wherein the buffer is a citrate buffer.

6. The pharmaceutical composition of claim 2, wherein pH of the pharmaceutical composition is 3.5 to 5.5.

7. The pharmaceutical composition of claim 2, further comprising a cyclodextrin-based solubilizer.

8. The pharmaceutical composition of claim 7, wherein the cyclodextrin-based solubilizer is sulfobutylether-β-cyclodextrin.

9. The pharmaceutical composition of claim 2, further comprising saline.

10. The pharmaceutical composition of claim 9, wherein the saline is an isotonic saline.

11. A method of treating a subject having synovial sarcoma, the method comprising administering to the subject an effective amount of the citrate salt of claim 1.

12. A method treating a viral infection related to BAF47 in a subject in need thereof, the method comprising administering to the subject an effective amount of the citrate salt of claim 1.

* * * * *